(12) United States Patent
Schalk et al.

(10) Patent No.: US 12,241,110 B2
(45) Date of Patent: Mar. 4, 2025

(54) CYTOCHROME P450 MONOOXYGENASE CATALYZED OXIDATION OF SESQUITERPENES

(71) Applicant: FIRMENICH SA, Satigny (CH)

(72) Inventors: Michel Schalk, Satigny (CH); Letizia Rocci, Satigny (CH); Fabienne Deguerry, Satigny (CH)

( * ) Notice: Subject to any disclaimer, the term of this patent is extended or adjusted under 35 U.S.C. 154(b) by 868 days.

(21) Appl. No.: 16/766,225

(22) PCT Filed: Jan. 16, 2019

(86) PCT No.: PCT/EP2019/051070
§ 371 (c)(1),
(2) Date: May 21, 2020

(87) PCT Pub. No.: WO2019/141739
PCT Pub. Date: Jul. 25, 2019

(65) Prior Publication Data
US 2023/0151393 A1    May 18, 2023

(30) Foreign Application Priority Data
Jan. 18, 2018 (EP) .................................... 18152363

(51) Int. Cl.
| | |
|---|---|
| *C12P 7/02* | (2006.01) |
| *C12N 5/10* | (2006.01) |
| *C12N 9/02* | (2006.01) |
| *C12N 15/52* | (2006.01) |
| *C12N 15/63* | (2006.01) |
| *C12P 5/00* | (2006.01) |

(52) U.S. Cl.
CPC .................. *C12P 7/02* (2013.01); *C12N 5/10* (2013.01); *C12N 9/0077* (2013.01); *C12N 15/52* (2013.01); *C12N 15/63* (2013.01); *C12P 5/007* (2013.01); *C12Y 114/15006* (2013.01)

(58) Field of Classification Search
CPC ... C12P 7/02; C12P 5/007; C12N 5/10; C12N 9/0077; C12N 15/52; C12N 15/63; C12N 9/0071; C12Y 114/15006
See application file for complete search history.

(56) References Cited

U.S. PATENT DOCUMENTS

| | | | | |
|---|---|---|---|---|
| 8,703,454 | B2 * | 4/2014 | Schalk .................. | C12P 15/00 435/166 |
| 9,909,145 | B2 | 3/2018 | Daviet et al. | |
| 10,000,773 | B2 * | 6/2018 | Schalk .................. | C12P 5/007 |
| 11,293,040 | B2 * | 4/2022 | Schalk .................. | C12N 15/70 |
| 2011/0167514 | A1 | 7/2011 | Brover et al. | |

FOREIGN PATENT DOCUMENTS

| | | | |
|---|---|---|---|
| EP | 2090662 | A2 | 3/2008 |
| JP | 2016533707 | | 11/2016 |
| WO | 2006134523 | A2 | 12/2006 |
| WO | 2010134004 | A1 | 11/2010 |
| WO | 2013064411 | A1 | 5/2013 |
| WO | 2018015453 | A2 | 1/2018 |

OTHER PUBLICATIONS

Banerjee et al., Improving enzymes for biomass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Dictionary optional meaning; one page, downloaded on Dec. 7, 2023 (Year: 2023).*
Citron et al., Terpenoids are Widespread in Actinomycetes: A Correlation of Secondary Metabolism and Genome Data. ChemBiochem., 2012, vol. 13: 202-214. (Year: 2012).*
Nist Chem WebBook, 2 pages downloaded on Feb. 2, 2024. (Year: 2024).*
Weyerstahl et al., 1,7-Cyclogermacra-1(10),4-dien-15-al, a sesquiterpene with a novel skeleton, and other sesquiterpenes from Haitian vetiver oil. Flav. Frag., 2000, vol. 15: 61-83. (Year: 2000).*

(Continued)

*Primary Examiner* — Ganapathirama Raghu
(74) *Attorney, Agent, or Firm* — Armstrong Teasdale LLP

(57) ABSTRACT

Described herein are the nucleic acid and the amino acid sequences of a cytochrome P450 capable of oxidizing terpene molecules. Also described herein are methods of oxidizing terpene molecules including contacting the cytochrome P450 with the terpene molecule intended to be oxidized. In particular, the method may be carried out in vitro or in vivo to produce oxidized terpene molecules, which may be used in different technical fields such as for example perfumery and flavoring. Also described herein is an expression vector containing the nucleic acid. A non-human host organism or a cell transformed with the nucleic acid is also an object of the disclosure.

9 Claims, 26 Drawing Sheets

Specification includes a Sequence Listing.

(56) References Cited

OTHER PUBLICATIONS

International Search Report and Written Opinion for corresponding PCT/EP2019/051070 mailed Apr. 17, 2019, 19 pages.

* cited by examiner

-Figure 1A-

Compound 1

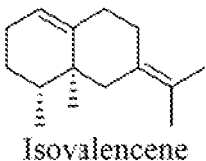

Isovalencene (4S,5R)-4a,5-dimethyl-3-(propan-2-ylidene)-1,2,3,4,4a,5,6,7-octahydronaphthalene
4β,5α-eremophila-1(10),7(11)-diene
CAS Registry Number 16641-26-2

Compound 2

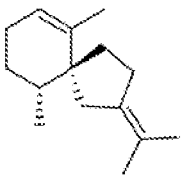

spirovetiva-1(10),7(11)-diene (5RS,6RS)-2-ISOPROPYLIDENE-6,10-DIMETHYL-SPIRO[4.5]DEC-6-ENE
(5R,10R)-6,10-dimethyl-2-(propan-2-ylidene)spiro[4.5]dec-6-ene
CAS Registry Number 39850-96-9

Compound 3

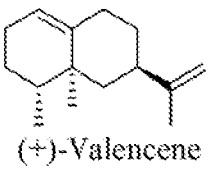

(+)-Valencene

4βH,5α-Eremophila-1(10),11-diene
(3R,4aS,5R)-3-isopropyl-4a,5-dimethyl-1,2,3,4,4a,5,6,7-octahydronaphthalene
CAS Registry Number 4630-07-3

-Figure 1B-
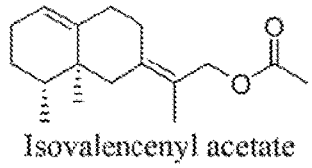
Isovalencenyl acetate
CAS Registry Number 352461-71-3
(E)-Eremophila-1(10),7(11)-dien-12-yl acetate
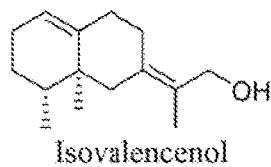
Isovalencenol
CAS Registry Number 22387-74-2
4βH,5α-Eremophila-1(10),7(11)-dien-12-ol
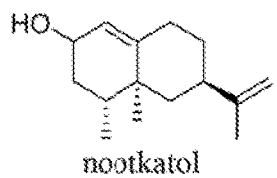
nootkatol
CAS Registry Number 840474-83-1
(4R,4aS,6R)-2-Naphthalenol, 2,3,4,4a,5,6,7,8-octahydro-4,4a-dimethyl-6-(1-methylethenyl)
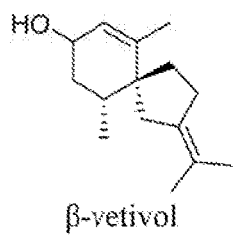
β-vetivol
6,10-Dimethyl-2-(1-methylethylidene)spiro[4.5]dec-6-en-8-ol
CAS Registry Number 39850-92-5

-Figure 1C-
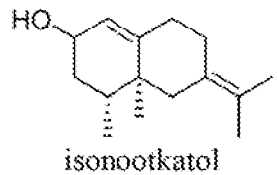
isonootkatol
2,3,4,4a,5,6,7,8-Octahydro-4,4a-dimethyl-6-(1-methylethylidene)-2-naphthalenol
CAS Registry Number 39850-91-4
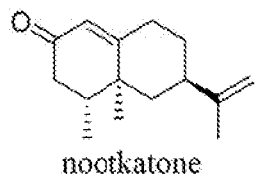
nootkatone
(4R,4aS,6R)-
2(3H)-Naphthalenone, 4,4a,5,6,7,8-hexahydro-4,4a-dimethyl-6-(1-methylethenyl)-,
CAS Registry Number 4674-50-4
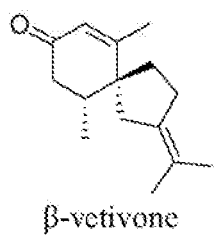
β-vetivone
6,10-dimethyl-2-(1-methylethylidene)-Spiro[4.5]dec-6-en-8-one
CAS Registry Number 859739-66-5

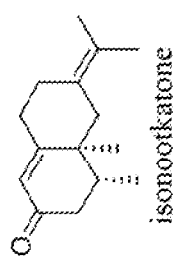
-Figure 1D-
isonootkatone
(4R,4aS)-4,4a,5,6,7,8-Hexahydro-4,4a-dimethyl-6-(1-methylethylidene)-2(3H)-naphthalenone
CAS Registry Number 15764-04-2

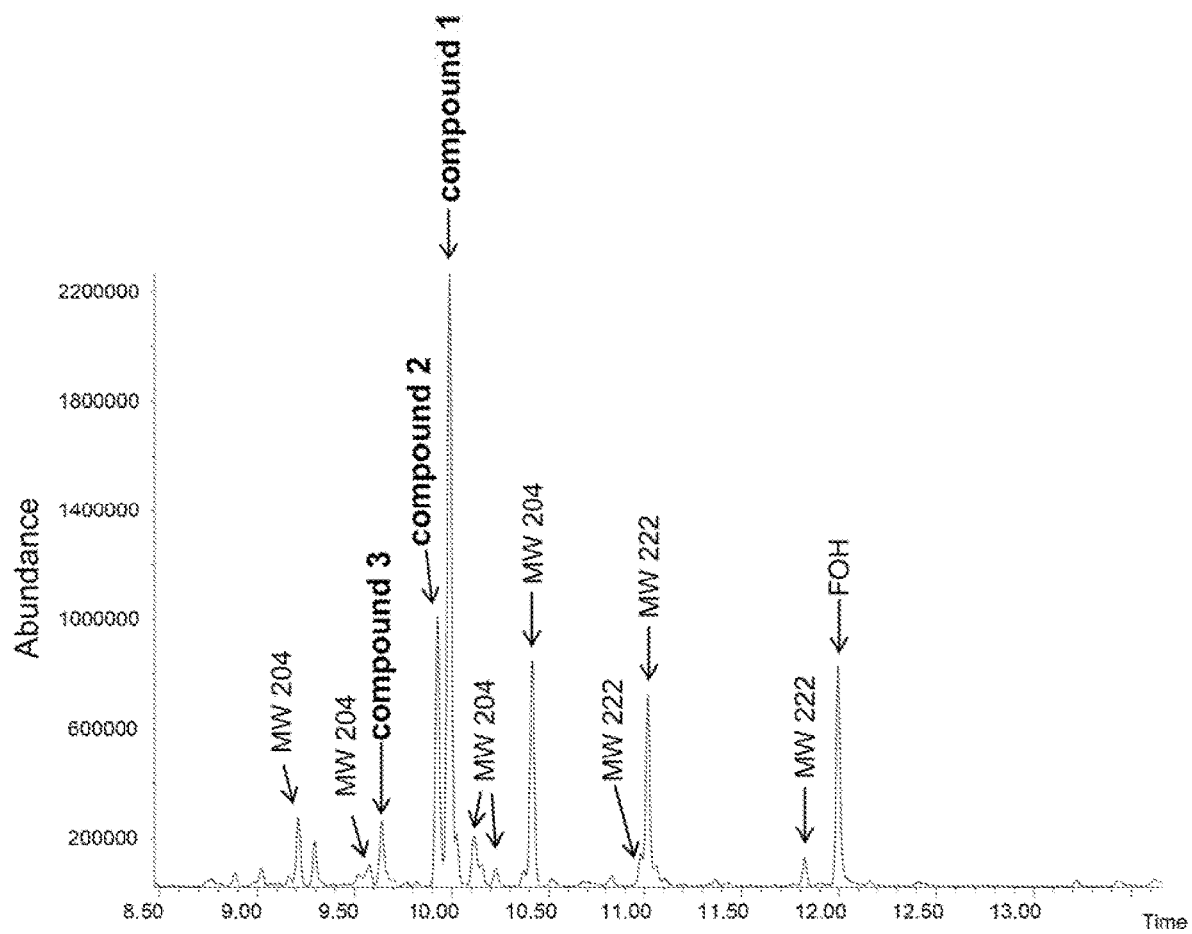
- Figure 2 -

Mass spectrum of compound 1 in Figure 2

Mass spectrum of isovalencene standard

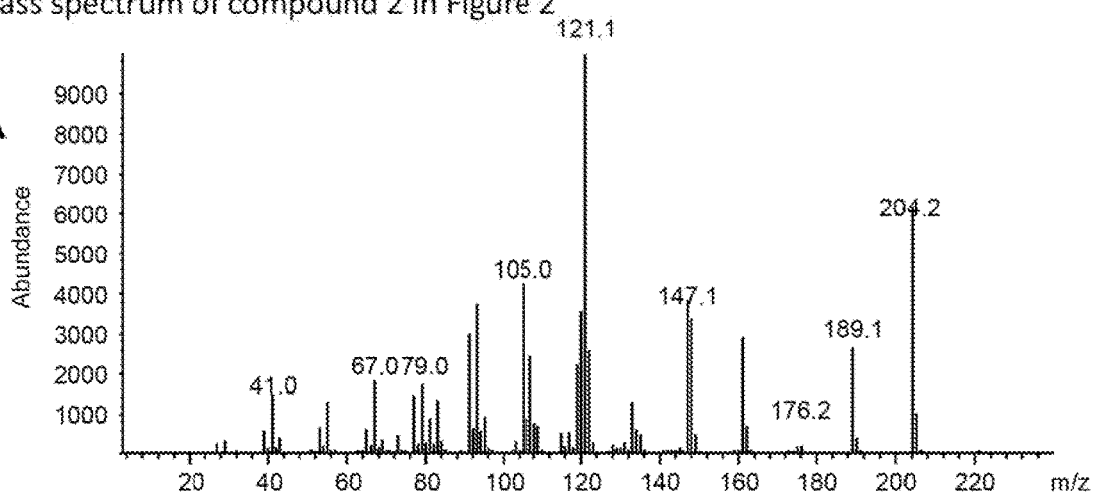
Fig. 4A — Mass spectrum of compound 2 in Figure 2
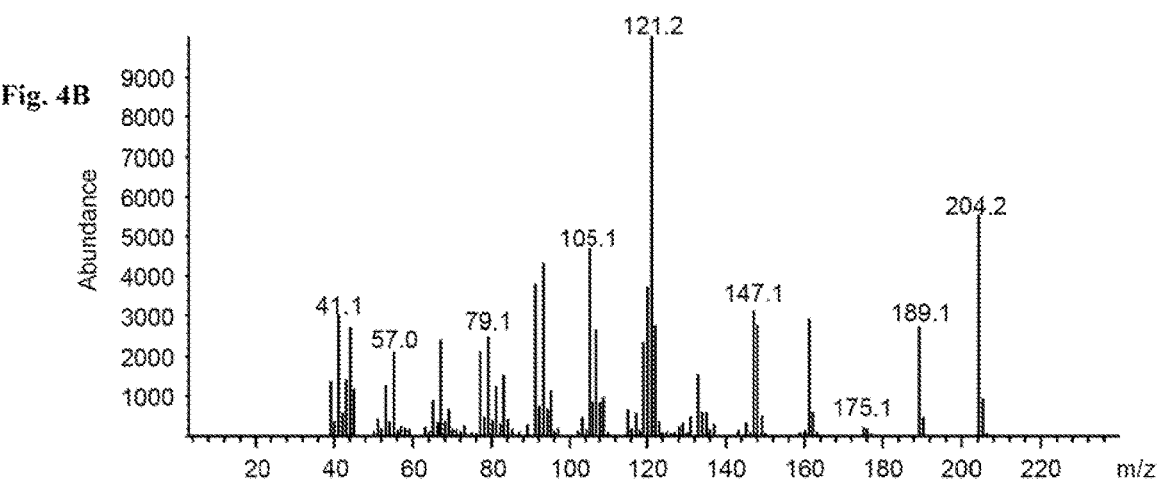
Fig. 4B — Mass spectrum of spirovetiva-1(10),7(11)-diene standard

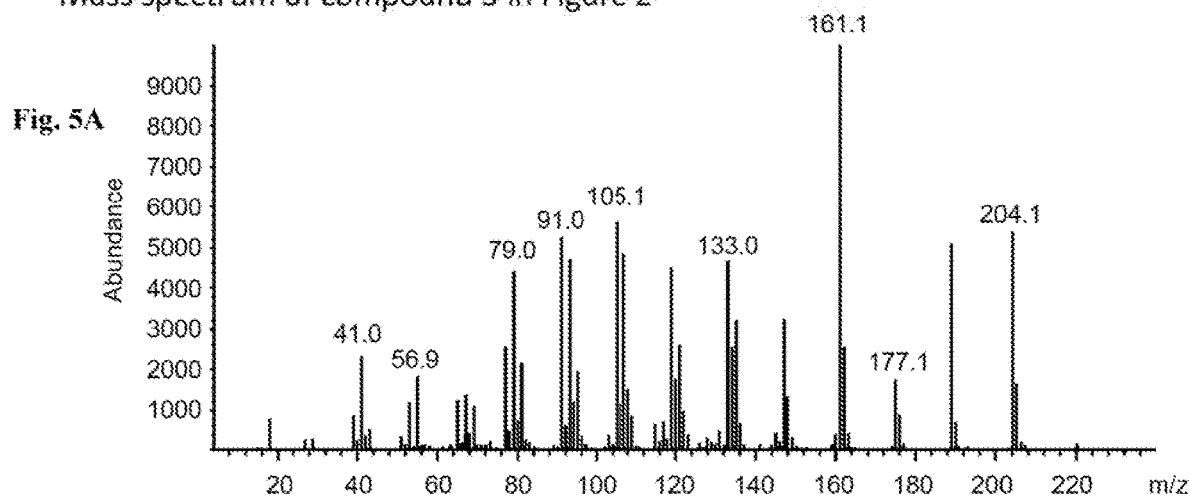
Fig. 5A — Mass spectrum of compound 3 in Figure 2
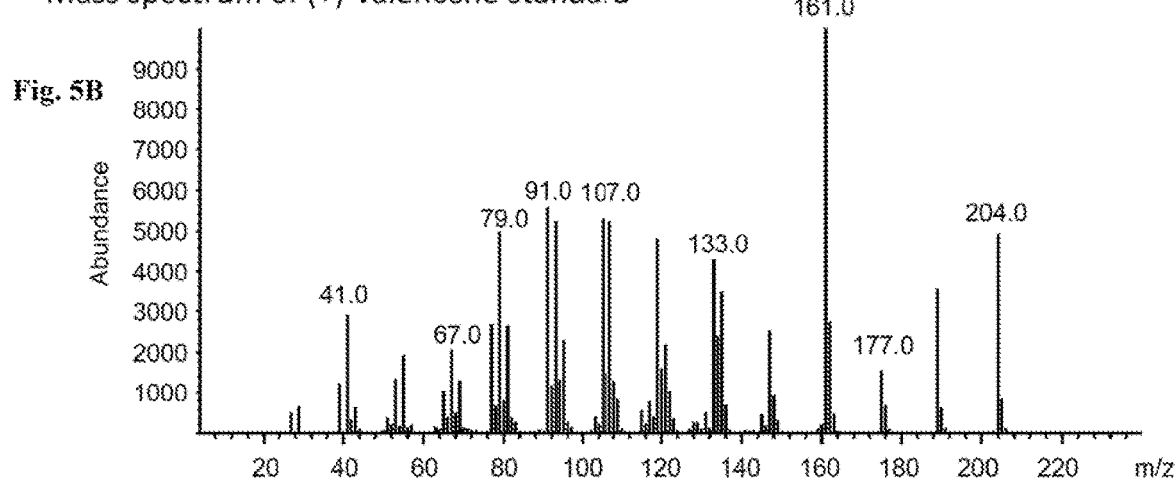
Fig. 5B — Mass spectrum of (+)-valencene standard

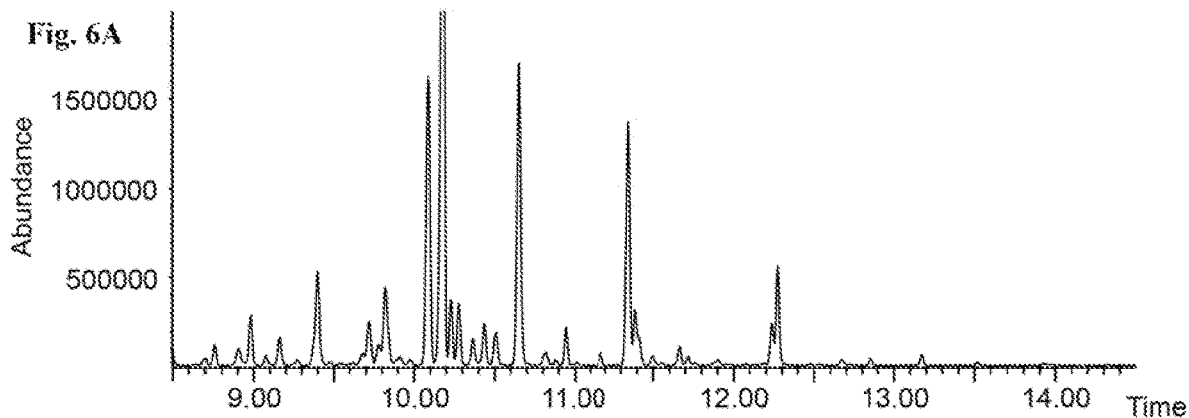
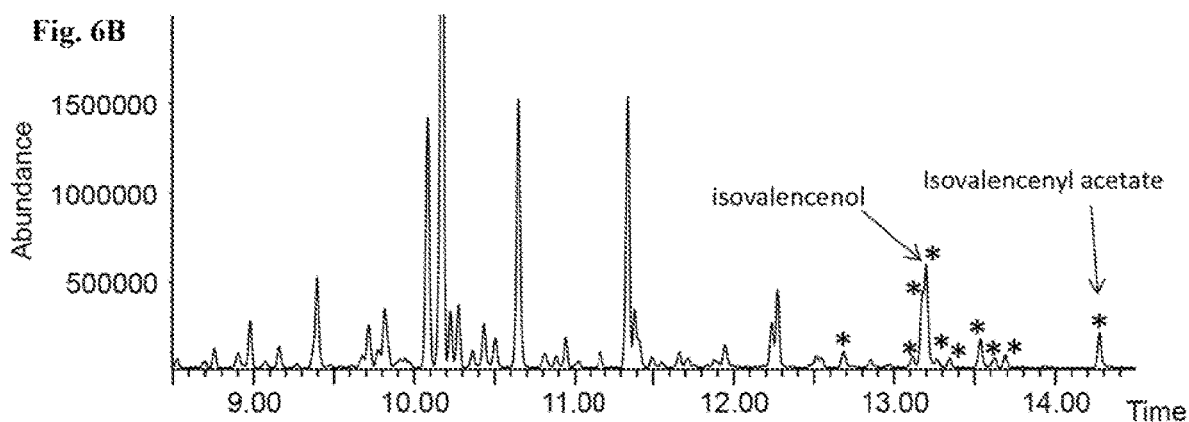
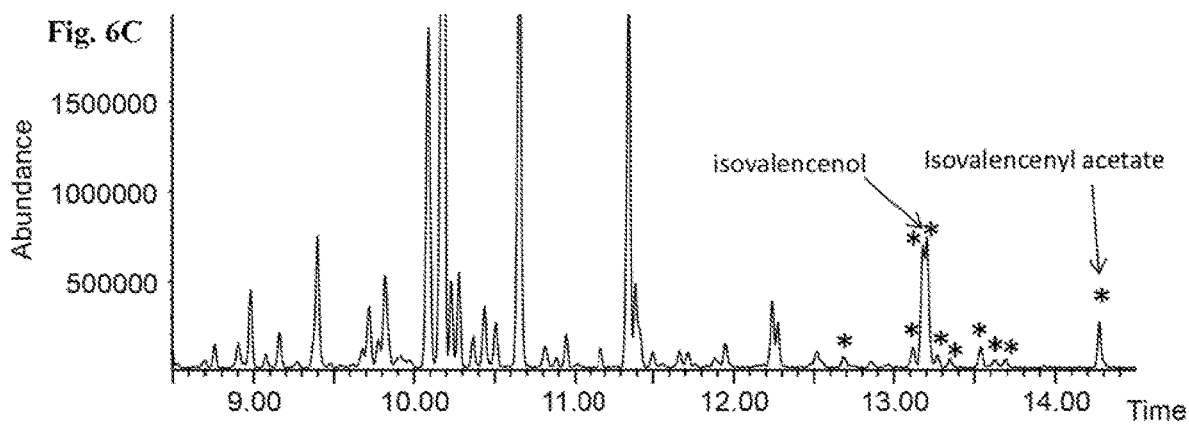

Mass spectrum of the peak identified as isovalencenol in figure 6B and C.

Mass spectrum of an isovalencenol authentic standard.

Mass spectrum of the peak identified as isovalencenyl acetate in figure 6B and C.

Mass spectrum of an isovalencenol authentic standard.

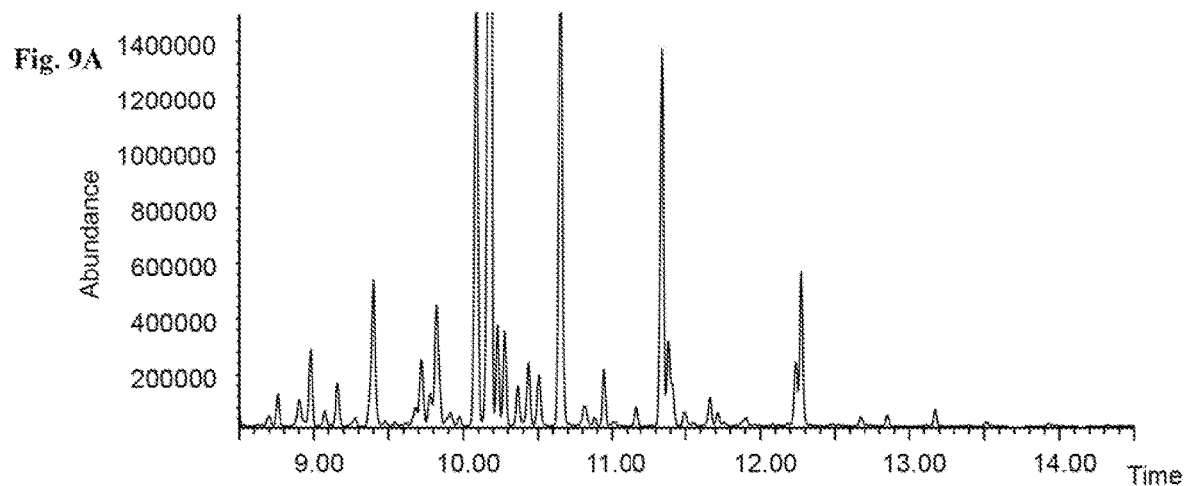
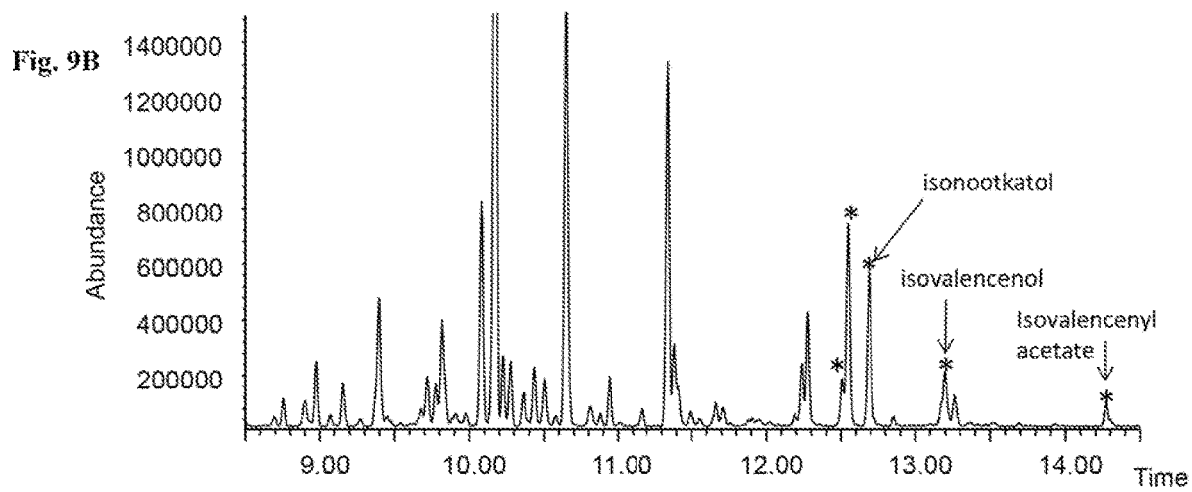

Mass spectrum of the peak identified as isonootkatol in figure 9B.

Mass spectrum of an isonootkatol authentic standard.

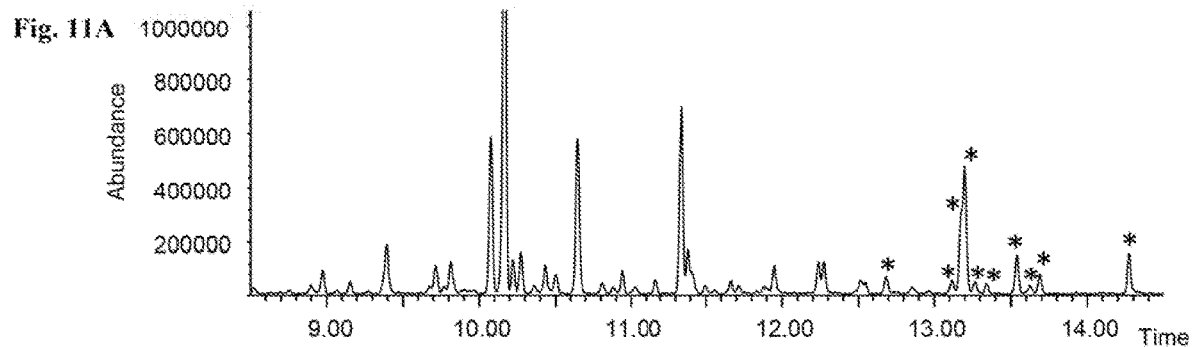
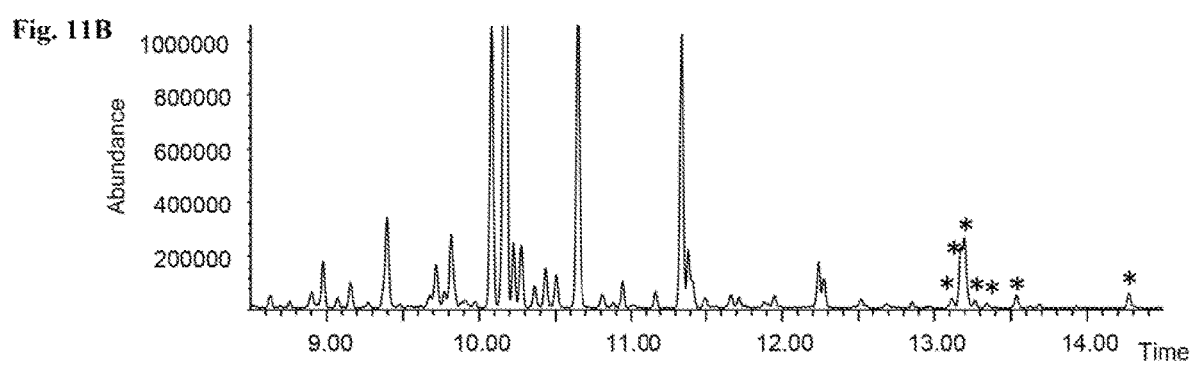
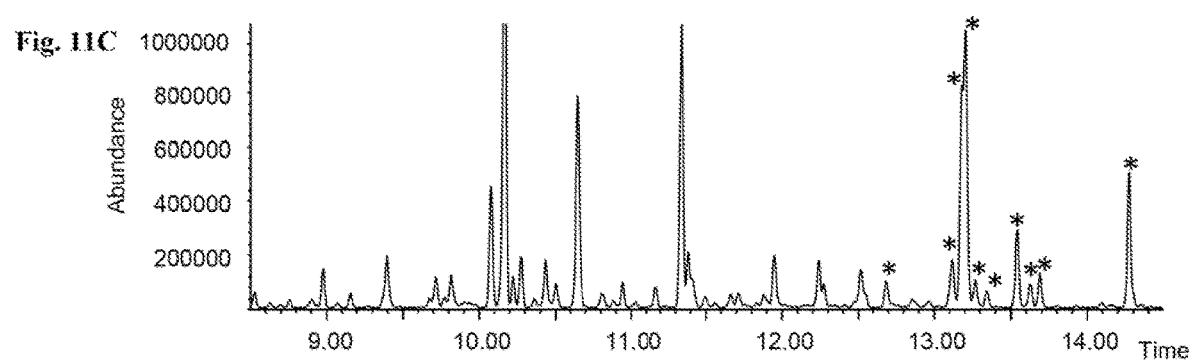

-Figure 12A-
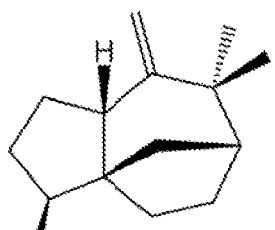
(+)-Zizaene
CAS Registry Number 18444-94-5
(3S,3aS,6R,8aS)-1*H*-3a,6-Methanoazulene, octahydro-3,7,7-trimethyl-8-methylene
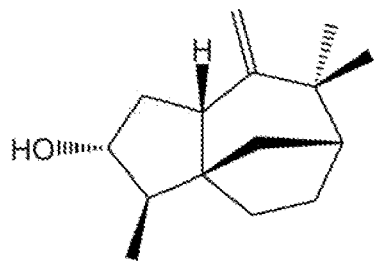
α-Zizaenol
CAS Registry Number 28102-79-6
(2R,3R,3aR,6R,8aS)-1H-3a,6-Methanoazulen-2-ol, octahydro-3,7,7-trimethyl-8-methylene
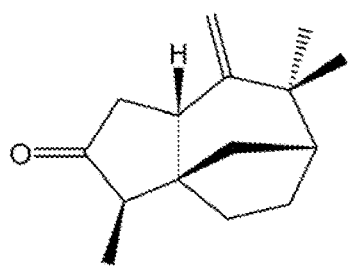
Zizaenone
CAS Registry Number 28051-97-0
(3R,3aR,6R,8aS)-1H-3a,6-Methanoazulen-2(3H)-one, hexahydro-3,7,7-trimethyl-8-methylene -Figure 12B-
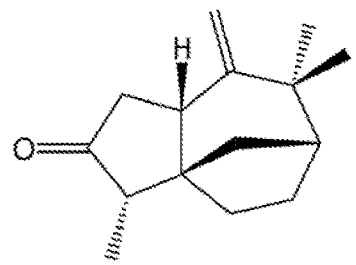
*epi*-Zizaenone
CAS Registry Number 28624-27-3
(3S,3aR,6R,8aS)-1H-3a,6-Methanoazulen-2(3H)-one, hexahydro-3,7,7-trimethyl-8-methylene
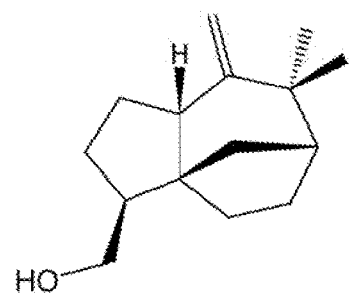
Khusimol
CAS Registry Number 16223-63-5
(3S,3aR,6R,8aS)-1H-3a,6-Methanoazulene-3-methanol, octahydro-7,7-dimethyl-8-methylene

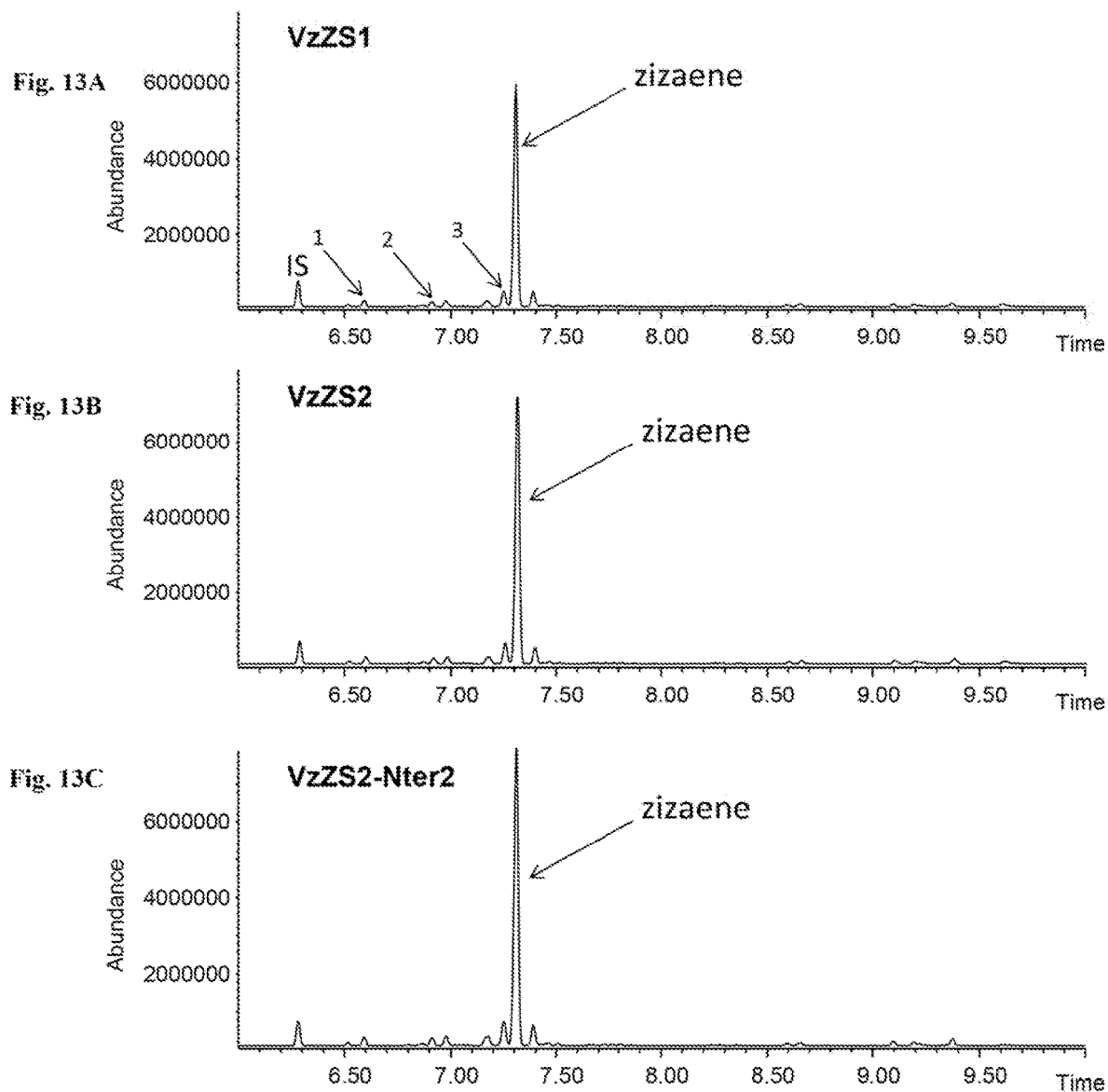

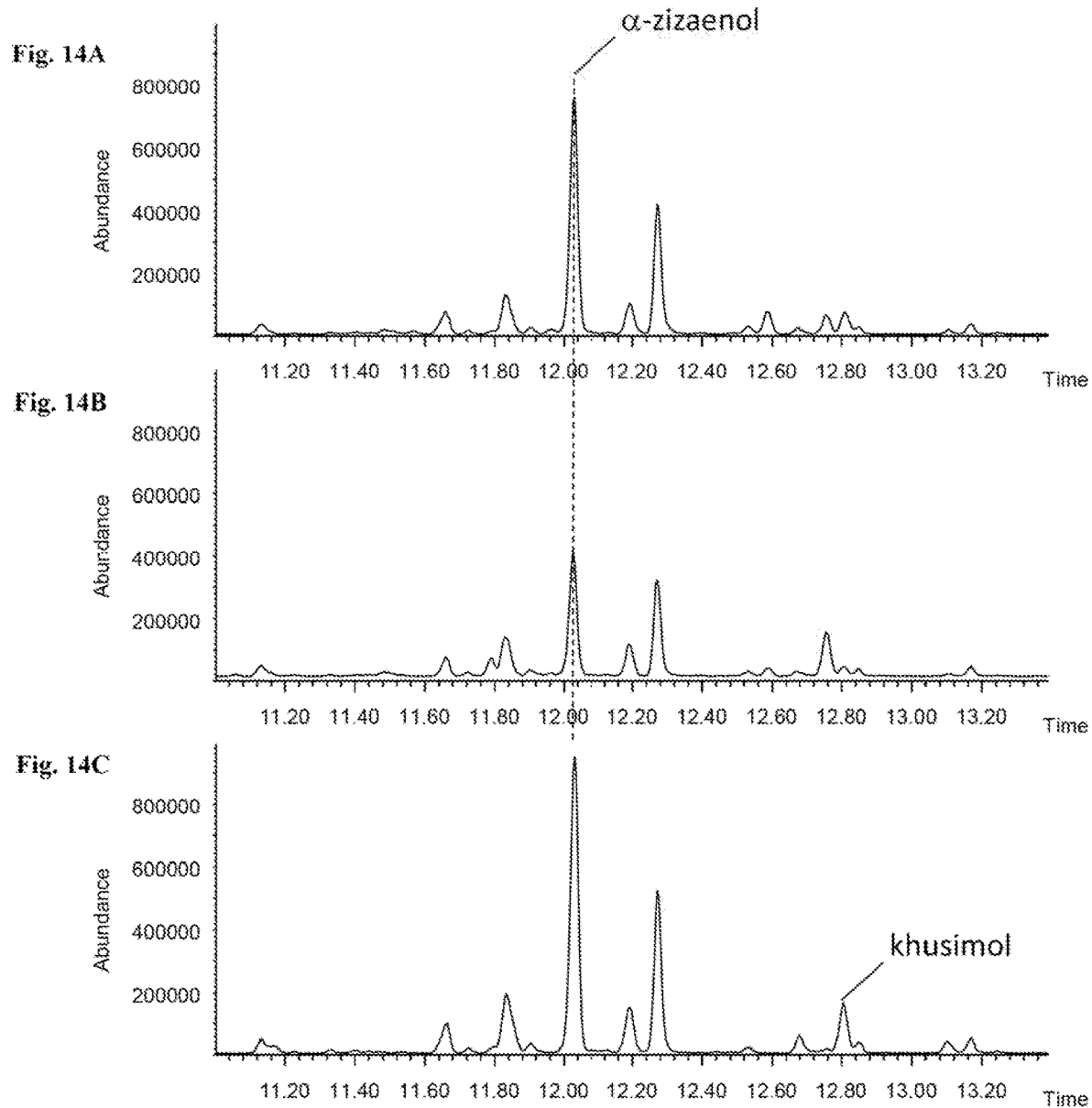

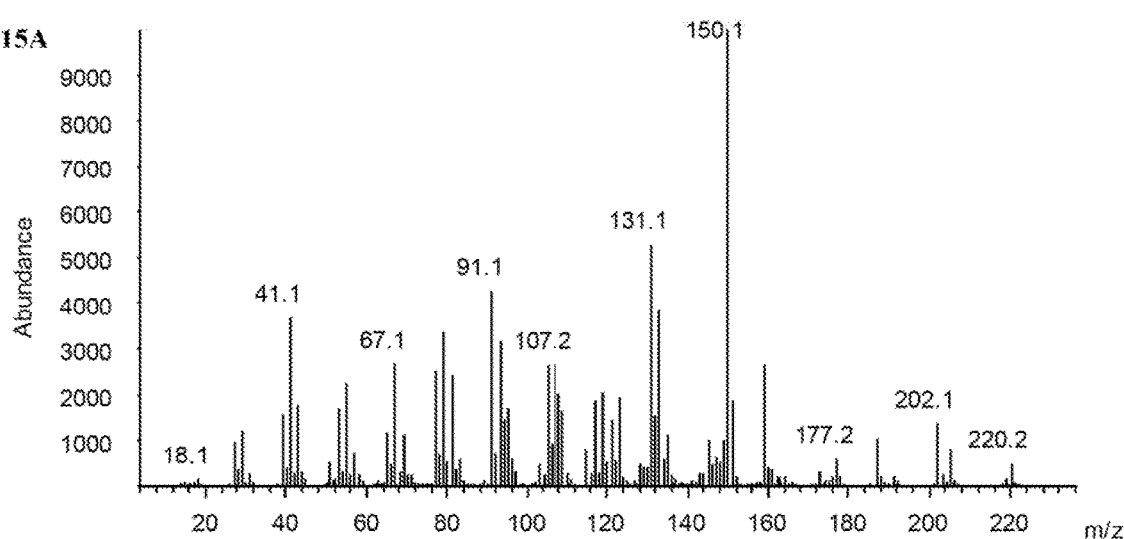
Fig. 15A. Mass spectrum of the peak at 12.03 minutes in figure 14.
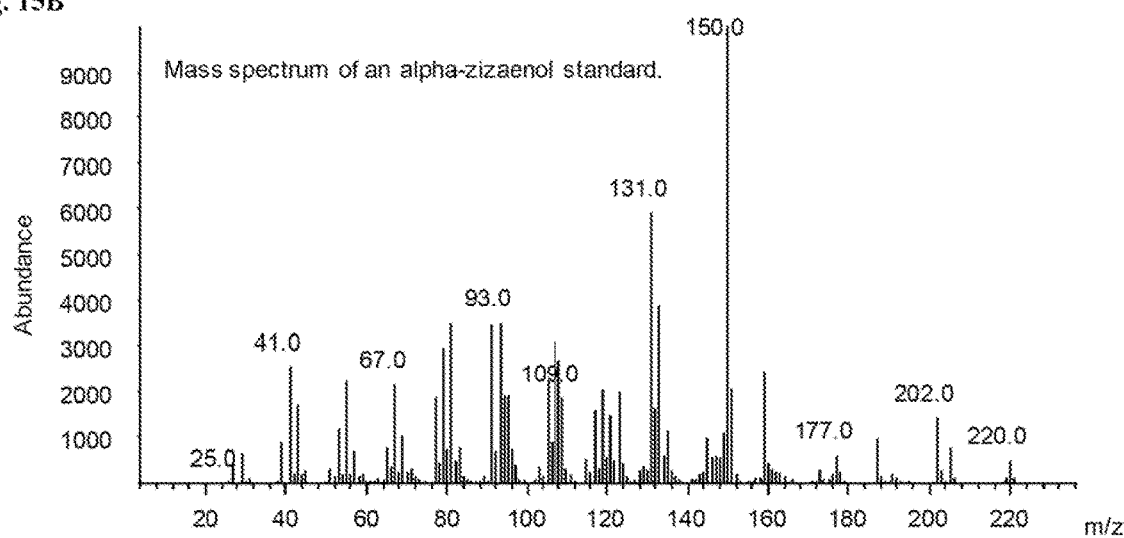
Fig. 15B. Mass spectrum of an alpha-zizaenol standard.

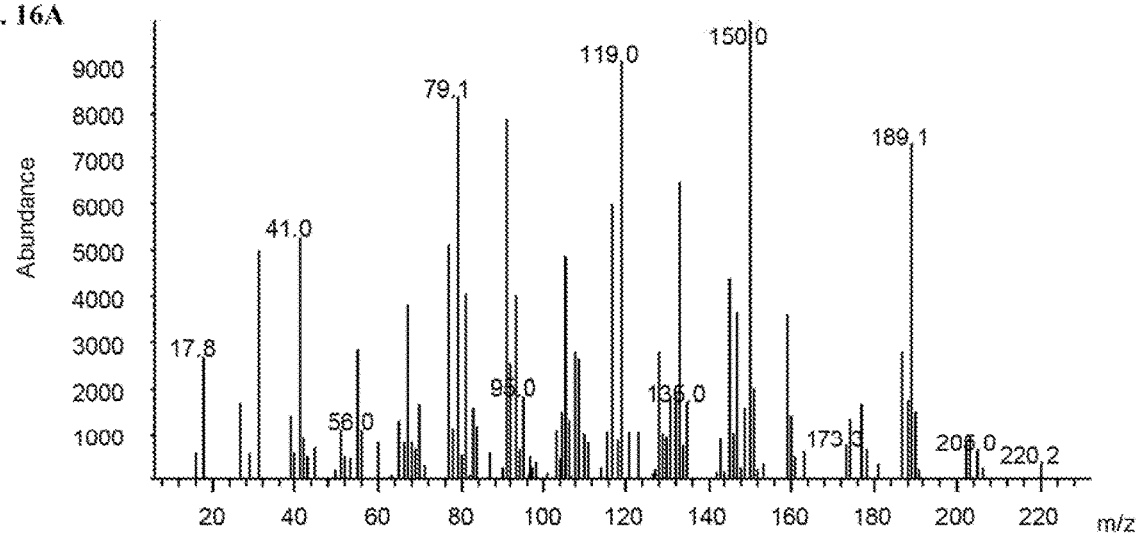
Fig. 16A — Mass spectrum of the peak at 12.8 min. in figure 14C
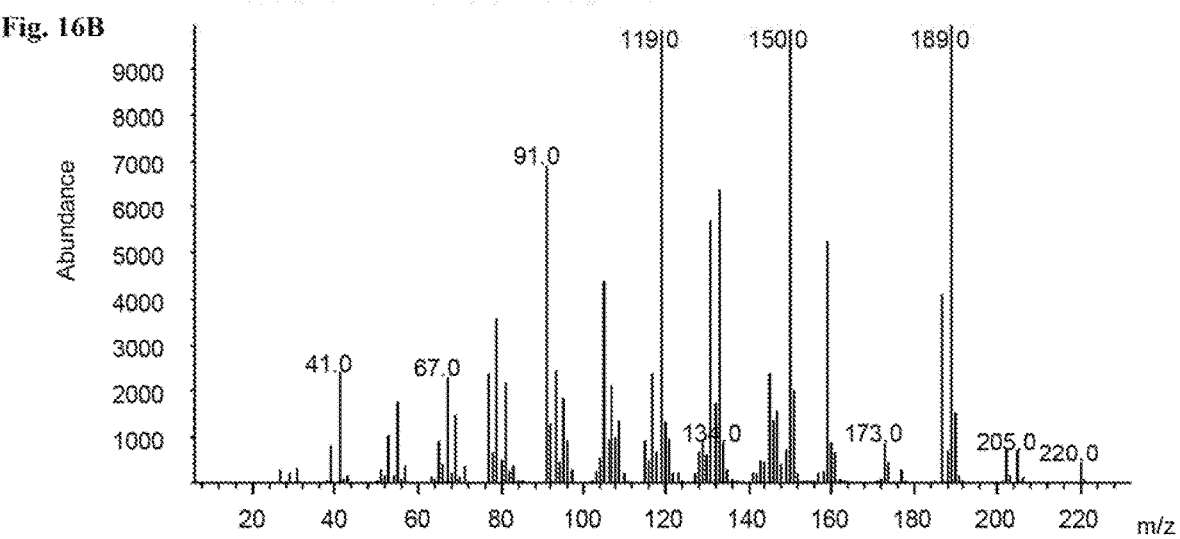
Fig. 16B — Mass spectrum of an khusimol standard.

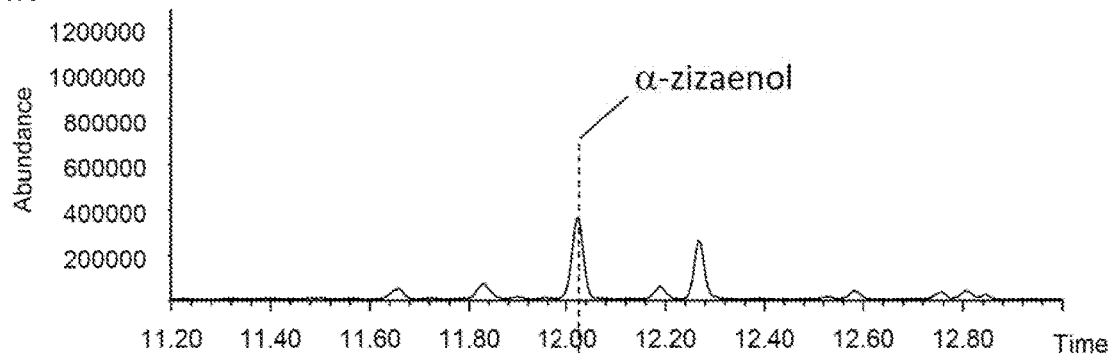
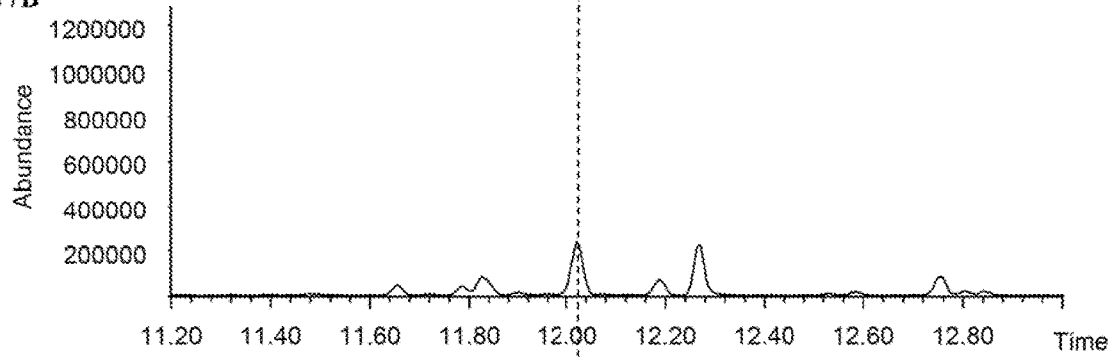
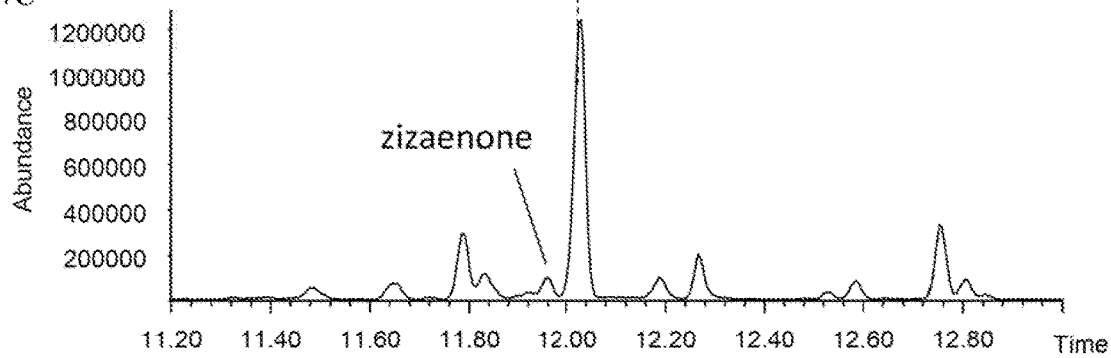

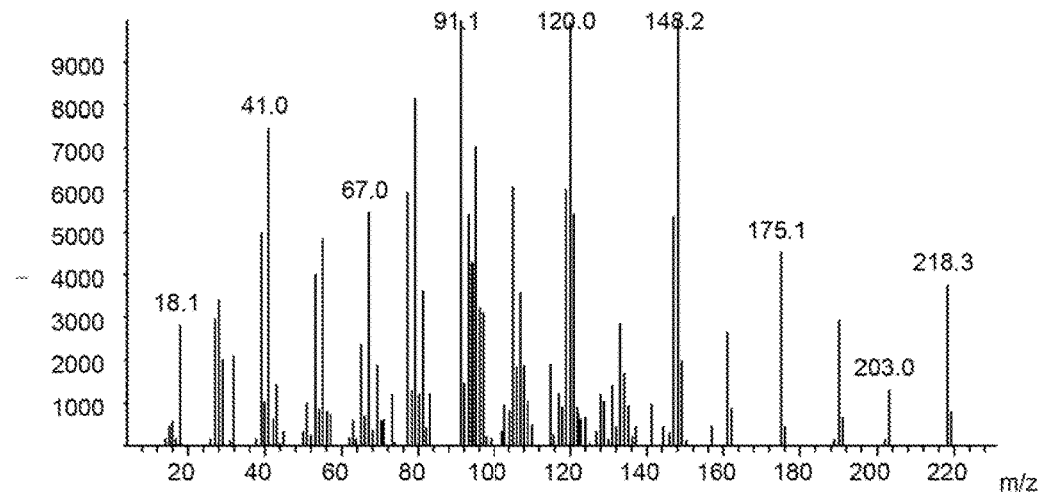
Fig. 18A  Mass spectrum of the peak at 11.96 minutes in figure 17C
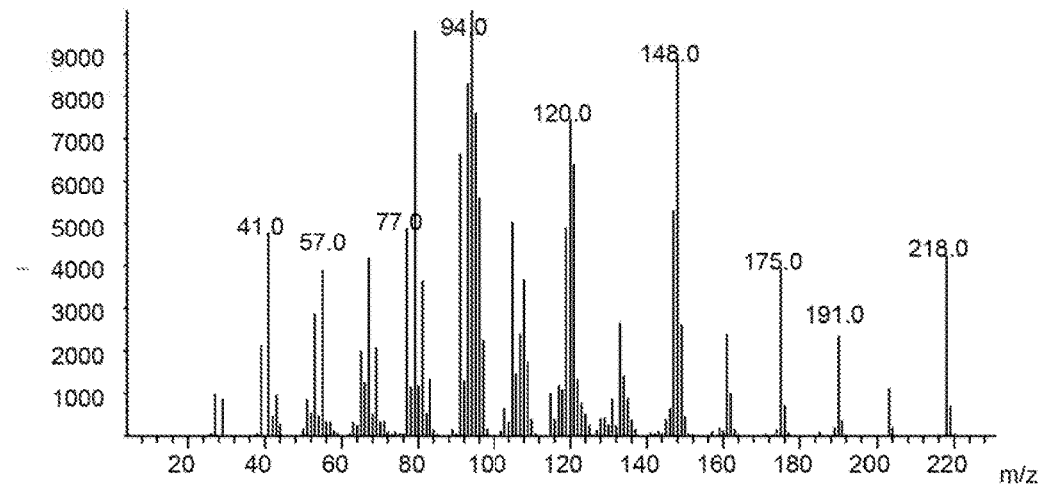
Fig. 18B  Mass spectrum of an zizaenone standard

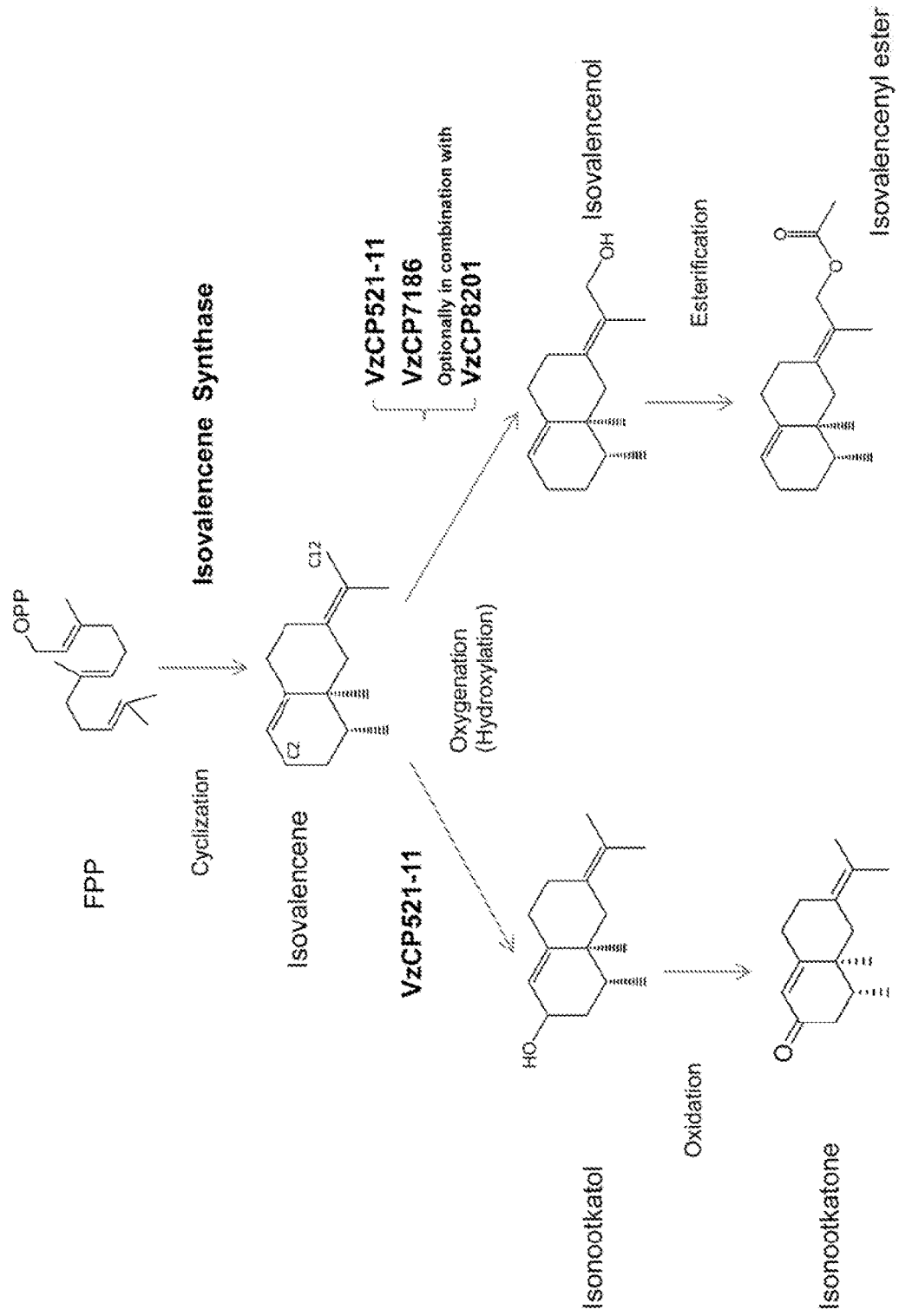

- Figure 20 -
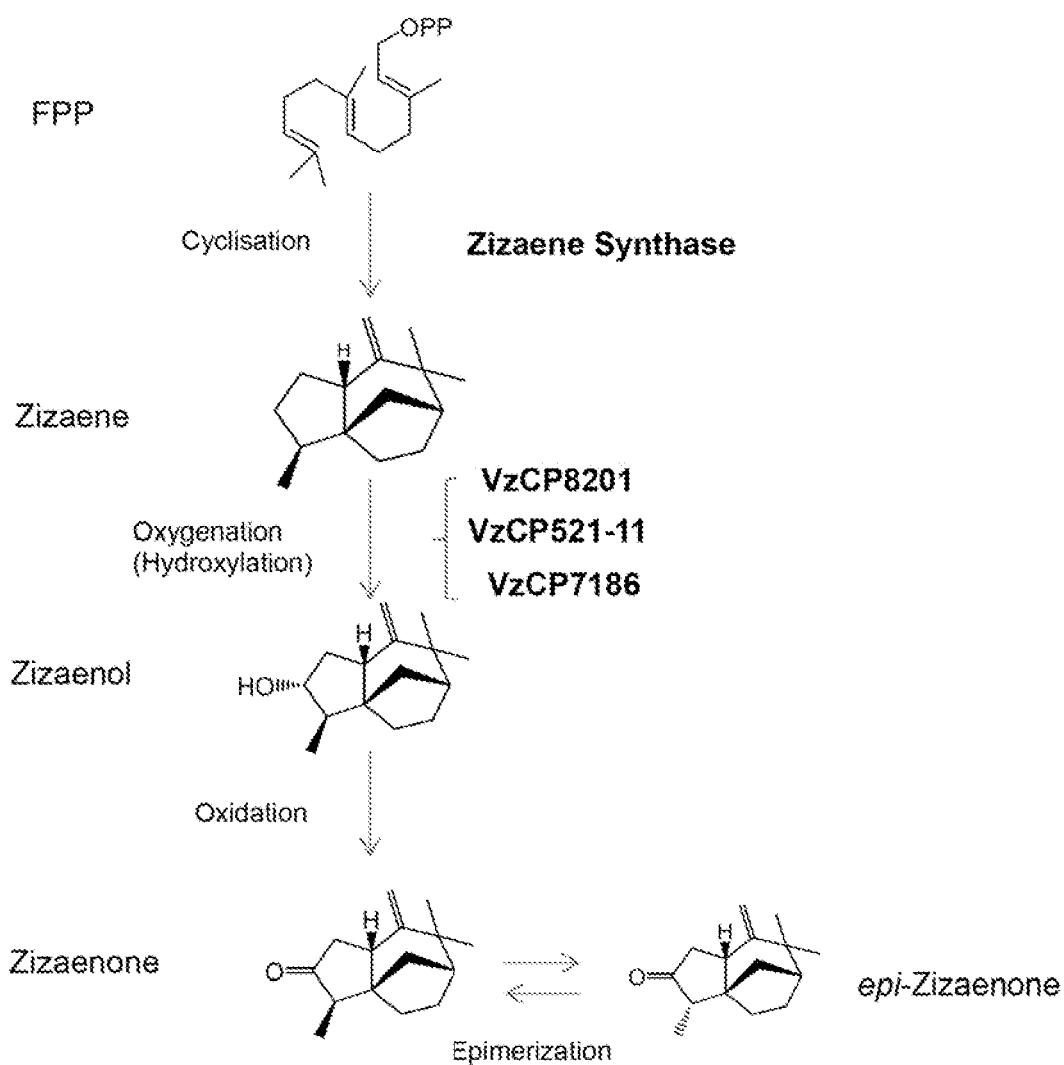

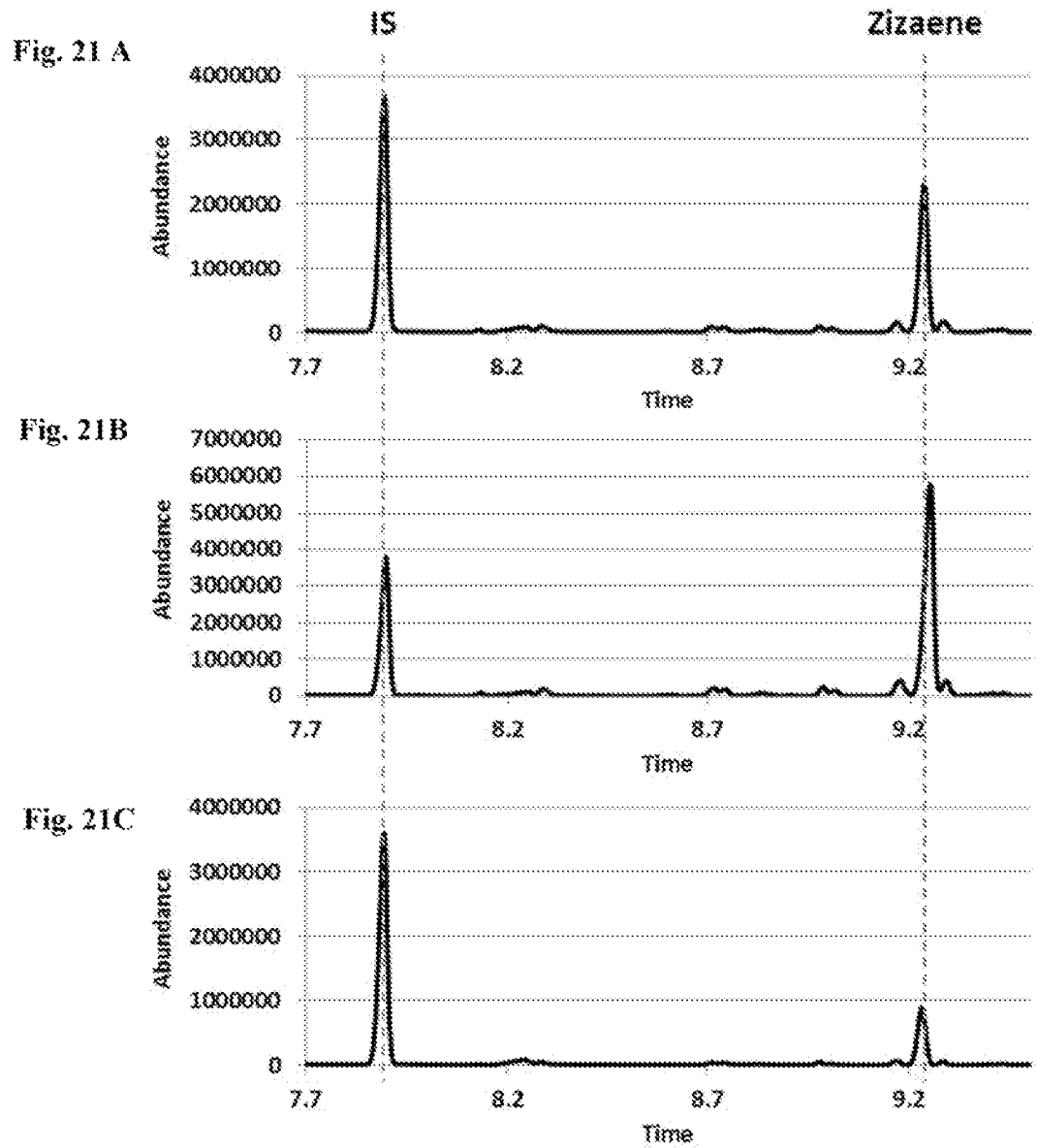

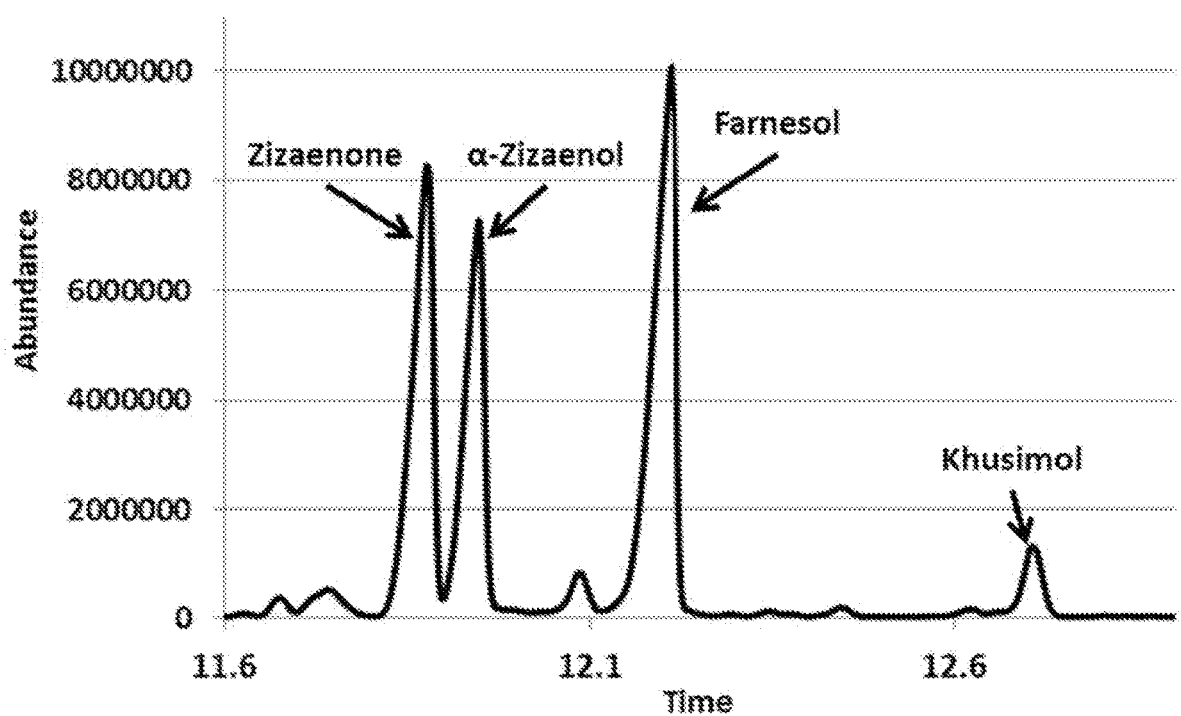
- Figure 22 -

CYTOCHROME P450 MONOOXYGENASE CATALYZED OXIDATION OF SESQUITERPENES

CROSS-REFERENCE TO RELATED APPLICATIONS

This application is a U.S. National Phase Application of PCT/EP2019/051070, filed on Jan. 16, 2019, which claims the benefit of priority to European Patent Application Number 18152363.0, filed Jan. 18, 2018, the entire contents of which are hereby incorporated by reference herein.

SEQUENCE LISTING

This application contains a sequence listing in paper format and in computer readable format, the teachings and content of which are hereby incorporated by reference.

TECHNICAL FIELD

The present invention provides a method of oxidizing sesquiterpene molecules comprising contacting certain cytochrome P450 monooxygenases with the sesquiterpene molecule intended to be oxidized. It also provides a novel cytochrome P450 monooxygenase capable of oxidizing sesquiterpene molecules, corresponding coding sequences, expression vectors, recombinant non-human host organism applicable in the production of said novel enzyme and mutants thereof.

BACKGROUND OF THE INVENTION

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Diterpenes, for example, are widely found in the plant kingdom and over 2500 diterpene structures have been described (Connolly and Hill, Dictionary of terpenoids, 1991, Chapman & Hall, London). Vetiver oil extracted from roots of the plant *Vetiveria zizanoides* is a valuable source of numerous bi- and tricyclic sesquiterpenes in different oxidation stage (alcohols, ketones, aldehydes and carboxylic acids) (see also M. Maffei, Vetriveria, 2002). Terpene molecules and their oxidized derivatives have been of interest for thousands of years because of their flavor and fragrance properties and their cosmetic, medicinal and antimicrobial effects. Plant extracts obtained by different means such as steam distillation or solvent extraction are used as source of oxidized derivatives of terpene molecules. Alternatively, terpene molecules found in plant extracts or obtained by biosynthetic processes are oxidized using chemical and enzymatic processes.

Enzymatic oxidation of terpenes often involves enzymes called cytochrome P450s (P450s), which are typically capable of catalyzing the transformation of a hydrophobic substrate, such as a terpene molecule, in a more hydrophilic one. Cytochrome P450 enzymes form a superfamily of hemoproteins found in bacteria, archaea and eukaryotes. In one of the most common activities, cytochrome P450 acts as a monooxygenase, by inserting one oxygen atom of molecular oxygen into a substrate molecule, while the other oxygen atom is reduced to water.

This catalytic reaction requires two electrons for the activation of molecular oxygen. P450s from eukaryotes use NADPH as the external reductant and source of electrons. The two electrons are transferred one at a time to the cytochrome P450 active site and this transfer requires an electron donor protein, a cytochrome P450 reductase (CPR). One CPR is not specific for one cytochrome P450. A CPR is the electron donor protein for several P450s in a given organism. In addition, a CPR from one organism can act as the electron donor protein for P450s from other organisms. In some cases P450s can also be coupled to a cytochrome b5 protein that can act as the electron donor protein or can improve the efficiency of the electron transfer from the CPR to the P450. In eukaryotic cells and particularly in plants, P450s and CPRs are generally membrane-bound proteins and are associated with the endoplasmic reticulum. These proteins are anchored to the membrane by an N-terminal trans-membrane helix.

Many P450s have low substrate specificity and are therefore able to catalyze the oxidation of many diverse structures such as for example different terpene molecules. Most of these enzymes have a particular regio- and stereo-selectivity with a given substrate but they often produce a mixture of several products from a particular substrate. Such P450s are usually involved in the breakdown and detoxification of molecules such as xenobiotics and are generally found in bacteria and animals. On the other hand, P450s involved in biosynthetic pathways show usually specificity for certain types of substrates and regio- and stereo-selectivity. This is the case for most plant P450s.

A large number of P450s can be found in nature and particularly in plants. One plant genome can contain several hundreds of genes encoding for P450s. Many plant P450s have been characterized but considering the extremely large number of P450s present in plants, most of their functions remain unknown.

It is therefore desirable to search for new cytochrome P450s capable of catalyzing the enzymatic production of valuable oxygenated compounds such as oxidized sesquiterpenes which otherwise would be accessible only via difficult and expensive classical isolation steps from natural oils like vetiver oil.

It is also desirable to identify per se known P450 enzymes for their applicability in such enzymatic productions.

It is a particular objective of the present invention to provide enzyme-catalyzed methods for making oxygenated sesquiterpenes terpenes, in particular isovalencenol, isonootkatol, and/or zizaenol and further oxidized derivatives thereof useful as perfumery and/or aroma ingredients.

It is a further objective to provide novel cytochrome P450 enzymes capable of oxidizing sesquiterpene molecules, in particular isovalencene, and/or zizaene and/or valencene and/or spirovetiva-1(10),7(11)-diene WO 2013/064411 describes isolation, characterization and use of two cytochrome P450 enzymes VzCP521-11 and VzCP521-16 from *Vetiveria zizanoides*. The bioconversion of (+) zizaene to khusimol via oxidation specifically in position C12 of (+) zizaene is reported therein. The bioconversion of isovalencene as well as the conversion of zizaene to zizaenol is not reported.

Earlier, not yet published PCT/EP2017/068268, filed Jul. 19, 2017, discloses, i.a., a cytochrome P450 enzyme from *Vetiveria zizanoides* and variants thereof. The bioconversion of isovalencene to isovalencenol by oxidation in position C12 of isovalencene with the VzCP8201 P450 enzymes as well as the subsequent esterification by *E. coli* background enzyme activity are described. The bioconversion of zizaene is not described for said P450 enzyme.

Abbreviations Used bp base pair
CoA Coenzyme A
DMAPP dimethylallyl diphosphate
DNA deoxyribonucleic acid
cDNA complementary DNA
CPR cytochrome P450-reductase
EDTA ethylenediaminetetraacetic acid
FAD flavine adenosine dinucleotide
FMN flavine mononucleotide
FPP farnesyl pyrophosphate
GPP geranyl pyrophosphate
GGPP geranylgeranyl pyrophosphate
GC gas chromatography
HMG Hydroxymethylglutaryl
IPP isopentenyl diphosphate
IPTG isopropyl-D-thiogalacto-pyranoside
LB lysogeny broth
MS mass spectrometry
NADP nicotinamide adenine dinucleotide phosphate
NADPH nicotinamide adenine dinucleotide phosphate, reduced form
P450 cytochrome P450
PCR polymerase chain reaction
RMCE recombinase-mediated cassette exchange
RT-PCR reverse transcription—polymerase chain reaction
RNA ribonucleic acid
mRNA messenger ribonucleic acid
RBS Ribosome binding site.
VzZs Zizaene synthase from *Vetiveria zizanoides*
VzCp Cytochrome P450 from *Vetiveria zizanoides*
VzTps Terpene synthase from *Vetiveria zizanoides*
VzTrspt Transcript from *Vetiveria zizanoides*

SUMMARY OF THE INVENTION

The above-mentioned problems were surprisingly solved by:
the provision of a novel cytochrome P450 monooxygenase (VzCP7186; SEQ ID NO: 20) having the ability to oxidize (+) zizaene in C3 position to form zizaenol, and having the ability to oxidize isovalencene in C12 position to isovalencenol;
the provision of a process of oxidation of (+) zizaene to zizaneol by applying one or more cytochrome P450 enzymes selected from VzCP7186 (comprising SEQ ID NO: 20); VzCP521-11 (comprising SEQ ID NO: 21) and VzCP8201 (comprising SEQ ID NO: 19) oxidizing zizaene in C3 position;
the provision of a process of oxidation of isovalencene to isovalencenol, isonootkatol or mixtures comprising the same by applying one or more cytochrome P450 enzymes selected from VzCP7186 (SEQ ID NO: 20) and VzCP521-11 (SEQ ID NO: 21) optionally in combination with VzCP8201 (SEQ ID NO: 19). While VzCP7186 (SEQ ID NO: 20) per se and optionally in combination with VzCP8201 (SEQ ID NO: 19) oxidizes isovalencene specifically in position C12, the enzyme VzCP521-11 (SEQ ID NO: 21) has the ability to oxidize isovalencene in positions C2 and C12, as further specified below;

combining the above reactions with further chemical or enzymatic oxidation steps zizaneone and/or epi-zizaenone are accessible from zizaene; and isonootkatone and/or isovalencenyl esters are accessible from isovalencene; and
by providing suitable combinations of terpene synthase enzymes, in particular isovalencene synthases (SEQ ID NO: 3) and zizaene synthases (SEQ ID NO: 33, 38 or 42) with the respective cytochrome P450 enzymes as described herein.

DESCRIPTION OF THE DRAWINGS

FIG. 1A-D. Structures and names of the major products of VzTps1718, oxidation products of VzCP521-11, VzCP7186 and VzCP8201 and examples of derivatives.

FIG. 2. GC-MS analysis of the sesquiterpenes produced in vivo by the recombinant VzTps1718 enzyme in engineered bacteria cells. The peaks corresponding to identified products are indicated: isovalencene (compound 1), spirovetiva-1(10),7(11)-diene (compound 2) and valencene (compound 3). The peaks labeled as MW 204 and MW 222 correspond to sesquiterpene hydrocarbons and sesquiterpene alcohols, respectively for which the structures where not determined. FOH: farnesol produced by hydrolysis of FPP by *E. coli* endogenous enzymatic activity.

FIG. 4A-B. Mass spectrum of compound 2 in the VzTps1718 product mixture (FIG. 2) (A) and mass spectrum of a spirovetiva-1(10),7(11)-diene authentic standard (B).

FIG. 5A-B. Mass spectrum of compound 3 in the VzTps1718 product mixture (FIG. 2) (A) and mass spectrum of a (+)-valencene authentic standard (B).

FIG. 6A-C. GC-MS analysis of the sesquiterpene compounds produced by *E. coli* cells engineered to produce the recombinant VzTps1718 sesquiterpene synthase alone (A) and together with a functional VzCP8201 cytochrome P450 enzyme (B) or a functional VzCP7186 cytochrome P450 enzyme (C). The peaks marked with asterisks correspond to the oxygenated compounds produced by the cytochrome P450 enzymes by oxidation of sesquiterpene hydrocarbons. The peaks identified as isovalencenol and isovalencenyl acetate are indicated. All other peaks are sesquiterpene compounds produced by the VzTps1718 sesquiterpene synthase.

FIG. 9A-B. GC-MS analysis of the sesquiterpene compounds produced by *E. coli* cells engineered to produce the recombinant VzTps1718 sesquiterpene synthase alone (A), and together with a functional VzCP521-11 cytochrome P450 enzyme (B). The peaks marked with asterisks correspond to the oxygenated compounds produced by the cytochrome P450 enzymes by oxidation of sesquiterpene hydrocarbons. The peaks identified as isonootkatol, isovalencenol and isovalencenyl acetate are indicated. All other peaks are sesquiterpene compounds produced by the VzTps1718 sesquiterpene synthase.

FIG. 11A-C. GC-MS analysis of the sesquiterpene compounds produced by *E. coli* cells engineered to produce the recombinant VzTps1718 sesquiterpene synthase together with a functional VzCP8201 cytochrome P450 enzyme (A), together with a functional VzCP7186 cytochrome P450 enzyme (B) or together with functional VzCP8201 and VzCP7186 cytochrome P450 enzymes (C). The peaks marked with asterisks correspond to the oxygenated compounds produced by the cytochrome P450 enzymes by oxidation of sesquiterpene hydrocarbons.

FIG. 12A-B. Structure of the sesquiterpene compounds produced by *Vetiveria zizanoides* (+)-zizaene synthase (VzZS) and the cytochrome-P450 monooxygenases.

FIG. 13A-C. GC-MS total ion chromatogram of the sesquiterpenes produced in vivo by the recombinant zizaene synthases (A) VsZS1, (B) VzZS2 and (C) VzZS2-Nter2, expressed in engineered bacteria cells. The peak corresponding to zizaene is indicated. α-Funebrene, β-funebrene and prezizaene were also detected amongst the minor product of the recombinant enzyme (labels 1, 2 and 3, respectively). IS, internal standard.

FIG. 14A-C. GC-MS total ion chromatogram of the sesquiterpenes produced by *E. coli* cells expressing a zizaene synthase and a functional VzCP8201 cytochrome P450 enzyme (A), a functional VzCP7186 cytochrome P450 enzyme (B) or a functional VzCP521-11 cytochrome P450 enzyme (C). The peaks identified as alpha-zizaenol and khusimol are indicated.

FIG. 15A-B. Mass spectrum of the peak with a retention time of 12.03 minutes in FIG. 14 (A) and the mass spectrum of an authentic alpha-zizaenol standard (B).

FIG. 16A-B. Mass spectrum of the peak with a retention time of 12.8 minutes in FIG. 14C and the mass spectrum of an authentic khusimol standard.

FIG. 17A-C. GC-MS total ion chromatogram of the sesquiterpenes produced by *E. coli* cells expressing a zizaene synthase in combination with a functional VzCP8201 cytochrome P450 enzyme (A) or in combination with functional VzCP7186 (B) or in combination with a VzCP8201 and VzCP7186 cytochrome P450 enzyme (C). The peaks identified as alpha-zizaenol and zizaenone are indicated.

FIG. 18A-B. Mass spectrum of the peak with a retention time of 11.96 minutes in FIG. 17C (A) and the mass spectrum of an authentic zizaenone standard (B).

FIG. 19. Schematic illustration of isovalencene oxygenation sequence of the invention. The reaction scheme according to a preferred embodiment stating the main products of the respective reaction steps is shown.

FIG. 20. Schematic illustration of zizaene oxygenation sequence of the invention. The reaction scheme according to a preferred embodiment stating the main products of the respective reaction steps is shown.

FIG. 21A-C. GC-MS chromatogram of the sesquiterpenes produced by engineered *Saccharomyces cerevisiae* cells expressing different zizaene synthases: (A) VZZS1, (B) VzZS2 and (C) VzZS2-Nter2 from in vivo constructed plasmids. The peak for the internal standard (IS) and the peak identified as zizaene are indicated.

FIG. 22. GC-MS analysis of the oxygenated sesquiterpenes produced by engineered *Saccharomyces cerevisiae* strain YST124 expressing VzZS2 zizaene synthase and VzCP521-11 cytochrome P450. The peaks identified as farnesol, zizaenone, zizaenol and khusimol are indicated.

SPECIFIC DEFINITIONS

Figure 3A:
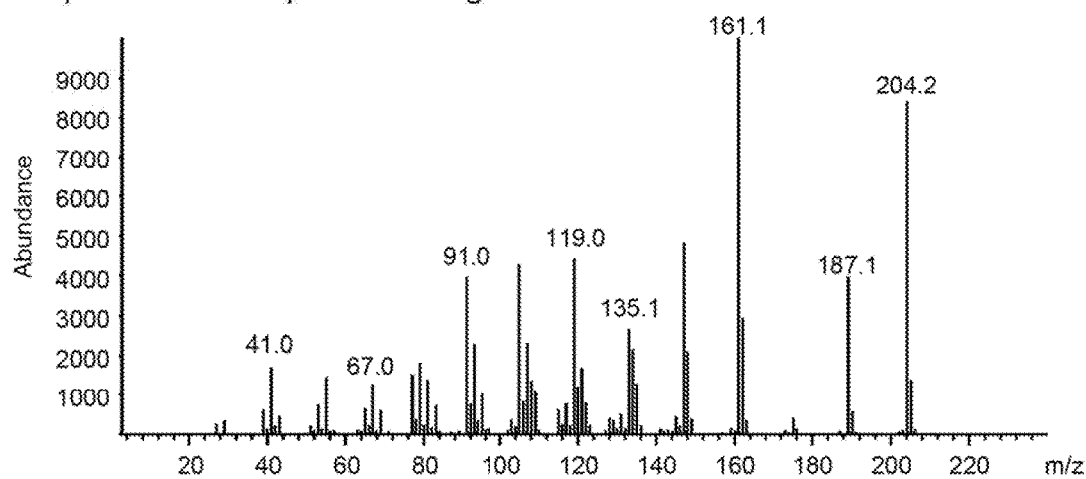
FIG. 3A-B. Mass spectrum of compound 1 in the VzTps1718 product mixture (FIG. 2) (A) and mass spectrum of an isovalencene authentic standard (B).

As intended in the present application, all compounds cited in the present application are defined by the way of their formula as represented in FIGS. 1 and 12.

A "cytochrome P450", or a "polypeptide having a cytochrome P450 activity" or a "cytochrome P450 oxidizing activity" is intended for the purpose of the present invention as a polypeptide capable of catalyzing the oxidation of a terpene molecule to form an oxygenated compound such as an alcohol, an aldehyde, a ketone or a carboxylic acid. According to a particular embodiment, the cytochrome P450 acts as a "cytochrome P450 monooxygenase", i.e. shows "cytochrome P450 monooxygenase activity" by adding, in each catalytic cycle, only one oxygen atom to compound, like in particular a terpene and more particularly a sesquiterpene, compound. The ability of a polypeptide to catalyze the oxidation of a particular terpene, like in particular a sesquiterpene, can be simply confirmed by performing the enzyme assay as detailed in the experimental part.

A "cytochrome P450 oxidizing activity" or "cytochrome P450 monooxygenase activity" in the context of the present invention is understood as the ability of the enzyme to catalyze an oxidation reaction of a terpene substrate, selected from mono-, sesqui- and or diterpene substrates, and more particular of at least one sesquiterpene substrate, preferably selected from zizaene and isovalencene, or a combination of both substrates. In a first aspect, it is understood to describe the ability of the enzyme to catalyze an oxidation reaction of zizaene in position C3 and, in particular, to form zizaenol. In particular zizaenol is formed as a "main product". In a second aspect, it is also understood to describe the ability of the enzyme to catalyze an oxidation reaction of isovalencene in position C2 and/or C12 and, in particular, to form isovalencenol and/or isonootkatol as a "main product". In a third aspect it is understood to describe the enzyme activity according to above aspects one and two.

A "terpene synthase" encompasses according to the present invention the ability to form from a non-cyclic terpene precursors selected from GPP, FPP or GGPP, in particular FPP, at least one linear, and in particular at least one mono or polycyclic terpene. In a first particular embodiment a terpene synthase of the invention encompasses the ability to convert FPP to isovalencene or a mixture of sesquiterpenes including isovalencene and optionally spirovetiva-1(10),7(11)-diene and valencene. In a second particular embodiment a terpene synthase of the invention encompasses the ability to convert FPP to zizaene a mixture of sesquiterpenes including zizaene.

"Sesquiterpene oxidizing activity" is determined under "standard conditions" as described herein below in more detail in the examples: They can be determined using cultivated recombinant cytochrome P450 expressing host cells, disrupted cytochrome P450 expressing cells, fractions of these or enriched or purified cytochrome P450 enzyme, in a culture medium or a reaction medium, preferably buffered, having a pH in the range of 6 to 11, preferably 6 to 8, in the presence of molecular oxygen, at a temperature in the range of about 20 to 45° C. preferably about 25 to 40° C., like 35 to 38° C. and in the presence of a reference substrate, here zizaene and/or isovalencene, either added at an initial concentration in the range of 1 to 10 mg/ml, preferably 3 to 7 mg/ml, or endogenously produced by the host sell.

"Terpene synthase activity" is determined under "standard conditions" as described herein below: They can be determined using recombinant terpene synthase expressing host cells, disrupted terpene synthase expressing cells, fractions of these or enriched or purified terpene synthase enzyme, in a culture medium or reaction medium, preferably buffered, having a pH in the range of 6 to 11, preferably 6 to 8, at a temperature in the range of about 20 to 45° C. preferably about 25 to 40° C., like 35 to 38° C. and in the presence of a reference substrate, here in particular FPP, either added at an initial concentration in the range of 1 to 10 mg/ml, preferably 3 to 7 mg/ml, or endogenously produced by the host sell.

The "mevalonate pathway" also known as the "isoprenoid pathway" or "HMG-CoA reductase pathway" is an essential metabolic pathway present in eukaryotes, archaea, and some bacteria. The mevalonate pathway begins with acetyl-CoA and produces two five-carbon building blocks called isopentenyl pyrophosphate (IPP) and dimethylallyl pyrophosphate (DMAPP). Key enzymes are acetoacetyl-CoA thiolase (atoB), HMG-CoA synthase (mvaS), HMG-CoA reductase (mvaA), mevalonate kinase (MvaK1), phosphomevalonate kinase (MvaK2), a mevalonate diphosphate decarboxylase (MvaD), and an isopentenyl diphosphate isomerase (idi). Combining the mevalonate pathway with enzyme activity to generate the terpene precursors GPP, FPP or GGPP, like in particular FPP synthase (ERG20), allows the recombinant cellular production of terpenes.

The terms "biological function," "function," "biological activity" or "activity" refer to the ability of the terpene synthesizing or terpene oxidizing enzymes as herein defined to catalyse the formation of a terpene or an oxidized terpene from the respective substrate.

As used herein, the term "host cell" or "transformed cell" refers to a prokaryotic or eukaryotic cell or organism altered to harbor at least one nucleic acid molecule, for instance, a recombinant gene encoding a desired protein or nucleic acid sequence which upon transcription yields a polypeptide for use as described herein. The host cell is particularly a bacterial cell, a fungal cell or a plant cell. The host cell may contain a recombinant gene which has been integrated into the nuclear or organelle genomes of the host cell. Alternatively, the host may contain the recombinant gene extrachromosomally.

"Homologous" sequences include orthologous or paralogous sequences. Methods of identifying orthologs or paralogs including phylogenetic methods, sequence similarity and hybridization methods are known in the art and are described herein.

"Paralogs" or paralogous sequences result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

"Orthologs", or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homologous sequences is by comparing of the transcript profiles in host cells or organisms, such as plants or microorganisms, overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

A particular host is meant to be "capable of producing" a terpene or oxidized terpene when it produces said terpene or oxidized terpene naturally or when it does not produce said terpene naturally but is transformed to produce said terpene or oxidized terpene, either prior to the transformation with a nucleic acid as described herein or together with said nucleic acid. Hosts transformed to produce a higher amount of a terpene or oxidized terpene than the naturally occurring host are also encompassed by the "hosts capable of producing" or "organisms or cells capable of producing" a terpene or oxidized terpene The terms "purified," "substantially purified," and "isolated" as used herein refer to the state of being free of other, dissimilar compounds with which a compound of the invention is normally associated in its natural state, so that the "purified," "substantially purified," and "isolated" subject comprises at least 0.5%, 1%, 5%, 10%, or 20%, or at least 50% or 75% of the mass, by weight, of a given sample. In one embodiment, these terms refer to the compound of the invention comprising at least 95, 96, 97, 98, 99 or 100%, of the mass, by weight, of a given sample. As used herein, the terms "purified," "substantially purified," and "isolated" "isolated," when referring to a nucleic acid or protein, of nucleic acids or proteins, also refers to a state of purification or concentration different than that which occurs naturally, for example in an prokaryotic or eukaryotic environment, like, for example in a bacterial or fungal cell, or in the mammalian, especially human body. Any degree of purification or concentration greater than that which occurs naturally, including (1) the purification from other associated structures or compounds or (2) the association with structures or compounds to which it is not normally associated in said prokaryotic or eukaryotic environment, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

In the context of the descriptions provided herein and of the appended claims, the use of "or" means "and/or" unless stated otherwise.

Similarly, "comprise," "comprises," "comprising", "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "about" indicates a potential variation of +25% of the stated value, in particular ±15%, ±10%, more particularly ±5%, ±2% or ±1%.

The term "substantially" describes a range of values of from about 80 to 100%, such as, for example, 85-99.9%, in particular 90 to 99.9%, more particularly 95 to 99.9%, or 98 to 99.9% and especially 99 to 99.9%.

"Predominantly" refers to a proportion in the range of above 50%, as for example in the range of 51 to 100%, particularly in the range of 75 to 99.9%; more particularly 85 to 98.5%, like 95 to 99%.

A "main product" in the context of the present invention designates a single compound or a group of at least 2 compounds, like 2, 3, 4, 5 or more, particularly 2 or 3 compounds, which single compound or group of compounds is "predominantly" prepared by a reaction as described herein, and is contained in said reaction in a predominant proportion based on the total amount of the constituents of the product formed by said reaction. Said proportion may be a molar proportion, a weight proportion or, preferably based on chromatographic analytics, an area proportion calculated from the corresponding chromatogram of the reaction products.

A "side product" in the context of the present invention designates a single compound or a group of at least 2 compounds, like 2, 3, 4, 5 or more, particularly 2 or 3 compounds, which single compound or group of compounds is not "predominantly" prepared by a reaction as described herein.

Because of the reversibility of enzymatic reactions, the present invention relates, unless otherwise stated, to the enzymatic or biocatalytic reactions described herein in both directions of reaction.

"Functional mutants" of herein described polypeptides include the "functional equivalents" of such polypeptides as defined below.

The term "stereoisomers" includes in particular conformational isomers.

Included in general are, according to the invention, all "stereoisomeric forms" of the compounds described herein, such as constitutional isomers and, in particular, stereoisomers and mixtures thereof, e.g. optical isomers, or geometric isomers, such as E- and Z-isomers, and combinations thereof. If several asymmetric centers are present in one molecule, the invention encompasses all combinations of different conformations of these asymmetry centers, e.g. enantiomeric pairs "Stereoselectivity" describes the ability to produce a particular stereoisomer of a compound in a stereoisomerically pure form or to specifically convert a particular stereoisomer in an enzyme catalyzed method as described herein out of a plurality of stereoisomers. More specifically, this means that a product of the invention is enriched with respect to a specific stereoisomer, or an educt may be depleted with respect to a particular stereoisomer. This may be quantified via the purity % ee-parameter calculated according to the formula:

$$\%ee=[X_A-X_B]/[X_A+X_B]*100,$$

wherein $X_A$ and $X_B$ represent the molar ratio of the stereoisomers A and B.

"Yield" and/or the "conversion rate" of a reaction according to the invention is determined over a defined period of, for example, 4, 6, 8, 10, 12, 16, 20, 24, 36 or 48 hours, in which the reaction takes place. In particular, the reaction is carried out under precisely defined conditions, for example at "standard conditions" as herein defined.

The different yield parameters ("Yield" or YP/S; "Specific Productivity Yield"; or Space-Time-Yield (STY)) are well known in the art and are determined as described in the literature.

"Yield" and "YP/S" (each expressed in mass of product produced/mass of material consumed) are herein used as synonyms.

A "terpene" unless otherwise specified encompasses mono-, sesqui- and diterpenes. A particular terpene is a sesquiterpene, like isovalencene and zizaene The specific productivity-yield describes the amount of a product, like a terpene or oxidized terpene, that is produced per h and L fermentation broth (or culture medium) per g of biomass. The amount of wet cell weight stated as WCW describes the quantity of biologically active microorganism in a biochemical reaction. The value is given as g product per g WCW per h (i.e. $g/gWCW^{-1}\ h^{-1}$).

The term "fermentative production" or "fermentation" refers to the ability of a microorganism (assisted by enzyme activity contained in or generated by said microorganism) to produce a chemical compound in cell culture utilizing at least one nutritive source, for example comprising a carbon source, added to the incubation.

The term "fermentation broth" is understood to mean a liquid, particularly aqueous or aqueous/organic solution which is based on a fermentative process and has not been worked up or has been worked up, for example, as described herein.

An "enzymatically catalyzed" or "biocatalytic" method means that said method is performed under the catalytic action of an enzyme, including enzyme mutants, as herein defined. Thus the method can either be performed in the presence of said enzyme in isolated (purified, enriched) or crude form or in the presence of a cellular system, in particular, natural or recombinant microbial cells containing said enzyme in active form, and having the ability to catalyze the conversion reaction as disclosed herein.

The terms "selectively converting" or "increasing the selectivity" in general means that a particular stereoisomeric form, For example, the (+)-form, of an hydrocarbon, is converted in a higher proportion or amount (compared on a molar basis) than the corresponding (−)-form, either during the entire course of said reaction (i.e. between initiation and termination of the reaction), at a certain point of time of said reaction, or during an "interval" of said reaction. In particular, said selectivity may be observed during an "interval" corresponding 1 to 99%, 2 to 95%, 3 to 90%, 5 to 85%, 10 to 80%, 15 to 75%, 20 to 70%, 25 to 65%, 30 to 60, or 40 to 50% conversion of the initial amount of the substrate. Said higher proportion or amount may, for example, be expressed in terms of:

a higher maximum yield of an isomer observed during the entire course of the reaction or said interval thereof;

a higher relative amount of an isomer at a defined % degree of conversion value of the substrate; and/or an identical relative amount of an isomer at a higher % degree of conversion value;

each of which preferably being observed relative to a reference method, said reference method being performed under otherwise identical condition with known chemical or biochemical means.

"Generally also comprised in accordance with the invention are all "isomeric forms" of the compounds described herein, such as constitutional isomers and in particular stereoisomers and mixtures of these, such as, for example, optical isomers or geometric isomers, such as E- and Z-isomers, and combinations of these. If several centers of asymmetry are present in a molecule, then the invention comprises all combinations of different conformations of these centers of asymmetry, such as, for example, pairs of enantiomers, or any mixtures of stereoisomeric forms.

If the present disclosure refers to features, parameters and ranges thereof of different degree of preference (including general, not explicitly preferred features, parameters and ranges thereof) then, unless otherwise stated, any combination of two or more of such features, parameters and ranges thereof, irrespective of their respective degree of preference, is encompassed by the disclosure of the present description.

DETAILED DESCRIPTION a. Particular Embodiments of the Invention

The present invention particularly refers to the following embodiments:

a1. Zizaene Oxidation

1. A method for producing an oxidized zizaene compound, which method comprises
   a. contacting zizaene or a zizaene containing composition with a polypeptide having Cytochrome P450 monooxygenase activity, selected from:
      i. VzCP8201 comprising an amino acid sequence having at least 70%, 75%, 80%, 85%, 90%, 95%, 96%, 97%, 98%, 99% or 100% sequence identity to SEQ ID NO: 19,
      ii. VzCP521-11 comprising an amino acid sequence having at least 70%, 75%, 80%, 85%, 90%, 95%, 96%, 97%, 98%, 99% or 100% sequence identity to SEQ ID NO: 21,
      iii. VzCP7186 comprising an amino acid sequence having at least 70%, 75%, 80%, 85%, 90%, 95%, 96%, 97%, 98%, 99% or 100% sequence identity to SEQ ID NO: 20,
      iv. or combinations of at least two of said polypeptides;
      thereby obtaining at least one oxidation product of zizaene, in particular by converting zizaene to zizaenol, preferably comprising alpha- and/or beta-zizaenol, in particular alpha-zizaenol (i.e. (+)-zizaenol), or an oxidation product containing such zizaenol, particularly an oxidation product containing predominantly such zizaenol; and
   b. optionally isolating at least one oxidation product as obtained in step a.; such as zizaenol, in particular alpha-zizaenol.

The step b may be performed with or without previous isolation of one or more oxidation products of the preceding step.

"Zizaenol" encompasses unless otherwise stated, alpha- and/or beta zizaenol optionally in combination with any other zizaenone precursor.

An "oxidation product of zizaene" or an "oxidation product comprising zizaenol" encompasses alpha- and/or beta zizaenol, optionally in combination with further oxidation products: structurally different alcohols, like khusimol, any other zizaenone precursors; and/or further oxidized products thereof, like zizaenone; and/or any isomers of the foregoing zizaene oxidation products, like epi-zizaenone. Said further oxidation products may be obtained as main product or in particular as side product.

The above method can be carried out in vitro as well as in vivo, as will be explained in details further on.

2. The method of embodiment 1, wherein step a. is performed in vivo in cell culture containing at least one of said polypeptides having Cytochrome P450 monooxygenase activity and in the presence of molecular oxygen; or in vitro in a liquid culture or reaction medium in the presence of molecular oxygen and at least one of said polypeptides having Cytochrome P450 monooxygenase activity in isolated form.

3. The method of any one of embodiments 1 and 2, wherein step a. is carried out in vivo by cultivating a recombinant non-human host organism or cell expressing, in particular a recombinant host transformed to express, at least one of said polypeptides having Cytochrome P450 monooxygenase activity in the presence of zizaene or a zizaene containing composition under conditions conducive to the oxidation of zizaene.

4. The method of one of the preceding embodiments, wherein the conversion of zizaene in step a. is performed in the presence of a polypeptide having P450 reductase (CPR) activity; and optionally in the presence of added redox equivalents, in particular NAD(P)H.

For catalytic activity, the above P450s have to be used in combination with a P450-reductase (CPR) which is capable of transferring electrons from NADPH (Nicotinamide adenine dinucleotide phosphate, reduced form) to the P450 active site, so as to reconstitute the P450 activity. The CPR must be present both for carrying out the process in vitro and in vivo. When the method is carried out in vivo, the CPR can either be present naturally in the host organism or cell, or such organism or cell can be transformed to express a CPR prior to, simultaneously with or after transformation to express the polypeptide of the invention. In a preferred embodiment of the invention the host cell or organism is transformed with a fusion polypeptide comprising both the P450 polypeptide of the invention and the CPR. In another preferred embodiment the CPR is a plant CPR. Most preferably it is derived from a *Mentha piperita* CPR.

When the method is carried out in vitro, the cytochrome P450 to be contacted with the terpene compound and the CPR can be obtained by extraction from any organism expressing it, using standard protein or enzyme extraction technologies. If the host organism is an unicellular organism or cell releasing the polypeptide of the invention into the culture medium, for example when no membrane anchor is present, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate. When P450s and CPRs comprise a membrane anchor sequence, such as natural P450s and CPRs in plants, they are associated with membranes and are therefore located in the membrane fraction of cells lysates. The membrane fraction (microsoms) can be easily separated from the other protein fractions by differential centrifugations of the crude cell lysate using known methods.

For the in vitro method the P450 and the CPR can independently be provided in isolated form or as part of a protein extract and is suspended in a buffer solution at optimal pH. If adequate, salts, DTT, NADPH, NADH, FAD, FMN and other kinds of enzymatic co-factors, may be added in order to optimize enzyme activity. Appropriate conditions are described in more details in the Examples further on.

5. The method of embodiment 4, wherein said CPR comprising an amino acid sequence having at least 70%, 75%, 80%, 85%, 90%, 95%, 96%, 97%, 98%, 99% or 100% sequence identity to SEQ ID NO: 23.

In one particular aspect of any of the embodiments herein, the CPR is encoded by a nucleic acid comprising a nucleotide sequence having at least 70%, 75%, 80%, 85%, 90%, 95%, 96%, 97%, 98%, 99% or 100% sequence identity to SEQ ID NO: 22.

6. The method of one of the preceding embodiments, further comprising, prior to step a. the cyclisation of farnesyl diphosphate (FPP) in the presence of a polypeptide having zizaene synthase activity.

7. The method of embodiment 6, wherein said polypeptide having zizaene synthase activity comprises an amino acid sequence having at least 70%, 75%, 80%, 85%, 90%, 95%, 96%, 97%, 98%, 99% or 100% sequence identity to SEQ ID NO: 33, 38 or 42.

8. The method of one of the preceding embodiments, performed in cell culture by applying a host endogenously producing FPP or a host genetically modified to produce FPP or genetically modified to produce FPP in increased amounts (relative to the non-modified host).

9. The method of embodiment 8, wherein said host is genetically modified to produce increased amounts of FPP, in particular genetically modified so as to express the enzyme set (comprising acetoacetyl-CoA thiolase (atoB), HMG-CoA synthase (mvaS), HMG-CoA reductase (mvaA), mevalonate kinase (MvaK1), phosphomevalonate kinase (MvaK2), a mevalonate diphosphate decarboxylase (MvaD), and an isopentenyl diphosphate isomerase (idi)) catalysing the mevalonate metabolic pathway.

10. The method of one of the preceding embodiments, further comprising as step c. the conversion of zizaenol, i.p. (+)-zizaenol, to zizaenone, or to a mixture comprising zizaenone and epi-zizaenone.

The step c may be performed with or without previous isolation of one or more reaction products of the preceding step.

11. The method of embodiment 10, wherein step c. comprises either a chemical oxidation or a biochemical oxidation; said biochemical oxidation may be performed in vivo in cell culture or in vitro in a liquid reaction medium and in the presence of at least one polypeptide having zizaenol oxidizing activity, in particular in the presence of a polypeptide having zizaenol dehydrogenating activity, and optionally in the presence of added redox equivalents, in particular NAD(P)H, and optionally a suitable enzyme based cofactor regenerating system.

12. The method of embodiment 11, wherein step c. is carried out by cultivating a non-human host organism, in particular recombinant host, or cell expressing, in particular genetically modified so as to express and more particularly transformed to express, at least one polypeptide having zizaenol dehydrogenating activity in the presence of zizaenol i.p. (+)-zizaenol, or a zizaenol containing composition like a reaction product containing predominantly zizaenol, in particular alpha-zizaenol, under conditions conducive to the oxidation (dehydrogenation) of zizaenol.

13. The method of one of the preceding embodiments, wherein said polypeptide having Cytochrome P450 monooxygenase activity is selected from:
   i. VzCP8201 comprising an amino acid sequence having at least 70% sequence identity to SEQ ID NO: 19, N-terminally extended by at least one amino acid residue,
   ii. VzCP521-11 comprising an amino acid sequence having at least 70% sequence identity to SEQ ID NO:21, N-terminally extended by at least one amino acid residue; and
   iii. VzCP7186 comprising an amino acid sequence having at least 70% sequence identity to SEQ ID NO:20, N-terminally extended by at least one amino acid residue.

As for example the polypeptide may be extended by a single natural amino acid residue, in particular a methionine residue, or any sequence containing 1 to 50, 1 to 40, 1 to 30, 1 to 25, in particular 5 to 25 or 15 to 25 consecutive amino acid residues. The sequence may have different functionality; for example, it may function as membrane anchor sequence, it may improve protein expression or it may improve enzyme function.

14. The method of embodiment 13, wherein said polypeptide having Cytochrome P450 monooxygenase activity is selected from:
   i. VzCP8201 comprising an amino acid sequence having at least 70% sequence identity to SEQ ID NO:19, N-terminally extended by methionine or its natural or a synthetic membrane anchor sequence,
   ii. VzCP521-11 comprising an amino acid sequence having at least 70% sequence identity to SEQ ID NO:21, N-terminally extended by methionine or its natural or a synthetic membrane anchor sequence; and
   iii. VzCP7186 comprising an amino acid sequence having at least 70% sequence identity to SEQ ID NO:20, N-terminally extended by methionine or its natural or a synthetic membrane anchor sequence.

In particular, the respective natural anchor sequence may be derived from the respective full-length sequences as herein disclosed. Artificial N-terminal sequences which may also function as anchor sequence may be easily synthesized. As example there may be mention the N-terminal peptide comprising an amino acid sequence of SEQ ID NO:24, or a functionally equivalent sequence or analog sequence having at least 70%, 75%, 80%, 85%, 90%, 95%, 96%, 97%, 98%, 99% sequence identity thereto.

15. The method of embodiment 14, wherein said polypeptide having Cytochrome P450 monooxygenase activity is selected from
   i. VzCP8201 comprising an amino acid sequence having at least 70% sequence identity to SEQ ID NO:7 or 10;
   ii. VzCP521-11 comprising an amino acid sequence having at least 70% sequence identity to SEQ ID NO:18; and
   iii. VzCP7186 comprising an amino acid sequence having at least 70% sequence identity to SEQ ID NO:13.

a2. Isovalencene Oxidation

16. A method for producing an oxidized isovalencene compound, which method comprises
   a. contacting isovalencene or a isovalencene containing composition with a polypeptide having Cytochrome P450 monooxygenase activity, selected from:
     i. VzCP521-11 comprising an amino acid sequence having at least 70%, 75%, 80%, 85%, 90%, 95%, 96%, 97%, 98%, 99% or 100% sequence identity to SEQ ID NO:21,
     ii. VzCP7186 comprising an amino acid sequence having at least 70%, 75%, 80%, 85%, 90%, 95%, 96%, 97%, 98%, 99% or 100% sequence identity to SEQ ID NO:20,
     iii. or combinations of at least two of said polypeptides;
     iv. or combinations of i., ii. or iii. with VzCP8201 comprising an amino acid sequence having at least 70%, 75%, 80%, 85%, 90%, 95%, 96%, 97%, 98%, 99% or 100% sequence identity to SEQ ID NO:19
     thereby converting isovalencene to at least one oxidation product, in particular by either converting isovalencene to isovalencenol or to an oxidation product containing isovalencenol, particularly an oxidation product containing predominantly isovalencenol; or converting isovalencene to isonootkatol or to an oxidation product containing isonootkatol, particularly an oxidation product containing predominantly isonootkatol; or converting isovalencene to a mixture comprising isovalencenol and isonootkatol or to an oxidation product predominantly containing isovalencenol and isonootkatol; if isovalencenol is obtained, the oxidation product may also contain an isovalencenyl ester;

and b. optionally isolating at least one oxidization product as obtained in step a.—

The step b may be performed with or without previous isolation of one or more reaction products of the preceding step.

In particular, an "oxidation product of isovalencene" encompasses isovalencenol and/or isonootkatol as main products; and optionally as further main or side products, in particular as side product, one or more further oxidized products thereof, like isoonootkatone and/or isovalencenyl esters. It may also contain non-oxidized compounds like siprovetiva-1(10).7(11)-diene, (+)-valencene, and in particular corresponding oxidized products thereof, like nootkatool, nootkatone, beta-vetivol and beta-vetivone (see also FIG. 1).

The above method can be carried out in vitro as well as in vivo, as will be explained in details further on.

In one particular aspect of this embodiment as the main product a combination of isonootkatol with isovalencenol and optionally an isovalencenyl ester is prepared. More particularly this conversion is performed by applying a P450 monooxygenase selected from a) VzCP521-11 comprising an amino acid sequence having at least 70%, 75%, 80%, 85%, 90%, 95%, 96%, 97%, 98%, 99% or 100% sequence identity to SEQ ID NO:21;

b) a combination of a) with VzCP8201 comprising an amino acid sequence having at least 70%, 75%, 80%, 85%, 90%, 95%, 96%, 97%, 98%, 99% or 100% sequence identity to SEQ ID NO:19.

c) a combination of a) with VzCP7186 comprising an amino acid sequence having at least 70%, 75%, 80%, 85%, 90%, 95%, 96%, 97%, 98%, 99% or 100% sequence identity to SEQ ID NO:20, or d) a combination of a) with VzCP8201 comprising an amino acid sequence having at least 70%, 75%, 80%, 85%, 90%, 95%, 96%, 97%, 98%, 99% or 100% sequence identity to SEQ ID NO:19; and VzCP7186 comprising an amino acid sequence having at least 70%, 75%, 80%, 85%, 90%, 95%, 96%, 97%, 98%, 99% or 100% sequence identity to SEQ ID NO:20.

The isovalencenyl ester may be produced in the presence of an ester forming enzyme activity, as for example esterase or lipase or acyl transferase enzyme activity. Said esterase activity may be added to the reaction mixture containing isovalencenol or said conversion may be catalysed by enzyme activity endogenously present, in case said method is performed in vivo by use of a host system. The isovalencenyl ester preferably is selected from carboxylic acid esters, in particular saturated short chain carboxylic acid esters, more particularly $C_2$-$C_4$ carboxylic acid esters, i.p. isovalencenyl acetate.

In another particular aspect of this embodiment the main product is isovalencenol optionally in combination with an isovalencenyl ester. More particularly this conversion is performed by applying a P450 monooxygenase selected from a) VzCP7186 comprising an amino acid sequence having at least 70%, 75%, 80%, 85%, 90%, 95%, 96%, 97%, 98%, 99% or 100% sequence identity to SEQ ID NO:20, or b) a combination of a) with VzCP8201 comprising an amino acid sequence having at least 70%, 75%, 80%, 85%, 90%, 95%, 96%, 97%, 98%, 99% or 100% sequence identity to SEQ ID NO: 19.

The isovalencenyl ester may be produced in the presence of, for example esterase, lipase, acyl transferase or acetyl transferase enzyme activity. Said enzyme activity may be added to the reaction mixture containing isovalencenol or said conversion may be catalysed by enzyme activity endogenously present, in case said method is performed in vivo by use of a host system. The isovalencenyl ester preferably is selected from carboxylic acid esters, in particular saturated short chain carboxylic acid esters, more particularly $C_2$-$C_4$ carboxylic acid esters, i.p. isovalencenyl acetate.

17. The method of embodiment 16, wherein step a. is performed in vivo in cell culture containing at least one of said polypeptides having Cytochrome P450 monooxygenase activity and in the presence of molecular oxygen; or in vitro in a liquid reaction medium in the presence of molecular oxygen and at least one of said polypeptides having Cytochrome P450 monooxygenase activity in isolated form.

18. The method of any one of embodiments 16 and 17, wherein step a. is carried out by cultivating a recombinant non-human host organism or cell expressing, in particular a recombinant cell transformed to express at least one of said polypeptides having Cytochrome P450 monooxygenase activity in the presence of isovalencene or an isovalencene containing composition under conditions conducive to the oxidation of isovalencene.

19. The method of one of the embodiments 16 to 18, wherein the conversion of isovalencene in step a. is performed in the presence of a polypeptide having P450 reductase (CPR) activity and optionally in the presence of added redox equivalents, in particular NAD(P)H.

For catalytic activity, the above P450s have to be used in combination with a P450-reductase (CPR) which is capable of transferring electrons from NADPH (Nicotinamide adenine dinucleotide phosphate, reduced form) to the P450 active site, so as to reconstitute the P450 activity. The CPR must be present both for carrying out the process in vitro and in vivo. When the method is carried out in vivo, the CPR can either be present naturally in the host organism or cell, or such organism or cell can be transformed to express a CPR prior to, simultaneously with or after transformation to express the cytochrome P450 polypeptide of the invention. In a preferred embodiment of the invention the host cell or organism is transformed with a fusion polypeptide comprising both the polypeptide of the invention and the CPR. In another preferred embodiment the CPR is a plant CPR. Most preferably it is derived from a *Mentha piperita* CPR.

When the method is carried out in vitro, the cytochrome P450 to be contacted with the terpene compound and the CPR can be obtained by extraction from any organism expressing it, using standard protein or enzyme extraction technologies. If the host organism is an unicellular organism or cell releasing the polypeptide of the invention into the culture medium, for example when no membrane anchor is present, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate. When P450s and CPRs comprise a membrane anchor sequence, such as natural P450s and CPRs in plants, they are associated with membranes and are therefore located in the membrane fraction of cells lysates. The membrane fraction (microsoms) can be easily separated from the other protein fractions by differential centrifugations of the crude cell lysate using known methods.

For the in vitro method the P450 and the CPR can independently be provided in isolated form or as part of a protein extract and is suspended in a buffer solution at optimal pH. If adequate, salts, DTT, NADPH, NADH, FAD, FMN and other kinds of enzymatic co-factors, may be added in order to optimize enzyme activity. Appropriate conditions are described in more details in the Examples further on.

20. The method of embodiment 19, wherein said CPR comprising an amino acid sequence having at least 70%, 75%, 80%, 85%, 90%, 95%, 96%, 97%, 98%, 99% or 100% sequence identity to SEQ ID NO: 23.

21. The method of one of the embodiments 16 to 20, further comprising, prior to step a. the cyclisation of farnesyl diphosphate (FPP) in the presence of a polypeptide having isovalencene synthase activity.

22. The method of embodiment 21, wherein said polypeptide having isovalencene synthase activity comprises an amino acid sequence having at least 70%, 75%, 80%, 85%, 90%, 95%, 96%, 97%, 98%, 99% or 100% sequence identity to SEQ ID NO:3.

23. The method of one of the embodiments 16 to 22, performed in cell culture by applying a host endogenously producing FPP or a host genetically modified to produce FPP or genetically modified to produce FPP in increased amounts (relative to the non-modified host).

24. The method of embodiment 23, wherein said host is genetically modified to produce increased amounts of FPP, in particular genetically modified so as to express the enzyme set (comprising acetoacetyl-CoA thiolase (atoB), HMG-CoA synthase (mvaS), HMG-CoA reductase (mvaA), mevalonate kinase (MvaK1), phosphomevalonate kinase (MvaK2), a mevalonate diphosphate decarboxylase (MvaD), and an isopentenyl diphosphate isomerase (idi) catalysing the mevalonate metabolic pathway.

25. The method of one of the embodiments 16 to 4, further comprising as step c a method of chemically or biochemically modifying isovalencenol The step c may be performed with or without previous isolation of one or more reaction products of the preceding step.

26. The method of embodiment 25, comprising
    a. as step c1. the esterification of isovalencenol to an isovalencenyl carboxylic acid ester; and/or
    b. as step c2. the oxidation of isonootkatol to isonootkatone.

27. The method of embodiment 26, wherein
    a. step c1. comprises either a chemical esterification or a biochemical esterification, said biochemical esterification may be performed in vivo in cell culture or in vitro in a liquid reaction medium and in the presence of at least one polypeptide having isovalencenol esterifying activity, in particular in the presence of a polypeptide having esterase, lipase, acyl transferase or acetyl transferase activity;
    b. step c2. comprises either a chemical oxidation or a biochemical oxidation, said biochemical oxidation may be performed in vivo in cell culture or in vitro in a liquid reaction medium and in the presence of at least one polypeptide having isonootkatol oxidizing activity, in particular in the presence of a polypeptide having isonootkatol dehydrogenating activity, and optionally in the presence of added redox equivalents, in particular NAD(P)H and optionally a suitable enzyme based cofactor regenerating system.

28. The method of embodiment 27, wherein
    i. step c1. is carried out by cultivating a non-human host organism, in particular recombinant host or cell expressing, in particular genetically modified to express, and more particularly transformed to express at least one polypeptide having isovalencenol esterifying activity in the presence of isovalencenol or a isovalencenol containing composition, like a reaction product containing predominantly isovalencenol, under conditions conducive to the esterification of isovalencenol; or
    ii. step c2. is carried out by cultivating a non-human host organism, in particular recombinant host or cell expressing, in particular genetically modified to express and more particularly transformed to express at least one polypeptide having isonootkatol oxidizing activity in the presence of isonootkatol or a isonootkatol containing composition, like a reaction product containing predominantly isonootkatol, under conditions conducive to the oxidation (dehydrogenation) of isonootkatol.

29. The method of one of the embodiments 16 to 28, wherein said polypeptide having Cytochrome P450 monooxygenase activity is selected from:
    i. VzCP8201 comprising an amino acid sequence having at least 70% sequence identity to SEQ ID NO: 19, N-terminally extended by at least one amino acid residue,
    ii. VzCP521-11 comprising an amino acid sequence having at least 70% sequence identity to SEQ ID NO:21, N-terminally extended by at least one amino acid residue; and
    iii. VzCP7186 comprising an amino acid sequence having at least 70% sequence identity to SEQ ID NO:20, N-terminally extended by at least one amino acid residue.

As for example the polypeptide may be extended by a single natural amino acid residue, in particular a methionine residue, or any sequence containing 1 to 50, 1 to 40, 1 to 30, 1 to 25, in particular 5 to 25 or 15 to 25 consecutive amino acid residues. The sequence may have different functionality; for example, it may function as membrane anchor sequence, it may improve protein expression or it may improve enzyme function.

30. The method of embodiment 29, wherein said polypeptide having Cytochrome P450 monooxygenase activity is selected from:
    i. VzCP8201 comprising an amino acid sequence having at least 70% sequence identity to SEQ ID NO:19, N-terminally extended by methionine or its natural or a synthetic membrane anchor sequence,
    ii. VzCP521-11 comprising an amino acid sequence having at least 70% sequence identity to SEQ ID NO:21, N-terminally extended by methionine or its natural or a synthetic membrane anchor sequence; and
    iii. VzCP7186 comprising an amino acid sequence having at least 70% sequence identity to SEQ ID NO:20, N-terminally extended by methionine or its natural or a synthetic membrane anchor sequence.

In particular, the respective natural anchor sequence may be derived from the respective full-length sequences as herein disclosed. Artificial N-terminal sequences which may also function as anchor sequence may be easily synthesized. As example there may be mention the N-terminal peptide comprising an amino acid sequence of SEQ ID NO:24, or a functionally equivalent sequence or analog sequence having at least 70%, 75%, 80%, 85%, 90%, 95%, 96%, 97%, 98%, 99% sequence identity thereto.

31. The method of embodiment 30, wherein said polypeptide having Cytochrome P450 monooxygenase activity is selected from
  i. VzCP8201 comprising an amino acid sequence having at least 70% sequence identity to SEQ ID NO:7 or 10;
  ii. VzCP521-11 comprising an amino acid sequence having at least 70% sequence identity to SEQ ID NO:18; and
  iii. VzCP7186 comprising an amino acid sequence having at least 70% sequence identity to SEQ ID NO:13.

Isonootkatol can be easily oxidized to the corresponding ketones, for example biochemically or chemically (see for example *Oxidation of Alcohols to Aldehydes and Ketones*, G. Tojo and M Fernadez, in *Basic Reactions in Organic Synthesis* (2007)) to produce isonootkatone, one of the major vetiver oil constituents. Similarly, beta-vetivone can be obtained from beta-vetivol and nootkatone from nootkatol.

a3. Novel Cytochrome P450 Enzymes

32. A polypeptide comprising an amino acid sequence at least 70%, 75%, 80%, 85%, 90%, 95%, 96%, 97%, 98%, 99% or 100% identical to SEQ ID NO:20 (VzCP7186) and having a cytochrome P450 monooxygenase activity, in particular the ability to convert zizaene to zizaenol, in particular alpha-zizaenol (i.e. (+)-zizaenol), or to a reaction product containing predominantly zizaenol, in particular alpha-zizaenol, and/or having the ability to convert isovalencene to isovalencenol or to a reaction product containing predominantly isovalencenol.

33. The polypeptide of embodiment 32, further comprising a membrane anchor sequence.

34. The polypeptide of embodiment 32 or 33 selected from polypeptides comprising an amino acid sequence selected from SEQ ID NO: 13 and 15 or comprising an amino acid sequence at least 70%, 75%, 80%, 85%, 90%, 95%, 96%, 97%, 98%, 99% or 100% identical to SEQ ID NO: 13 or 15.

35. A nucleic acid encoding the polypeptide of any one of embodiments 32 to 34.

36. The nucleic acid of embodiment 35, comprising a coding nucleotide sequence encoding a polypeptide having at least 70%, 75%, 80%, 85%, 90%, 95%, 96%, 97%, 98%, 99% or 100% identity to SEQ ID NO: 13, 15 or 20; or the complement thereof.

37. An expression vector comprising the coding nucleic acid of any one of embodiments 35 and 36.

38. The expression vector of embodiment 37, in the form of a viral vector, a bacteriophage or a plasmid.

39. The expression vector of embodiment 37 or 38, wherein the coding nucleic acid is linked to at least one regulatory sequence, which for example controls transcription, translation initiation or termination, such as a transcriptional promoter, operator or enhancer or an mRNA ribosomal binding site, and, optionally, including at least one selection marker.

40. A non-human host organism or cell harboring at least one nucleic acid according to any one of embodiments 35 and 36.

41. The non-human host organism of embodiment 40, wherein said non-human host organism is an eukaryote or a prokaryote, in particular a plant, a bacterium or a fungus, in particular a yeast.

42. The non-human host organism of embodiment 41, wherein said bacterium is of the genus *Escherichia*, in particular *E. coli* and said yeast is of the genus *Saccharomyces*, in particular *S. cerevisiae*.

43. The non-human host cell of embodiment 40, which is a plant cell.

44. A method for producing at least one polypeptide according to any one of embodiments 32 to 34 comprising:
  a) culturing a non-human host organism or cell harboring at least one nucleic acid according to any one of embodiments 35 and 36 and expressing or overexpressing at least one polypeptide according to any one of embodiments 32 to 34;
  b) optionally isolating said polypeptide from the non-human host organism or cell cultured in step a.

According to a preferred embodiment, said method further comprises, prior to step a), transforming a non-human host organism or cell with at least one nucleic acid according to the invention so that it expresses or overexpresses a polypeptide according to the invention. Gene transfer, as for example by transformation, and culture of the non-human host organism or cell can be carried out as described herein for the method of producing an oxidized terpene in vivo.

Step b) may be performed using any technique well known in the art to isolate a particular polypeptide from an organism or cell.

45. The method of embodiment 44, further comprising, prior to step a., providing a non-human host organism or cell with at least one nucleic acid according to any one of embodiments 35 and 36 so that it expresses or overexpresses the polypeptide according to any one of embodiments 32 to 24.

46. A method for preparing a mutant polypeptide capable of oxidizing a terpene compound comprising the steps of:
  a. selecting a nucleic acid according to any one of embodiments 35 and 36;
  b. modifying the selected nucleic acid to obtain at least one mutant nucleic acid;
  c. providing host cells or unicellular organisms with the mutant nucleic acid sequence to express a polypeptide encoded by the mutant nucleic acid sequence;
  d. screening for at least one mutant polypeptide with activity in oxidizing terpene compounds;
  e. optionally, if the mutated polypeptide has no desired activity, repeating the process steps a. to d. until a polypeptide with a desired activity is obtained; and,
  f. optionally, if a mutant polypeptide having a desired activity was identified in step d. or e., isolating the corresponding mutant nucleic acid.

In step (b), a large number of mutant nucleic acid sequences may be created, for example by random mutagenesis, site-specific mutagenesis, or DNA shuffling. As described in more detail below.

Accordingly, a nucleic acid encoding the polypeptide comprising SEQ ID NO: 13 or 15 or the complement thereof may be recombined with any other nucleic acid encoding a cytochrome P450, for example isolated from an organism other than Vetiveria zizanioides (L.) Nash. Thus, mutant nucleic acids may be obtained and separated, which may be used for transforming a host cell according to standard procedures, for example such as disclosed in the present Examples.

In step (d), the polypeptide obtained in step (c) is screened for at least one modified cytochrome P450 activity. Examples of desired modified cytochrome P450 activity, for which an expressed polypeptide may be screened, include enhanced or reduced enzymatic activity, as measured by $K_M$ or $V_{max}$ value, modified regio-chemistry or stereochemistry and altered substrate utilization or product distribution. The screening of enzymatic activity can be performed according to procedures familiar to the skilled person and those disclosed in the present Examples.

Step (e) provides for repetition of process steps (a)-(d), which may preferably be performed in parallel. Accordingly, by creating a significant number of mutant nucleic acids, many host cells may be transformed with different mutant nucleic acids at the same time, allowing for the subsequent screening of an elevated number of polypeptides. The chances of obtaining a desired variant polypeptide may thus be increased at the discretion of the skilled person. In each of the above embodiments the degrees of sequence identity are independently of each other preferably at least 90%, more preferably at least 95% and even more preferably at least 98% to the sequence of the respective SEQ ID NO. According to a more preferred embodiment, the mentioned polypeptide comprises the sequence of the respective SEQ ID NO. Even more preferably it consists of the sequence of the respective SEQ ID NO.

47. A method for preparing an oxidized terpene, which method comprises
    a. contacting at least one terpene substrate with a polypeptide having a cytochrome P450 monooxygenase activity as defined in anyone of the embodiment 32 to 34, or encoded by a nucleic acid as defined in anyone of the embodiments 35 and 36
        thereby converting at least one terpene to at least one oxidation product; and
    b. optionally isolating at least one oxidation product as obtained in step a.

In the above embodiments of the invention the sequences for cytochrome P450s may also comprises a membrane anchor sequence. Percentage of identity preferably refers, unless otherwise stated, to said part of the polypeptide that provides the P450 activity.—In eukaryotes, the P450 monooxygenases are membrane-bound proteins and the N-terminal sequence of these proteins constitute a membrane anchor essential for the membrane localization of these enzymes. This part of the protein, usually delimited by a proline-rich domain, is not essential for the control of the specificity of the enzymatic activity. This region can thus be modified by deletion, insertion or mutation without effect on the catalytic activity. However, specific modification of the N-terminal region of eukaryotic P450s, including plant P450s, have been shown to have a positive effect on the levels of functional recombinant proteins when expressed in microorganisms (Halkier et al (1995) *Arch. Biochem. Biophys.* 322, 369-377; Haudenschield et al (2000) *Arch. Biochem. Biophys.* 379, 127-136). Thus, based on these previous observations the membrane anchor region of can be redesigned to obtain an anchor sequences suitable with the organism in which the polypeptide is expressed and sequences designed for common types of host organisms are known to the person skilled in the art. Any suitable anchor sequence can be used in combination with the polypeptide of the present invention.

The P450 enzymes and terpene synthases as used herein are preferably encoded by the nucleic acid is isolated from *Vetiveria zizanioides* (L.) Nash.

For P450 enzymes it is known that they may catalyze the successive oxidation of an alcohol at the same carbon atom to corresponding aldehydes, ketones and/or carboxylic acids. Therefore, in the above embodiments zizaenol oxidation to zizaenone or other corresponding oxidation products may be catalyzed by the same P450 enzyme or by another zizaenol oxidizing activity. Further, in the above embodiments isovalencenol or isonootkatol oxidation to other isovalencenol oxidation products (aldehydes or ketones) or to isonootkatone or other corresponding oxidation products may be catalyzed by the same P450 enzyme or by another isovalencenol or isonootkatol oxidizing activity.

In one particular aspect of any of the embodiments herein, including the methods, vectors, or non-human host organism, the VzCP8201 polypeptide having Cytochrome P450 monooxygenase activity comprises an amino acid sequence having at least 70%, 75%, 80%, 85%, 90%, 95%, 96%, 97%, 98%, 99% or 100% sequence identity to SEQ ID NO: 7, SEQ ID NO: 10, or SEQ ID NO: 19.

In one particular aspect of any of the embodiments herein, including the methods, vectors, or non-human host organism, the VzCP8201 polypeptide having Cytochrome P450 monooxygenase activity is encoded by a nucleic acid comprising a nucleotide sequence having at least 70%, 75%, 80%, 85%, 90%, 95%, 96%, 97%, 98%, 99% or 100% sequence identity to SEQ ID NO: 6, SEQ ID NO: 7, SEQ ID NO: 8, SEQ ID NO: 9, or SEQ ID NO: 55.

In one particular aspect of any of the embodiments herein, including the methods, vectors, or non-human host organism, the VzCP521-11 polypeptide having Cytochrome P450 monooxygenase activity comprises an amino acid sequence having at least 70%, 75%, 80%, 85%, 90%, 95%, 96%, 97%, 98%, 99% or 100% sequence identity to SEQ ID NO: 18 or SEQ ID NO: 21.

In one particular aspect of any of the embodiments herein, including the methods, vectors, or non-human host organism, the VzCP521-11 polypeptide having Cytochrome P450 monooxygenase activity is encoded by a nucleic acid comprising a nucleotide sequence having at least 70%, 75%, 80%, 85%, 90%, 95%, 96%, 97%, 98%, 99% or 100% sequence identity to SEQ ID NO: 16, SEQ ID NO: 17, or SEQ ID NO: 54.

In one particular aspect of any of the embodiments herein, including the methods, vectors, or non-human host organism, the VzCP7186 polypeptide having Cytochrome P450 monooxygenase activity comprises an amino acid sequence having at least 70%, 75%, 80%, 85%, 90%, 95%, 96%, 97%, 98%, 99% or 100% sequence identity to SEQ ID NO: 13, SEQ ID NO: 15, or SEQ ID NO: 20.

In one particular aspect of any of the embodiments herein, including the methods, vectors, or non-human host organism, the VzCP7186 polypeptide having Cytochrome P450 monooxygenase activity is encoded by a nucleic acid comprising a nucleotide sequence having at least 70%, 75%, 80%, 85%, 90%, 95%, 96%, 97%, 98%, 99% or 100% sequence identity to SEQ ID NO: 11, SEQ ID NO: 12, or SEQ ID NO: 14.

In one particular aspect of any of the embodiments herein, including the methods, vectors, or non-human host organism, the polypeptide having zizaene synthase activity is VzZS1 (a) comprising an amino acid sequence having at least 70%, 75%, 80%, 85%, 90%, 95%, 96%, 97%, 98%, 99% or 100% sequence identity to SEQ ID NO: 33, or (b) encoded by a nucleic acid comprising a nucleotide sequence having at least 70%, 75%, 80%, 85%, 90%, 95%, 96%, 97%, 98%, 99% or 100% sequence identity to SEQ ID NO: 31, SEQ ID NO: 32, SEQ ID NO: 34, or SEQ ID NO: 51.

In one particular aspect of any of the embodiments herein, including the methods, vectors, or non-human host organism, the polypeptide having zizaene synthase activity is VzZS2 (a) comprising an amino acid sequence having at least 70%, 75%, 80%, 85%, 90%, 95%, 96%, 97%, 98%, 99% or 100% sequence identity to SEQ ID NO: 38, or (b) encoded by a nucleic acid comprising a nucleotide sequence having at least 70%, 75%, 80%, 85%, 90%, 95%, 96%, 97%, 98%, 99% or 100% sequence identity to SEQ ID NO: 35, SEQ ID NO: 36, SEQ ID NO: 37, or SEQ ID NO: 52.

In one particular aspect of any of the embodiments herein, including the methods, vectors, or non-human host organism, the polypeptide having zizaene synthase activity is VzZS2-Nter2 (a) comprising an amino acid sequence having at least 70%, 75%, 80%, 85%, 90%, 95%, 96%, 97%, 98%, 99% or 100% sequence identity to SEQ ID NO: 42, or (b) encoded by a nucleic acid comprising a nucleotide sequence having at least 70%, 75%, 80%, 85%, 90%, 95%, 96%, 97%, 98%, 99% or 100% sequence identity to SEQ ID NO: 39, SEQ ID NO: 40, SEQ ID NO: 41, or SEQ ID NO: 53.

In one particular aspect of any of the embodiments herein, including the methods, vectors, or non-human host organism, the CPR is encoded by a nucleic acid comprising a nucleotide sequence having at least 70%, 75%, 80%, 85%, 90%, 95%, 96%, 97%, 98%, 99% or 100% sequence identity to SEQ ID NO: 22.

b. Polypeptides Applicable According to the Invention

In this context the following definitions apply:

The term "polypeptide" means an amino acid sequence of consecutively polymerized amino acid residues, for instance, at least 15 residues, at least 30 residues, at least 50 residues. In some embodiments herein, a polypeptide comprises an amino acid sequence that is an enzyme, or a fragment, or a variant or mutant thereof.

The term "protein" refers to an amino acid sequence of any length wherein amino acids are linked by covalent peptide bonds, and includes oligopeptide, peptide, polypeptide and full-length protein whether naturally occurring or synthetic.

The term "isolated" polypeptide refers to an amino acid sequence that is removed from its natural environment by any method or combination of methods known in the art and includes recombinant, biochemical and synthetic methods.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

"Membrane anchor peptide" refers to the N-terminal part of eukaryotic cytochrome P450s essential for the membrane localization of these enzymes.

The present invention also relates to "functional equivalents" (also designated as "analogs" or "functional mutations" or "variants") of the polypeptides specifically described herein.

For example, "functional equivalents" refer to polypeptides which, in a test used for determining an enzymatic activity of an enzyme referred to herein, as for example an isovalencene or zizaene oxidizing activity or a zizaene synthase activity or isovalencene synthase activity display at least a 1 to 10%, or at least 20%, or at least 50%, or at least 75%, or at least 90% higher or lower activity, as compared to the activity of a particular polypeptide specifically described herein.

Such "functional equivalents" or "variants" of the polypeptides of the invention may be used to attain for example desired enhanced or reduced enzymatic activity, modified regiochemistry or stereochemistry, or altered substrate utilization or product distribution, increased affinity for the substrate, improved specificity for the production of one or more desired compounds, increased velocity of the enzyme reaction, higher activity or stability in a specific environment (pH, temperature, solvent, etc), or improved expression level in a desired expression system. A variant or mutant may be made by any method known in the art. Variants and derivatives of native polypeptides can be obtained by isolating naturally-occurring variants, or the nucleotide sequence of variants, of other or same plant lines or species, or by artificially programming mutations of nucleotide sequences coding for the polypeptides of the invention. Alterations of the native amino acid sequence can be accomplished by any of a number of conventional methods (see below)

"Functional equivalents", according to the invention, also cover particular mutants, which, in at least one sequence position of an amino acid sequences stated herein, have an amino acid that is different from that concretely stated one, but nevertheless possess one of the aforementioned biological activities, as for example an enzyme activity, like isovalencene oxidizing activity, zizaene oxidizing activity, zizaene synthase activity or isovalencene synthase activity. "Functional equivalents" thus comprise mutants obtainable by one or more, like 1 to 20, in particular 1 to 15 or 5 to 10 amino acid additions, substitutions, in particular conservative substitutions, deletions and/or inversions, where the stated changes can occur in any sequence position, provided they lead to a mutant with the profile of properties according to the invention. Functional equivalence is in particular also provided if the activity patterns coincide qualitatively between the mutant and the unchanged polypeptide, i.e. if, for example, interaction with the same agonist or antagonist or substrate, however at a different rate, (i.e. expressed by a $EC_{50}$ or $IC_{50}$ value or any other parameter suitable in the present technical field) is observed. Examples of suitable (conservative) amino acid substitutions are shown in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The effects of such substitutions can be calculated using substitution score matrices such a PAM-120, PAM-200, and PAM-250 as discussed in Altschul, (J. Mol. Biol. 219:555-65, 1991). Other such conservative substitutions, for example substitutions of entire regions having similar hydrophobicity characteristics, are well known. The polypeptides of the invention can also be subjected to non-conservative substitutions, so as to generate more diverse variants, provided that such variants retain the desired enzyme activity. Variants can also be produced by substitution, deletion and insertion of nucleotide(s) into the nucleic acid sequence encoding for the variant polypeptide.

"Functional equivalents" in the above sense are also "precursors" of the polypeptides described herein, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent polypeptides can be determined on the basis of the concrete parameters of the invention.

"Functional equivalents" also comprise "fragments", like individual domains or sequence motifs, of the polypeptides according to the invention, or N- and or C-terminally truncated forms, which may or may not display the desired biological function. Preferably such "fragments" retain the desired biological function at least qualitatively.

"Functional equivalents" are, moreover, fusion proteins, which have one of the polypeptide sequences stated herein or functional equivalents derived there from and at least one further, functionally different, heterologous sequence in functional N-terminal or C-terminal association (i.e. without substantial mutual functional impairment of the fusion protein parts). Such fusion polypeptides can be used to enhance expression of the polypeptides of interest, be useful in the purification of the protein or improve the enzymatic activity of the polypeptide in a desired environment or expression system. Non-limiting examples of these heterologous sequences are e.g. signal peptides, histidine anchors, membrane anchors or other enzymes.

"Functional equivalents" which are also comprised in accordance with the invention are homologs to the specifically disclosed polypeptides. These have at least 60%, preferably at least 75%, in particular at least 80 or 85%, such as, for example, 90, 91, 92, 93, 94, 95, 96, 97, 98 or 99%, homology (or identity) to one of the specifically disclosed amino acid sequences, calculated by the algorithm of Pearson and Lipman, Proc. Natl. Acad, Sci. (USA) 85(8), 1988, 2444-2448. A homology or identity, expressed as a percentage, of a homologous polypeptide according to the invention means in particular an identity, expressed as a percentage, of the amino acid residues based on the total length of one of the amino acid sequences described specifically herein.

The identity data, expressed as a percentage, may also be determined with the aid of BLAST alignments, algorithm blastp (protein-protein BLAST), or by applying the Clustal settings specified herein below.

In the case of a possible protein glycosylation, "functional equivalents" according to the invention comprise polypeptides as described herein in deglycosylated or glycosylated form as well as modified forms that can be obtained by altering the glycosylation pattern.

Functional equivalents or homologues of the polypeptides according to the invention can be produced by mutagenesis, e.g. by point mutation, lengthening or shortening of the protein or as described in more detail below.

Functional equivalents or homologs of the polypeptides according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art.

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues.

An embodiment provided herein provides orthologs and paralogs of polypeptides disclosed herein as well as methods for identifying and isolating such orthologs and paralogs.

c. Coding Nucleic Acid Sequences Applicable According to the Invention

In this context the following definitions apply:

The terms "nucleic acid sequence," "nucleic acid," "nucleic acid molecule" and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U). The term "nucleotide sequence" should also be understood as comprising a polynucleotide molecule or an oligonucleotide molecule in the form of a separate fragment or as a component of a larger nucleic acid.

An "isolated nucleic acid" or "isolated nucleic acid sequence" relates to a nucleic acid or nucleic acid sequence that is in an environment different from that in which the nucleic acid or nucleic acid sequence naturally occurs and can include those that are substantially free from contaminating endogenous material. The term "naturally-occurring" as used herein as applied to a nucleic acid refers to a nucleic acid that is found in a cell of an organism in nature and which has not been intentionally modified by a human in the laboratory.

A "fragment" of a polynucleotide or nucleic acid sequence refers to contiguous nucleotides that is particularly at least 15 bp, at least 30 bp, at least 40 bp, at least 50 bp and/or at least 60 bp in length of the polynucleotide of an embodiment herein. Particularly the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

As used herein, the term "hybridization" or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein below. Appropriate hybridization conditions can also be selected by those skilled in the art with minimal experimentation as exemplified in Ausubel et al. (1995, *Current Protocols in Molecular Biology*, John Wiley & Sons, sections 2, 4, and 6). Additionally, stringency conditions are described in Sambrook et al. (1989, *Molecular Cloning: A Laboratory Manual*, 2nd ed., Cold Spring Harbor Press, chapters 7, 9, and 11).

"Recombinant nucleic acid sequences" are nucleic acid sequences that result from the use of laboratory methods (for example, molecular cloning) to bring together genetic material from more than on source, creating or modifying a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002, Cold Spring Harbor Lab Press; and Sambrook et al., 1989, Cold Spring Harbor, NY, Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

"Polycistronic" refers to nucleic acid molecules, in particular mRNAs, which can encode two or more polypeptides separately within the same nucleic acid molecule. A polycistronic nucleic acid contains more than one open reading frame (ORFs) and the information of each ORF is translated in polypeptide. The ORF sequences in polycistronic nucleic acid are separated by noncoding sequences generally including a ribosome binding site (RBS) for the initiation of the translation.

A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3'end") refers to the nucleic acid sequence found downstream of the coding sequence of a gene, which comprises, for example, a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

The term "primer" refers to a short nucleic acid sequence that is hybridized to a template nucleic acid sequence and is used for polymerization of a nucleic acid sequence complementary to the template.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

The term "transformed", if not otherwise stated, has to be understood broadly in the context of the invention, as it refers to the fact that a host was subjected to genetic engineering to comprise one, two or more copies of each of the nucleic acids required in any of the above-described embodiment. Preferably the term "transformed" relates to hosts heterologously expressing the polypeptides encoded by the nucleic acid with which they are transformed, as well as overexpressing said polypeptides. Accordingly, in an embodiment, the present invention provides a transformed organism, in which the polypeptides are expressed in higher quantity than in the same organism not so transformed.

In one embodiment, transformed DNA is integrated into a chromosome of a host organism and/or cell such that a stable recombinant system results. Any chromosomal integration method known in the art may be used in the practice of the invention, including but not limited to recombinase-mediated cassette exchange (RMCE), viral site-specific chromosomal insertion, adenovirus and pronuclear injection. The invention also relates to nucleic acid sequences that code for polypeptides as defined herein. In particular, the invention also relates to nucleic acid sequences (single-stranded and double-stranded DNA and RNA sequences, e.g. cDNA, genomic DNA and mRNA), coding for one of the above polypeptides and their functional equivalents, which can be obtained for example using artificial nucleotide analogs.

The invention relates both to isolated nucleic acid molecules, which code for polypeptides according to the invention or biologically active segments thereof, and to nucleic acid fragments, which can be used for example as hybridization probes or primers for identifying or amplifying coding nucleic acids according to the invention.

The present invention also relates to nucleic acids with a certain degree of "identity" to the sequences specifically disclosed herein. "Identity" between two nucleic acids means identity of the nucleotides, in each case over the entire length of the nucleic acid.

The "identity" between two nucleotide sequences (the same applies to peptide or amino acid sequences) is a function of the number of nucleotide residues (or amino acid residues) or that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web.

Particularly, the BLAST program (Tatiana et al, *FEMS Microbiol Lett.*, 1999, 174:247-250, 1999) set to the default parameters, available from the National Center for Biotechnology Information (NCBI) website at ncbi.nlm.nih.gov/BLAST/bl2seq/wblast2.cgi, can be used to obtain an optimal alignment of protein or nucleic acid sequences and to calculate the percentage of sequence identity.

In another example the identity may be calculated by means of the Vector NTI Suite 7.1 program of the company Informax (USA) employing the Clustal Method (Higgins D G, Sharp P M. ((1989))) with the following settings:

| Multiple alignment parameter: | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |
| Pairwise alignment parameter: | |
| FAST algorithm | on |
| K-tuple size | 1 |
| Gap penalty | 3 |
| Window size | 5 |
| Number of best diagonals | 5 |

Alternatively the identity may be determined according to Chenna, et al. (2003), the web page: www.ebi.ac.uk/Tools/clustalw/index.html #and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (as defined herein elsewhere) on at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, (1989)).

In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences according to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These "standard conditions" vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), (1985), Brown (ed) (1991).

"Hybridization" can in particular be carried out under stringent conditions. Such hybridization conditions are for example described in Sambrook (1989), or in Current Protocols in Molecular Biology, John Wiley & Sons, N.Y. (1989), 6.3.1-6.3.6.

As used herein, the term hybridization or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995, *Current Protocols in Molecular Biology*, John Wiley & Sons, sections 2, 4, and 6). Additionally, stringency conditions are described in Sambrook et al. (1989, *Molecular Cloning: A Laboratory Manual*, 2nd ed., Cold Spring Harbor Press, chapters 7, 9, and 11).

As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ 32P-labeled probe is used. Filters are incubated in hybridization mixture for 18-20 h at 40° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ 32P-labeled probe is used. Filters are incubated in hybridization mixture for 30 h at 50° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in the prehybridization mixture containing 100 µg/ml denatured salmon sperm DNA and 5-20×10$^6$ cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes.

Other conditions of low, moderate, and high stringency well known in the art (e.g., as employed for cross-species hybridizations) may be used if the above conditions are inappropriate (e.g., as employed for cross-species hybridizations).

A detection kit for nucleic acid sequences encoding a polypeptide of the invention may include primers and/or probes specific for nucleic acid sequences encoding the polypeptide, and an associated protocol to use the primers and/or probes to detect nucleic acid sequences encoding the polypeptide in a sample. Such detection kits may be used to determine whether a plant, organism, microorganism or cell has been modified, i.e., transformed with a sequence encoding the polypeptide.

To test a function of variant DNA sequences according to an embodiment herein, the sequence of interest is operably linked to a selectable or screenable marker gene and expression of said reporter gene is tested in transient expression assays, for example, with microorganisms or with protoplasts or in stably transformed plants.

The invention also relates to derivatives of the concretely disclosed or derivable nucleic acid sequences.

Thus, further nucleic acid sequences according to the invention can be derived from the sequences specifically disclosed herein and can differ from it by one or more, like 1 to 20, in particular 1 to 15 or 5 to 10 additions, substitutions, insertions or deletions of one or several (like for example 1 to 10) nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism.

According to a particular embodiment of the invention variant nucleic acids may be prepared in order to adapt its nucleotide sequence to a specific expression system. For example, bacterial expression systems are known to more efficiently express polypeptides if amino acids are encoded by particular codons. Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the polypeptides described herein may be optimized for increased expression in the host cell. For example, nucleic acids of an embodiment herein may be synthesized using codons particular to a host for improved expression.

The invention also encompasses naturally occurring variants, e.g. splicing variants or allelic variants, of the sequences described therein.

Allelic variants may have at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

The invention also relates to sequences that can be obtained by conservative nucleotide substitutions (i.e. as a result thereof the amino acid in question is replaced by an amino acid of the same charge, size, polarity and/or solubility).

The invention also relates to the molecules derived from the concretely disclosed nucleic acids by sequence polymorphisms. Such genetic polymorphisms may exist in cells from different populations or within a population due to natural allelic variation. Allelic variants may also include functional equivalents. These natural variations usually produce a variance of 1 to 5% in the nucleotide sequence of a gene. Said polymorphisms may lead to changes in the amino acid sequence of the polypeptides disclosed herein. Allelic variants may also include functional equivalents.

Furthermore, derivatives are also to be understood to be homologs of the nucleic acid sequences according to the invention, for example animal, plant, fungal or bacterial homologs, shortened sequences, single-stranded DNA or RNA of the coding and noncoding DNA sequence. For example, homologs have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

d. Generation of Functional Polypeptide Mutants

A person skilled in the art is familiar with methods for generating functional mutants, that is to say nucleotide sequences which code for a polypeptide with at least 80%, 81%, 82%, 83%, 84%, 85%, 86%, 87%, 88%, 89%, 90%, 91%, 92%, 93%, 94%, 95%, 96%, 97%, 98% or 99% sequence identity to anyone of amino acid related SEQ ID NOs as disclosed herein and/or encoded by a nucleic acid molecule comprising a nucleotide sequence having at least 70% sequence identity to anyone of the nucleotide related SEQ ID NOs as disclosed herein.

Depending on the technique used, a person skilled in the art can introduce entirely random or else more directed mutations into genes or else noncoding nucleic acid regions (which are for example important for regulating expression) and subsequently generate genetic libraries. The methods of molecular biology required for this purpose are known to the skilled worker and for example described in Sambrook and Russell, Molecular Cloning. 3rd Edition, Cold Spring Harbor Laboratory Press 2001.

Methods for modifying genes and thus for modifying the polypeptide encoded by them have been known to the skilled worker for a long time, such as, for example
- site-specific mutagenesis, where individual or several nucleotides of a gene are replaced in a directed fashion (Trower M K (Ed.) 1996; In vitro mutagenesis protocols. Humana Press, New Jersey),
- saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcirel R, Stunnenberg H G (1994) Nucleic Acids Res 22:541; Barik S (1995) Mol Biotechnol 3:1), error-prone polymerase chain reaction, where nucleotide sequences are mutated by error-prone DNA polymerases (Eckert K A, Kunkel T A (1990) Nucleic Acids Res 18:3739);

the SeSaM method (sequence saturation method), in which preferred exchanges are prevented by the polymerase. Schenk et al., Biospektrum, Vol. 3, 2006, 277-279 the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an *E. coli* mutator strain. In: Trower M K (Ed.) In vitro mutagenesis protocols. Humana Press, New Jersey), or DNA shuffling, in which a pool of closely related genes is formed and digested and the fragments are used as templates for a polymerase chain reaction in which, by repeated strand separation and reassociation, full-length mosaic genes are ultimately generated (Stemmer W P C (1994) Nature 370:389; Stemmer W P C (1994) Proc Natl Acad Sci USA 91:10747).

Using so-called directed evolution (described, inter alia, in Reetz M T and Jaeger K-E (1999), Topics Curr Chem 200:31; Zhao H, Moore J C, Volkov A A, Arnold F H (1999), Methods for optimizing industrial polypeptides by directed evolution, In: Demain A L, Davies J E (Ed.) Manual of industrial microbiology and biotechnology. American Society for Microbiology), a skilled worker can produce functional mutants in a directed manner and on a large scale. To this end, in a first step, gene libraries of the respective polypeptides are first produced, for example using the methods given above. The gene libraries are expressed in a suitable way, for example by bacteria or by phage display systems.

The relevant genes of host organisms which express functional mutants with properties that largely correspond to the desired properties can be submitted to another mutation cycle. The steps of the mutation and selection or screening can be repeated iteratively until the present functional mutants have the desired properties to a sufficient extent. Using this iterative procedure, a limited number of mutations, for example 1, 2, 3, 4 or 5 mutations, can be performed in stages and assessed and selected for their influence on the activity in question. The selected mutant can then be submitted to a further mutation step in the same way. In this way, the number of individual mutants to be investigated can be reduced significantly.

The results according to the invention also provide important information relating to structure and sequence of the relevant polypeptides, which is required for generating, in a targeted fashion, further polypeptides with desired modified properties. In particular, it is possible to define so-called "hot spots", i.e. sequence segments that are potentially suitable for modifying a property by introducing targeted mutations.

Information can also be deduced regarding amino acid sequence positions, in the region of which mutations can be effected that should probably have little effect on the activity, and can be designated as potential "silent mutations".

e. Constructs for Expressing Polypeptides of the Invention

In this context the following definitions apply:

"Expression of a gene" encompasses "heterologous expression" and "overexpression" and involves transcription of the gene and translation of the mRNA into a protein.

Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for a RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one "regulatory sequence", which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

An "expression system" as used herein encompasses any combination of nucleic acid molecules required for the co-expression of two or more polypeptides. The respective coding sequences may either be located on a single nucleic acid molecule or vector, as for example a vector containing more than one promoter sequence, or on a polycistronic nucleic acid, or may be distributed over two or more physically distinct vectors.

As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific and/or degenerate oligonucleotide primer pairs, oligo dT primer) for amplifying (e.g., by polymerase chain reaction, PCR) naturally expressed (e.g., genomic DNA or mRNA) or recombinant (e.g., cDNA) nucleic acids of the invention in vivo, ex vivo or in vitro.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

A "promoter", a "nucleic acid with promoter activity" or a "promoter sequence" is understood as meaning, in accordance with the invention, a nucleic acid which, when functionally linked to a nucleic acid to be transcribed, regulates the transcription of said nucleic acid. "Promoter" in particular refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

In this context, a "functional" or "operative" linkage is understood as meaning for example the sequential arrangement of one of the nucleic acids with a regulatory sequence. For example, the sequence with promoter activity and of a nucleic acid sequence to be transcribed and optionally further regulatory elements, for example nucleic acid sequences which ensure the transcription of nucleic acids, and for example a terminator, are linked in such a way that each of the regulatory elements can perform its function upon transcription of the nucleic acid sequence. This does not necessarily require a direct linkage in the chemical sense. Genetic control sequences, for example enhancer sequences, can even exert their function on the target sequence from more remote positions or even from other DNA molecules. Preferred arrangements are those in which the nucleic acid sequence to be transcribed is positioned downstream (i.e. at the 3'-end of) the promoter sequence so that the two sequences are joined together covalently. The distance between the promoter sequence and the nucleic acid sequence to be expressed recombinantly can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, CA (1990).

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the organism to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of a terpene compound as herein specified in the cell or organism.

The nucleotide sequence as described herein above may be part of an "expression cassette". The terms "expression cassette" and "expression construct" are used synonymously. The (preferably recombinant) expression construct contains a nucleotide sequence which encodes a polypeptide according to the invention and which is under genetic control of regulatory nucleic acid sequences.

In a process applied according to the invention, the expression cassette may be part of an "expression vector", in particular of a recombinant expression vector.

An "expression unit" is understood as meaning, in accordance with the invention, a nucleic acid with expression activity which comprises a promoter as defined herein and, after functional linkage with a nucleic acid to be expressed or a gene, regulates the expression, i.e. the transcription and the translation of said nucleic acid or said gene. It is therefore in this connection also referred to as a "regulatory nucleic acid sequence". In addition to the promoter, other regulatory elements, for example enhancers, can also be present.

An "expression cassette" or "expression construct" is understood as meaning, in accordance with the invention, an expression unit which is functionally linked to the nucleic acid to be expressed or the gene to be expressed. In contrast to an expression unit, an expression cassette therefore comprises not only nucleic acid sequences which regulate transcription and translation, but also the nucleic acid sequences that are to be expressed as protein as a result of transcription and translation.

The terms "expression" or "overexpression" describe, in the context of the invention, the production or increase in intracellular activity of one or more polypeptides in a microorganism, which are encoded by the corresponding DNA. To this end, it is possible for example to introduce a gene into an organism, replace an existing gene with another gene, increase the copy number of the gene(s), use a strong promoter or use a gene which encodes for a corresponding polypeptide with a high activity; optionally, these measures can be combined.

Preferably such constructs according to the invention comprise a promoter 5'-upstream of the respective coding sequence and a terminator sequence 3'-downstream and optionally other usual regulatory elements, in each case in operative linkage with the coding sequence.

Nucleic acid constructs according to the invention comprise in particular a sequence coding for a polypeptide for example derived from the amino acid related SEQ ID NOs as described therein or the reverse complement thereof, or derivatives and homologs thereof and which have been linked operatively or functionally with one or more regulatory signals, advantageously for controlling, for example increasing, gene expression.

In addition to these regulatory sequences, the natural regulation of these sequences may still be present before the actual structural genes and optionally may have been genetically modified so that the natural regulation has been switched off and expression of the genes has been enhanced. The nucleic acid construct may, however, also be of simpler construction, i.e. no additional regulatory signals have been inserted before the coding sequence and the natural promoter, with its regulation, has not been removed. Instead, the natural regulatory sequence is mutated such that regulation no longer takes place and the gene expression is increased.

A preferred nucleic acid construct advantageously also comprises one or more of the already mentioned "enhancer" sequences in functional linkage with the promoter, which sequences make possible an enhanced expression of the nucleic acid sequence. Additional advantageous sequences may also be inserted at the 3'-end of the DNA sequences, such as further regulatory elements or terminators. One or more copies of the nucleic acids according to the invention may be present in a construct. In the construct, other markers, such as genes which complement auxotrophisms or antibiotic resistances, may also optionally be present so as to select for the construct.

Examples of suitable regulatory sequences are present in promoters such as cos, tac, trp, tet, trp-tet, lpp, lac, lpp-lac, lacI$^q$, T7, T5, T3, gal, tre, ara, rhaP (rhaP$_{BAD}$)SP6, lambda-P$_R$ or in the lambda-P$_L$ promoter, and these are advantageously employed in Gram-negative bacteria. Further advantageous regulatory sequences are present for example in the Gram-positive promoters amy and SPO2, in the yeast or fungal promoters ADC1, MFalpha, AC, P-60, CYC1, GAPDH, TEF, rp28, ADH. Artificial promoters may also be used for regulation.

For expression in a host organism, the nucleic acid construct is inserted advantageously into a vector such as, for example, a plasmid or a phage, which makes possible optimal expression of the genes in the host. Vectors are also understood as meaning, in addition to plasmids and phages, all the other vectors which are known to the skilled worker, that is to say for example viruses such as SV40, CMV, baculovirus and adenovirus, transposons, IS elements, phasmids, cosmids and linear or circular DNA or artificial chromosomes. These vectors are capable of replicating autonomously in the host organism or else chromosomally. These vectors are a further development of the invention. Binary or cpo-integration vectors are also applicable.

Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-II$^{113}$-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The abovementioned plasmids are a small selection of the plasmids which are possible. Further plasmids are well known to the skilled worker and can be found for example in the book Cloning Vectors (Eds. Pouwels P. H. et al. Elsevier, Amsterdam-New York-Oxford, 1985, ISBN 0 444 904018).

In a further development of the vector, the vector which comprises the nucleic acid construct according to the invention or the nucleic acid according to the invention can advantageously also be introduced into the microorganisms in the form of a linear DNA and integrated into the host organism's genome via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences to match the specific "codon usage" used in the organism. The "codon usage" can be determined readily by computer evaluations of other, known genes of the organism in question.

An expression cassette according to the invention is generated by fusing a suitable promoter to a suitable coding nucleotide sequence and a terminator or polyadenylation signal. Customary recombination and cloning techniques are used for this purpose, as are described, for example, in T. Maniatis, E. F. Fritsch and J. Sambrook, Molecular Cloning: A Laboratory Manual, Cold Spring Harbor Laboratory, Cold Spring Harbor, NY (1989) and in T. J. Silhavy, M. L. Berman and L. W. Enquist, Experiments with Gene Fusions, Cold Spring Harbor Laboratory, Cold Spring Harbor, NY (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which makes possible optimal expression of the genes in the host. Vectors are well known to the skilled worker and can be found for example in "cloning vectors" (Pouwels P. H. et al., Ed., Elsevier, Amsterdam-New York-Oxford, 1985).

An alternative embodiment of an embodiment herein provides a method to "alter gene expression" in a host cell. For instance, the polynucleotide of an embodiment herein may be enhanced or overexpressed or induced in certain contexts (e.g. upon exposure to certain temperatures or culture conditions) in a host cell or host organism.

Alteration of expression of a polynucleotide provided herein may also result in ectopic expression which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity.

In one embodiment, provided herein is also an isolated, recombinant or synthetic polynucleotide encoding a polypeptide or variant polypeptide provided herein.

In one embodiment, several polypeptide encoding nucleic acid sequences are co-expressed in a single host, particularly under control of different promoters. In another embodiment, several polypeptide encoding nucleic acid sequences can be present on a single transformation vector or be co-transformed at the same time using separate vectors and selecting transformants comprising both chimeric genes. Similarly, one or polypeptide encoding genes may be expressed in a single plant, cell, microorganism or organism together with other chimeric genes.

f. Hosts to be Applied for the Present Invention

Depending on the context, the term "host" (or "host cell or organism") can mean the wild-type hosts or genetically altered, recombinant hosts or both. A "host organisms" comprises any prokaryotic or eukaryotic organisms, including plants, fungi, prokaryotes, or cultures of higher eukaryotic, like mammalian hosts. Microorganisms in particular comprise prokaryotes, fungi and yeasts.

Using the vectors according to the invention, recombinant hosts can be produced, which are for example transformed with at least one vector according to the invention and can be used for producing the polypeptides according to the invention and or for performing the enzyme-catalyzed conversion reactions as herein defined. Advantageously, the recombinant constructs according to the invention, described above, are introduced into a suitable host system and expressed. Preferably common cloning and transfection methods, known by a person skilled in the art, are used, for example coprecipitation, protoplast fusion, electroporation, retroviral transfection and the like, for expressing the stated nucleic acids in the respective expression system. For the creation of transgenic plants, for example, current methods include: electroporation of plant protoplasts, liposome-mediated transformation, agrobacterium-mediated transformation, polyethylene-glycol-mediated transformation, particle bombardement, microinjection of plant cells, and transformation using viruses.

Suitable systems are described for example in Current Protocols in Molecular Biology, F. Ausubel et al., Ed., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, NY, 1989. Cloning and expression vectors for higher plants and/or plant cells in particular are available to the skilled person. See for example Schardl et al. Gene 61: 1-11, 1987.

In principle, all prokaryotic or eukaryotic organisms, including plants, fungi, prokaryotes, or cultures of higher eukaryotic, like mammalian hosts, may be considered as recombinant host organisms for the nucleic acid according to the invention or the nucleic acid construct. Advantageously, microorganisms such as bacteria, fungi/yeasts are used as host organisms. Advantageously, gram-positive or gram-negative bacteria are used, preferably bacteria of the families Enterobacteriaceae, Pseudomonadaceae, Rhizobiaceae, Streptomycetaceae or Nocardiaceae, especially preferably bacteria of the genera *Escherichia, Pseudomonas, Streptomyces, Nocardia, Burkholderia, Salmonella, Agrobacterium, Clostridium* or *Rhodococcus*. The genus and species *Escherichia coli* is quite especially preferred. Furthermore, other advantageous bacteria are to be found in the group of alpha-Proteobacteria, beta-Proteobacteria or gamma-Proteobacteria.

Depending on the host organism, the organisms used in the method according to the invention are grown or cultured in a manner known by a person skilled in the art. Culture can be batchwise, semi-batchwise or continuous. Nutrients can be present at the beginning of fermentation or can be supplied later, semicontinuously or continuously. This is also described in more detail below.

As mentioned above, host organism or cells may be applied according to the invention in the recombinant production of novel polypeptides as well as in a method of producing oxidized terpene compounds.

To carry out the production of oxidized terpenes in vivo, the host is cultivated under conditions conducive to the production of the oxidized terpene. Such conditions are any conditions leading to growth of the host organism or cell. Preferably, such conditions are designed for optimal growth of the host. Accordingly, if the host is a transgenic plant, optimal growth conditions are provided, such as optimal light, water and nutrient conditions, for example. If the host is a unicellular organism, conditions conducive to the production of the oxidized terpene may comprise addition of suitable cofactors to the culture medium of the host. In addition, a culture medium may be selected, so as to maximize terpene oxidation. Optimal culture conditions are known to the person skilled in the art and are not specific to the present invention. Examples of suitable conditions are described in a more detailed manner in the following Examples.

Non-human hosts suitable to carry out the method of the invention in vivo may be any non-human multicellular or unicellular organisms. In a preferred embodiment, the non-human host used to carry out the invention in vivo is a plant, a prokaryote or a fungus. Any plant, prokaryote or fungus can be used. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Minta*. Preferably, the plant belongs to the species of *Nicotiana tabacum*.

In a more preferred embodiment the host used to carry out the method of the invention in vivo is a microorganism. Any microorganism can be used but according to an even more preferred embodiment said microorganism is a bacteria or fungus. Preferably said fungus is yeast. Most preferably, said bacteria is *E. coli* and said yeast is *Saccharomyces cerevisiae*.

Several of these organisms do not produce the terpene to be oxidized naturally. To be suitable to carry out the method of the invention, these organisms have to be transformed to produce said terpene. They can be so transformed either prior to, simultaneously with or after transformation with the nucleic acid described according to any of the above embodiments, as explained above. Methods to transform organisms, for example microorganisms, so that they express a terpene synthase are already known in the art. Such methods can for example be found in WO 2010/134004, which describes transformation of diverse host organisms and cells with a zizaene synthase, i.e. an enzyme capable of catalyzing the production of zizaene from farnesyl pyrophosphate. In particular, they can advantageously be further transformed with at least one gene encoding a polypeptide involved in the metabolism of production of acyclic terpene precursor such as geranyl pyrophosphate, or geranylgeranyl pyrophosphate and in particular farnesyl pyrophosphate. Such polypeptides include for example enzymes of the MEP pathway, of the MVA pathway and/or prenyl transferases. Transforming an organism or cell capable of producing a terpene compound with a polypeptide of the invention and with a CPR, or with a fusion polypeptide comprising both, as described in any of the embodiments of the invention, is sufficient for the oxidation of the terpene to take place. Nevertheless, further transformation with at least one enzyme involved in the production of an acyclic terpene precursor and/or of isopentenyl diphosphate (IPP) or dimethylallyl diphosphate (DMAPP), has the advantage of increasing the amount of terpene available to be oxidized.

In a particular embodiment, such host heterologously expresses or overexpresses a polypeptide according to any embodiment of the present invention.

According to a preferred embodiment, if the host expresses a terpene oxidizing enzyme, like a cytochrome P450 enzyme as herein defined, it further expresses a P450-reductase (CPR), as described above. The CPR can either be present naturally in the host organism or cell or such organism or cell can be transformed to express a CPR prior to, simultaneously with or after transformation to express the cytochrome P450. In a preferred embodiment of the invention the host cell or organism is transformed to express a fusion polypeptide comprising both the cytochrome P450 and the CPR.

In another preferred embodiment, the host is capable of producing the terpene to be oxidized. This is the case when the host expresses a terpene synthase capable of catalyzing the formation of said terpene.

In an alternative embodiment, the terpene compound to be oxidized can be added to the culture medium of said host. The terpene compound will permeate through the membrane of the host, thus being available for reaction with the P450 of the invention expressed by said host.

g. Recombinant Production of Polypeptides According to the Invention

The invention further relates to methods for recombinant production of polypeptides according to the invention or functional, biologically active fragments thereof, wherein a polypeptide-producing microorganism is cultured, optionally the expression of the polypeptides is induced and these are isolated from the culture. The polypeptides can also be produced in this way on an industrial scale, if desired.

The microorganisms produced according to the invention can be cultured continuously or discontinuously in the batch method or in the fed-batch method or repeated fed-batch method. A summary of known cultivation methods can be found in the textbook by Chmiel (Bioprozesstechnik 1. Einfihrung in die Bioverfahrenstechnik [Bioprocess technology 1. Introduction to bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Braunschweig/Wiesbaden, 1994)).

The culture medium to be used must suitably meet the requirements of the respective strains. Descriptions of culture media for various microorganisms are given in the manual "Manual of Methods for General Bacteriology" of the American Society for Bacteriology (Washington D. C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via malt extract, complex compounds, such as molasses, or other by-products of sugar refining. It can also be advantageous to add mixtures of different carbon sources. Other possible carbon sources are oils and fats, for example soybean oil, sunflower oil, peanut oil and coconut oil, fatty acids, for example palmitic acid, stearic acid or linoleic acid, alcohols, for example glycerol, methanol or ethanol and organic acids, for example acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soya flour, soya protein, yeast extract, meat extract and others. The nitrogen sources can be used alone or as a mixture.

Inorganic salt compounds that can be present in the media comprise the chloride, phosphorus or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, as well as organic sulfur compounds, such as mercaptans and thiols, can be used as the sulfur source.

Phosphoric acid, potassium dihydrogen phosphate or dipotassium hydrogen phosphate or the corresponding sodium-containing salts can be used as the phosphorus source.

Chelating agents can be added to the medium, in order to keep the metal ions in solution. Especially suitable chelating agents comprise dihydroxyphenols, such as catechol or protocatechuate, or organic acids, such as citric acid. EDTA can also be added.

The fermentation media used according to the invention usually also contain other growth factors, such as vitamins or growth promoters, which include for example biotin, riboflavin, thiamine, folic acid, nicotinic acid, pantothenate and pyridoxine. Growth factors and salts often originate from the components of complex media, such as yeast extract, malt extract, molasses, corn-steep liquor and the like. Moreover, suitable precursors can be added to the culture medium. The exact composition of the compounds in the medium is strongly dependent on the respective experiment and is decided for each specific case individually. Information on media optimization can be found in the textbook "Applied Microbiol. Physiology, A Practical Approach" (Ed. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the medium are sterilized, either by heat (20 min at 1.5 bar and 121° C.) or by sterile filtration. The components can either be sterilized together, or separately if necessary. All components of the medium can be present at the start of culture or can be added either continuously or batchwise.

The culture temperature is normally between 15° C. and 45° C., preferably 25° C. to 40° C. and can be varied or kept constant during the experiment. The pH of the medium should be in the range from 5 to 8.5, preferably around 7.0. The pH for growing can be controlled during growing by adding basic compounds such as sodium hydroxide, potassium hydroxide, ammonia or ammonia water or acid compounds such as phosphoric acid or sulfuric acid. Antifoaming agents, for example fatty acid polyglycol esters, can be used for controlling foaming. To maintain the stability of plasmids, suitable selective substances, for example antibiotics, can be added to the medium. To maintain aerobic conditions, oxygen or oxygen-containing gas mixtures, for example ambient air, are fed into the culture. The temperature of the culture is normally in the range from 20° C. to 45° C. The culture is continued until a maximum of the desired product has formed. This target is normally reached within 10 hours to 160 hours.

The fermentation broth is then processed further. Depending on requirements, the biomass can be removed from the fermentation broth completely or partially by separation techniques, for example centrifugation, filtration, decanting or a combination of these methods or can be left in it completely.

If the polypeptides are not secreted in the culture medium, the cells can also be lysed and the product can be obtained from the lysate by known methods for isolation of proteins. The cells can optionally be disrupted with high-frequency ultrasound, high pressure, for example in a French press, by osmolysis, by the action of detergents, lytic enzymes or organic solvents, by means of homogenizers or by a combination of several of the aforementioned methods.

The polypeptides can be purified by known chromatographic techniques, such as molecular sieve chromatography (gel filtration), such as Q-sepharose chromatography, ion exchange chromatography and hydrophobic chromatography, and with other usual techniques such as ultrafiltration, crystallization, salting-out, dialysis and native gel electrophoresis. Suitable methods are described for example in Cooper, T. G., Biochemische Arbeitsmethoden [Biochemical processes], Verlag Walter de Gruyter, Berlin, New York or in Scopes, R., Protein Purification, Springer Verlag, New York, Heidelberg, Berlin.

For isolating the recombinant protein, it can be advantageous to use vector systems or oligonucleotides, which lengthen the cDNA by defined nucleotide sequences and therefore code for altered polypeptides or fusion proteins, which for example serve for easier purification. Suitable modifications of this type are for example so-called "tags" functioning as anchors, for example the modification known as hexa-histidine anchor or epitopes that can be recognized as antigens of antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be used as packing in a chromatography column, or can be used on a microtiter plate or on some other carrier.

At the same time these anchors can also be used for recognition of the proteins. For recognition of the proteins, it is moreover also possible to use usual markers, such as fluorescent dyes, enzyme markers, which form a detectable reaction product after reaction with a substrate, or radioactive markers, alone or in combination with the anchors for derivatization of the proteins.

h. Polypeptide Immobilization

The enzymes or polypeptides according to the invention can be used free or immobilized in the methods described herein. An immobilized enzyme is an enzyme that is fixed to an inert carrier. Suitable carrier materials and the enzymes immobilized thereon are known from EP-A-1149849, EP-A-1 069 183 and DE-OS 100193773 and from the references cited therein. Reference is made in this respect to the disclosure of these documents in their entirety. Suitable carrier materials include for example clays, clay minerals, such as kaolinite, diatomaceous earth, perlite, silica, aluminum oxide, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For making the supported enzymes, the carrier materials are usually employed in a finely-divided, particulate form, porous forms being preferred. The particle size of the carrier material is usually not more than 5 mm, in particular not more than 2 mm (particle-size distribution curve). Similarly, when using dehydrogenase as whole-cell catalyst, a free or immobilized form can be selected. Carrier materials are e.g. Ca-alginate, and carrageenan. Enzymes as well as cells can also be crosslinked directly with glutaraldehyde (cross-linking to CLEAs). Corresponding and other immobilization techniques are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out methods according to the invention are also given for example in Rehm et al. (Ed.) Biotechnology, 2nd Edn, Vol 3, Chapter 17, VCH, Weinheim.

i. Reaction Conditions for Biocatalytic Production Methods of the Invention

The at least one polypeptide/enzyme which is present during a method of the invention or an individual step of a multistep-method as defined herein above, can be present in living cells naturally or recombinantly producing the enzyme or enzymes, in harvested cells, in dead cells, in permeabilized cells, in crude cell extracts, in purified extracts, or in essentially pure or completely pure form. The at least one enzyme may be present in solution or as an enzyme immobilized on a carrier. One or several enzymes may simultaneously be present in soluble and/or immobilised form.

The methods according to the invention can be performed in common reactors, which are known to those skilled in the art, and in different ranges of scale, e.g. from a laboratory scale (few millilitres to dozens of litres of reaction volume) to an industrial scale (several litres to thousands of cubic meters of reaction volume). If the polypeptide is used in a form encapsulated by non-living, optionally permeabilized cells, in the form of a more or less purified cell extract or in purified form, a chemical reactor can be used. The chemical reactor usually allows controlling the amount of the at least one enzyme, the amount of the at least one substrate, the pH, the temperature and the circulation of the reaction medium. When the at least one polypeptide/enzyme is present in living cells, the process will be a fermentation. In this case the biocatalytic production will take place in a bioreactor (fermenter), where parameters necessary for suitable living conditions for the living cells (e.g. culture medium with nutrients, temperature, pH, stirring, aeration, presence or absence of oxygen or other gases, antibiotics, and the like) can be controlled. Those skilled in the art are familiar with chemical reactors or bioreactors, e.g. with procedures for up-scaling chemical or biotechnological methods from laboratory scale to industrial scale, or for optimizing process parameters, which are also extensively described in the literature (for biotechnological methods see e.g. Crueger und Crueger, Biotechnologie—Lehrbuch der angewandten Mikrobiologie, 2. Ed., R. Oldenbourg Verlag, München, Wien, 1984).

Cells containing the at least one enzyme can be permeabilized by physical or mechanical means, such as ultrasound or radiofrequency pulses, French presses, or chemical means, such as hypotonic media, lytic enzymes and detergents present in the medium, or combination of such methods. Examples for detergents are digitonin, n-dodecylmaltoside, octylglycoside, Triton® X-100, Tween® 20, deoxycholate, CHAPS (3-[(3-Cholamidopropyl)dimethylammonio]-1-propansulfonate), Nonidet® P40 (Ethylphenolpoly(ethyleneglycolether), and the like.

If the at least one enzyme is immobilised, it is attached to an inert carrier as described above.

The conversion reaction can be carried out batch wise, semi-batch wise or continuously. Reactants (and optionally nutrients) can be supplied at the start of reaction or can be supplied subsequently, either semi-continuously or continuously.

The reaction of the invention, depending on the particular reaction type, may be performed in an aqueous, aqueous-organic or non-aqueous reaction medium.

An aqueous or aqueous-organic medium may contain a suitable buffer in order to adjust the pH to a value in the range of 5 to 11, like 6 to 10.

In an aqueous-organic medium an organic solvent miscible, partly miscible or immiscible with water may be applied. Non-limiting examples of suitable organic solvents are listed below. Further examples are mono- or polyhydric, aromatic or aliphatic alcohols, in particular polyhydric aliphatic alcohols like glycerol.

The non-aqueous medium may contain is substantially free of water, i.e. will contain less that about 1 wt.-% or 0.5 wt.-% of water.

Biocatalytic methods may also be performed in an organic non-aqueous medium. As suitable organic solvents there may be mentioned aliphatic hydrocarbons having for example 5 to 8 carbon atoms, like pentane, cyclopentane, hexane, cyclohexane, heptane, octane or cyclooctane; aromatic carbohydrates, like benzene, toluene, xylenes, chlorobenzene or dichlorobenzene, aliphatic acyclic and ethers, like diethylether, methyl-tert.-butylether, ethyl-tert.-butylether, dipropylether, diisopropylether, dibutylether; or mixtures thereof.

The concentration of the reactants/substrates may be adapted to the optimum reaction conditions, which may depend on the specific enzyme applied. For example, the initial substrate concentration may be in the 0.1 to 0.5 M, as for example 10 to 100 mM.

The reaction temperature may be adapted to the optimum reaction conditions, which may depend on the specific enzyme applied. For example, the reaction may be performed at a temperature in a range of from 0 to 70° C., as for example 20 to 50 or 25 to 40° C. Examples for reaction temperatures are about 30° C., about 35° C., about 37° C., about 40° C., about 45° C., about 50° C., about 55° C. and about 60° C.

The process may proceed until equilibrium between the substrate and then product(s) is achieved, but may be stopped earlier. Usual process times are in the range from 1 minute to 25 hours, in particular 10 min to 6 hours, as for example in the range from 1 hour to 4 hours, in particular 1.5 hours to 3.5 hours.

If the host is a transgenic plant, optimal growth conditions can be provided, such as optimal light, water, pH and nutrient conditions, for example.

k. Fermentative In Vivo Production of an Oxidized Terpene

The invention also relates to methods for the fermentative production of an oxidized terpene as herein defined.

A fermentation as used according to the present invention can, for example, be performed in stirred fermenters, bubble columns and loop reactors. A comprehensive overview of the possible method types including stirrer types and geometric designs can be found in "Chmiel: Bioprozesstechnik: Einfuhrung in die Bioverfahrenstechnik, Band 1". In the process of the invention, typical variants available are the following variants known to those skilled in the art or explained, for example, in "Chmiel, Hammes and Bailey: Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D. C., USA, 1981).

These media that can be used according to the invention may comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soy-bean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, di-thionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (1997) Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 1 hour to 160 hours.

If not produced intrinsically during fermentation, the concentration of the substrate to be converted should be in adapted to a value in a range of for example 0.1 to 50 mg/L.

The methodology of the present invention can further include a step of recovering such oxidized terpene.

The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Before the intended isolation the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value.

In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

1. Product Isolation

The methodology of the present invention can further include a step of recovering an end or intermediate product, optionally in stereoisomerically or enantiomerically substantially pure form. The term "recovering" includes extracting, harvesting, isolating or purifying the compound from culture or reaction media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Identity and purity of the isolated product may be determined by known techniques, like High Performance Liquid Chromatography (HPLC), gas chromatography (GC), Spektroskopy (like IR, UV, NMR), Colouring methods, TLC, NIRS, enzymatic or microbial assays. (see for example: Patek et al. (1994) Appl. Environ. Microbiol. 60:133-140; Malakhova et al. (1996) Biotekhnologiya 11 27-32; und Schmidt et al. (1998) Bioprocess Engineer. 19:67-70. Ullmann's Encyclopedia of Industrial Chemistry (1996) Bd. A27, VCH: Weinheim, S. 89-90, S. 521-540, S. 540-547, S. 559-566, 575-581 und S. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Bd. 17.)

All the publications mentioned in this application are incorporated by reference to disclose and describe the methods and/or materials in connection with which the publications are cited.

The following examples are illustrative only and are not meant to limit the scope of invention as set forth in the Summary, Description or in the Claims.

The numerous possible variations that will become immediately evident to a person skilled in the art after heaving considered the disclosure provided herein also fall within the scope of the invention.

EXPERIMENTAL PART

The invention will now be described in further detail by way of the following Examples.

Materials

Unless otherwise stated, all chemical and biochemical materials and microorganisms or cells employed herein are commercially available products.

Unless otherwise specified, recombinant proteins are cloned and expressed by standard methods, such as, for example, as described by Sambrook, J., Fritsch, E. F. and Maniatis, T., Molecular cloning: A Laboratory Manual, $2^{nd}$ Edition, Cold Spring Harbor Laboratory, Cold Spring Harbor Laboratory Press, Cold Spring Harbor, NY, 1989.

Methods

Enzyme Assay as Applied (Standard) (In Vivo Production of Terpene Compounds Using Cultures of E. Col Cells)

KRX *E. coli* cells (Promega) transformed with one or more expression plasmid carrying nucleic sequences encoding for enzymes allowing to increase the intra-cellular pool of terpene precursors and carrying one or more nucleic sequence encoding for terpene biosynthetic enzymes are used to produce terpene compounds. Transformed cells are selected on LB-agar plates supplemented with the appropriate antibiotic(s) and cells from single colonies are used to inoculate 5 mL liquid LB medium supplemented with the same antibiotic(s). The cultures are incubated overnight at 37° C. The next day 2 mL of TB medium supplemented with the same antibiotics are inoculated with 0.2 mL of the overnight culture. After 6 hours incubation at 37° C., the culture was cooled down to 20° C. and 0.1 mM IPTG and 0.02% rhamnose were added to each tube. The cultures were incubated for 48 hours at 20° C. The cultures are then extracted twice with 2 volumes of MTBE, the organic phase are concentrated to 500 µL and analyzed by GC-MS.

Gas Chromatography Mass Spectrometry (GC-MS)

Gas Chromatography Mass Spectrometry (GC-MS) was carried out with using an Agilent 6890 Series GC system connected to an Agilent 5975 mass detector. The GC was equipped with 0.25 mm inner diameter by 30 m DB-1MS capillary column (Agilent). The carrier gas was Helium at a constant flow of 1 mL/min. The inlet temperature was set at 250° C. The initial oven temperature was 80° C. followed by a gradient of 10° C./min to 220° C. and a second gradient of 30° C./min to 280° C. The identification of the products was based on the comparison of the mass spectra and retention indices with authentic standards and internal mass spectra databases.

1. Examples—Isovalencene Oxygenation

Example 1: Plant Material and Total RNA Extraction

Vetiver (*Vetiveria zizanoides*) plants were obtained from a plant nursery (The Austral Plants Company, Les Avirons, The Reunion Island, France). The plants were cultivated in pots in a greenhouse (Lullier Agronomy research Station, Geneva, Switzerland) and were propagated vegetatively by dividing six months to one-year-old clumps. For harvesting of the roots, the plants were removed from the pots and rinsed with tap water.

For extraction of RNA, roots from several plants were combined, including young plants (4 to 6 months after propagation), old plants with a well-developed dense root system (1 to 2 years after propagation) and young plants dried at room temperature for 24 to 36 hours after being removed from the pots. The roots were cut off from the aerial part of the plants and frozen in liquid nitrogen. The roots were first roughly chopped in liquid nitrogen using a Waring Blendor (Waring Laboratory, Torrington, USA) and then ground to a fine powder using a mortar and pestle. Total RNA was extracted following the procedure described in Kolosova et al (Kolosova N, Miller B, Ralph S, Ellis B E, Douglas C, Ritland K, and Bohlmann J, Isolation of high-quality RNA from gymnosperm and angiosperm trees. *J. Biotechniques*, 36(5), 821-4, 2004) with the following modifications. A volume of 20 mL of extraction buffer was used for 2 grams of ground tissue and the extraction buffer was supplemented with 2% (w/v) of PVP (polyvinylpyrrolidone, Sigma-Aldrich). For the CTAB (cethyltrimethylammonium bromide, Sigma-Aldrich) extraction step, the nucleic acid pellet was resuspended in 2 mL TE buffer (10 mM Tris-HCl, pH 8, 1 mM EDTA) and the extraction was performed with 2 mL of 5M NaCl and 1 mlL 10% CTAB. For the isopropanol precipitation, the nucleic acid pellet was dissolved in 500 µL TE. The final RNA pellet was resuspended in 50 µL water.

Example 2: Transcriptome Sequencing

The Vetiver roots transcriptome was sequenced using the Illumina technology. All sequencing steps were performed by Fasteris SA (Plan-les-Ouates, CH-1228, Switzerland). The mRNA library was prepared using the TruSeq Stranded mRNA Library Preparation Kit (Illumina Inc.). The fragmentation and size selection were adapted to select and purify DNA fragments between 500 and 550 bp of length. The DNA sequencing was performed on a MiSeq sequencer using the MiSeq Reagent Kit V3 (Illumina Inc.). One full flow cell was used for the sequencing of the library and 2×300 sequencing cycles were performed. This sequencing provided 17'453'393 of 2×300 overlapping paired reads (10.5 mega bases in total).

The paired reads were first preprocessed using FastqJoin to join paired-end reads on the overlapping ends. In this step 58.3% of the paired-end reads could be joined and 8.5 millions of joined-reads with an average size of 430 bases were obtained. These new reads as well as the non-joined paired-end reads were then assembled using the CLC bio de novo assembly tool of the CLC Genomic Workbench 7 (CLC bio). Finally, the assembled vetiver roots transcriptome contained 333'633 unique contig sequences with an average length of 577 bases, a maximum length of 15'800 bases and an N50 of 546 bases.

Example 3: Isolation of Terpene Synthase-Encoding cDNA from Vetiver Root Transcriptome The transcriptome data were searched using the tBlastn algorithm (Altschul et al, J. Mol. Biol. 215, 403-410, 1990) and using as query the amino acid sequences of known sesquiterpene synthases isolated from the same plants and described previously (WO2010134004 and WO2006134523). Using this approach a new sesquiterpene encoding sequence was obtained. This cDNA (VzTps1718) (SEQ ID NO:1) was 1835 base-pairs long and contained an open reading frame (SEQ ID NO: 2) encoding for a 567 amino acid length protein (SEQ ID NO:3).

The DNA sequence of VzTps1718 was codon-optimized (SEQ ID NO: 4), synthesized in vitro and cloned in the pJ401 expression plasmid (ATUM, Newark, CA, USA). The pJ401-VzTps1718 expression construct can be used to produce sesquiterpene compounds in *E. coli* cells. To increase the productivity of the cells, a heterologous FPP synthase and the enzymes from a complete heterologous mevalonate (MVA) pathway were expressed in the same cells. The construction of the expression plasmid containing an FPP synthase gene and the gene for a complete MVA pathway was described in patent WO2013064411 or in Schalk et al (2013) J. Am. Chem. Soc. 134, 18900-18903. Briefly, an expression plasmid was prepared containing two operons composed of the genes encoding the enzymes for a complete mevalonate pathway. A first synthetic operon consisting of an *E. coli* acetoacetyl-CoA thiolase (atoB), a *Staphylococcus aureus* HMG-CoA synthase (mvaS), a *Staphylococcus aureus* HMG-CoA reductase (mvaA) and a *Saccharomyces cerevisiae* FPP synthase (ERG20) genes was synthetized in vitro (ATUM, Newark, CA, USA) and ligated into the NcoI-BamHI digested pACYCDuet-1 vector (Invitrogen) yielding pACYC-29258. A second operon containing a mevalonate kinase (MvaK1), a phosphomevalonate kinase (MvaK2), a mevalonate diphosphate decarboxylase (MvaD), and an isopentenyl diphosphate isomerase (idi) was amplified from genomic DNA of *Streptococcus pneumoniae* (ATCC BAA-334) and ligated into the second multicloning site of pACYC-29258 providing the plasmid pACYC-29258-4506. This plasmid thus contains the genes encoding all enzymes of the biosynthetic pathway leading from acetyl-coenzyme A to FPP.

Figure 3B:
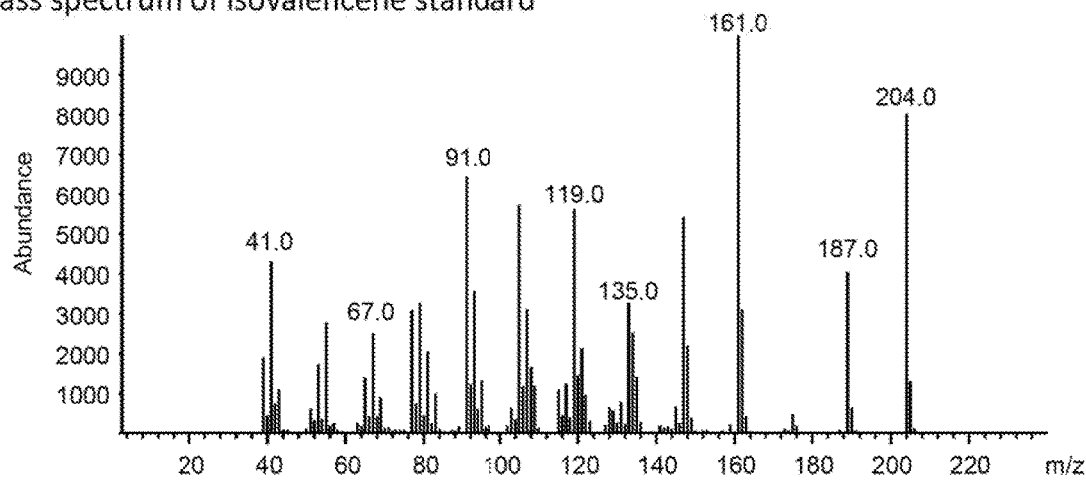

KRX *E. coli* cells (Promega) were co-transformed with the plasmid pACYC-29258-4506 and the plasmid pJ401-VzTps1718 and transformed cells were selected on kanamycin (50 µg/mL) and chloramphenicol (34 µg/mL) LBagar plates. Production and identification of terpene compounds by the engineered cells was performed as described in the Methods section. In these conditions, the VzTps1718 enzyme (SEQ ID NO: 3) showed sesquiterpene synthase activity and converted FPP to several terpene products including sesquiterpene hydrocarbons and oxygenated sesquiterpenes (FIG. 2). The major products were sesquiterpenes with the eremophilane, vetispirane and eudesmane skeleton. Amongst the products, some compounds could be identified based on the coincidence of the retention index and mass spectrum (FIG. 3 to 5): isovalencene (compound 1), spirovetiva-1(10),7(11)-diene (compound 2) and valencene (compound 3) (cf. FIG. 1). The relative composition of the product mixture obtained with VzTps1718 is detailed in subsequent table 1. For the identified sesquiterpene products, spirovetiva-1(10),7(11)-diene, isovalencene and valencene, the relative abundance in the product mixture were 14.7%, 39.0% and 5.1%, respectively.

TABLE 1

Composition of the product mixture obtained in vivo with the recombinant VzTps1718 sesquiterpene synthase.

|  | Relative composition in product mixture | Ret Time [min] | Measured Linear retention Index (LRI) | Reference LRI |
|---|---|---|---|---|
| sesquiterpene hydrocarbon | 1.0% | 8.43 | 1392 |  |
| sesquiterpene hydrocarbon | 0.9% | 8.92 | 1432 |  |
| sesquiterpene hydrocarbon | 1.4% | 9.06 | 1444 |  |
| sesquiterpene hydrocarbon | 4.5% | 9.25 | 1460 |  |
| sesquiterpene hydrocarbon | 2.0% | 9.62 | 1490 |  |
| valencene | 5.1% | 9.68 | 1495 | 1494 |
| spirovetiva-1(10),7(11)-diene | 14.7% | 9.97 | 1519 | 1523 |
| isovalencene | 39.0% | 10.03 | 1524 | 1527 |
| sesquiterpene hydrocarbon | 3.5% | 10.15 | 1535 |  |
| sesquiterpene hydrocarbon | 1.4% | 10.20 | 1545 |  |
| sesquiterpene hydrocarbon | 1.5% | 10.26 | 1565 |  |
| sesquiterpene hydrocarbon | 12.7% | 10.452 | 1561 |  |
| oxygenated sesquiterpene | 0.9% | 11.023 | 1610 |  |
| oxygenated sesquiterpene | 9.3% | 11.06 | 1614 |  |
| oxygenated sesquiterpene | 2.0% | 11.86 | 1686 |  |

Sesquiterpene synthases producing this mixture of products or synthases producing compound 1 or compound 2 were not known before. Oxygenated derivatives of the product of VzTps1718, especially alcohol, ketones, aldehydes and carboxylic acids are known constituents of vetiver oil and some of these derivatives contribute to the typical complex vetiver odour.

Example 4: Identification of Cytochrome P450-Encoding cDNAs from the Vetiver Root Transcriptome In order to produce oxygenated derivatives of the sesquiterpene hydrocarbons produced by the VzTps1718 enzyme, a number of cytochrome P450 enzymes were selected, all derived from the roots of vetiver.

The vetiver roots transcriptome data were searched for cytochrome P450 encoding sequences using the tBlastn algorithm (Altschul et al, J. Mol. Biol. 215, 403-410, 1990) and using as query the amino acid sequences of known cytochrome P450s with terpene hydroxylase activity such as the SEQ ID NO:1 and 2 of WO2013064411. Several cytochrome P450-encoding transcripts were isolated. The transcript VzTrspt-9 Locus 8201-12 (SEQ ID NO: 5) contained an open reading frame of 1521 base-pairs (SEQ ID NO: 6) and encoded for a 506 amino acid protein, VzCP8201-12 (SEQ ID NO:7) showing homology with cytochrome P450 amino acid sequences. The closest publicly available sequences are putative cytochrome P450 proteins from *Sorghum bicolor* (such as the sequence with the NCBI accession number XP_002466860.1 or XP_002466859.2, annotated as diterpene hydroxylase) with less than 84% sequence identity compared to VzCP8201-12.

Another transcript, VzTrsp7_contig_7186 (SEQ TD NO: 11), contained an open reading frame of 1521 (SEQ ID NO: 12) and encoding for a 506 amino acid putative cytochrome P450 protein, VzCP7186 (SEQ ID NO: 13), was also selected. The closest sequence in public sequence databases is the sequence with the accession number XP_002466859.2 from *Sorghum bicolor* with 86% sequence identity.

A third cytochrome P450 enzyme was selected, VzCP521-11 (WO2013064411) (SEQ ID NO: 18) encoded by SEQ ID NO: 16. This cytochrome P450 enzyme was previously shown to have terpene hydroxylase activity on various sesquiterpenes.

Example 5: DNA Sequences Optimization for Heterologous Expression of Cytochrome P450

Cytochrome P450s from plants are membrane-bound proteins possessing an N-terminal anchor peptide. The membrane anchor sequence and the catalytic domain of a cytochrome P450s are usually delimited by a proline-rich region. The catalytic part of VzCP8201, VzCP7186 and VzCP521-11 (SEQ ID NO: 19, 20 and 21, respectively) carries the enzymatic activity of the proteins. The N-terminal membrane anchor peptide is involved in the association of the cytochrome P450 enzyme to the membranes. The N-terminal sequence can thus be modified without altering the catalytic activity of the enzyme. Modification of the 5'-end of a P450-encoding cDNA to change the amino acid sequence of the membrane anchor peptide can improve the expression of the enzyme in a microbial host cell.

Thus, a cDNA (SEQ ID NO: 8) sequence encoding for the full-length VzCP 8201-12 (SEQ ID NO: 7) protein was designed with a codon usage for optimal expression in bacteria and a second cDNA (SEQ ID NO: 9) encoding for an N-terminal modified variant of VzCP8201-12 (designated VzCP8201bov, SEQ ID NO: 10) was also designed. This modification include deletion of the 20 first N-terminal amino acids and replacement by the MALL-LAVFLGLSCLLLLSLW peptide (SEQ ID NO: 24). The two cDNAs were synthesized and sub-cloned in the pCWori expression plasmid (Barnes, H. J. Method Enzymol. 272, 3-14; (1996)) providing the pCWori-VzCP8201-12 and pCWori-VzCP8201Bov plasmids, respectively.

For VzCP7186, a variant (VzCP7186op, SEQ ID NO: 15) with a similar modification of the N-terminal region amino acid sequence was designed to replace the 20 first amino acids by MALLLAVFLGLSCLLLLSLW sequence (SEQ TD NO: 24) and a new cDNA was synthesized with a codon usage optimization for *E. coli* expression (SEQ ID NO: 14) and cloned in the pJ401 plasmid (ATUM, Newark, CA, USA).

For VzCP521-11, the wild-type amino acid sequence (SEQ ID NO: 18) was conserved for the heterologous expression in *E. coli* and a cDNA was synthesized only with a codon optimized sequence (SEQ ID NO: 17) and cloned in the pJ401 plasmid (ATUM, Newark, CA, USA).

For functional characterization of the vetiver P450 enzymes, the proteins were heterologously expressed in *E. coli* cells. To reconstitute the activity of plant P450s, the presence of a second membrane protein is necessary. This protein, a P450-reductase (CPR), is involved in the transfer of electrons from the cofactor NADPH (reduced Nicotinamide adenine dinucleotide phosphate) to the P450 active site. It has been shown that a CPR from one plant can complement the activity of a cytochrome P450 enzyme from another plant (Jensen and Moller (2010) Photochemistry 71, 132-141). Several CPR-encoding DNA sequences have been reported from different plant sources. We selected a CPR previously isolated from *Mentha piperita* (CPRm, unpublished data, SEQ ID NO:23) optimized the codon usage of the full-length cDNA (SEQ ID NO: 22) and cloned it into the NcoI and HindIII restriction sites of the pACYCDuet-1 expression plasmid (Novagen) providing the plasmid pACYC-CPRm.

Example 6: Construction of Expression Plasmids for Co-Expression of a Cytochrome P450, a Cytochrome P450-Reductases and a Terpene Synthase Plasmids were constructed comprising the pCWori+ plasmid (Barnes H. J (1996) Method Enzymol. 272, 3-14) containing a synthetic operon composed of a P450, a CPR and the terpene synthase encoding cDNA. The constructs were designed to insert upstream of each cDNA a ribosome binding site (RBS). The pCWori-VzCP8201Bov plasmid described in Example 5 contains the VzCP8201Bov-encoding cDNA (SEQ ID NO:9) that was designed to include the NdeI recognition sequence upstream of the VzCP8201Bov-encoding cDNA and a polylinker DNA sequence (GTCGACAATTAACCATGGTTAATTAAGCT-TATATATG GTACCATATATGAATTCATTAATCTCGAG (SEQ ID NO: 25) downstream of the VzCP8201Bov-encoding cDNA and containing the SalI, NcoI, HindIII, KpnI, EcoRI and XhoI recognition sequences. The optimized CPRm cDNA was modified to add at the 5'-end, before the start codon, a 26 bp extension containing a spacer sequence, the SalI recognition sequence and the RBS sequence (GTCGACAATTAGGTAAAAAATAAACC (SEQ ID NO:26) and to add a HindIII recognition sequence at the 3'-end. The optimized CPRm cDNA (SEQ ID NO:22) was sub-cloned between the SalI and HindIII sites of the pCWori-VzCP8201Bov plasmid providing the pCWori-VzCP8201Bov-CPRm plasmid. The optimized cDNA sequence of VzTps1718 (SEQ ID NO:4) cloned in the pJ401 plasmid (DNA2.0, Menlo Park, CA, USA) contains a 5' non-coding sequence composed of a HindIII recognition sequence and a RBS sequence (AAGCT-TAAGGAGGTAAAAA) (SEQ ID NO:27) and a 3' non-coding sequence composed of the KpnI, EcoRI and XhoI recognition sites (GGTACCATATATGAATTCAT-TAATCTCGAG) (SEQ ID NO:28). The insert form the VzTps1718-pJ401 plasmid was digested using the HindIII and XhoI restriction enzymes and sub-cloned between the same restriction enzyme recognition sites of the pCWori-VzCP8201Bov-CPRm plasmid. The resulting plasmid pCWori:VzCP8201Bov:CPRm:VzTps1718 contains thus an operon including the VzCP8201Bov-encoding cDNA, the CPRm-encoding cDNA and the VzTps1718-encoding cDNA.

The optimized cDNA (SEQ ID NO: 14) encoding for the N-terminal modified VzCP7186 protein (SEQ ID NO: 15) was transferred from the original pJ401 plasmid (Example 5) into the pCWori:VzCP8201Bov:CPRm:VzTps1718 by digestion/ligation using the NdeI and HindIII restriction enzymes. The new plasmid, pCWori:VzCp7186:CPRm:VzTps1718, thus contained an operon including the VzCP7186opt-encoding cDNA, the CPRm-encoding cDNA and the VzTps1718-encoding cDNA.

Similarly the pCWori:VzCP521-11:CPRm:VzTps1718 plasmid was constructed by subcloning the VzCP521-11 optimized cDNA from the pJ401 plasmid into the NdeI and HindIII digested pCWori:VzCP8201Bov:CPRm:VzTps1718 plasmid.

Finally, a polycistronic plasmid was constructed to combine one copy of the VzCP8201-encoding cDNA and one copy of the VzCP7186-encoding cDNA with the CPR and the terpene synthase encoding cDNA. The VzCP7186 cDNA was amplified with the primers Inf8201-7186-Fw (TAATTTTATTCCGAACTAAGTCGAAGGAGG TAATATGGCGTTGCTGTTGGCTGTTTTTCTGG) (SEQ ID NO: 29) and Infn201-7186-Rev (ATTTTTTACCTAAT-TGTCGACTTAGTTCGGAATAAAGTTATTGTAC GGAC). (SEQ ID NO: 30). The amplified DNA fragment was cloned in the pCWori:VzCP8201Bov:CPRm:VzTps1718 plasmid linearized with the SalI restriction enzyme. The cloning reaction was performed using the In-Fusion® technique (Clontech, Takara Bio Europe). The resulting plasmid pCWori:VzCP8201:VzCP7186:CPRm:VzTps1718 thus contains the cDNAs encoding for VzCP8201, VzCP7186, CPRm and VzTps1718 in a single operon.

Example 7. In Vivo Production of Oxygenated Sesquiterpene Compounds Using VzTps1718 and Cytochrome P450 Enzymes The KRX *E. coli* cells (Promega) were co-transformed with one of the four pCWori plasmids described in Example 6 and with plasmid pACYC-29258-4506 carrying a complete mevalonate pathway (Example 3). Transformed cells were cultivated and the production of terpene compounds was evaluated as described in the experimental section except that 75 µg/L of 6-aminolevulinic acid (Sigma) was added to the culture medium.

Figure 7A:
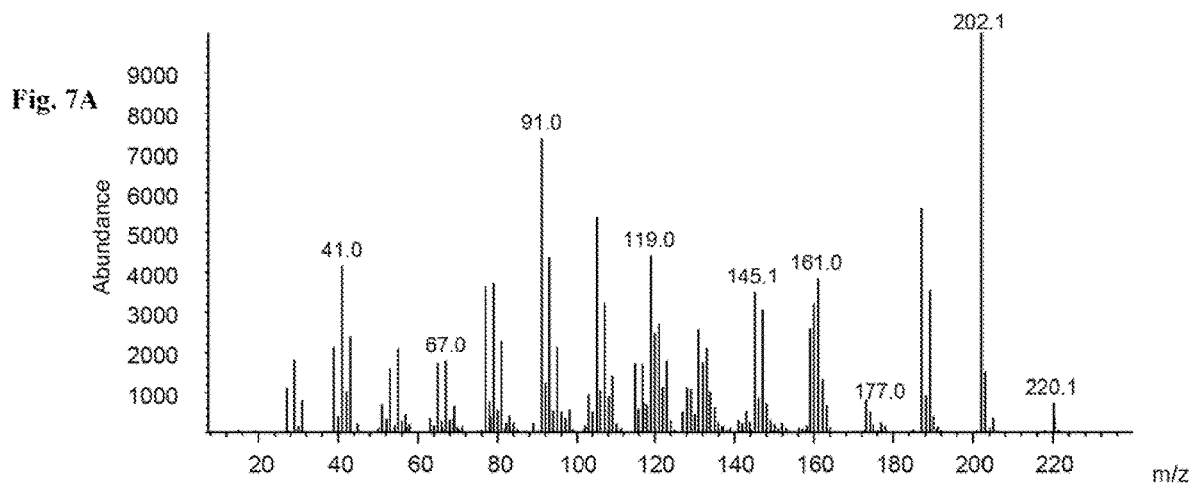
FIG. 7A-B. Mass spectrum of the peak with a retention time of 13.02 minutes in FIGS. 6B and 6C (A) and the mass spectrum of an authentic isovalencenol standard (B).
Figure 7B:
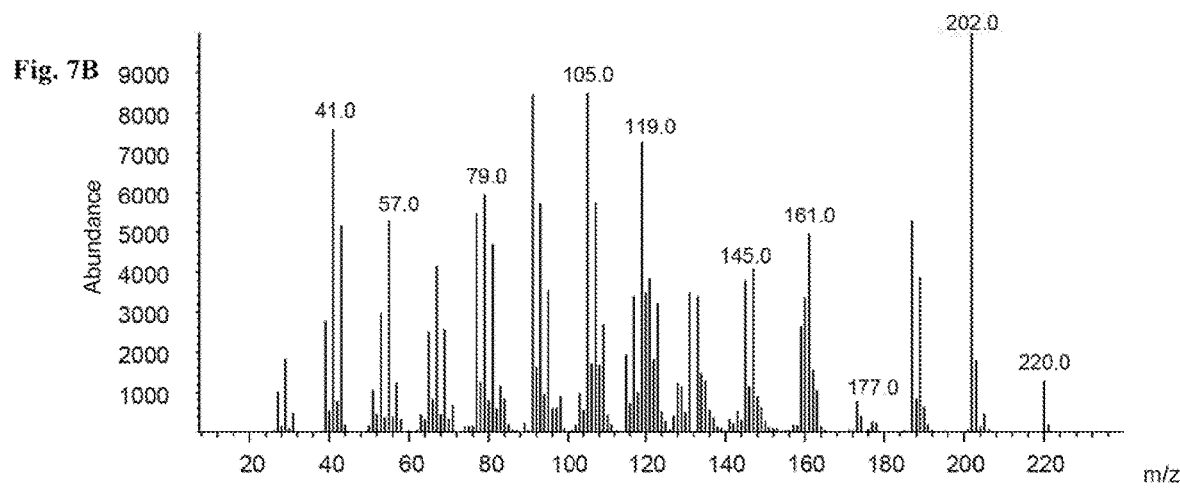
Figure 8A:
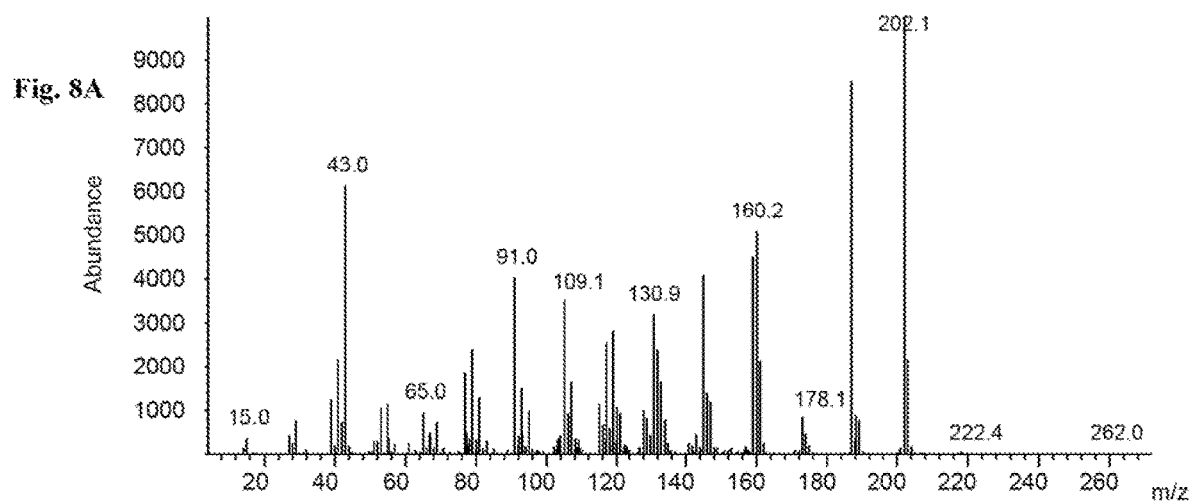
FIG. 8A-B. Mass spectrum of the peak with a retention time of 14.25 minutes in FIGS. 6B and 6C (A) and the mass spectrum of an authentic isovalencenyl acetate standard (B).
Figure 8B:
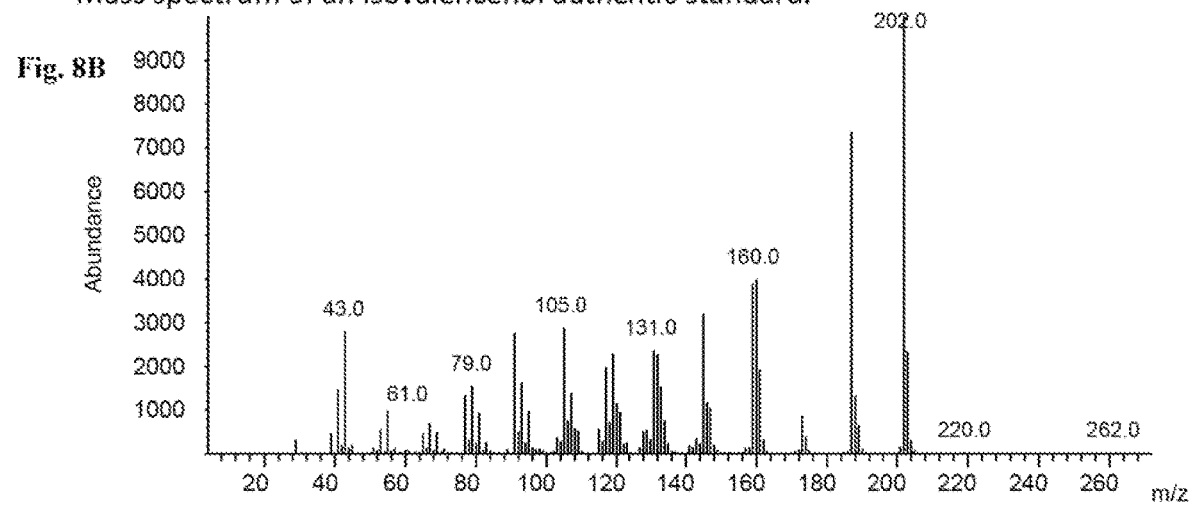

FIG. 6 shows the GC-MS analysis of the products formed using *E. coli* cells engineered to produce the recombinant VzTps1718 sesquiterpene synthase either alone or together with the VzCP8201 or the VzCP7186 cytochrome P450 enzymes. Several oxygenated sesquiterpene compounds were formed during this bioconversion including isovalencenol (FIG. 7) and isovalencenyl acetate (FIG. 8). The isovalencenol product is formed by oxidation of isovalencene by VzCP8201 or VzCP7186. The isovalencenyl acetate product is formed by acetylation of isovalencenol by background *E. coli* enzymatic activity. FIG. 6 shows also that the selectivity of hydroxylation reaction catalyzed by VzCP8201 and VzCp7186 are similar.

Figure 10A:
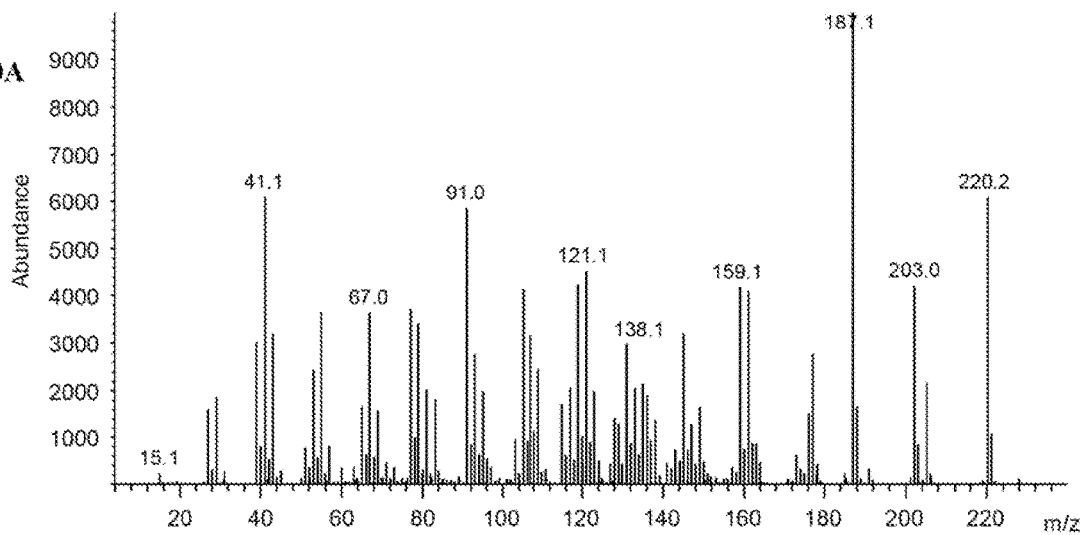
FIG. 10A-B. Mass spectrum of the peak with a retention time of 13.2 minutes in FIG. 9B (A) and the mass spectrum of an authentic isonootkatol standard (B).
Figure 10B:
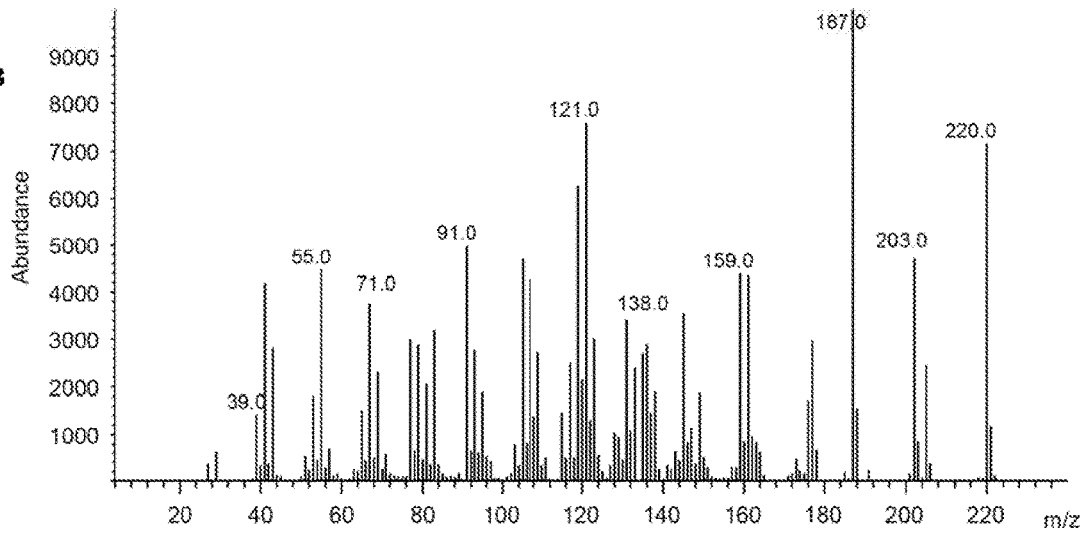

FIG. 9 shows the GC-MS analysis of the products formed using *E. coli* cells engineered to produce the recombinant VzTps1718 sesquiterpene synthase together with the VzCP521-11 cytochrome P450 enzyme. Several oxygenated sesquiterpene compounds were formed during this bioconversion including. Some of these products, in particular isovalencenol and isovalencenol acetate, were also observed with VzCP8201 or VzCP7186. Amongst the major oxidation products of VzCP521-11, isonootkatol could be observed by matching of the mass spectrum with an authentic standard (FIG. 10). Isonootkatol can be easily oxidized to the corresponding ketones, for example biochemically or chemically (Oxidation of Alcohols to Aldehydes and Ketones, G. Tojo and M. Fernadez, in Basic Reactions in Organic Synthesis (2007)) to produce α-vetivone, one of the major vetiver oil constituents.

FIG. 11 shows the GC-MS analysis of the products formed using *E. coli* cells engineered to produce the recombinant VzTps1718 sesquiterpene synthase together with the VzCP8201 and the VzCP7186 cytochrome P450 enzymes. The analysis shows an increase of the amounts of oxidized sesquiterpenes and an increase of the ratio of oxygenated sesquiterpenes versus non oxygenated sesquiterpenes.

2. Examples—Zizaene Oxygenation

Example 8: Identification of Variants of Zizaene Synthase

Terpene synthases having zizaene synthase activity are described in WO2010134004. The new transcriptome data were searched using the tBlastn algorithm (Altschul et al, J. Mol. Biol. 215, 403-410, 1990) and using as query the amino acid sequence SEQ ID No 1 of WO2010134004. This approach allowed the identification of two new cDNA (VzTrspt_4_contig_995 (SEQ ID NO:35); full-length cDNA with open reading frame is shown in SEQ ID NO: 36) and VzTrspt 10_contig_49 (SEQ ID NO:39; full-length cDNA with open reading frame is shown in SEQ ID NO: 40) encoding for variants of the zizaene synthase VzZS2 (SEQ ID NO 38) and VzZS2-Nter2 (SEQ ID NO: 42, respectively). The two variants differ by 12 and 17 amino acids respectively from the previously identified zizaene synthase (VzZS1, SEQ ID NO 33). The corresponding full-length cDNA encoding for VzZS1, including non-coding regions is shown in SEQ ID NO:31 and the open reading frame is shown in SEQ ID NO:32.

Codon optimized DNAs encoding for VzZS2 (SEQ ID NO:37) and VzZS2-Nter2 (SEQ ID NO:41) as well as for VzZS1 (SEQ ID NO: 1 of WO2010134004) (herein VzZS1 amino acid sequence=SEQ ID NO:33; codon optimized cDNA=SEQ ID NO:34) were synthesized and cloned in the pJ401 expression plasmid (ATUM, Newark, CA, USA). These three expression plasmids were used to transform *E. coli* cells and to produce sesquiterpene compounds using the procedure described in the Methods section except that for the GC-MS analysis the oven temperature was initially set at 100° C. for one minute followed by increase at 12° C./min to 240° C. and a second increase at 50° C./min to 300° C.

In these conditions, all three recombinant proteins produced zizaene (FIG. 12) as major product. Compared to the previously identified synthase (VzZS1), the VzZS2 and VzZS2-Nter2 produced 38% and 42% higher quantities of zizaene (FIG. 13).

Example 9: Construction of Expression Plasmids for Co-Expression of a Cytochrome P450, a Cytochrome P450-Reductase and a Zizaene Synthase The optimized cDNA sequence of VzZS2-Nter2 cloned in the pJ401 plasmid (DNA2.0, Menlo Park, CA, USA) contains a 5' non-coding sequence composed of a HindIII recognition sequence and a RBS sequence (AAGCT-TAAGGAGGTAAAAA SEQ ID NO: 27) and a 3' non-coding sequence composed of the KpnI, EcoRI and XhoI recognition sites (GGTACCATATATGAATTCAT-TAATCTCGAG (SEQ ID NO: 28). The insert form the VzZS2-Nter2-pJ401 plasmid was cut out using the HindIII and XhoI restriction enzymes and sub-cloned between the same restriction enzyme recognition of each of the three tricistronic plasmids described in Example 6 to replace the terpene synthase-encoding cDNA. This resulted in three new plasmids pCWori:VzCP8201Bov:CPRm:VzZS2-Nter2, pCWori:VzCp7186:CPRm:VzZS2-Nter2 and pCWori:VzCp521-11:CPRm:VzZS2-Nter2, each carrying a CPRm-encoding cDNA, a zizaene synthase-encoding cDNA and one of the three cytochrome P450-encoding cDNAs.

Example 10: In Vivo Production of Oxygenated Sesquiterpene Compounds Using VzZS2-Nter2 and Cytochrome P450 Enzymes The KRX *E. coli* cells (Promega) were co-transformed with one of the pCWori plasmids described in Example 9 and with plasmid pACYC-29258-4506 carrying a complete mevalonate pathway (Example 3) and the transformed cells were evaluated for the production of terpene compounds as described in the Methods section.

FIG. 14 shows the GC-MS analysis of the products formed using *E. coli* cells engineered to produce the recombinant zizaene synthase (VzZS2-Nter2) with the VzCP8201, the VzCP7186 or the VzCP521-11 cytochrome P450 enzymes. The α-zizaenol was produced with each of three cytochrome P450 enzymes (FIG. 15). With VzCP521-11, khusimol was produced as a minor product in addition to α-zizaenol (FIG. 16).

Example 11: Co-Expression of Zizaene Synthase, the VzCP8201 Cytochrome P450 and the VzCP7186 Cytochrome P450 in the Same Cells A polycistronic plasmid was constructed to combine one copy of the VzCP8201-encoding cDNA and one copy of the VzCP7186-encoding cDNA with the CPR and the zizaene synthase encoding cDNAs. The VzCP7186 cDNA was amplified with the primers Inf8201-7186-Fw (TAATTTT-ATTCCGAACTAAGTCGAAGGAGGTAATATGGC GTTGCTGTTGGCTGTTTTTCTGG) (SEQ ID NO: 29) and Inf8201-7186-Rev (ATTTTTTACCTAATTGTCGACT-TAGTTCGGAATAAAGTTATTGTACGGAC). (SEQ ID NO: 30) The amplified DNA fragment was cloned in the pCWori:VzCP8201Bov:CPRm:VzZS2-Nter2 plasmid linearized with the SalI restriction enzyme. The cloning reaction was performed using the In-Fusion® technique (Clontech, Takara Bio Europe). The resulting plasmid pCWori: VzCP8201:VzCP7186:CPRm:VzZS2-Nter2 thus contains the cDNAs encoding for VzCP8201, VzCP7186, CPRm and VzZS2-Nter2 in a single operon.

FIG. 17C shows the GC-MS analysis of the products formed using *E. coli* cells engineered to produce the recombinant zizaene synthase together with the VzCP8201 and the VzCP7186 cytochrome P450 enzymes compared to cells containing only the VzCP8201 or the VzCP7186 (FIGS. 17A and 1713). The analysis shows an increase of amounts of α-zizaenol produced in cells co-expressing the VzCP8201 and the VzCP7186 cytochrome P450 enzymes. In these conditions, the oxidized derivative of zizaenol, zizaenone, was also detected (FIG. 17C and FIG. 18).

Example 12: In Vivo Zizaene Production in *Saccharomyces cerevisiae* Cells Using Variants of Zizaene Synthase For the production of zizaene, the genes coding for three different zizaene synthases; VzZS1 (SEQ ID NO: 33), VzZS2 (SEQ ID NO: 38) and VzZS2-Nter2 (SEQ ID NO: 42); were expressed in engineered *Saccharomyces cerevisiae* cells with increased level of endogenous farnesyl-diphosphate (FPP).

To increase the level of endogenous farnesyl-diphosphate (FPP) pool in *S. cerevisiae* cells, an extra copy of all the yeast endogenous genes involved in the mevalonate pathway, from ERG10 coding for acetyl-CoA C-acetyltransferase to ERG20 coding for FPP synthetase, were integrated in the genome of the *S. cerevisiae* strain CEN.PK2-1C (Euroscarf, Frankfurt, Germany) under the control of galactose-inducible promoters, similarly as described in Paddon et al., Nature, 2013, 496:528-532. Briefly, three cassettes were integrated in the LEU2, TRP1 and URA3 loci respectively. A first cassette containing the genes ERG20 and a truncated HMG1 (tHMG1 as described in Donald et al., *Proc Natl Acad Sci USA*, 1997, 109:E111-8) under the control of the bidirectional promoter of GAL10/GAL1 and the genes ERG19 and ERG13 also under the control of GAL10/GAL1 promoter, the cassette was flanked by two 100 nucleotides regions corresponding to the up- and down-stream sections of LEU2. A second cassette where the genes IDI1 and tHMG1 were under the control of the GAL10/GAL1 promoter and the gene ERG13 under the control of the promoter region of GAL7, the cassette was flanked by two 100 nucleotides regions corresponding to the up- and down-stream sections of TRP1. A third cassette with the genes ERG10, ERG12, tHMG1 and ERG8, all under the control of GAL10/GAL1 promoters, the cassette was flanked by two 100 nucleotides regions corresponding to the up- and down-stream sections of URA3. All genes in the three cassettes included 200 nucleotides of their own terminator regions. Also, an extra copy of GAL4 under the control of a mutated version of its own promoter, as described in Griggs and Johnston, *Proc Natl Acad Sci USA*, 1991, 88:8597-8601, was integrated upstream the ERG9 promoter region. In addition, the expression of ERG9 was modified by promoter exchange. The GAL7, GAL10 and GAL1 genes were deleted using a cassette containing the HIS3 gene with its own promoter and terminator. The resulting strain was mated with the strain CEN.PK2-1D (Euroscarf, Frankfurt, Germany) obtaining a diploid strain termed YST045 which was induced for sporulation according to Solis-Escalante et al, *FEMS Yeast Res*, 2015, 15:2. Spore separation was achieved by resuspension of asci in 200 µL 0.5M sorbitol with 2 µL zymolyase (1000 U mL$^{-1}$, Zymo research, Irvine, CA) and incubated at 37° C. for 20 minutes. The mix then was plated on media containing 20 g/L peptone, 10 g/L yeast extract and 20 g/L agar, one germinated spore was isolated and termed YST075.

For expression of VzZS1, VzZS2 and VzZS2-Nter2 in YST075 a set of plasmids were constructed in vivo using yeast endogenous homologous recombination as previously described in Kuijpers et al., *Microb Cell Fact.*, 2013, 12:47. The plasmids are composed of five DNA fragments which were used for *S. cerevisiae* co-transformation. The fragments were:

a) LEU2 yeast marker, constructed by PCR using the primers 5'AGGTGCAGTTCGCGTGCAAT-TATAACGTCGTGGCAACTGTTATCAGT CGTACCGCGCCATTCGACTACGTCGTAAGGCC-3' (SEQ ID NO: 43) and 5'TCGTGGT-CAAGGCGTGCAATTCTCAACACGAGAGTGAT-TCTTCGGCG TTGTTGCTGACCATCGACGGTCGAG-GAGAACTT-3' (SEQ ID NO: 44) with the plasmid pESC-LEU (Agilent Technologies, California, USA) as template;

b) AmpR *E. coli* marker, constructed by PCR using the primers 5'-TGGTCAGCAACAACGCCGAAGAAT-CACTCTCGTGTTGAGAATTGCACG CCTTGAC-CACGACACGTTAAGGGATTTTGGTCATGAG-3' (SEQ ID NO: 45) and 5'-AACGCGTACCCTAAGTACGGCAC-CACAGTGACTATGCAG TCCGCACTTTGC-CAATGCCAAAAATGTGCGCGGAACCCCTA-3' (SEQ ID NO: 46) with the plasmid pESC-URA as template;

c) Yeast origin of replication, obtained by PCR using the primers 5'-TTGGCATTGGCAAAGTGCGGACTG-CATAGTCACTGTGGTGCCGTACTT AGGGTACGCGTTCCT-GAACGAAGCATCTGTGCTTCA-3' (SEQ ID NO: 5y) and 5'-CCGAGATGCCAAAGGATAGGTGC-TATGTTGATGACTACGACACA GAACTGCGGGTGACATAATGATAGCATT-GAAGGATGAGACT-3' (SEQ ID NO: 48) with pESC-URA as template;

d) *E. coli* replication origin, obtained by PCR using the primers 5'-ATGT-CACCCGCAGTTCTGTGTCGTAGTCATCAACAT-AGCACCTATCCTT TGGCATCTCGGT-GAGCAAAAGGCCAGCAAAAGG-3' (SEQ ID NO: 49) and 5'-CTCAGATGTACGGTGATCGCCAC-CATGTGACGGAAGCTATCCTGACAG TGTAGCAAGTGCTGAGCGTCA-GACCCCGTAGAA-3' (SEQ ID NO: 50) with the plasmid pESC-URA as template;

e) a fragment composed by the last 60 nucleotides of the fragment "d", 200 nucleotides downstream the stop codon of the yeast gene PGK1, one of the tested zizaene synthases coding genes codon optimized for their expression in *S. cerevisiae* (SEQ ID NO: 51, SEQ ID NO: 52, SEQ ID NO: 53 for VzZS1, VzZS2 and VzZS2-Nter2 respectively), the yeast promoter GAL1 and 60 nucleotides corresponding to the beginning of the fragment "a", these fragments were obtained by DNA synthesis (ATUM, Menlo Park, CA 94025) and PCR overlap extension (Yolov and Shabarova., *Nucleic Acids Res.* 1990, 18(13):3983-6).

YST075 was transformed with the fragments required for in vivo plasmid assembly. Yeast transformations were performed with the lithium acetate protocol as described in Gietz and Woods, Methods Enzymol., 2002, 350:87-96. Transformation mixture was plated on Sm Leu-media containing 6.7 g/L of Yeast Nitrogen Base without amino acid (BD Difco, New Jersey, USA), 1.6 g/L Dropout supplement without leucine (Sigma Aldrich, Missouri, USA), 20 g/L glucose and 20 g/L agar. Plate was incubated for 3-4 days at 30° C. Individual colonies were used to produce zizaene in glass tubes containing media as described in Westfall et al., *Proc Natl Acad Sci USA*, 2012, 109:E111-118 and dodecane as organic overlay. The cultures were incubated for 3-4 days at 30° C. The production of zizaene was identified and quantified using GC-MS analysis with an internal standard.

Under these culture conditions, all tested zizaene synthases produced zizaene as main product. Compared to the previously identified synthase VzZS1 (SEQ ID NO: 1 of WO2010134004), VzZS2 and VzZS2-Nter2 produced 286% and 42.3% quantities of zizaene (FIG. 21). VzZS2 delivered the highest production of zizaene.

Example 13: In Vivo Production of Oxygenated Sesquiterpene Compounds in *Saccharomyces cerevisiae* Cells Using Zizaene Synthases and Cytochrome P450 Enzymes For the production of oxygenated sesquiterpenes compounds, the genes coding for the zizaene synthases VzZS1, VzZS2 and VzZS2-Nter2, and the genes encoding the cytochrome P450's VzCP521-11 (SEQ ID NO 54) and VzCP8201 (SEQ ID NO 55) were expressed in engineered *Saccharomyces cerevisiae* cells. All genes were codon optimized for their expression in *S. cerevisiae*.

The codon optimized versions of the genes encoding for the cytochrome reductase AaCPR and the cytochrome b5 CYB5 (form *Artemisia annua*, GenBank accession JF951732 and JQ582841, respectively; as described by Paddon et al., Nature, 2013, 496:528-532) were integrated into the genome of YST075. Expression of the genes coding for AaCPR and CYB5 were under the control of the promoter regions of GAL3 and GAL7 genes respectively. The generated strain was termed YST091.

For expression of the different tested genes in YST091 a set of six plasmids were constructed in vivo using yeast endogenous homologous recombination as previously described in Kuijpers et al., *Microb Cell Fact.*, 2013, 12:47. The plasmids are composed of five DNA fragments similarly as described in Example 12 with the difference that fragment "e" contained one tested zizaene synthase and one tested cytochrome P450, both regulated by the bidirectional GAL10/GAL1 promoter. YST091 was transformed with the fragments required for in vivo plasmid assembly and tested as described in Example 12 using deep well plates instead of glass tubes. Deep well plates contained media as described in Westfall et al., *Proc Natl Acad Sci USA*, 2012, 109:E111-118 and paraffin oil (Sigma Aldrich, Missouri, USA) as organic overlay. The deep well plates were incubated for 3-4 days at 30° C. To extract the produced molecules by the yeast cells, ethyl acetate containing an internal standard was added to each well. The production of zizaene and zizaenol was identified using GC-MS analysis and quantified by GC-FID.

Under these culture conditions, oxygenated zizaene was not identified when VzCP8201 was expressed in yeast cells. In contrast, the three combinations of zizaene synthases and the P450 VzCP521-11 resulted in production of both zizaene and zizaenol. The highest amount of zizaenol was obtained with the plasmid harboring the genes coding for VzZS2 and VzCP521-11, while the other two combinations, VzZS1/VzCP521-11 and VzZS2-Nter2/VzCP521-11, generated 53% and 11%, respectively, of the highest amount of zizaenol.

With the aim to construct a stable yeast strain, the DNA fragment used for plasmid construction containing the genes coding for VzZS2 and VzCP521-11 was integrated two times into the genome of YST091 in two sequential recombination events with the aid of the LEU2 and TRP1 marker genes. In addition, a third integration with a DNA fragment containing only the gene coding for VzCP521-11 under the control of GAL10 promoter was performed using the URA3 marker gene. The resulting strain was termed YST124.

YST124 was evaluated for the production of oxygenated sesquiterpenes similarly as described in Westfall et al., *Proc Natl Acad Sci USA*, 2012, 109:E111-118. FIG. 22 shows the GC-MS analysis of the oxygenated sesquiterpenes formed in cultures of YST124, not only zizaenol was formed but also zizaenone and, in lower amount, khusimol.

| SEQ ID NO | Name | Source | Type |
|---|---|---|---|
| 1 | VzTps1718 wild type cDNA includes non-coding regions | Vetiveria zizanoides | NA |
| 2 | VzTps1718 wild type cDNA open reading frame | Vetiveria zizanoides | NA |
| 3 | VzTps1718 wild type | Vetiveria zizanoides | AA |
| 4 | VzTps1718 wild type cDNA codon optimized. | artificial | NA |
| 5 | VzTrspt-9 Locus 8201-12 | Vetiveria zizanoides | NA |
| 6 | VzCp8201-12 wild type cDNA | Vetiveria zizanoides | NA |
| 7 | VzCp8201-12 wild type | Vetiveria zizanoides | AA |
| 8 | VzCP8201-228093, optimized cDNA, encoding VzCP8201-12, | artificial | NA |
| 9 | VzCP8201-228092, optimized cDNA, encoding VzCP8201-12-bov | artificial | NA |
| 10 | VzCP8201-12-bov | artificial | AA |
| 11 | VzTrspt7 contig 7186, | Vetiveria zizanoides | NA |
| 12 | VzTrspt7 contig 7186 wild type cDNA | Vetiveria zizanoides | NA |
| 13 | VzCP7186, wild type | Vetiveria zizanoides | AA |
| 14 | Optimized cDNA of N-terminal variant of VzCP7186 | artificial | NA |
| 15 | N-terminal variant of VzCP7186 = VzCP7186op | artificial | AA |
| 16 | VzCP521-11 wild type cDNA open reading frame | Vetiveria zizanoides | NA |
| 17 | VzCP521-11 cDNA optimized sequence | artificial | NA |
| 18 | VzCP521-11, wild type | Vetiveria zizanoides | AA |
| 19 | Catalytic domain of VzCP8201 | Vetiveria zizanoides | AA |
| 20 | Catalytic domain of VzCP7186 | Vetiveria zizanoides | AA |
| 21 | Catalytic domain of VzCP521-11 | Vetiveria zizanoides | AA |

-continued

| SEQ ID NO | Name | Source | Type |
|---|---|---|---|
| 22 | P450 reductase (CPRm) | *Mentha piperita* | NA |
| 23 | P450 reductase (CPRm) | *Mentha piperita* | AA |
| 24 | N-terminal peptide | artificial | AA |
| 25 | polylinker | artificial | NA |
| 26 | extension sequence | artificial | NA |
| 27 | 5' non-coding sequence | artificial | NA |
| 28 | 3' non-coding sequence | artificial | NA |
| 29 | Inf8201-7186-Fw | Primer | NA |
| 30 | Inf8201-7186-Rev | Primer | NA |
| 31 | Vzctg306 full-length cDNA encoding for VzZS1, includes non-coding regions | *Vetiveria zizanoides* | NA |
| 32 | Vzctg306 full-length cDNA encoding for VzZS1, ORF only | *Vetiveria zizanoides* | NA |
| 33 | VzZS1 | *Vetiveria zizanoides* | AA |
| 34 | Codon optimized cDNA encoding for VzZS1 | artificial | NA |
| 35 | VzTrspt_4_contig_995, full-length cDNA encoding for VzZS2, including non-coding regions | *Vetiveria zizanoides* | NA |
| 36 | VzTrspt_4_contig_995, full-length cDNA encoding for VzZS2, open reading frame only | *Vetiveria zizanoides* | NA |
| 37 | Codon optimized cDNA encoding for VzZS2 | artificial | NA |
| 38 | VzZS2 | *Vetiveria zizanoides* | AA |
| 39 | VzTrspt_10_contig_49, full-length cDNA encoding for VzZS2-Nter2, including non-coding regions | *Vetiveria zizanoides* | NA |
| 40 | VzTrspt_10_contig_49, full-length cDNA encoding for VzZS2-Nter2, open reading frame only | *Vetiveria zizanoides* | NA |
| 41 | Codon optimized cDNA encoding for VzZS2-Nter2 SR opt | Artificial | NA |
| 42 | VzZS2-Nter2 | *Vetiveria zizanoides* | AA |
| 43 | Primer for LEU2 marker PCR | Primer | NA |
| 44 | Primer for LEU2 marker PCR | Primer | NA |
| 45 | Primer for AmpR, *E. coli* marker PCR | Primer | NA |
| 46 | Primer for AmpR, *E. coli* marker PCR | Primer | NA |
| 47 | Primer for Yeast origin of replication PCR | Primer | NA |
| 48 | Primer for Yeast origin of replication PCR | Primer | NA |
| 49 | Primer for *E. coli* origin of replication PCR | Primer | NA |
| 50 | Primer for *E. coli* origin of replication PCR | Primer | NA |
| 51 | VzZS1 DNA codon optimized for *Saccharomyces cerevisiae* | Artificial | NA |
| 52 | VzZS2 DNA codon optimized for *Saccharomyces cerevisiae* | Artificial | NA |
| 53 | VzZS2-Nter2 DNA codon optimized for *Saccharomyces cerevisiae* | Artificial | NA |
| 54 | VzCP521-11 DNA codon optimized for *Saccharomyces cerevisiae* | Artificial | NA |
| 55 | VzCP8201 DNA codon optimized for *Saccharomyces cerevisiae* | Artificial | NA |

NA = Nucleic Acid
AA = Amino Acid

SEQUENCE LISTING

<160> NUMBER OF SEQ ID NOS: 55

<210> SEQ ID NO 1
<211> LENGTH: 1835
<212> TYPE: DNA
<213> ORGANISM: Vetiveria zizanoides
<220> FEATURE:
<221> NAME/KEY: misc_feature
<223> OTHER INFORMATION: VzTps1718 wild type cDNA (including 3' and 5' non coding regions)

<400> SEQUENCE: 1

```
actggagttc agacgtgtgc tcttccgatc tatcggagtg aagttgagca gctaacttca      60
cgactcgttt gcaggctagc tcgcaacaga atagagagtg ttactgctgg tatatatata     120
tatatatata tggctgcgag cattactgtc gccgccgcac atgggcctcc tgctgcaatc     180
ccagagacca aacgcagcac tgtagacgac gttcctttcc aatcctctgt gtggggcgac     240
tactttgtaa actacacacc tcctgcatca cagaggtcgg aggaatggat gagggagagg     300
```

```
gttgatgaac tcaggggtga agtgcgccgg aagttcaaaa cgacgatgag catggccgag    360
acgatggtgc tggtggacac actggagcgc ctcgccatcg acggccattt ccgcaaggat    420
attgacttgg cgttgagcca aatccacatg gaggggaagc cggccggtat tagcagctcc    480
aacaagcttt acatcgtcgc cctgggattc cgcttgctta ggcaacatgg cttctgggta    540
tccgcagacg tgtttgacaa gtttagggat agcacgggca agcttagcaa gggtctgagc    600
ggcgacgtga agggtctgct gagcctatac aacgcggctc acatggcggt tcccggcgag    660
aaaagcctgg acgaagccat cgacttcaca aggcgctgcc tcgagtctgc caaggacagg    720
ctcgtggcgc cgatgtcggt gcaggtgtcg cgcgccctca gcattcctct cccccgctac    780
ctgccgcggc tagaggccat gcactacatc tcagagtatg ggcaggagga ggaccatgac    840
gccaagatcc tggagcttgc gaggctggac tatgcccttg tccagtctct ctatctcaag    900
gagctcaggg agctcacctt gtggtggaag gagctgtatc acagcgtgaa tctgcccaac    960
acacgggacc gcatcgtgga gatgtacttc tttgcatttg gtatgctgca gacgaggag    1020
tactctcggg cgcgcctgat tgatagcaag ataattgcac tggtcagcct gatggatgac    1080
atttacgacg aacacgctag ctttgaggaa gcccaaaaat tcaatgaagc catacagaga    1140
tggaatgaaa gtgcggtctc agacctacca gaatacatgc gcatgctata cacccaaata    1200
ctaagcacct tcgccaaatt tgaggaagtt ttggggccca acgaaaagta ccgcgtgtct    1260
tacgccaaag aggcgtacaa attgcagtcg atgtattact ttctggagaa caaatggtgt    1320
cacgagaacc acatgccaag cttcggagag cacatacatc tttcttccat gtcggcaggc    1380
ttgcaggtgt tgatcgttgg ggcatggata ggcgcccacc acgccattgc caaggagtca    1440
ctagagtggg caatcaccta ccctgaagtc ttccgggcag caggagatgt tggccgtctc    1500
ctcaacgata tcgcttcatt taagaagagg aaaaacagca aggacgcgcc caacgcgctg    1560
gagtgctacg tcagagaaca tggcgtcacg ggggaggaag ctgcggccgc gtgtgcagcc    1620
attgtagagc tcgggtggag gaagatcaac agggcccgta tggagataca tcctatgctg    1680
gtacccgcgg cacaaatgga tgcgaaaatc aacctgacca gggtgtgcga gattttatac    1740
taccgtggta tggatggcta cacctttgga agcgacctcc gggatgtcat cacttctctc    1800
ttcatcaagc cggcggccgg gggccctgca taatt                               1835
```

```
<210> SEQ ID NO 2
<211> LENGTH: 1704
<212> TYPE: DNA
<213> ORGANISM: Vetiveria zizanoides
<220> FEATURE:
<221> NAME/KEY: misc_feature
<223> OTHER INFORMATION: VzTps1718 wild type cDNA (open reading frame
      sequence)
<220> FEATURE:
<221> NAME/KEY: CDS
<222> LOCATION: (1)..(1704)

<400> SEQUENCE: 2 atg gct gcg agc att act gtc gcc gcc gca cat ggg cct cct gct gca      48
Met Ala Ala Ser Ile Thr Val Ala Ala Ala His Gly Pro Pro Ala Ala
1               5                   10                  15 atc cca gag acc aaa cgc agc act gta gac gac gtt cct ttc caa tcc      96
Ile Pro Glu Thr Lys Arg Ser Thr Val Asp Asp Val Pro Phe Gln Ser
            20                  25                  30 tct gtg tgg ggc gac tac ttt gta aac tac aca cct cct gca tca cag     144
Ser Val Trp Gly Asp Tyr Phe Val Asn Tyr Thr Pro Pro Ala Ser Gln
        35                  40                  45
```

```
agg tcg gag gaa tgg atg agg gag agg gtt gat gaa ctc agg ggt gaa    192
Arg Ser Glu Glu Trp Met Arg Glu Arg Val Asp Glu Leu Arg Gly Glu
    50              55                  60 gtg cgc cgg aag ttc aaa acg acg atg agc atg gcc gag acg atg gtg    240
Val Arg Arg Lys Phe Lys Thr Thr Met Ser Met Ala Glu Thr Met Val
65              70                  75                  80 ctg gtg gac aca ctg gag cgc ctc gcc atc gac ggc cat ttc cgc aag    288
Leu Val Asp Thr Leu Glu Arg Leu Ala Ile Asp Gly His Phe Arg Lys
                85                  90                  95 gat att gac ttg gcg ttg agc caa atc cac atg gag ggg aag ccg gcc    336
Asp Ile Asp Leu Ala Leu Ser Gln Ile His Met Glu Gly Lys Pro Ala
            100                 105                 110 ggt att agc agc tcc aac aag ctt tac atc gtc gcc ctg gga ttc cgc    384
Gly Ile Ser Ser Ser Asn Lys Leu Tyr Ile Val Ala Leu Gly Phe Arg
        115                 120                 125 ttg ctt agg caa cat ggc ttc tgg gta tcc gca gac gtg ttt gac aag    432
Leu Leu Arg Gln His Gly Phe Trp Val Ser Ala Asp Val Phe Asp Lys
    130                 135                 140 ttt agg gat agc acg ggc aag ctt agc aag ggt ctg agc ggc gac gtg    480
Phe Arg Asp Ser Thr Gly Lys Leu Ser Lys Gly Leu Ser Gly Asp Val
145                 150                 155                 160 aag ggt ctg ctg agc cta tac aac gcg gct cac atg gcg gtt ccc ggc    528
Lys Gly Leu Leu Ser Leu Tyr Asn Ala Ala His Met Ala Val Pro Gly
                165                 170                 175 gag aaa agc ctg gac gaa gcc atc gac ttc aca agg cgc tgc ctc gag    576
Glu Lys Ser Leu Asp Glu Ala Ile Asp Phe Thr Arg Arg Cys Leu Glu
            180                 185                 190 tct gcc aag gac agg ctc gtg gcg ccg atg tcg gtg cag gtg tcg cgc    624
Ser Ala Lys Asp Arg Leu Val Ala Pro Met Ser Val Gln Val Ser Arg
        195                 200                 205 gcc ctc agc att cct ctc ccc cgc tac ctg ccg cgg cta gag gcc atg    672
Ala Leu Ser Ile Pro Leu Pro Arg Tyr Leu Pro Arg Leu Glu Ala Met
    210                 215                 220 cac tac atc tca gag tat ggg cag gag gag gac cat gac gcc aag atc    720
His Tyr Ile Ser Glu Tyr Gly Gln Glu Glu Asp His Asp Ala Lys Ile
225                 230                 235                 240 ctg gag ctt gcg agg ctg gac tat gcc ctt gtc cag tct ctc tat ctc    768
Leu Glu Leu Ala Arg Leu Asp Tyr Ala Leu Val Gln Ser Leu Tyr Leu
                245                 250                 255 aag gag ctc agg gag ctc acc ttg tgg tgg aag gag ctg tat cac agc    816
Lys Glu Leu Arg Glu Leu Thr Leu Trp Trp Lys Glu Leu Tyr His Ser
            260                 265                 270 gtg aat ctg ccc aac aca cgg gac cgc atc gtg gag atg tac ttc ttt    864
Val Asn Leu Pro Asn Thr Arg Asp Arg Ile Val Glu Met Tyr Phe Phe
        275                 280                 285 gca ttt ggt atg ctg cag acg gag gag tac tct cgg gcg cgc ctg att    912
Ala Phe Gly Met Leu Gln Thr Glu Glu Tyr Ser Arg Ala Arg Leu Ile
    290                 295                 300 gat agc aag ata att gca ctg gtc agc ctg atg gat gac att tac gac    960
Asp Ser Lys Ile Ile Ala Leu Val Ser Leu Met Asp Asp Ile Tyr Asp
305                 310                 315                 320 gaa cac gct agc ttt gag gaa gcc caa aaa ttc aat gaa gcc ata cag    1008
Glu His Ala Ser Phe Glu Glu Ala Gln Lys Phe Asn Glu Ala Ile Gln
                325                 330                 335 aga tgg aat gaa agt gcg gtc tca gac cta cca gaa tac atg cgc atg    1056
Arg Trp Asn Glu Ser Ala Val Ser Asp Leu Pro Glu Tyr Met Arg Met
            340                 345                 350 cta tac acc caa ata cta agc acc ttc gcc aaa ttt gag gaa gtt ttg    1104
Leu Tyr Thr Gln Ile Leu Ser Thr Phe Ala Lys Phe Glu Glu Val Leu
```

```
                   355                 360                 365
ggg ccc aac gaa aag tac cgc gtg tct tac gcc aaa gag gcg tac aaa     1152
Gly Pro Asn Glu Lys Tyr Arg Val Ser Tyr Ala Lys Glu Ala Tyr Lys
370                 375                 380 ttg cag tcg atg tat tac ttt ctg gag aac aaa tgg tgt cac gag aac     1200
Leu Gln Ser Met Tyr Tyr Phe Leu Glu Asn Lys Trp Cys His Glu Asn
385                 390                 395                 400 cac atg cca agc ttc gga gag cac ata cat ctt tct tcc atg tcg gca     1248
His Met Pro Ser Phe Gly Glu His Ile His Leu Ser Ser Met Ser Ala
                405                 410                 415 ggc ttg cag gtg ttg atc gtt ggg gca tgg ata ggc gcc cac cac gcc     1296
Gly Leu Gln Val Leu Ile Val Gly Ala Trp Ile Gly Ala His His Ala
            420                 425                 430 att gcc aag gag tca cta gag tgg gca atc acc tac cct gaa gtc ttc     1344
Ile Ala Lys Glu Ser Leu Glu Trp Ala Ile Thr Tyr Pro Glu Val Phe
        435                 440                 445 cgg gca gca gga gat gtt ggc cgt ctc ctc aac gat atc gct tca ttt     1392
Arg Ala Ala Gly Asp Val Gly Arg Leu Leu Asn Asp Ile Ala Ser Phe
    450                 455                 460 aag aag agg aaa aac agc aag gac gcg ccc aac gcg ctg gag tgc tac     1440
Lys Lys Arg Lys Asn Ser Lys Asp Ala Pro Asn Ala Leu Glu Cys Tyr
465                 470                 475                 480 gtc aga gaa cat ggc gtc acg ggg gag gaa gct gcg gcc gcg tgt gca     1488
Val Arg Glu His Gly Val Thr Gly Glu Glu Ala Ala Ala Ala Cys Ala
                485                 490                 495 gcc att gta gag ctc ggg tgg agg aag atc aac agg gcc cgt atg gag     1536
Ala Ile Val Glu Leu Gly Trp Arg Lys Ile Asn Arg Ala Arg Met Glu
            500                 505                 510 ata cat cct atg ctg gta ccc gcg gca caa atg gat gcg aaa atc aac     1584
Ile His Pro Met Leu Val Pro Ala Ala Gln Met Asp Ala Lys Ile Asn
        515                 520                 525 ctg acc agg gtg tgc gag att tta tac tac cgt ggt atg gat ggc tac     1632
Leu Thr Arg Val Cys Glu Ile Leu Tyr Tyr Arg Gly Met Asp Gly Tyr
    530                 535                 540 acc ttt gga agc gac ctc cgg gat gtc atc act tct ctc ttc atc aag     1680
Thr Phe Gly Ser Asp Leu Arg Asp Val Ile Thr Ser Leu Phe Ile Lys
545                 550                 555                 560 ccg gcg gcc ggg ggc cct gca taa                                      1704
Pro Ala Ala Gly Gly Pro Ala
                565

<210> SEQ ID NO 3
<211> LENGTH: 567
<212> TYPE: PRT
<213> ORGANISM: Vetiveria zizanoides

<400> SEQUENCE: 3

Met Ala Ala Ser Ile Thr Val Ala Ala Ala His Gly Pro Pro Ala Ala
1               5                   10                  15

Ile Pro Glu Thr Lys Arg Ser Thr Val Asp Asp Val Pro Phe Gln Ser
                20                  25                  30

Ser Val Trp Gly Asp Tyr Phe Val Asn Tyr Thr Pro Pro Ala Ser Gln
            35                  40                  45

Arg Ser Glu Glu Trp Met Arg Glu Arg Val Asp Glu Leu Arg Gly Glu
        50                  55                  60

Val Arg Arg Lys Phe Lys Thr Thr Met Ser Met Ala Glu Thr Met Val
65                  70                  75                  80

Leu Val Asp Thr Leu Glu Arg Leu Ala Ile Asp Gly His Phe Arg Lys
                85                  90                  95
```

```
Asp Ile Asp Leu Ala Leu Ser Gln Ile His Met Glu Gly Lys Pro Ala
            100                 105                 110

Gly Ile Ser Ser Asn Lys Leu Tyr Ile Val Ala Leu Gly Phe Arg
        115                 120                 125

Leu Leu Arg Gln His Gly Phe Trp Val Ser Ala Asp Val Phe Asp Lys
    130                 135                 140

Phe Arg Asp Ser Thr Gly Lys Leu Ser Lys Gly Leu Ser Gly Asp Val
145                 150                 155                 160

Lys Gly Leu Leu Ser Leu Tyr Asn Ala Ala His Met Ala Val Pro Gly
                165                 170                 175

Glu Lys Ser Leu Asp Glu Ala Ile Asp Phe Thr Arg Arg Cys Leu Glu
            180                 185                 190

Ser Ala Lys Asp Arg Leu Val Ala Pro Met Ser Val Gln Val Ser Arg
        195                 200                 205

Ala Leu Ser Ile Pro Leu Pro Arg Tyr Leu Pro Arg Leu Glu Ala Met
    210                 215                 220

His Tyr Ile Ser Glu Tyr Gly Gln Glu Glu Asp His Asp Ala Lys Ile
225                 230                 235                 240

Leu Glu Leu Ala Arg Leu Asp Tyr Ala Leu Val Gln Ser Leu Tyr Leu
                245                 250                 255

Lys Glu Leu Arg Glu Leu Thr Leu Trp Trp Lys Glu Leu Tyr His Ser
            260                 265                 270

Val Asn Leu Pro Asn Thr Arg Asp Arg Ile Val Glu Met Tyr Phe Phe
        275                 280                 285

Ala Phe Gly Met Leu Gln Thr Glu Glu Tyr Ser Arg Ala Arg Leu Ile
    290                 295                 300

Asp Ser Lys Ile Ile Ala Leu Val Ser Leu Met Asp Asp Ile Tyr Asp
305                 310                 315                 320

Glu His Ala Ser Phe Glu Glu Ala Gln Lys Phe Asn Glu Ala Ile Gln
                325                 330                 335

Arg Trp Asn Glu Ser Ala Val Ser Asp Leu Pro Glu Tyr Met Arg Met
            340                 345                 350

Leu Tyr Thr Gln Ile Leu Ser Thr Phe Ala Lys Phe Glu Glu Val Leu
        355                 360                 365

Gly Pro Asn Glu Lys Tyr Arg Val Ser Tyr Ala Lys Glu Ala Tyr Lys
    370                 375                 380

Leu Gln Ser Met Tyr Tyr Phe Leu Glu Asn Lys Trp Cys His Glu Asn
385                 390                 395                 400

His Met Pro Ser Phe Gly Glu His Ile His Leu Ser Ser Met Ser Ala
                405                 410                 415

Gly Leu Gln Val Leu Ile Val Gly Ala Trp Ile Gly Ala His His Ala
            420                 425                 430

Ile Ala Lys Glu Ser Leu Glu Trp Ala Ile Thr Tyr Pro Glu Val Phe
        435                 440                 445

Arg Ala Ala Gly Asp Val Gly Arg Leu Leu Asn Asp Ile Ala Ser Phe
    450                 455                 460

Lys Lys Arg Lys Asn Ser Lys Asp Ala Pro Asn Ala Leu Glu Cys Tyr
465                 470                 475                 480

Val Arg Glu His Gly Val Thr Gly Glu Glu Ala Ala Ala Cys Ala
                485                 490                 495

Ala Ile Val Glu Leu Gly Trp Arg Lys Ile Asn Arg Ala Arg Met Glu
            500                 505                 510
```

```
Ile His Pro Met Leu Val Pro Ala Ala Gln Met Asp Ala Lys Ile Asn
            515                 520                 525

Leu Thr Arg Val Cys Glu Ile Leu Tyr Tyr Arg Gly Met Asp Gly Tyr
        530                 535                 540

Thr Phe Gly Ser Asp Leu Arg Asp Val Ile Thr Ser Leu Phe Ile Lys
545                 550                 555                 560

Pro Ala Ala Gly Gly Pro Ala
                565

<210> SEQ ID NO 4
<211> LENGTH: 1704
<212> TYPE: DNA
<213> ORGANISM: Artificial Sequence
<220> FEATURE:
<223> OTHER INFORMATION: VzTps1718 wild type cDNA codon optimized
<220> FEATURE:
<221> NAME/KEY: misc_feature
<223> OTHER INFORMATION: Terpene synthase from Vetiveria zizanoides,
      codon optimized cDNA sequence

<400> SEQUENCE: 4
atggcagcaa gcatcacggt cgccgcagca cacggtccgc cagcagcaat cccggaaacc      60
aaacgcagca ccgtggatga cgttccattt caatcctcgg tgtggggcga ctacttcgtc     120
aactatacgc cgccggcgag ccagcgttcc gaagagtgga tgcgtgaacg cgttgacgaa     180
ctgcgtggcg aagtgcgtcg taagttcaag actaccatga gcatggctga accatggtt     240 ctggttgata ccctggagcg ccttgcaatc gatggtcatt tcgtaaaga tattgacctg     300 gcactgagcc agatccacat ggagggtaaa ccggcgggta ttagctcgtc taacaagctg     360
tatatcgttg cgctgggctt tcgtttgttg cgtcagcacg gtttctgggt gagcgccgat     420
gttttcgata aatttcgtga tagcacgggc aaactgtcca agggcctgag cggcgacgtc     480
aagggcctgc tgtcactgta taatgccgca cacatggctg tcccgggtga gaaatctctg     540
gatgaagcga ttgactttac gcgtcgctgc ctggaaagcg ccaaagatcg tttggtggcc     600
ccgatgagcg tccaggttag ccgcgccctg agcatcccgc tgccgcgtta tctgccgcgc     660
ctggaagcga tgcattacat cagcgagtat ggtcaagagg aagatcacga cgctaagatc     720
ctggaattgg cgcgcctgga ctacgcgctg gtccaaagcc tgtacctgaa gaactgcgc     780 gagctgaccc tgtggtggaa agaactgtac cactccgtta atctgccgaa cacccgtgac     840
cgcatcgtcg agatgtattt cttttgcgttt ggtatgttgc agaccgaaga gtactctcgt     900
gctcgcctga tcgatagcaa gattatcgcc ctggtgagcc tgatggatga catttatgat     960
gagcatgcca gcttcgagga agctcaaaag tttaacgaag caatccaacg ttggaatgaa    1020
agcgcggtta cgacttgcc ggagtatatg cgcatgctgt acacccaaat cctgagcacc    1080
ttcgcgaagt ttgaagaggt tctgggtccg aacgaaaaat atcgcgtgag ctatgcgaaa    1140
gaggcgtaca gctgcaatc catgtactat ttcctggaga caaatggtg tcatgagaat    1200 cacatgccga gcttcggtga gcacattcac ctgagctcca gtccgcgggg tttgcaagtg    1260
ttgattgtgg gtgcttggat cggcgcacat catgccattg caaaagagag cctggagtgg    1320
gcgattacct accctgaagt ttttcgtgcc gcgggcgatg tgggtcgtct gttgaatgac    1380
attgcaagct tcaaaaagcg taagaactct aaagacgccc cgaacgcgct ggagtgttat    1440
gtccgtgaac acggcgtgac tggcgaagaa gcggcagctg cctgcgcagc tattgttgag    1500
ctgggttggc gtaagatcaa ccgtgcgcgc atggaaatcc atccgatgct ggtcccggcg    1560
gcgcagatgg acgcgaaaat caatttgacc cgtgtgtgcg agatcctgta ctaccgtggc    1620
```

```
atggatggtt acaccttcgg tagcgattta cgcgatgtga ttacgagcct cttcattaag    1680
cctgcggctg gcggcccggc gtaa                                          1704

<210> SEQ ID NO 5
<211> LENGTH: 1825
<212> TYPE: DNA
<213> ORGANISM: Vetiveria zizanoides
<220> FEATURE:
<221> NAME/KEY: misc_feature
<223> OTHER INFORMATION: VzTrspt-9_Locus_8201-12, full length transcript
      containing 5' and 3 non-translated sequences

<400> SEQUENCE: 5
gatcgtttca cgtgactgga gttcagacgt gtgctcttcc gatctcaaaa aatggacttt     60
ctcagaatcc cgtttcttgt agccttcgtc ttcctcgccg tccttctcag gctcatccgg    120
agctacatca catcctcagc tcttcgcctg ccaccggggc catggcagct gccgctcatc    180
ggcagcctgc accacctcct gctgtcgcgc ttcagcgacc tccctcaccg ggctttgcgc    240
gagatgtccg gcacctacgg gcccctcatg ctgctccgct tcggctccgt gcccacgctg    300
gtggtctcct ccgccgaggc tgcccggag gtgatgagga cccacgacct cgccttctgc    360
gaccgccacc tcggcgtcac tctcgacatc gtcacctgcg gcgcaagga catcatctgc    420 tcccctaca cgcccactg gcgcgagctc cgtaagctgt gcatggtcga gatcttgagc    480
cagcggcgcg tgctctcgtt ccggagcatc cgggaagagg aggtggcgag cctcgtccgc    540
tccatctccg acgagtgcgg cggtggccag cagcccgtca acctcactga agggataagc    600
cgcatgataa acgacgtcgc cgcgcgcacg gtcgtcggcg accggtgcaa gtaccaggat    660
gaatacatgc atgagctgga cgaagtggtg cggctggccg gcgggttcaa cctggcggac    720
ctgtacccgt cctcgcggct ggtacggcgg ttcagcgccg ccgcgaggga cgcgaggagg    780
tgccagagga acatgtaccg tatcatccag agcatcatcc aggagcgtga agccatgccg    840
acgccagagc gagacgagga ggacctcctc ggcgtcctcc tcaggctgca gagagaaggt    900
ggcctgcagt ttgctctcac caatgagata gtcagcaccg tcatttacga tattttttct    960
gctggtagtg aaacatcatc aactgttcta gtatgggcaa tgtcggagct tgttaagaat   1020
ccacaagtca tgcgtaaggc ccagtcagag gtgagggata ccttcaaagg aaacaacaag   1080
ataactgaaa gtgatttgat caagttaaga tatctacaac tggtgatcaa ggagacttta   1140
cggttgcatg ctccggtacc actcttgctc cctcgagaat gccgtgagtc atgtcagatt   1200
atgggttacg atgtgctaaa gggaaccaag gtatttgtga atgcttgggc aatagcaagg   1260
gacacgggat tatggtgtga tggagaggaa tttaggccag aaaggtttga aagtagcaat   1320
attgatttca ggggtaatga ctttgagttc acaccgtttg gggcaggcag agagtatgc    1380 cctggcatca cacttggact ggccaaccta gaactagcgc ttgctagcct tctttatcat   1440
tttgattggg atctgcccaa tggtgccagg ttggaagatc ttgatatggc agaggccttt   1500
ggtataacgt taaaaggaa gtccatgctc tggctcaagg ccaaaccta caataatttt    1560 ataccaaatt aatcaggtga tttgtgatgt gaactatccc ggttgctact tagtttatta   1620
tacccagaaa gagtgtgatg gtaattgtac tatcaatctt tactgcagaa cagtaaatat   1680
atccagagtt ggttctatgc ttctgttata atgtttcatc actctgtatt aagtgtgtag   1740
ttatctgttt gttacttttt tttgtaatga ttaaacgatt atctaatgag agtacaagaa   1800
tcaaatgaga ctggtctaaa aaaaa                                        1825
```

<210> SEQ ID NO 6
<211> LENGTH: 1521
<212> TYPE: DNA
<213> ORGANISM: Vetiveria zizanoides
<220> FEATURE:
<221> NAME/KEY: misc_feature
<223> OTHER INFORMATION: VzCp8201-12 wild type cDNA sequence, open read frame only
<220> FEATURE:
<221> NAME/KEY: CDS
<222> LOCATION: (1)..(1521)

<400> SEQUENCE: 6

```
atg gac ttt ctc aga atc ccg ttt ctt gta gcc ttc gtc ttc ctc gcc      48
Met Asp Phe Leu Arg Ile Pro Phe Leu Val Ala Phe Val Phe Leu Ala
1               5                   10                  15 gtc ctt ctc agg ctc atc cgg agc tac atc aca tcc tca gct ctt cgc      96
Val Leu Leu Arg Leu Ile Arg Ser Tyr Ile Thr Ser Ser Ala Leu Arg
            20                  25                  30 ctg cca ccg ggg cca tgg cag ctg ccg ctc atc ggc agc ctg cac cac     144
Leu Pro Pro Gly Pro Trp Gln Leu Pro Leu Ile Gly Ser Leu His His
        35                  40                  45 ctc ctg ctg tcg cgc ttc agc gac ctc cct cac cgg gct ttg cgc gag     192
Leu Leu Leu Ser Arg Phe Ser Asp Leu Pro His Arg Ala Leu Arg Glu
    50                  55                  60 atg tcc ggc acc tac ggg ccc ctc atg ctg ctc cgc ttc ggc tcc gtg     240
Met Ser Gly Thr Tyr Gly Pro Leu Met Leu Leu Arg Phe Gly Ser Val
65                  70                  75                  80 ccc acg ctg gtg gtc tcc tcc gcc gag gct gcc cgg gag gtg atg agg     288
Pro Thr Leu Val Val Ser Ser Ala Glu Ala Ala Arg Glu Val Met Arg
                85                  90                  95 acc cac gac ctc gcc ttc tgc gac cgc cac ctc ggc gtc act ctc gac     336
Thr His Asp Leu Ala Phe Cys Asp Arg His Leu Gly Val Thr Leu Asp
            100                 105                 110 atc gtc acc tgc ggc ggc aag gac atc atc tgc tcc ccc tac aac gcc     384
Ile Val Thr Cys Gly Gly Lys Asp Ile Ile Cys Ser Pro Tyr Asn Ala
        115                 120                 125 cac tgg cgc gag ctc cgt aag ctg tgc atg gtc gag atc ttg agc cag     432
His Trp Arg Glu Leu Arg Lys Leu Cys Met Val Glu Ile Leu Ser Gln
    130                 135                 140 cgg cgc gtg ctc tcg ttc cgg agc atc cgg gaa gag gag gtg gcg agc     480
Arg Arg Val Leu Ser Phe Arg Ser Ile Arg Glu Glu Glu Val Ala Ser
145                 150                 155                 160 ctc gtc cgc tcc atc tcc gac gag tgc ggc ggt ggc cag cag ccc gtc     528
Leu Val Arg Ser Ile Ser Asp Glu Cys Gly Gly Gly Gln Gln Pro Val
                165                 170                 175 aac ctc act gaa ggg ata agc cgc atg ata aac gac gtc gcc gcg cgc     576
Asn Leu Thr Glu Gly Ile Ser Arg Met Ile Asn Asp Val Ala Ala Arg
            180                 185                 190 acg gtc gtc ggc gac cgg tgc aag tac cag gat gaa tac atg cat gag     624
Thr Val Val Gly Asp Arg Cys Lys Tyr Gln Asp Glu Tyr Met His Glu
        195                 200                 205 ctg gac gaa gtg gtg cgg ctg gcc ggc ggg ttc aac ctg gcg gac ctg     672
Leu Asp Glu Val Val Arg Leu Ala Gly Gly Phe Asn Leu Ala Asp Leu
    210                 215                 220 tac ccg tcc tcg cgg ctg gta cgg cgg ttc agc gcc gcc gcg agg gac     720
Tyr Pro Ser Ser Arg Leu Val Arg Arg Phe Ser Ala Ala Ala Arg Asp
225                 230                 235                 240 gcg agg agg tgc cag agg aac atg tac cgt atc atc cag agc atc atc     768
Ala Arg Arg Cys Gln Arg Asn Met Tyr Arg Ile Ile Gln Ser Ile Ile
                245                 250                 255
```

| | | | | | | | | | | | | | | | | |
|---|---|---|---|---|---|---|---|---|---|---|---|---|---|---|---|---|
| cag | gag | cgt | gaa | gcc | atg | ccg | acg | cca | gag | cga | gac | gag | gag | gac | ctc | 816 |
| Gln | Glu | Arg | Glu | Ala | Met | Pro | Thr | Pro | Glu | Arg | Asp | Glu | Glu | Asp | Leu | |
| | | 260 | | | | | 265 | | | | | 270 | | | | |

| | | | | | | | | | | | | | | | | |
|---|---|---|---|---|---|---|---|---|---|---|---|---|---|---|---|---|
| ctc | ggc | gtc | ctc | ctc | agg | ctg | cag | aga | gaa | ggt | ggc | ctg | cag | ttt | gct | 864 |
| Leu | Gly | Val | Leu | Leu | Arg | Leu | Gln | Arg | Glu | Gly | Gly | Leu | Gln | Phe | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| ctc | acc | aat | gag | ata | gtc | agc | acc | gtc | att | tac | gat | att | ttt | tct | gct | 912 |
| Leu | Thr | Asn | Glu | Ile | Val | Ser | Thr | Val | Ile | Tyr | Asp | Ile | Phe | Ser | Ala | |
| | | | 290 | | | | | 295 | | | | | 300 | | | |

| | | | | | | | | | | | | | | | | |
|---|---|---|---|---|---|---|---|---|---|---|---|---|---|---|---|---|
| ggt | agt | gaa | aca | tca | tca | act | gtt | cta | gta | tgg | gca | atg | tcg | gag | ctt | 960 |
| Gly | Ser | Glu | Thr | Ser | Ser | Thr | Val | Leu | Val | Trp | Ala | Met | Ser | Glu | Leu | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| gtt | aag | aat | cca | caa | gtc | atg | cgt | aag | gcc | cag | tca | gag | gtg | agg | gat | 1008 |
| Val | Lys | Asn | Pro | Gln | Val | Met | Arg | Lys | Ala | Gln | Ser | Glu | Val | Arg | Asp | |
| | | | | 325 | | | | | 330 | | | | | 335 | | |

| | | | | | | | | | | | | | | | | |
|---|---|---|---|---|---|---|---|---|---|---|---|---|---|---|---|---|
| acc | ttc | aaa | gga | aac | aac | aag | ata | act | gaa | agt | gat | ttg | atc | aag | tta | 1056 |
| Thr | Phe | Lys | Gly | Asn | Asn | Lys | Ile | Thr | Glu | Ser | Asp | Leu | Ile | Lys | Leu | |
| | | | 340 | | | | | 345 | | | | | 350 | | | |

| | | | | | | | | | | | | | | | | |
|---|---|---|---|---|---|---|---|---|---|---|---|---|---|---|---|---|
| aga | tat | cta | caa | ctg | gtg | atc | aag | gag | act | tta | cgg | ttg | cat | gct | ccg | 1104 |
| Arg | Tyr | Leu | Gln | Leu | Val | Ile | Lys | Glu | Thr | Leu | Arg | Leu | His | Ala | Pro | |
| | | 355 | | | | | 360 | | | | | 365 | | | | |

| | | | | | | | | | | | | | | | | |
|---|---|---|---|---|---|---|---|---|---|---|---|---|---|---|---|---|
| gta | cca | ctc | ttg | ctc | cct | cga | gaa | tgc | cgt | gag | tca | tgt | cag | att | atg | 1152 |
| Val | Pro | Leu | Leu | Leu | Pro | Arg | Glu | Cys | Arg | Glu | Ser | Cys | Gln | Ile | Met | |
| 370 | | | | | 375 | | | | | 380 | | | | | | |

| | | | | | | | | | | | | | | | | |
|---|---|---|---|---|---|---|---|---|---|---|---|---|---|---|---|---|
| ggt | tac | gat | gtg | cta | aag | gga | acc | aag | gta | ttt | gtg | aat | gct | tgg | gca | 1200 |
| Gly | Tyr | Asp | Val | Leu | Lys | Gly | Thr | Lys | Val | Phe | Val | Asn | Ala | Trp | Ala | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| ata | gca | agg | gac | acg | gga | tta | tgg | tgt | gat | gga | gag | gaa | ttt | agg | cca | 1248 |
| Ile | Ala | Arg | Asp | Thr | Gly | Leu | Trp | Cys | Asp | Gly | Glu | Glu | Phe | Arg | Pro | |
| | | | | 405 | | | | | 410 | | | | | 415 | | |

| | | | | | | | | | | | | | | | | |
|---|---|---|---|---|---|---|---|---|---|---|---|---|---|---|---|---|
| gaa | agg | ttt | gaa | agt | agc | aat | att | gat | ttc | agg | ggt | aat | gac | ttt | gag | 1296 |
| Glu | Arg | Phe | Glu | Ser | Ser | Asn | Ile | Asp | Phe | Arg | Gly | Asn | Asp | Phe | Glu | |
| | | | 420 | | | | | 425 | | | | | 430 | | | |

| | | | | | | | | | | | | | | | | |
|---|---|---|---|---|---|---|---|---|---|---|---|---|---|---|---|---|
| ttc | aca | ccg | ttt | ggg | gca | ggc | agg | aga | gta | tgc | cct | ggc | atc | aca | ctt | 1344 |
| Phe | Thr | Pro | Phe | Gly | Ala | Gly | Arg | Arg | Val | Cys | Pro | Gly | Ile | Thr | Leu | |
| | | 435 | | | | | 440 | | | | | 445 | | | | |

| | | | | | | | | | | | | | | | | |
|---|---|---|---|---|---|---|---|---|---|---|---|---|---|---|---|---|
| gga | ctg | gcc | aac | cta | gaa | cta | gcg | ctt | gct | agc | ctt | ctt | tat | cat | ttt | 1392 |
| Gly | Leu | Ala | Asn | Leu | Glu | Leu | Ala | Leu | Ala | Ser | Leu | Leu | Tyr | His | Phe | |
| 450 | | | | | 455 | | | | | 460 | | | | | | |

| | | | | | | | | | | | | | | | | |
|---|---|---|---|---|---|---|---|---|---|---|---|---|---|---|---|---|
| gat | tgg | gat | ctg | ccc | aat | ggt | gcc | agg | ttg | gaa | gat | ctt | gat | atg | gca | 1440 |
| Asp | Trp | Asp | Leu | Pro | Asn | Gly | Ala | Arg | Leu | Glu | Asp | Leu | Asp | Met | Ala | |
| 465 | | | | | 470 | | | | | 475 | | | | | 480 | |

| | | | | | | | | | | | | | | | | |
|---|---|---|---|---|---|---|---|---|---|---|---|---|---|---|---|---|
| gag | gcc | ttt | ggt | ata | acg | tta | aaa | agg | aag | tcc | atg | ctc | tgg | ctc | aag | 1488 |
| Glu | Ala | Phe | Gly | Ile | Thr | Leu | Lys | Arg | Lys | Ser | Met | Leu | Trp | Leu | Lys | |
| | | | | 485 | | | | | 490 | | | | | 495 | | |

| | | | | | | | | | |
|---|---|---|---|---|---|---|---|---|---|
| gcc | aaa | cct | tac | aat | aat | ttt | ata | cca | aat | taa | 1521 |
| Ala | Lys | Pro | Tyr | Asn | Asn | Phe | Ile | Pro | Asn | | |
| | | | 500 | | | | | 505 | | | |

<210> SEQ ID NO 7
<211> LENGTH: 506
<212> TYPE: PRT
<213> ORGANISM: Vetiveria zizanoides

<400> SEQUENCE: 7

Met Asp Phe Leu Arg Ile Pro Phe Leu Val Ala Phe Val Phe Leu Ala
1               5                   10                  15

Val Leu Leu Arg Leu Ile Arg Ser Tyr Ile Thr Ser Ser Ala Leu Arg
            20                  25                  30

Leu Pro Pro Gly Pro Trp Gln Leu Pro Leu Ile Gly Ser Leu His His

```
                    35                  40                  45
Leu Leu Leu Ser Arg Phe Ser Asp Leu Pro His Arg Ala Leu Arg Glu
     50                  55                  60

Met Ser Gly Thr Tyr Gly Pro Leu Met Leu Leu Arg Phe Gly Ser Val
 65                  70                  75                  80

Pro Thr Leu Val Val Ser Ser Ala Glu Ala Arg Glu Val Met Arg
                     85                  90                  95

Thr His Asp Leu Ala Phe Cys Asp Arg His Leu Gly Val Thr Leu Asp
                100                 105                 110

Ile Val Thr Cys Gly Gly Lys Asp Ile Ile Cys Ser Pro Tyr Asn Ala
             115                 120                 125

His Trp Arg Glu Leu Arg Lys Leu Cys Met Val Glu Ile Leu Ser Gln
         130                 135                 140

Arg Arg Val Leu Ser Phe Arg Ser Ile Arg Glu Glu Val Ala Ser
145                 150                 155                 160

Leu Val Arg Ser Ile Ser Asp Glu Cys Gly Gly Gln Gln Pro Val
                165                 170                 175

Asn Leu Thr Glu Gly Ile Ser Arg Met Ile Asn Asp Val Ala Ala Arg
             180                 185                 190

Thr Val Gly Asp Arg Cys Lys Tyr Gln Asp Glu Tyr Met His Glu
         195                 200                 205

Leu Asp Glu Val Val Arg Leu Ala Gly Gly Phe Asn Leu Ala Asp Leu
 210                 215                 220

Tyr Pro Ser Ser Arg Leu Val Arg Arg Phe Ser Ala Ala Arg Asp
225                 230                 235                 240

Ala Arg Arg Cys Gln Arg Asn Met Tyr Arg Ile Ile Gln Ser Ile Ile
                245                 250                 255

Gln Glu Arg Glu Ala Met Pro Thr Pro Glu Arg Asp Glu Asp Leu
             260                 265                 270

Leu Gly Val Leu Leu Arg Leu Gln Arg Glu Gly Gly Leu Gln Phe Ala
         275                 280                 285

Leu Thr Asn Glu Ile Val Ser Thr Val Ile Tyr Asp Ile Phe Ser Ala
 290                 295                 300

Gly Ser Glu Thr Ser Ser Thr Val Leu Val Trp Ala Met Ser Glu Leu
305                 310                 315                 320

Val Lys Asn Pro Gln Val Met Arg Lys Ala Gln Ser Glu Val Arg Asp
                325                 330                 335

Thr Phe Lys Gly Asn Asn Lys Ile Thr Glu Ser Asp Leu Ile Lys Leu
             340                 345                 350

Arg Tyr Leu Gln Leu Val Ile Lys Glu Thr Leu Arg Leu His Ala Pro
         355                 360                 365

Val Pro Leu Leu Leu Pro Arg Glu Cys Arg Glu Ser Cys Gln Ile Met
 370                 375                 380

Gly Tyr Asp Val Leu Lys Gly Thr Lys Val Phe Val Asn Ala Trp Ala
385                 390                 395                 400

Ile Ala Arg Asp Thr Gly Leu Trp Cys Asp Gly Glu Phe Arg Pro
                405                 410                 415

Glu Arg Phe Glu Ser Ser Asn Ile Asp Phe Arg Gly Asn Asp Phe Glu
             420                 425                 430

Phe Thr Pro Phe Gly Ala Gly Arg Arg Val Cys Pro Gly Ile Thr Leu
         435                 440                 445

Gly Leu Ala Asn Leu Glu Leu Ala Leu Ala Ser Leu Leu Tyr His Phe
 450                 455                 460
```

Asp Trp Asp Leu Pro Asn Gly Ala Arg Leu Glu Asp Leu Asp Met Ala
465                 470                 475                 480

Glu Ala Phe Gly Ile Thr Leu Lys Arg Lys Ser Met Leu Trp Leu Lys
            485                 490                 495

Ala Lys Pro Tyr Asn Asn Phe Ile Pro Asn
            500                 505

<210> SEQ ID NO 8
<211> LENGTH: 1524
<212> TYPE: DNA
<213> ORGANISM: Artificial Sequence
<220> FEATURE:
<223> OTHER INFORMATION: VzCP8201-228093, optimized DNA, encoding for
      VzCP8201-12, including NdeI site at 5'end and polylinker at 3'end

<400> SEQUENCE: 8

```
atggcactgt tgttggctgt ttttttgggt ttgagctgtt tgttgctgtt gagcttgtgg     60
cgtctgatcc gcagctacat tacttccagc gcgctgcgcc tgccgccggg tccgtggcag    120
ctgcctctga ttggcagcct gcaccacttg ctgctgagcc gcttcagcga cttgccgcat    180
cgcgcgctga gagagatgag cggcacctac ggtccgctga tgctgctgcg tttcggtagc    240
gtcccgaccc tggttgtctc tagcgcggaa gcggctcgtg aagtcatgcg tacccacgat    300
ctggcgtttt gcgatcgtca cctgggtgtg acgctggaca tcgtaacctg tggtggcaaa    360
gacatcatct gcagcccata caacgctcat tggcgtgagc tgcgcaagct gtgcatggtt    420
gaaatcctga ccagcgccg tgtgctgagc ttccgttcga ttcgtgaaga agaggtcgcg    480
agcctggtgc gttccattag cgatgagtgt ggtggcggcc agcaaccagt taacctgacc    540
gaaggcatct ctcgcatgat taatgacgtc gccgcacgta ccgtggtcgg tgaccgctgc    600
aagtaccaag acgagtacat gcatgaactg gacgaagttg ttcgtctggc gggtggcttc    660
aacctggccg atctgtatcc gagctcacgt ctggttcgtc gttttccgc agctgcgcgt    720
gacgcgcgtc gctgtcagcg taacatgtac cgcattattc aatctatcat ccaagagcgt    780
gaggcaatgc cgacgcctga cgcgacgaa gaagatcttc tgggtgtcct gctgcgtctg    840
cagcgcgagg gtggtctgca gtttgcgctg acgaacgaaa ttgtttcgac cgtgatttac    900
gatatcttca cgccggtag cgaaacctcc agcacggtgt tggtgtgggc aatgtctgaa    960
ctggtcaaaa atccgcaagt gatgcgcaaa gcgcaaagcg aagttcgtga cactttcaaa   1020
ggtaacaata agattaccga gcgacctg attaagctgc gctatctgca actggttatc   1080
aaagaaaccc tgcgcctgca cgcaccggtg ccgctgctgc tgccgcgtga gtgccgtgaa   1140
tcctgtcaga tcatgggcta tgacgttctg aagggtacga agtgttcgt taatgcctgg   1200
gcgattgcac gtgatacggg tctgtggtgc gacggcgaag agttccgtcc ggagcgtttc   1260
gagtccagca atatcgattt tcgtggtaat gattttgagt tcacgccgtt cggtgcgggc   1320
cgtcgtgtct gcccaggcat caccctgggc ctggccaact agaactggc cctcgcgagc   1380
ttgttatatc actttgactg ggatctgccg aacggcgcgc gcctggaaga tctggacatg   1440
gccgaggcat ttggtatcac gctgaagcgc aagagcatgc tgtggctgaa agcaaaaccg   1500
tacaataatt ttattccgaa ctaa                                          1524
```

<210> SEQ ID NO 9
<211> LENGTH: 1524
<212> TYPE: DNA
<213> ORGANISM: Artificial Sequence
<220> FEATURE:

<223> OTHER INFORMATION: VzCP8201-228092, optimized DNA sequence
       encoding for VzCP8201-12

```
                    275                 280                 285
gcg ctg acg aac gaa att gtt tcg acc gtg att tac gat atc ttc agc     912
Ala Leu Thr Asn Glu Ile Val Ser Thr Val Ile Tyr Asp Ile Phe Ser
    290                 295                 300 gcc ggt agc gaa acc tcc agc acg gtg ttg gtg tgg gca atg tct gaa     960
Ala Gly Ser Glu Thr Ser Ser Thr Val Leu Val Trp Ala Met Ser Glu
305                 310                 315                 320 ctg gtc aaa aat ccg caa gtg atg cgc aaa gcg caa agc gaa gtt cgt    1008
Leu Val Lys Asn Pro Gln Val Met Arg Lys Ala Gln Ser Glu Val Arg
                325                 330                 335 gac act ttc aaa ggt aac aat aag att acc gag agc gac ctg att aag    1056
Asp Thr Phe Lys Gly Asn Asn Lys Ile Thr Glu Ser Asp Leu Ile Lys
            340                 345                 350 ctg cgc tat ctg caa ctg gtt atc aaa gaa acc ctg cgc ctg cac gca    1104
Leu Arg Tyr Leu Gln Leu Val Ile Lys Glu Thr Leu Arg Leu His Ala
        355                 360                 365 ccg gtg ccg ctg ctg ctg ccg cgt gag tgc cgt gaa tcc tgt cag atc    1152
Pro Val Pro Leu Leu Leu Pro Arg Glu Cys Arg Glu Ser Cys Gln Ile
    370                 375                 380 atg ggc tat gac gtt ctg aag ggt acg aaa gtg ttc gtt aat gcc tgg    1200
Met Gly Tyr Asp Val Leu Lys Gly Thr Lys Val Phe Val Asn Ala Trp
385                 390                 395                 400 gcg att gca cgt gat acg ggt ctg tgg tgc gac ggc gaa gag ttc cgt    1248
Ala Ile Ala Arg Asp Thr Gly Leu Trp Cys Asp Gly Glu Glu Phe Arg
                405                 410                 415 ccg gag cgt ttc gag tcc agc aat atc gat ttt cgt ggt aat gat ttt    1296
Pro Glu Arg Phe Glu Ser Ser Asn Ile Asp Phe Arg Gly Asn Asp Phe
            420                 425                 430 gag ttc acg ccg ttc ggt gcg ggc cgt cgt gtc tgc cca ggc atc acc    1344
Glu Phe Thr Pro Phe Gly Ala Gly Arg Arg Val Cys Pro Gly Ile Thr
        435                 440                 445 ctg ggc ctg gcc aac tta gaa ctg gcc ctc gcg agc ttg tta tat cac    1392
Leu Gly Leu Ala Asn Leu Glu Leu Ala Leu Ala Ser Leu Leu Tyr His
    450                 455                 460 ttt gac tgg gat ctg ccg aac ggc gcg cgc ctg gaa gat ctg gac atg    1440
Phe Asp Trp Asp Leu Pro Asn Gly Ala Arg Leu Glu Asp Leu Asp Met
465                 470                 475                 480 gcc gag gca ttt ggt atc acg ctg aag cgc aag agc atg ctg tgg ctg    1488
Ala Glu Ala Phe Gly Ile Thr Leu Lys Arg Lys Ser Met Leu Trp Leu
                485                 490                 495 aaa gca aaa ccg tac aat aat ttt att ccg aac taa                    1524
Lys Ala Lys Pro Tyr Asn Asn Phe Ile Pro Asn
                500                 505

<210> SEQ ID NO 10
<211> LENGTH: 507
<212> TYPE: PRT
<213> ORGANISM: Artificial Sequence
<220> FEATURE:
<223> OTHER INFORMATION: Synthetic Construct

<400> SEQUENCE: 10

Met Ala Leu Leu Leu Ala Val Phe Leu Gly Leu Ser Cys Leu Leu Leu
1               5                   10                  15

Leu Ser Leu Trp Arg Leu Ile Arg Ser Tyr Ile Thr Ser Ser Ala Leu
            20                  25                  30

Arg Leu Pro Pro Gly Pro Trp Gln Leu Pro Leu Ile Gly Ser Leu His
        35                  40                  45

His Leu Leu Leu Ser Arg Phe Ser Asp Leu Pro His Arg Ala Leu Arg
    50                  55                  60
```

```
Glu Met Ser Gly Thr Tyr Gly Pro Leu Met Leu Arg Phe Gly Ser
 65                  70                  75                  80

Val Pro Thr Leu Val Ser Ser Ala Glu Ala Ala Arg Glu Val Met
                 85                  90                  95

Arg Thr His Asp Leu Ala Phe Cys Asp Arg His Leu Gly Val Thr Leu
                100                 105                 110

Asp Ile Val Thr Cys Gly Gly Lys Asp Ile Ile Cys Ser Pro Tyr Asn
                115                 120                 125

Ala His Trp Arg Glu Leu Arg Lys Leu Cys Met Val Glu Ile Leu Ser
    130                 135                 140

Gln Arg Arg Val Leu Ser Phe Arg Ser Ile Arg Glu Glu Val Ala
145                 150                 155                 160

Ser Leu Val Arg Ser Ile Ser Asp Glu Cys Gly Gly Gln Gln Pro
                165                 170                 175

Val Asn Leu Thr Glu Gly Ile Ser Arg Met Ile Asn Asp Val Ala Ala
                180                 185                 190

Arg Thr Val Val Gly Asp Arg Cys Lys Tyr Gln Asp Glu Tyr Met His
                195                 200                 205

Glu Leu Asp Glu Val Val Arg Leu Ala Gly Gly Phe Asn Leu Ala Asp
210                 215                 220

Leu Tyr Pro Ser Ser Arg Leu Val Arg Arg Phe Ser Ala Ala Ala Arg
225                 230                 235                 240

Asp Ala Arg Arg Cys Gln Arg Asn Met Tyr Arg Ile Ile Gln Ser Ile
                245                 250                 255

Ile Gln Glu Arg Glu Ala Met Pro Thr Pro Glu Arg Asp Glu Asp
                260                 265                 270

Leu Leu Gly Val Leu Leu Arg Leu Gln Arg Glu Gly Gly Leu Gln Phe
                275                 280                 285

Ala Leu Thr Asn Glu Ile Val Ser Thr Val Ile Tyr Asp Ile Phe Ser
    290                 295                 300

Ala Gly Ser Glu Thr Ser Ser Thr Val Leu Val Trp Ala Met Ser Glu
305                 310                 315                 320

Leu Val Lys Asn Pro Gln Val Met Arg Lys Ala Gln Ser Glu Val Arg
                325                 330                 335

Asp Thr Phe Lys Gly Asn Asn Lys Ile Thr Glu Ser Asp Leu Ile Lys
                340                 345                 350

Leu Arg Tyr Leu Gln Leu Val Ile Lys Glu Thr Leu Arg Leu His Ala
                355                 360                 365

Pro Val Pro Leu Leu Leu Pro Arg Glu Cys Arg Glu Ser Cys Gln Ile
                370                 375                 380

Met Gly Tyr Asp Val Leu Lys Gly Thr Lys Val Phe Val Asn Ala Trp
385                 390                 395                 400

Ala Ile Ala Arg Asp Thr Gly Leu Trp Cys Asp Gly Glu Glu Phe Arg
                405                 410                 415

Pro Glu Arg Phe Glu Ser Ser Asn Ile Asp Phe Arg Gly Asn Asp Phe
                420                 425                 430

Glu Phe Thr Pro Phe Gly Ala Gly Arg Arg Val Cys Pro Gly Ile Thr
                435                 440                 445

Leu Gly Leu Ala Asn Leu Glu Leu Ala Leu Ala Ser Leu Leu Tyr His
                450                 455                 460

Phe Asp Trp Asp Leu Pro Asn Gly Ala Arg Leu Glu Asp Leu Asp Met
465                 470                 475                 480
```

Ala Glu Ala Phe Gly Ile Thr Leu Lys Arg Lys Ser Met Leu Trp Leu
            485                 490                 495

Lys Ala Lys Pro Tyr Asn Asn Phe Ile Pro Asn
        500                 505

<210> SEQ ID NO 11
<211> LENGTH: 1717
<212> TYPE: DNA
<213> ORGANISM: Vetiveria zizanoides
<220> FEATURE:
<221> NAME/KEY: misc_feature
<223> OTHER INFORMATION: VzTrspt7_contig_7186, full length transcript
      containing 5' and 3 non-translated sequences

<400> SEQUENCE: 11
tggtcacgta gttgcctgca aaattgtccc atcccctggc aaaaaatgga cattatcagt      60
atcccgtttc ttgtagcctt cgtcttcctc ctcgccgtcc ttctcaggct catccggagc     120
tacatcacat cctcagcgct tcgcctgcca ccggggccat ggcagctgcc gctcatcggc     180
agcctgcacc acctcctgct gtcgcgcttc agcgacctgc ctcaccgggc gctgcgcgag     240
atgtccggcg cctacggtcc cctcatgctc ctccgcttcg gcgccgtgcc cacgctggtg     300
gcctcctccg ccgaggctgc ccgggaggtg atgaggaccc acgacctcgc cttctgcaac     360
cgccatctcg gcgtcacctt cgacaccatc acctgcggcg gcaaggacat catcggctcc     420
ccctacaacg cccagtggcg cgagctccgc aagctgtgca tgctcgagat cttcagccag     480
cggcgcgtgc tctcgttccg gagcatccgg gaagaggagg tggcgaacct cgtccgctcc     540
atctccgacg agtgcggcgg tggccggcag cccgtcaacc tcaccgaggg gatctgccgc     600
atgatcaacg acgtcgccgc gcgcacggcc gtcggtgacc ggtgcaggta ccgggacgag     660
tacatgcacg agctggacga agtggtgcgg ctggtgagcg ggttcaacct ggcggacctg     720
tacccgtcct cgtggctggt gcggcggttc agcgccgccg cgagggacgc gaggaggtgc     780
cagaggaaca tgtaccgcat catccagagc atcatcgagg aacgtgaagc catgccgacg     840
ccagagcgag acgaggacct tctgggtgtc ctcctgaggc tgcagaagga aggtggcctg     900
cagttcgccc tcaccaacga gattgtcagc accgtcattt tcgacatttt ctctgctggg     960
agtgagacat catcaaccgt tctagtatgg gcaatgtcag aacttgttaa gaacccgcag    1020
gtcatgcata aggcccggtc agaggtgagg gagaccttca gaggacaaga caagataagt    1080
gaagatgatc tggtcaagtt aagatatcta caactggtga taaaggagac tttacggctg    1140
catgctccag taccactctt gctccctcga gaatgtcgtg agtcatgtca ggttatgggt    1200
tacgacgtgc caaagggaac caaggtgttt gtgaatgttt gggcaatagc aagggacgtg    1260
aaactgtggc atgatgcgga ggtattcaaa ccagaaagat tgaaagtag cagtatcgat    1320 tttaggggta atgactttga gttcactcca ttcggggcag gcaggagaat gtgccctggc    1380
gttacactcg gactggccaa cctagagctg gcacttgcta gccttcttta ccattttgat    1440
tgggatctgc cggatggcat cgggttagaa gaactcgata tgtcagagac ctctggtata    1500
acgttaagaa agaagtccat gctctggctc aaggctagac cttacaataa ttttataccg    1560
aattaatcag gtgctctgtg ttgtgaacta tgtcctgttc ctgttactac ttaatttgta    1620
ccagaaagag tgtgattata attgtcatat caatctgtac tgcatgataa taaatatatg    1680
catagtttgt atatactatg cttgtgttat actgttt                             1717

<210> SEQ ID NO 12
<211> LENGTH: 1521

<212> TYPE: DNA
<213> ORGANISM: Vetiveria zizanoides
<220> FEATURE:
<221> NAME/KEY: misc_feature
<223> OTHER INFORMATION: VzTrspt7_contig_7186 wild type cDNA (open read frame only)
<220> FEATURE:
<221> NAME/KEY: CDS
<222> LOCATION: (1)..(1521)

<400> SEQUENCE: 12

```
atg gac att atc agt atc ccg ttt ctt gta gcc ttc gtc ttc ctc ctc      48
Met Asp Ile Ile Ser Ile Pro Phe Leu Val Ala Phe Val Phe Leu Leu
1               5                   10                  15 gcc gtc ctt ctc agg ctc atc cgg agc tac atc aca tcc tca gcg ctt      96
Ala Val Leu Leu Arg Leu Ile Arg Ser Tyr Ile Thr Ser Ser Ala Leu
            20                  25                  30 cgc ctg cca ccg ggg cca tgg cag ctg ccg ctc atc ggc agc ctg cac     144
Arg Leu Pro Pro Gly Pro Trp Gln Leu Pro Leu Ile Gly Ser Leu His
        35                  40                  45 cac ctc ctg ctg tcg cgc ttc agc gac ctg cct cac cgg gcg ctg cgc     192
His Leu Leu Leu Ser Arg Phe Ser Asp Leu Pro His Arg Ala Leu Arg
50                  55                  60 gag atg tcc ggc gcc tac ggt ccc ctc atg ctc ctc cgc ttc ggc gcc     240
Glu Met Ser Gly Ala Tyr Gly Pro Leu Met Leu Leu Arg Phe Gly Ala
65                  70                  75                  80 gtg ccc acg ctg gtg gcc tcc tcc gcc gag gct gcc cgg gag gtg atg     288
Val Pro Thr Leu Val Ala Ser Ser Ala Glu Ala Ala Arg Glu Val Met
                85                  90                  95 agg acc cac gac ctc gcc ttc tgc aac cgc cat ctc ggc gtc acc ttc     336
Arg Thr His Asp Leu Ala Phe Cys Asn Arg His Leu Gly Val Thr Phe
            100                 105                 110 gac acc atc acc tgc ggc ggc aag gac atc atc ggc tcc ccc tac aac     384
Asp Thr Ile Thr Cys Gly Gly Lys Asp Ile Ile Gly Ser Pro Tyr Asn
        115                 120                 125 gcc cag tgg cgc gag ctc cgc aag ctg tgc atg ctc gag atc ttc agc     432
Ala Gln Trp Arg Glu Leu Arg Lys Leu Cys Met Leu Glu Ile Phe Ser
    130                 135                 140 cag cgg cgc gtg ctc tcg ttc cgg agc atc cgg gaa gag gag gtg gcg     480
Gln Arg Arg Val Leu Ser Phe Arg Ser Ile Arg Glu Glu Glu Val Ala
145                 150                 155                 160 aac ctc gtc cgc tcc atc tcc gac gag tgc ggc ggt ggc cgg cag ccc     528
Asn Leu Val Arg Ser Ile Ser Asp Glu Cys Gly Gly Gly Arg Gln Pro
                165                 170                 175 gtc aac ctc acc gag ggg atc tgc cgc atg atc aac gac gtc gcc gcg     576
Val Asn Leu Thr Glu Gly Ile Cys Arg Met Ile Asn Asp Val Ala Ala
            180                 185                 190 cgc acg gcc gtc ggt gac cgg tgc agg tac cgg gac gag tac atg cac     624
Arg Thr Ala Val Gly Asp Arg Cys Arg Tyr Arg Asp Glu Tyr Met His
        195                 200                 205 gag ctg gac gaa gtg gtg cgg ctg gtg agc ggg ttc aac ctg gcg gac     672
Glu Leu Asp Glu Val Val Arg Leu Val Ser Gly Phe Asn Leu Ala Asp
    210                 215                 220 ctg tac ccg tcc tcg tgg ctg gtg cgg cgg ttc agc gcc gcc gcg agg     720
Leu Tyr Pro Ser Ser Trp Leu Val Arg Arg Phe Ser Ala Ala Ala Arg
225                 230                 235                 240 gac gcg agg agg tgc cag agg aac atg tac cgc atc atc cag agc atc     768
Asp Ala Arg Arg Cys Gln Arg Asn Met Tyr Arg Ile Ile Gln Ser Ile
                245                 250                 255 atc gag gaa cgt gaa gcc atg ccg acg cca gag cga gac gag gac ctt     816
Ile Glu Glu Arg Glu Ala Met Pro Thr Pro Glu Arg Asp Glu Asp Leu
            260                 265                 270
```

| | | | | | | | | | | | | | | | |
|---|---|---|---|---|---|---|---|---|---|---|---|---|---|---|---|
| ctg | ggt | gtc | ctc | ctg | agg | ctg | cag | aag | gaa | ggt | ggc | ctg | cag | ttc | gcc | 864 |
| Leu | Gly | Val | Leu | Leu | Arg | Leu | Gln | Lys | Glu | Gly | Gly | Leu | Gln | Phe | Ala |
| | | 275 | | | | | 280 | | | | | 285 | | | | ctc acc aac gag att gtc agc acc gtc att ttc gac att ttc tct gct    912
Leu Thr Asn Glu Ile Val Ser Thr Val Ile Phe Asp Ile Phe Ser Ala
    290             295                 300 ggg agt gag aca tca tca acc gtt cta gta tgg gca atg tca gaa ctt    960
Gly Ser Glu Thr Ser Ser Thr Val Leu Val Trp Ala Met Ser Glu Leu
305             310                 315                 320 gtt aag aac ccg cag gtc atg cat aag gcc cgg tca gag gtg agg gag   1008
Val Lys Asn Pro Gln Val Met His Lys Ala Arg Ser Glu Val Arg Glu
                325                 330                 335 acc ttc aga gga caa gac aag ata agt gaa gat gat ctg gtc aag tta   1056
Thr Phe Arg Gly Gln Asp Lys Ile Ser Glu Asp Asp Leu Val Lys Leu
            340                 345                 350 aga tat cta caa ctg gtg ata aag gag act tta cgg ctg cat gct cca   1104
Arg Tyr Leu Gln Leu Val Ile Lys Glu Thr Leu Arg Leu His Ala Pro
        355                 360                 365 gta cca ctc ttg ctc cct cga gaa tgt cgt gag tca tgt cag gtt atg   1152
Val Pro Leu Leu Leu Pro Arg Glu Cys Arg Glu Ser Cys Gln Val Met
    370                 375                 380 ggt tac gac gtg cca aag gga acc aag gtg ttt gtg aat gtt tgg gca   1200
Gly Tyr Asp Val Pro Lys Gly Thr Lys Val Phe Val Asn Val Trp Ala
385                 390                 395                 400 ata gca agg gac gtg aaa ctg tgg cat gat gcg gag gta ttc aaa cca   1248
Ile Ala Arg Asp Val Lys Leu Trp His Asp Ala Glu Val Phe Lys Pro
                405                 410                 415 gaa aga ttt gaa agt agc agt atc gat ttt agg ggt aat gac ttt gag   1296
Glu Arg Phe Glu Ser Ser Ser Ile Asp Phe Arg Gly Asn Asp Phe Glu
            420                 425                 430 ttc act cca ttc ggg gca ggc agg aga atg tgc cct ggc gtt aca ctc   1344
Phe Thr Pro Phe Gly Ala Gly Arg Arg Met Cys Pro Gly Val Thr Leu
        435                 440                 445 gga ctg gcc aac cta gag ctg gca ctt gct agc ctt ctt tac cat ttt   1392
Gly Leu Ala Asn Leu Glu Leu Ala Leu Ala Ser Leu Leu Tyr His Phe
    450                 455                 460 gat tgg gat ctg ccg gat ggc atc ggg tta gaa gaa ctc gat atg tca   1440
Asp Trp Asp Leu Pro Asp Gly Ile Gly Leu Glu Glu Leu Asp Met Ser
465                 470                 475                 480 gag acc tct ggt ata acg tta aga aag aag tcc atg ctc tgg ctc aag   1488
Glu Thr Ser Gly Ile Thr Leu Arg Lys Lys Ser Met Leu Trp Leu Lys
                485                 490                 495 gct aga cct tac aat aat ttt ata cca aat taa                       1521
Ala Arg Pro Tyr Asn Asn Phe Ile Pro Asn
            500                 505

<210> SEQ ID NO 13
<211> LENGTH: 506
<212> TYPE: PRT
<213> ORGANISM: Vetiveria zizanoides

<400> SEQUENCE: 13

Met Asp Ile Ile Ser Ile Pro Phe Leu Val Ala Phe Val Phe Leu Leu
1               5                   10                  15

Ala Val Leu Leu Arg Leu Ile Arg Ser Tyr Ile Thr Ser Ser Ala Leu
            20                  25                  30

Arg Leu Pro Pro Gly Pro Trp Gln Leu Pro Leu Ile Gly Ser Leu His
        35                  40                  45

His Leu Leu Leu Ser Arg Phe Ser Asp Leu Pro His Arg Ala Leu Arg

```
            50                  55                  60
Glu Met Ser Gly Ala Tyr Gly Pro Leu Met Leu Leu Arg Phe Gly Ala
 65                  70                  75                  80

Val Pro Thr Leu Val Ala Ser Ser Ala Glu Ala Ala Arg Glu Val Met
                 85                  90                  95

Arg Thr His Asp Leu Ala Phe Cys Asn Arg His Leu Gly Val Thr Phe
                100                 105                 110

Asp Thr Ile Thr Cys Gly Gly Lys Asp Ile Ile Gly Ser Pro Tyr Asn
                115                 120                 125

Ala Gln Trp Arg Glu Leu Arg Lys Leu Cys Met Leu Glu Ile Phe Ser
130                 135                 140

Gln Arg Arg Val Leu Ser Phe Arg Ser Ile Arg Glu Glu Val Ala
145                 150                 155                 160

Asn Leu Val Arg Ser Ile Ser Asp Glu Cys Gly Gly Arg Gln Pro
                165                 170                 175

Val Asn Leu Thr Glu Gly Ile Cys Arg Met Ile Asn Asp Val Ala Ala
                180                 185                 190

Arg Thr Ala Val Gly Asp Arg Cys Arg Tyr Arg Asp Glu Tyr Met His
                195                 200                 205

Glu Leu Asp Glu Val Val Arg Leu Val Ser Gly Phe Asn Leu Ala Asp
210                 215                 220

Leu Tyr Pro Ser Ser Trp Leu Val Arg Arg Phe Ser Ala Ala Ala Arg
225                 230                 235                 240

Asp Ala Arg Arg Cys Gln Arg Asn Met Tyr Arg Ile Ile Gln Ser Ile
                245                 250                 255

Ile Glu Glu Arg Glu Ala Met Pro Thr Pro Glu Arg Asp Glu Asp Leu
                260                 265                 270

Leu Gly Val Leu Leu Arg Leu Gln Lys Glu Gly Gly Leu Gln Phe Ala
                275                 280                 285

Leu Thr Asn Glu Ile Val Ser Thr Val Ile Phe Asp Ile Phe Ser Ala
                290                 295                 300

Gly Ser Glu Thr Ser Ser Thr Val Leu Val Trp Ala Met Ser Glu Leu
305                 310                 315                 320

Val Lys Asn Pro Gln Val Met His Lys Ala Arg Ser Glu Val Arg Glu
                325                 330                 335

Thr Phe Arg Gly Gln Asp Lys Ile Ser Glu Asp Asp Leu Val Lys Leu
                340                 345                 350

Arg Tyr Leu Gln Leu Val Ile Lys Glu Thr Leu Arg Leu His Ala Pro
                355                 360                 365

Val Pro Leu Leu Leu Pro Arg Glu Cys Arg Glu Ser Cys Gln Val Met
                370                 375                 380

Gly Tyr Asp Val Pro Lys Gly Thr Lys Val Phe Val Asn Val Trp Ala
385                 390                 395                 400

Ile Ala Arg Asp Val Lys Leu Trp His Asp Ala Glu Val Phe Lys Pro
                405                 410                 415

Glu Arg Phe Glu Ser Ser Ser Ile Asp Phe Arg Gly Asn Asp Phe Glu
                420                 425                 430

Phe Thr Pro Phe Gly Ala Gly Arg Arg Met Cys Pro Gly Val Thr Leu
                435                 440                 445

Gly Leu Ala Asn Leu Glu Leu Ala Leu Ala Ser Leu Leu Tyr His Phe
                450                 455                 460

Asp Trp Asp Leu Pro Asp Gly Ile Gly Leu Glu Glu Leu Asp Met Ser
465                 470                 475                 480
```

```
Glu Thr Ser Gly Ile Thr Leu Arg Lys Lys Ser Met Leu Trp Leu Lys
                485                 490                 495
Ala Arg Pro Tyr Asn Asn Phe Ile Pro Asn
            500                 505

<210> SEQ ID NO 14
<211> LENGTH: 1521
<212> TYPE: DNA
<213> ORGANISM: Artificial Sequence
<220> FEATURE:
<223> OTHER INFORMATION: Optimized cDNA of N-terminal variant of
      VzCP7186
<220> FEATURE:
<221> NAME/KEY: misc_feature
<223> OTHER INFORMATION: Optimized cDNA encoding for an N-terminal
      variant of VzCP7186
<220> FEATURE:
<221> NAME/KEY: CDS
<222> LOCATION: (1)..(1521)

<400> SEQUENCE: 14 atg gcg ttg ctg ttg gct gtt ttt ctg ggt ttg tcg tgt ttg ttg ttg      48
Met Ala Leu Leu Leu Ala Val Phe Leu Gly Leu Ser Cys Leu Leu Leu
1               5                   10                  15 ttg tca ctg tgg cgc ttg atc cgt agc tat atc act agc agc gcg ttg      96
Leu Ser Leu Trp Arg Leu Ile Arg Ser Tyr Ile Thr Ser Ser Ala Leu
            20                  25                  30 cgt ctg cct ccg ggt cct tgg cag ctg ccg ctg att ggt agc ctg cac     144
Arg Leu Pro Pro Gly Pro Trp Gln Leu Pro Leu Ile Gly Ser Leu His
        35                  40                  45 cat ttg ctg ctg agc cgt ttc agc gat ctg ccg cac cgt gcg ttg cgc     192
His Leu Leu Leu Ser Arg Phe Ser Asp Leu Pro His Arg Ala Leu Arg
    50                  55                  60 gag atg agc ggt gcc tat ggc ccg ctg atg ctg tta cgt ttt ggt gca     240
Glu Met Ser Gly Ala Tyr Gly Pro Leu Met Leu Leu Arg Phe Gly Ala
65                  70                  75                  80 gtg ccg acc ctg gtg gca agc agc gca gaa gca gcg cgc gag gtg atg     288
Val Pro Thr Leu Val Ala Ser Ser Ala Glu Ala Ala Arg Glu Val Met
                85                  90                  95 cgc acc cat gac ctg gcc ttc tgc aat cgt cac ctg ggt gtc acc ttt     336
Arg Thr His Asp Leu Ala Phe Cys Asn Arg His Leu Gly Val Thr Phe
            100                 105                 110 gac acc atc acc tgt ggt ggc aaa gac att atc ggt agc cca tat aac     384
Asp Thr Ile Thr Cys Gly Gly Lys Asp Ile Ile Gly Ser Pro Tyr Asn
        115                 120                 125 gca caa tgg cgc gag ctg cgc aag ctg tgt atg ctg gag atc ttc agc     432
Ala Gln Trp Arg Glu Leu Arg Lys Leu Cys Met Leu Glu Ile Phe Ser
    130                 135                 140 caa cgt cgt gtg ctg agc ttc cgt agc att cgc gag gag gaa gtg gcc     480
Gln Arg Arg Val Leu Ser Phe Arg Ser Ile Arg Glu Glu Glu Val Ala
145                 150                 155                 160 aac ctg gtc cgc agc att agc gac gaa tgc ggt ggt ggc cgt caa ccg     528
Asn Leu Val Arg Ser Ile Ser Asp Glu Cys Gly Gly Gly Arg Gln Pro
                165                 170                 175 gtc aat ctg acc gag ggt atc tgt cgc atg atc aac gac gtg gct gcg     576
Val Asn Leu Thr Glu Gly Ile Cys Arg Met Ile Asn Asp Val Ala Ala
            180                 185                 190 cgt act gca gtc ggc gac cgt tgc cgt tac cgt gat gag tac atg cac     624
Arg Thr Ala Val Gly Asp Arg Cys Arg Tyr Arg Asp Glu Tyr Met His
        195                 200                 205 gaa ctg gat gaa gtt gtc cgc ctg gtt agc ggc ttc aac ctg gcg gat     672
Glu Leu Asp Glu Val Val Arg Leu Val Ser Gly Phe Asn Leu Ala Asp
```

```
                210                 215                 220
ctg tac ccg tcc tct tgg ctg gtt cgt cgt ttc tcg gca gct gct cgt       720
Leu Tyr Pro Ser Ser Trp Leu Val Arg Arg Phe Ser Ala Ala Ala Arg
225                 230                 235                 240 gac gcg cgc aga tgc cag cgt aat atg tat cgt atc att cag agc att       768
Asp Ala Arg Arg Cys Gln Arg Asn Met Tyr Arg Ile Ile Gln Ser Ile
                245                 250                 255 att gaa gaa cgt gag gca atg ccg acg ccg gaa cgt gac gag gat ttg       816
Ile Glu Glu Arg Glu Ala Met Pro Thr Pro Glu Arg Asp Glu Asp Leu
            260                 265                 270 ctg ggt gtg ctg ctg cgc ctg cag aag gag ggt ggc ttg cag ttc gcg       864
Leu Gly Val Leu Leu Arg Leu Gln Lys Glu Gly Gly Leu Gln Phe Ala
        275                 280                 285 ctg acc aac gaa atc gtc agc acg gtt atc ttt gac atc ttt tct gcg       912
Leu Thr Asn Glu Ile Val Ser Thr Val Ile Phe Asp Ile Phe Ser Ala
    290                 295                 300 ggt agc gag act agc agc acg gtg ctg gtc tgg gcc atg agc gaa ctg       960
Gly Ser Glu Thr Ser Ser Thr Val Leu Val Trp Ala Met Ser Glu Leu
305                 310                 315                 320 gtt aaa aat cct caa gtt atg cat aag gca cgc tct gag gtg cgc gaa      1008
Val Lys Asn Pro Gln Val Met His Lys Ala Arg Ser Glu Val Arg Glu
                325                 330                 335 acg ttt cgt ggc caa gac aaa atc tcc gag gac gat ctc gtc aag ctg      1056
Thr Phe Arg Gly Gln Asp Lys Ile Ser Glu Asp Asp Leu Val Lys Leu
                340                 345                 350 cgt tat ttg caa ctt gtt att aag gaa acc ctg cgt ctg cat gcg ccg      1104
Arg Tyr Leu Gln Leu Val Ile Lys Glu Thr Leu Arg Leu His Ala Pro
            355                 360                 365 gtt ccg tta ctg ctg cca cgc gag tgt cgt gag agc tgc caa gtg atg      1152
Val Pro Leu Leu Leu Pro Arg Glu Cys Arg Glu Ser Cys Gln Val Met
        370                 375                 380 ggt tac gat gtg cca aaa ggc acc aaa gtg ttc gtt aac gtc tgg gcg      1200
Gly Tyr Asp Val Pro Lys Gly Thr Lys Val Phe Val Asn Val Trp Ala
385                 390                 395                 400 att gcc cgc gac gtc aaa ctg tgg cac gat gca gag gtc ttt aaa ccg      1248
Ile Ala Arg Asp Val Lys Leu Trp His Asp Ala Glu Val Phe Lys Pro
                405                 410                 415 gag cgt ttc gag agc tct agc atc gat ttt cgt ggc aat gat ttc gag      1296
Glu Arg Phe Glu Ser Ser Ser Ile Asp Phe Arg Gly Asn Asp Phe Glu
                420                 425                 430 ttc acg ccg ttt ggc gct ggt cgt cgt atg tgc ccg ggt gtc acc ctg      1344
Phe Thr Pro Phe Gly Ala Gly Arg Arg Met Cys Pro Gly Val Thr Leu
            435                 440                 445 ggt ctg gcc aat ctg gaa ctg gcc ttg gcg tcc ctt ctg tac cac ttc      1392
Gly Leu Ala Asn Leu Glu Leu Ala Leu Ala Ser Leu Leu Tyr His Phe
        450                 455                 460 gat tgg gat ctc ccg gac ggc atc ggt ctg gaa gaa ctg gac atg agc      1440
Asp Trp Asp Leu Pro Asp Gly Ile Gly Leu Glu Glu Leu Asp Met Ser
465                 470                 475                 480 gaa acc tcc ggt atc acg ctg cgt aaa aag agc atg ctg tgg ctg aag      1488
Glu Thr Ser Gly Ile Thr Leu Arg Lys Lys Ser Met Leu Trp Leu Lys
                485                 490                 495 gcg cgt ccg tac aat aac ttt att ccg aac taa                           1521
Ala Arg Pro Tyr Asn Asn Phe Ile Pro Asn
                500                 505

<210> SEQ ID NO 15
<211> LENGTH: 506
<212> TYPE: PRT
<213> ORGANISM: Artificial Sequence
```

<220> FEATURE:
<223> OTHER INFORMATION: Synthetic Construct

<400> SEQUENCE: 15

Met Ala Leu Leu Leu Ala Val Phe Leu Gly Leu Ser Cys Leu Leu Leu
1               5                   10                  15

Leu Ser Leu Trp Arg Leu Ile Arg Ser Tyr Ile Thr Ser Ser Ala Leu
            20                  25                  30

Arg Leu Pro Pro Gly Pro Trp Gln Leu Pro Leu Ile Gly Ser Leu His
        35                  40                  45

His Leu Leu Leu Ser Arg Phe Ser Asp Leu Pro His Arg Ala Leu Arg
    50                  55                  60

Glu Met Ser Gly Ala Tyr Gly Pro Leu Met Leu Arg Phe Gly Ala
65                  70                  75                  80

Val Pro Thr Leu Val Ala Ser Ala Glu Ala Arg Glu Val Met
                85                  90                  95

Arg Thr His Asp Leu Ala Phe Cys Asn Arg His Leu Gly Val Thr Phe
            100                 105                 110

Asp Thr Ile Thr Cys Gly Gly Lys Asp Ile Ile Gly Ser Pro Tyr Asn
            115                 120                 125

Ala Gln Trp Arg Glu Leu Arg Lys Leu Cys Met Leu Glu Ile Phe Ser
    130                 135                 140

Gln Arg Arg Val Leu Ser Phe Arg Ser Ile Arg Glu Glu Glu Val Ala
145                 150                 155                 160

Asn Leu Val Arg Ser Ile Ser Asp Glu Cys Gly Gly Gly Arg Gln Pro
                165                 170                 175

Val Asn Leu Thr Glu Gly Ile Cys Arg Met Ile Asn Asp Val Ala Ala
            180                 185                 190

Arg Thr Ala Val Gly Asp Arg Cys Arg Tyr Arg Asp Tyr Met His
            195                 200                 205

Glu Leu Asp Glu Val Val Arg Leu Val Ser Gly Phe Asn Leu Ala Asp
    210                 215                 220

Leu Tyr Pro Ser Ser Trp Leu Val Arg Phe Ser Ala Ala Ala Arg
225                 230                 235                 240

Asp Ala Arg Arg Cys Gln Arg Asn Met Tyr Arg Ile Ile Gln Ser Ile
                245                 250                 255

Ile Glu Glu Arg Glu Ala Met Pro Thr Pro Glu Arg Asp Glu Asp Leu
            260                 265                 270

Leu Gly Val Leu Leu Arg Leu Gln Lys Glu Gly Gly Leu Gln Phe Ala
            275                 280                 285

Leu Thr Asn Glu Ile Val Ser Thr Val Ile Phe Asp Ile Phe Ser Ala
    290                 295                 300

Gly Ser Glu Thr Ser Ser Thr Val Leu Val Trp Ala Met Ser Glu Leu
305                 310                 315                 320

Val Lys Asn Pro Gln Val Met His Lys Ala Arg Ser Glu Val Arg Glu
                325                 330                 335

Thr Phe Arg Gly Gln Asp Lys Ile Ser Glu Asp Leu Val Lys Leu
            340                 345                 350

Arg Tyr Leu Gln Leu Val Ile Lys Glu Thr Leu Arg Leu His Ala Pro
            355                 360                 365

Val Pro Leu Leu Leu Pro Arg Glu Cys Arg Glu Ser Cys Gln Val Met
    370                 375                 380

Gly Tyr Asp Val Pro Lys Gly Thr Lys Val Phe Val Asn Val Trp Ala
385                 390                 395                 400

Ile Ala Arg Asp Val Lys Leu Trp His Asp Ala Glu Val Phe Lys Pro
                405                 410                 415

Glu Arg Phe Glu Ser Ser Ser Ile Asp Phe Arg Gly Asn Asp Phe Glu
            420                 425                 430

Phe Thr Pro Phe Gly Ala Gly Arg Arg Met Cys Pro Gly Val Thr Leu
        435                 440                 445

Gly Leu Ala Asn Leu Glu Leu Ala Leu Ala Ser Leu Leu Tyr His Phe
    450                 455                 460

Asp Trp Asp Leu Pro Asp Gly Ile Gly Leu Glu Glu Leu Asp Met Ser
465                 470                 475                 480

Glu Thr Ser Gly Ile Thr Leu Arg Lys Lys Ser Met Leu Trp Leu Lys
                485                 490                 495

Ala Arg Pro Tyr Asn Asn Phe Ile Pro Asn
            500                 505

<210> SEQ ID NO 16
<211> LENGTH: 1542
<212> TYPE: DNA
<213> ORGANISM: Vetiveria zizanoides
<220> FEATURE:
<221> NAME/KEY: misc_feature
<223> OTHER INFORMATION: VzCP521-11 wild type cDNA open reading frame
      sequence

<400> SEQUENCE: 16

```
atggaggaca ctaagatcct cgtcgccgcg gtgtccgtgt gcgtgcttct tgtggtcctc      60
tccaagctca agaagtccct gctgccggc gcgaaaccaa agcttaacct gcccccgggg     120
ccatggacgc tgccggtgat cggcagcctc caccacgtga tcacctaccc caacctccac     180
cgcgcactgc acgggctggc gcagaagtac ggtccggtga tgatgttccg gctcggcgag     240
gtgccaatga tggtggtgtc gtcgccggcg gccgcgcagg aggccctcaa gacgaacgac     300
atcgccttcg ccgaccggta caccaacgcc accatcggcg cgctcacctt ccatggcgag     360
gacatggcgt tcgcgcccta cggcgagcgg tggcgccagc tccgcaagat ctgcgtgctg     420
gagctgctca gcgccgcccg ggtgcagtcg ttccgccaca tccgggcgga ggaggtgtcg     480
cggctcgtcg ggaaactcgc cgcgtccgcc gccgccggcg aagctgtcca cctcaacaag     540
attgtcgcga agttcgtcaa cgacaccatc gtgagggagg cggtcggcag cgggagcaag     600
caccaggacg agtacctcaa ctccatcgac gtagccctcc ggcagacaat ggggtcgcc     660 ctcgccgacc tcttcccgtc ttcgaggctc atacagatga ttgacacggc accccggaag     720
gtgctcgcgg cccggaacaa catggagcgc atcctcgagg aaatcatcaa cgagaccaag     780
gaagccatgg accgcggcga cggccagaag aaggtggagg gcatcctcgg tgtcctgctg     840
aggctccaga aggaaggcag cacgccggtc ccgctcacca acgaggtcat cgttacggtg     900
atgtttgaca tgtttggcgc tggcagcgac acctcgtcga ccttgctgac ctggtgcatg     960
atggagctag tccggtcacc gccgacgatg gccaaagtgc aagacgaggt gcgagaggcc    1020
ttcaaaggga agaaggagag caccatcatc actgaagacg acctcaaggg gctcacctac    1080
ctcaagcaag tgatcaagga ggccctgagg atgcaccctc cggtgcccct cctgcttcca    1140
aggaagtgtc gcgagacgtg caaggtcatg ggctacgaca ttcccaaggg cacggtagtg    1200
ttcgctaacg catgggcaat cggcagggat cccaagtatt gggaggatcc agaggagttc    1260
aagccagagc gattcgacaa gagcaatgtg gactacaagg gaacaaactt tgagtacctg    1320
ccgtttggat ctggccgtcg gatttgtccc ggcataaacc taggcttgtg caacattgag    1380
```

```
ctcgcgttgg cgagccttct atatcacttt gactggaagc tgccgaacgg aatggagccc    1440
aaagacatag atatgggaga ggctcaaggg ttaatcgcca gtaagaaaac aaacctaacc    1500
ctgcaccctg tgactcgcat tgctccggcc ggttttaatt aa                      1542

<210> SEQ ID NO 17
<211> LENGTH: 1542
<212> TYPE: DNA
<213> ORGANISM: Artificial Sequence
<220> FEATURE:
<223> OTHER INFORMATION: VzCP521-11 cDNA optimized sequence
<220> FEATURE:
<221> NAME/KEY: misc_feature
<223> OTHER INFORMATION: Optimized cDNA seqeunce encoding for VzCP521-11
<220> FEATURE:
<221> NAME/K

```
ttc ccg agc tct cgc ctg atc cag atg atc gat acc gca ccg cgc aaa      720
Phe Pro Ser Ser Arg Leu Ile Gln Met Ile Asp Thr Ala Pro Arg Lys
225                 230                 235                 240 gtt ctg gcc gcg cgt aac aat atg gaa cgt atc ctg gaa gag atc att      768
Val Leu Ala Ala Arg Asn Asn Met Glu Arg Ile Leu Glu Glu Ile Ile
                245                 250                 255 aac gaa acc aaa gag gca atg gat cgt ggt gac ggc cag aag aaa gtc      816
Asn Glu Thr Lys Glu Ala Met Asp Arg Gly Asp Gly Gln Lys Lys Val
            260                 265                 270 gag ggc att ctg ggc gtc ttg ctg cgt ctg cag aaa gag ggt agc acc      864
Glu Gly Ile Leu Gly Val Leu Leu Arg Leu Gln Lys Glu Gly Ser Thr
        275                 280                 285 ccg gtg ccg ctg acc aat gag gtg atc gtt acc gtc atg ttc gat atg      912
Pro Val Pro Leu Thr Asn Glu Val Ile Val Thr Val Met Phe Asp Met
    290                 295                 300 ttc ggc gcg ggc agc gac acg agc agc acc ctg ttg acc tgg tgc atg      960
Phe Gly Ala Gly Ser Asp Thr Ser Ser Thr Leu Leu Thr Trp Cys Met
305                 310                 315                 320 atg gaa ttg gtt cgt agc cca cca aca atg gca aag gtc caa gac gaa     1008
Met Glu Leu Val Arg Ser Pro Pro Thr Met Ala Lys Val Gln Asp Glu
                325                 330                 335 gtg cgt gag gca ttt aaa ggc aag aaa gaa agc acc atc atc acc gag     1056
Val Arg Glu Ala Phe Lys Gly Lys Lys Glu Ser Thr Ile Ile Thr Glu
            340                 345                 350 gat gac ttg aag ggc ctg acc tac ctg aag cag gtc atc aaa gag gca     1104
Asp Asp Leu Lys Gly Leu Thr Tyr Leu Lys Gln Val Ile Lys Glu Ala
        355                 360                 365 ctg cgc atg cac cct ccg gtg ccg ttg ctg ctg ccg cgc aaa tgc cgc     1152
Leu Arg Met His Pro Pro Val Pro Leu Leu Leu Pro Arg Lys Cys Arg
    370                 375                 380 gaa acc tgc aaa gtt atg ggc tat gac atc ccg aaa ggt acg gtg gtt     1200
Glu Thr Cys Lys Val Met Gly Tyr Asp Ile Pro Lys Gly Thr Val Val
385                 390                 395                 400 ttt gca aat gcc tgg gcg att ggt cgc gat ccg aag tat tgg gaa gac     1248
Phe Ala Asn Ala Trp Ala Ile Gly Arg Asp Pro Lys Tyr Trp Glu Asp
                405                 410                 415 ccg gag gag ttc aaa cct gaa cgt ttc gat aag agc aac gtt gac tac     1296
Pro Glu Glu Phe Lys Pro Glu Arg Phe Asp Lys Ser Asn Val Asp Tyr
            420                 425                 430 aaa ggt act aac ttc gag tat ctg ccg ttc ggt tcg ggt cgt cgc att     1344
Lys Gly Thr Asn Phe Glu Tyr Leu Pro Phe Gly Ser Gly Arg Arg Ile
        435                 440                 445 tgc ccg ggt atc aac ttg ggt ctg tgt aac att gag ctg gcc ttg gct     1392
Cys Pro Gly Ile Asn Leu Gly Leu Cys Asn Ile Glu Leu Ala Leu Ala
    450                 455                 460 tcc ctg ttg tat cat ttc gat tgg aaa ctg ccg aat ggc atg gag ccg     1440
Ser Leu Leu Tyr His Phe Asp Trp Lys Leu Pro Asn Gly Met Glu Pro
465                 470                 475                 480 aag gac att gac atg ggt gag gca caa ggc ctg atc gca tcc aaa aag     1488
Lys Asp Ile Asp Met Gly Glu Ala Gln Gly Leu Ile Ala Ser Lys Lys
                485                 490                 495 acg aat ttg acg ctg cac ccg gtt act cgt atc gct ccg gca ggt ttt     1536
Thr Asn Leu Thr Leu His Pro Val Thr Arg Ile Ala Pro Ala Gly Phe
            500                 505                 510 aat tga                                                              1542
Asn

<210> SEQ ID NO 18
<211> LENGTH: 513
<212> TYPE: PRT
```

<213> ORGANISM: Artificial Sequence
<220> FEATURE:
<223> OTHER INFORMATION: Synthetic Construct

<400> SEQUENCE: 18

```
Met Glu Asp Thr Lys Ile Leu Val Ala Ala Val Ser Val Cys Val Leu
1               5                   10                  15

Leu Val Val Leu Ser Lys Leu Lys Ser Leu Leu Pro Gly Ala Lys
            20                  25                  30

Pro Lys Leu Asn Leu Pro Pro Gly Pro Trp Thr Leu Pro Val Ile Gly
        35                  40                  45

Ser Leu His His Val Ile Thr Tyr Pro Asn Leu His Arg Ala Leu His
    50                  55                  60

Gly Leu Ala Gln Lys Tyr Gly Pro Val Met Met Phe Arg Leu Gly Glu
65                  70                  75                  80

Val Pro Met Met Val Val Ser Pro Ala Ala Gln Glu Ala Leu
                85                  90                  95

Lys Thr Asn Asp Ile Ala Phe Ala Asp Arg Tyr Thr Asn Ala Thr Ile
                100                 105                 110

Gly Ala Leu Thr Phe His Gly Glu Asp Met Ala Phe Ala Pro Tyr Gly
            115                 120                 125

Glu Arg Trp Arg Gln Leu Arg Lys Ile Cys Val Leu Glu Leu Leu Ser
        130                 135                 140

Ala Ala Arg Val Gln Ser Phe Arg His Ile Arg Ala Glu Glu Val Ser
145                 150                 155                 160

Arg Leu Val Gly Lys Leu Ala Ala Ser Ala Ala Gly Glu Ala Val
                165                 170                 175

His Leu Asn Lys Ile Val Ala Lys Phe Val Asn Asp Thr Ile Val Arg
                180                 185                 190

Glu Ala Val Gly Ser Gly Ser Lys His Gln Asp Glu Tyr Leu Asn Ser
            195                 200                 205

Ile Asp Val Ala Leu Arg Gln Thr Met Gly Val Ala Leu Ala Asp Leu
        210                 215                 220

Phe Pro Ser Ser Arg Leu Ile Gln Met Ile Asp Thr Ala Pro Arg Lys
225                 230                 235                 240

Val Leu Ala Ala Arg Asn Asn Met Glu Arg Ile Leu Glu Glu Ile Ile
                245                 250                 255

Asn Glu Thr Lys Glu Ala Met Asp Arg Gly Asp Gly Gln Lys Lys Val
                260                 265                 270

Glu Gly Ile Leu Gly Val Leu Leu Arg Leu Gln Lys Glu Gly Ser Thr
            275                 280                 285

Pro Val Pro Leu Thr Asn Glu Val Ile Val Thr Val Met Phe Asp Met
        290                 295                 300

Phe Gly Ala Gly Ser Asp Thr Ser Ser Thr Leu Leu Thr Trp Cys Met
305                 310                 315                 320

Met Glu Leu Val Arg Ser Pro Pro Thr Met Ala Lys Val Gln Asp Glu
                325                 330                 335

Val Arg Glu Ala Phe Lys Gly Lys Lys Glu Ser Thr Ile Ile Thr Glu
            340                 345                 350

Asp Asp Leu Lys Gly Leu Thr Tyr Leu Lys Gln Val Ile Lys Glu Ala
        355                 360                 365

Leu Arg Met His Pro Pro Val Pro Leu Leu Pro Arg Lys Cys Arg
370                 375                 380

Glu Thr Cys Lys Val Met Gly Tyr Asp Ile Pro Lys Gly Thr Val Val
```

```
385                 390                 395                 400
    Phe Ala Asn Ala Trp Ala Ile Gly Arg Asp Pro Lys Tyr Trp Glu Asp
                    405                 410                 415

Pro Glu Glu Phe Lys Pro Glu Arg Phe Asp Lys Ser Asn Val Asp Tyr
                420                 425                 430

Lys Gly Thr Asn Phe Glu Tyr Leu Pro Phe Gly Ser Gly Arg Arg Ile
                435                 440                 445

Cys Pro Gly Ile Asn Leu Gly Leu Cys Asn Ile Glu Leu Ala Leu Ala
    450                 455                 460

Ser Leu Leu Tyr His Phe Asp Trp Lys Leu Pro Asn Gly Met Glu Pro
    465                 470                 475                 480

Lys Asp Ile Asp Met Gly Glu Ala Gln Gly Leu Ile Ala Ser Lys Lys
                    485                 490                 495

Thr Asn Leu Thr Leu His Pro Val Thr Arg Ile Ala Pro Ala Gly Phe
                500                 505                 510

Asn

<210> SEQ ID NO 19
<211> LENGTH: 469
<212> TYPE: PRT
<213> ORGANISM: Vetiveria zizanoides
<220> FEATURE:
<221> NAME/KEY: MISC_FEATURE
<223> OTHER INFORMATION: Catalytic domain of VzCP8201

<400> SEQUENCE: 19

Trp Gln Leu Pro Leu Ile Gly Ser Leu His His Leu Leu Ser Arg
    1               5                   10                  15

Phe Ser Asp Leu Pro His Arg Ala Leu Arg Glu Met Ser Gly Thr Tyr
                20                  25                  30

Gly Pro Leu Met Leu Leu Arg Phe Gly Ser Val Pro Thr Leu Val Val
                35                  40                  45

Ser Ser Ala Glu Ala Ala Arg Glu Val Met Arg Thr His Asp Leu Ala
            50                  55                  60

Phe Cys Asp Arg His Leu Gly Val Thr Leu Asp Ile Val Thr Cys Gly
    65                  70                  75                  80

Gly Lys Asp Ile Ile Cys Ser Pro Tyr Asn Ala His Trp Arg Glu Leu
                    85                  90                  95

Arg Lys Leu Cys Met Val Glu Ile Leu Ser Gln Arg Val Leu Ser
                100                 105                 110

Phe Arg Ser Ile Arg Glu Glu Val Ala Ser Leu Val Arg Ser Ile
                115                 120                 125

Ser Asp Glu Cys Gly Gly Gln Gln Pro Val Asn Leu Thr Glu Gly
            130                 135                 140

Ile Ser Arg Met Ile Asn Asp Val Ala Ala Arg Thr Val Val Gly Asp
    145                 150                 155                 160

Arg Cys Lys Tyr Gln Asp Glu Tyr Met His Glu Leu Asp Glu Val Val
                    165                 170                 175

Arg Leu Ala Gly Gly Phe Asn Leu Ala Asp Leu Tyr Pro Ser Ser Arg
                180                 185                 190

Leu Val Arg Arg Phe Ser Ala Ala Arg Asp Ala Arg Cys Gln
                195                 200                 205

Arg Asn Met Tyr Arg Ile Ile Gln Ser Ile Ile Gln Glu Arg Glu Ala
    210                 215                 220

Met Pro Thr Pro Glu Arg Asp Glu Glu Asp Leu Leu Gly Val Leu Leu
```

```
                225                 230                 235                 240
        Arg Leu Gln Arg Glu Gly Gly Leu Gln Phe Ala Leu Thr Asn Glu Ile
                        245                 250                 255

Val Ser Thr Val Ile Tyr Asp Ile Phe Ser Ala Gly Ser Glu Thr Ser
                        260                 265                 270

Ser Thr Val Leu Val Trp Ala Met Ser Glu Leu Val Lys Asn Pro Gln
                        275                 280                 285

Val Met Arg Lys Ala Gln Ser Glu Val Arg Asp Thr Phe Lys Gly Asn
                        290                 295                 300

Asn Lys Ile Thr Glu Ser Asp Leu Ile Lys Leu Arg Tyr Leu Gln Leu
        305                 310                 315                 320

Val Ile Lys Glu Thr Leu Arg Leu His Ala Pro Val Pro Leu Leu Leu
                        325                 330                 335

Pro Arg Glu Cys Arg Glu Ser Cys Gln Ile Met Gly Tyr Asp Val Leu
                        340                 345                 350

Lys Gly Thr Lys Val Phe Val Asn Ala Trp Ala Ile Ala Arg Asp Thr
                        355                 360                 365

Gly Leu Trp Cys Asp Gly Glu Glu Phe Arg Pro Glu Arg Phe Glu Ser
                        370                 375                 380

Ser Asn Ile Asp Phe Arg Gly Asn Asp Phe Glu Phe Thr Pro Phe Gly
        385                 390                 395                 400

Ala Gly Arg Arg Val Cys Pro Gly Ile Thr Leu Gly Leu Ala Asn Leu
                        405                 410                 415

Glu Leu Ala Leu Ala Ser Leu Leu Tyr His Phe Asp Trp Asp Leu Pro
                        420                 425                 430

Asn Gly Ala Arg Leu Glu Asp Leu Asp Met Ala Glu Ala Phe Gly Ile
                        435                 440                 445

Thr Leu Lys Arg Lys Ser Met Leu Trp Leu Lys Ala Lys Pro Tyr Asn
                        450                 455                 460

Asn Phe Ile Pro Asn
        465

<210> SEQ ID NO 20
        <211> LENGTH: 468
        <212> TYPE: PRT
        <213> ORGANISM: Vetiveria zizanoides
        <220> FEATURE:
        <221> NAME/KEY: MISC_FEATURE
        <223> OTHER INFORMATION: Catalytic doamin of VzCP7186

<400> SEQUENCE: 20

Trp Gln Leu Pro Leu Ile Gly Ser Leu His Leu Leu Leu Ser Arg
        1               5                   10                  15

Phe Ser Asp Leu Pro His Arg Ala Leu Arg Glu Met Ser Gly Ala Tyr
                        20                  25                  30

Gly Pro Leu Met Leu Leu Arg Phe Gly Ala Val Pro Thr Leu Val Ala
                        35                  40                  45

Ser Ser Ala Glu Ala Ala Arg Glu Val Met Arg Thr His Asp Leu Ala
                        50                  55                  60

Phe Cys Asn Arg His Leu Gly Val Thr Phe Asp Thr Ile Thr Cys Gly
        65                  70                  75                  80

Gly Lys Asp Ile Ile Gly Ser Pro Tyr Asn Ala Gln Trp Arg Glu Leu
                        85                  90                  95

Arg Lys Leu Cys Met Leu Glu Ile Phe Ser Gln Arg Arg Val Leu Ser
                        100                 105                 110
```

```
Phe Arg Ser Ile Arg Glu Glu Val Ala Asn Leu Val Arg Ser Ile
            115                 120                 125
Ser Asp Glu Cys Gly Gly Arg Gln Pro Val Asn Leu Thr Glu Gly
130                 135                 140
Ile Cys Arg Met Ile Asn Asp Val Ala Ala Arg Thr Ala Val Gly Asp
145                 150                 155                 160
Arg Cys Arg Tyr Arg Asp Glu Tyr Met His Glu Leu Asp Glu Val Val
                165                 170                 175
Arg Leu Val Ser Gly Phe Asn Leu Ala Asp Leu Tyr Pro Ser Ser Trp
            180                 185                 190
Leu Val Arg Arg Phe Ser Ala Ala Ala Arg Asp Ala Arg Arg Cys Gln
            195                 200                 205
Arg Asn Met Tyr Arg Ile Ile Gln Ser Ile Ile Glu Glu Arg Glu Ala
210                 215                 220
Met Pro Thr Pro Glu Arg Asp Glu Asp Leu Leu Gly Val Leu Leu Arg
225                 230                 235                 240
Leu Gln Lys Glu Gly Gly Leu Gln Phe Ala Leu Thr Asn Glu Ile Val
                245                 250                 255
Ser Thr Val Ile Phe Asp Ile Phe Ser Ala Gly Ser Glu Thr Ser Ser
            260                 265                 270
Thr Val Leu Val Trp Ala Met Ser Glu Leu Val Lys Asn Pro Gln Val
            275                 280                 285
Met His Lys Ala Arg Ser Glu Val Arg Glu Thr Phe Arg Gly Gln Asp
290                 295                 300
Lys Ile Ser Glu Asp Asp Leu Val Lys Leu Arg Tyr Leu Gln Leu Val
305                 310                 315                 320
Ile Lys Glu Thr Leu Arg Leu His Ala Pro Val Pro Leu Leu Leu Pro
                325                 330                 335
Arg Glu Cys Arg Glu Ser Cys Gln Val Met Gly Tyr Asp Val Pro Lys
            340                 345                 350
Gly Thr Lys Val Phe Val Asn Val Trp Ala Ile Ala Arg Asp Val Lys
            355                 360                 365
Leu Trp His Asp Ala Glu Val Phe Lys Pro Glu Arg Phe Glu Ser Ser
370                 375                 380
Ser Ile Asp Phe Arg Gly Asn Asp Phe Glu Phe Thr Pro Phe Gly Ala
385                 390                 395                 400
Gly Arg Arg Met Cys Pro Gly Val Thr Leu Gly Leu Ala Asn Leu Glu
                405                 410                 415
Leu Ala Leu Ala Ser Leu Leu Tyr His Phe Asp Trp Asp Leu Pro Asp
            420                 425                 430
Gly Ile Gly Leu Glu Glu Leu Asp Met Ser Glu Thr Ser Gly Ile Thr
            435                 440                 445
Leu Arg Lys Lys Ser Met Leu Trp Leu Lys Ala Arg Pro Tyr Asn Asn
450                 455                 460
Phe Ile Pro Asn
465

<210> SEQ ID NO 21
<211> LENGTH: 472
<212> TYPE: PRT
<213> ORGANISM: Vetiveria zizanoides
<220> FEATURE:
<221> NAME/KEY: MISC_FEATURE
<223> OTHER INFORMATION: Catalytic domain of VzCP521-11

<400> SEQUENCE: 21
```

```
Trp Thr Leu Pro Val Ile Gly Ser Leu His His Val Ile Thr Tyr Pro
1               5                   10                  15

Asn Leu His Arg Ala Leu His Gly Leu Ala Gln Lys Tyr Gly Pro Val
            20                  25                  30

Met Met Phe Arg Leu Gly Glu Val Pro Met Met Val Val Ser Ser Pro
            35                  40                  45

Ala Ala Ala Gln Glu Ala Leu Lys Thr Asn Asp Ile Ala Phe Ala Asp
        50                  55                  60

Arg Tyr Thr Asn Ala Thr Ile Gly Ala Leu Thr Phe His Gly Glu Asp
65                  70                  75                  80

Met Ala Phe Ala Pro Tyr Gly Glu Arg Trp Arg Gln Leu Arg Lys Ile
            85                  90                  95

Cys Val Leu Glu Leu Leu Ser Ala Ala Arg Val Gln Ser Phe Arg His
            100                 105                 110

Ile Arg Ala Glu Glu Val Ser Arg Leu Val Gly Lys Leu Ala Ala Ser
            115                 120                 125

Ala Ala Ala Gly Glu Ala Val His Leu Asn Lys Ile Val Ala Lys Phe
        130                 135                 140

Val Asn Asp Thr Ile Val Arg Glu Ala Val Gly Ser Gly Ser Lys His
145                 150                 155                 160

Gln Asp Glu Tyr Leu Asn Ser Ile Asp Val Ala Leu Arg Gln Thr Met
            165                 170                 175

Gly Val Ala Leu Ala Asp Leu Phe Pro Ser Ser Arg Leu Ile Gln Met
            180                 185                 190

Ile Asp Thr Ala Pro Arg Lys Val Leu Ala Ala Arg Asn Asn Met Glu
            195                 200                 205

Arg Ile Leu Glu Glu Ile Ile Asn Glu Thr Lys Glu Ala Met Asp Arg
210                 215                 220

Gly Asp Gly Gln Lys Lys Val Glu Gly Ile Leu Gly Val Leu Leu Arg
225                 230                 235                 240

Leu Gln Lys Glu Gly Ser Thr Pro Val Pro Leu Thr Asn Glu Val Ile
            245                 250                 255

Val Thr Val Met Phe Asp Met Phe Gly Ala Gly Ser Asp Thr Ser Ser
            260                 265                 270

Thr Leu Leu Thr Trp Cys Met Met Glu Leu Val Arg Ser Pro Pro Thr
            275                 280                 285

Met Ala Lys Val Gln Asp Glu Val Arg Glu Ala Phe Lys Gly Lys Lys
            290                 295                 300

Glu Ser Thr Ile Ile Thr Glu Asp Asp Leu Lys Gly Leu Thr Tyr Leu
305                 310                 315                 320

Lys Gln Val Ile Lys Glu Ala Leu Arg Met His Pro Pro Val Pro Leu
            325                 330                 335

Leu Leu Pro Arg Lys Cys Arg Glu Thr Cys Lys Val Met Gly Tyr Asp
            340                 345                 350

Ile Pro Lys Gly Thr Val Val Phe Ala Asn Ala Trp Ala Ile Gly Arg
            355                 360                 365

Asp Pro Lys Tyr Trp Glu Asp Pro Glu Glu Phe Lys Pro Glu Arg Phe
            370                 375                 380

Asp Lys Ser Asn Val Asp Tyr Lys Gly Thr Asn Phe Glu Tyr Leu Pro
385                 390                 395                 400

Phe Gly Ser Gly Arg Arg Ile Cys Pro Gly Ile Asn Leu Gly Leu Cys
            405                 410                 415
```

```
Asn Ile Glu Leu Ala Leu Ala Ser Leu Leu Tyr His Phe Asp Trp Lys
            420                 425                 430

Leu Pro Asn Gly Met Glu Pro Lys Asp Ile Asp Met Gly Glu Ala Gln
            435                 440                 445

Gly Leu Ile Ala Ser Lys Lys Thr Asn Leu Thr Leu His Pro Val Thr
    450                 455                 460

Arg Ile Ala Pro Ala Gly Phe Asn
465                 470

<210> SEQ ID NO 22
<211> LENGTH: 2130
<212> TYPE: DNA
<213> ORGANISM: Mentha piperita
<220> FEATURE:
<221> NAME/KEY: misc_feature
<223> OTHER INFORMATION: P450 reductase (CPRm)
<220> FEATURE:
<221> NAME/KEY: CDS
<222> LOCATION: (1)..(2130)

<400> SEQUENCE: 22
```

| | | | | | | | | | | | | | | | | |
|---|---|---|---|---|---|---|---|---|---|---|---|---|---|---|---|---|
| atg | gaa | cct | agc | tct | cag | aaa | ctg | tct | ccg | ttg | gaa | ttt | gtt | gct | gct | 48 |
| Met | Glu | Pro | Ser | Ser | Gln | Lys | Leu | Ser | Pro | Leu | Glu | Phe | Val | Ala | Ala | |
| 1 | | | | 5 | | | | | 10 | | | | | 15 | | |
| atc | ctg | aag | ggc | gac | tac | agc | agc | ggt | cag | gtt | gaa | ggt | ggt | cca | ccg | 96 |
| Ile | Leu | Lys | Gly | Asp | Tyr | Ser | Ser | Gly | Gln | Val | Glu | Gly | Gly | Pro | Pro | |
| | | | 20 | | | | | 25 | | | | | 30 | | | |
| cca | ggt | ctg | gca | gct | atg | ttg | atg | gaa | aat | aag | gat | ttg | gtg | atg | gtt | 144 |
| Pro | Gly | Leu | Ala | Ala | Met | Leu | Met | Glu | Asn | Lys | Asp | Leu | Val | Met | Val | |
| | | 35 | | | | | 40 | | | | | 45 | | | | |
| ctg | acg | acg | tcc | gtg | gca | gtc | ctg | atc | ggc | tgt | gtc | gtg | gtc | ctg | gca | 192 |
| Leu | Thr | Thr | Ser | Val | Ala | Val | Leu | Ile | Gly | Cys | Val | Val | Val | Leu | Ala | |
| | 50 | | | | | 55 | | | | | 60 | | | | | |
| tgg | cgt | cgt | gcg | gca | ggt | agc | ggt | aag | tac | aag | caa | cct | gaa | ctg | cct | 240 |
| Trp | Arg | Arg | Ala | Ala | Gly | Ser | Gly | Lys | Tyr | Lys | Gln | Pro | Glu | Leu | Pro | |
| 65 | | | | | 70 | | | | | 75 | | | | | 80 | |
| aaa | ctg | gtg | gtc | ccg | aaa | gca | gcc | gaa | ccg | gag | gag | gca | gag | gat | gat | 288 |
| Lys | Leu | Val | Val | Pro | Lys | Ala | Ala | Glu | Pro | Glu | Glu | Ala | Glu | Asp | Asp | |
| | | | | 85 | | | | | 90 | | | | | 95 | | |
| aaa | acc | aag | atc | agc | gtg | ttt | ttc | ggc | acc | caa | acc | ggt | acg | gca | gaa | 336 |
| Lys | Thr | Lys | Ile | Ser | Val | Phe | Phe | Gly | Thr | Gln | Thr | Gly | Thr | Ala | Glu | |
| | | | 100 | | | | | 105 | | | | | 110 | | | |
| ggt | ttc | gcg | aag | gct | ttt | gtt | gaa | gag | gcc | aag | gcg | cgt | tat | cag | cag | 384 |
| Gly | Phe | Ala | Lys | Ala | Phe | Val | Glu | Glu | Ala | Lys | Ala | Arg | Tyr | Gln | Gln | |
| | | 115 | | | | | 120 | | | | | 125 | | | | |
| gcc | cgt | ttc | aaa | gtt | atc | gac | ctg | gac | gac | tat | gcg | gca | gac | gat | gac | 432 |
| Ala | Arg | Phe | Lys | Val | Ile | Asp | Leu | Asp | Asp | Tyr | Ala | Ala | Asp | Asp | Asp | |
| | 130 | | | | | 135 | | | | | 140 | | | | | |
| gag | tac | gaa | gag | aaa | ctg | aag | aag | gaa | aac | ttg | gca | ttc | ttc | ttc | ttg | 480 |
| Glu | Tyr | Glu | Glu | Lys | Leu | Lys | Lys | Glu | Asn | Leu | Ala | Phe | Phe | Phe | Leu | |
| 145 | | | | | 150 | | | | | 155 | | | | | 160 | |
| gcg | tcc | tac | ggt | gac | ggc | gag | ccg | acg | gac | aac | gcg | gca | cgc | ttt | tac | 528 |
| Ala | Ser | Tyr | Gly | Asp | Gly | Glu | Pro | Thr | Asp | Asn | Ala | Ala | Arg | Phe | Tyr | |
| | | | | 165 | | | | | 170 | | | | | 175 | | |
| aaa | tgg | ttt | acg | gag | ggt | aag | gac | cgt | ggt | gaa | tgg | ctg | aac | aat | ctg | 576 |
| Lys | Trp | Phe | Thr | Glu | Gly | Lys | Asp | Arg | Gly | Glu | Trp | Leu | Asn | Asn | Leu | |
| | | | 180 | | | | | 185 | | | | | 190 | | | |
| cag | tac | ggc | gtt | ttt | ggt | ctg | ggt | aac | cgt | caa | tat | gag | cat | ttc | aat | 624 |
| Gln | Tyr | Gly | Val | Phe | Gly | Leu | Gly | Asn | Arg | Gln | Tyr | Glu | His | Phe | Asn | |
| | | 195 | | | | | 200 | | | | | 205 | | | | |
| aag | atc | gcc | att | gtc | gtc | gat | gat | ctg | atc | ttc | gag | caa | ggt | ggc | aag | 672 |

```
                                           -continued

Lys Ile Ala Ile Val Val Asp Asp Leu Ile Phe Glu Gln Gly Gly Lys
    210                 215                 220 aag ctg gtt ccg gtg ggt ctg ggt gac gat gac cag tgc att gag gat      720
Lys Leu Val Pro Val Gly Leu Gly Asp Asp Asp Gln Cys Ile Glu Asp
225                 230                 235                 240 gat ttt gcg gcg tgg cgt gaa ctg gtc tgg ccg gaa ctg gat aaa ctg      768
Asp Phe Ala Ala Trp Arg Glu Leu Val Trp Pro Glu Leu Asp Lys Leu
                245                 250                 255 ctg cgt aac gaa gac gac gct acc gtg gca acc ccg tac agc gcc gct      816
Leu Arg Asn Glu Asp Asp Ala Thr Val Ala Thr Pro Tyr Ser Ala Ala
            260                 265                 270 gtg ctg caa tac cgc gtg gtt ttc cac gat cac att gac ggc ctg att      864
Val Leu Gln Tyr Arg Val Val Phe His Asp His Ile Asp Gly Leu Ile
        275                 280                 285 agc gaa aac ggt agc ccg aac ggt cat gct aat ggc aat acc gtg tac      912
Ser Glu Asn Gly Ser Pro Asn Gly His Ala Asn Gly Asn Thr Val Tyr
    290                 295                 300 gat gcg caa cac ccg tgc cgt agc aac gtc gcg gtc aag aag gaa ttg      960
Asp Ala Gln His Pro Cys Arg Ser Asn Val Ala Val Lys Lys Glu Leu
305                 310                 315                 320 cat act ccg gcg agc gat cgc agc tgc acc cac ctg gaa ttt aac att     1008
His Thr Pro Ala Ser Asp Arg Ser Cys Thr His Leu Glu Phe Asn Ile
                325                 330                 335 agc ggt acc ggc ctg atg tac gag acg ggt gac cac gtc ggt gtg tat     1056
Ser Gly Thr Gly Leu Met Tyr Glu Thr Gly Asp His Val Gly Val Tyr
            340                 345                 350 tgc gag aac ctg ttg gaa acc gtg gag gag gcc gag aag ttg ttg aac     1104
Cys Glu Asn Leu Leu Glu Thr Val Glu Glu Ala Glu Lys Leu Leu Asn
        355                 360                 365 ctg agc ccg cag acg tac ttc tcc gtt cac acc gac aac gag gac ggt     1152
Leu Ser Pro Gln Thr Tyr Phe Ser Val His Thr Asp Asn Glu Asp Gly
    370                 375                 380 acg ccg ttg agc ggc agc agc ctg ccg cca ccg ttt ccg ccg tgc acc     1200
Thr Pro Leu Ser Gly Ser Ser Leu Pro Pro Pro Phe Pro Pro Cys Thr
385                 390                 395                 400 ttg cgc acg gca ttg acc aaa tac gca gac ttg act tct gca ccg aaa     1248
Leu Arg Thr Ala Leu Thr Lys Tyr Ala Asp Leu Thr Ser Ala Pro Lys
                405                 410                 415 aag tcg gtg ctg gtg gcg ctg gcc gag tac gca tct gac cag ggt gaa     1296
Lys Ser Val Leu Val Ala Leu Ala Glu Tyr Ala Ser Asp Gln Gly Glu
            420                 425                 430 gcg gat cgt ttg cgt ttc ttg gcg agc ccg agc ggc aaa gag gaa tat     1344
Ala Asp Arg Leu Arg Phe Leu Ala Ser Pro Ser Gly Lys Glu Glu Tyr
        435                 440                 445 gca cag tac atc ttg gca agc cag cgc acg ctg ctg gag gtc atg gcg     1392
Ala Gln Tyr Ile Leu Ala Ser Gln Arg Thr Leu Leu Glu Val Met Ala
    450                 455                 460 gag ttc ccg tcg gcg aaa ccg ccg ctg ggt gtc ttt ttc gcg ggt gtc     1440
Glu Phe Pro Ser Ala Lys Pro Pro Leu Gly Val Phe Phe Ala Gly Val
465                 470                 475                 480 gct ccg cgc ctg cag ccg cgt ttc tat tcc att agc tct agc ccg aag     1488
Ala Pro Arg Leu Gln Pro Arg Phe Tyr Ser Ile Ser Ser Ser Pro Lys
                485                 490                 495 atc gca ccg ttc cgt att cac gtg acc tgc gcc ctg gtt tat gac aaa     1536
Ile Ala Pro Phe Arg Ile His Val Thr Cys Ala Leu Val Tyr Asp Lys
            500                 505                 510 tcc cct acc ggt cgc gtt cat aag ggc atc tgt agc acg tgg atg aaa     1584
Ser Pro Thr Gly Arg Val His Lys Gly Ile Cys Ser Thr Trp Met Lys
        515                 520                 525
```

| | | | | | | | | | | | | | | | |
|---|---|---|---|---|---|---|---|---|---|---|---|---|---|---|---|
| aat | gcg | gtc | ccg | ctg | gaa | gaa | agc | aac | gat | tgt | tcc | tgg | gct | ccg | atc | 1632 |
| Asn | Ala | Val | Pro | Leu | Glu | Glu | Ser | Asn | Asp | Cys | Ser | Trp | Ala | Pro | Ile | |
| | 530 | | | | | 535 | | | | | 540 | | | | | |
| ttc | gtc | cgc | aac | agc | aac | ttc | aag | ctg | ccg | acc | gac | ccg | aag | gtt | ccg | 1680 |
| Phe | Val | Arg | Asn | Ser | Asn | Phe | Lys | Leu | Pro | Thr | Asp | Pro | Lys | Val | Pro | |
| 545 | | | | | 550 | | | | | 555 | | | | | 560 | |
| att | atc | atg | att | ggt | ccg | ggt | acc | ggt | ctg | gcc | cct | ttt | cgt | ggc | ttt | 1728 |
| Ile | Ile | Met | Ile | Gly | Pro | Gly | Thr | Gly | Leu | Ala | Pro | Phe | Arg | Gly | Phe | |
| | | | | 565 | | | | | 570 | | | | | 575 | | |
| ttg | caa | gag | cgc | ttg | gcg | ttg | aaa | gag | agc | ggt | gct | gaa | ttg | ggt | ccg | 1776 |
| Leu | Gln | Glu | Arg | Leu | Ala | Leu | Lys | Glu | Ser | Gly | Ala | Glu | Leu | Gly | Pro | |
| | | 580 | | | | | 585 | | | | | 590 | | | | |
| gcg | atc | ttg | ttc | ttt | ggt | tgc | cgt | aac | cgt | aaa | atg | gac | ttt | att | tac | 1824 |
| Ala | Ile | Leu | Phe | Phe | Gly | Cys | Arg | Asn | Arg | Lys | Met | Asp | Phe | Ile | Tyr | |
| | | 595 | | | | | 600 | | | | | 605 | | | | |
| gag | gat | gaa | ctg | aat | gat | ttc | gtc | aaa | gcg | ggc | gtt | gtc | agc | gag | ctg | 1872 |
| Glu | Asp | Glu | Leu | Asn | Asp | Phe | Val | Lys | Ala | Gly | Val | Val | Ser | Glu | Leu | |
| | 610 | | | | | 615 | | | | | 620 | | | | | |
| atc | gtc | gct | ttt | agc | cgc | gaa | ggc | ccg | atg | aaa | gaa | tac | gtg | caa | cac | 1920 |
| Ile | Val | Ala | Phe | Ser | Arg | Glu | Gly | Pro | Met | Lys | Glu | Tyr | Val | Gln | His | |
| 625 | | | | | 630 | | | | | 635 | | | | | 640 | |
| aaa | atg | agc | caa | cgt | gcc | tcc | gat | gtg | tgg | aac | atc | att | agc | gac | ggt | 1968 |
| Lys | Met | Ser | Gln | Arg | Ala | Ser | Asp | Val | Trp | Asn | Ile | Ile | Ser | Asp | Gly | |
| | | | | 645 | | | | | 650 | | | | | 655 | | |
| ggt | tat | gtt | tat | gtt | tgc | ggt | gac | gcg | aag | ggt | atg | gct | cgt | gat | gtt | 2016 |
| Gly | Tyr | Val | Tyr | Val | Cys | Gly | Asp | Ala | Lys | Gly | Met | Ala | Arg | Asp | Val | |
| | | | | 660 | | | | | 665 | | | | | 670 | | |
| cac | cgt | acc | ctg | cat | acc | atc | gca | cag | gag | caa | ggt | agc | atg | tcc | agc | 2064 |
| His | Arg | Thr | Leu | His | Thr | Ile | Ala | Gln | Glu | Gln | Gly | Ser | Met | Ser | Ser | |
| | | 675 | | | | | 680 | | | | | 685 | | | | |
| tcg | gag | gcc | gaa | ggt | atg | gtc | aaa | aac | ctg | caa | acc | acc | ggt | cgt | tac | 2112 |
| Ser | Glu | Ala | Glu | Gly | Met | Val | Lys | Asn | Leu | Gln | Thr | Thr | Gly | Arg | Tyr | |
| | 690 | | | | | 695 | | | | | 700 | | | | | |
| ctg | cgt | gat | gtg | tgg | taa | | | | | | | | | | | 2130 |
| Leu | Arg | Asp | Val | Trp | | | | | | | | | | | | |
| 705 | | | | | | | | | | | | | | | | |

<210> SEQ ID NO 23
<211> LENGTH: 709
<212> TYPE: PRT
<213> ORGANISM: Mentha piperita

<400> SEQUENCE: 23

Met Glu Pro Ser Ser Gln Lys Leu Ser Pro Leu Glu Phe Val Ala Ala
1               5                   10                  15

Ile Leu Lys Gly Asp Tyr Ser Ser Gly Gln Val Glu Gly Pro Pro
            20                  25                  30

Pro Gly Leu Ala Ala Met Leu Met Glu Asn Lys Asp Leu Val Met Val
            35                  40                  45

Leu Thr Thr Ser Val Ala Val Leu Ile Gly Cys Val Val Leu Ala
        50                  55                  60

Trp Arg Arg Ala Ala Gly Ser Gly Lys Tyr Lys Gln Pro Glu Leu Pro
65              70                  75                  80

Lys Leu Val Val Pro Lys Ala Ala Glu Pro Glu Glu Ala Glu Asp Asp
                85                  90                  95

Lys Thr Lys Ile Ser Val Phe Phe Gly Thr Gln Thr Gly Thr Ala Glu
            100                 105                 110

Gly Phe Ala Lys Ala Phe Val Glu Glu Ala Lys Ala Arg Tyr Gln Gln
        115                 120                 125

```
Ala Arg Phe Lys Val Ile Asp Leu Asp Asp Tyr Ala Asp Asp Asp
            130                 135                 140

Glu Tyr Glu Glu Lys Leu Lys Lys Glu Asn Leu Ala Phe Phe Phe Leu
145                 150                 155                 160

Ala Ser Tyr Gly Asp Gly Glu Pro Thr Asp Asn Ala Ala Arg Phe Tyr
                165                 170                 175

Lys Trp Phe Thr Glu Gly Lys Asp Arg Gly Glu Trp Leu Asn Asn Leu
            180                 185                 190

Gln Tyr Gly Val Phe Gly Leu Gly Asn Arg Gln Tyr Glu His Phe Asn
            195                 200                 205

Lys Ile Ala Ile Val Val Asp Asp Leu Ile Phe Glu Gln Gly Gly Lys
            210                 215                 220

Lys Leu Val Pro Val Gly Leu Gly Asp Asp Gln Cys Ile Glu Asp
225                 230                 235                 240

Asp Phe Ala Ala Trp Arg Glu Leu Val Trp Pro Glu Leu Asp Lys Leu
                245                 250                 255

Leu Arg Asn Glu Asp Asp Ala Thr Val Ala Thr Pro Tyr Ser Ala Ala
            260                 265                 270

Val Leu Gln Tyr Arg Val Val Phe His Asp His Ile Asp Gly Leu Ile
            275                 280                 285

Ser Glu Asn Gly Ser Pro Asn Gly His Ala Asn Gly Asn Thr Val Tyr
290                 295                 300

Asp Ala Gln His Pro Cys Arg Ser Asn Val Ala Val Lys Lys Glu Leu
305                 310                 315                 320

His Thr Pro Ala Ser Asp Arg Ser Cys Thr His Leu Glu Phe Asn Ile
                325                 330                 335

Ser Gly Thr Gly Leu Met Tyr Glu Thr Gly Asp His Val Gly Val Tyr
            340                 345                 350

Cys Glu Asn Leu Leu Glu Thr Val Glu Glu Ala Glu Lys Leu Leu Asn
            355                 360                 365

Leu Ser Pro Gln Thr Tyr Phe Ser Val His Thr Asp Asn Glu Asp Gly
            370                 375                 380

Thr Pro Leu Ser Gly Ser Ser Leu Pro Pro Phe Pro Pro Cys Thr
385                 390                 395                 400

Leu Arg Thr Ala Leu Thr Lys Tyr Ala Asp Leu Thr Ser Ala Pro Lys
                405                 410                 415

Lys Ser Val Leu Val Ala Leu Ala Glu Tyr Ala Ser Asp Gln Gly Glu
            420                 425                 430

Ala Asp Arg Leu Arg Phe Leu Ala Ser Pro Ser Gly Lys Glu Glu Tyr
            435                 440                 445

Ala Gln Tyr Ile Leu Ala Ser Gln Arg Thr Leu Leu Glu Val Met Ala
            450                 455                 460

Glu Phe Pro Ser Ala Lys Pro Pro Leu Gly Val Phe Ala Gly Val
465                 470                 475                 480

Ala Pro Arg Leu Gln Pro Arg Phe Tyr Ser Ile Ser Ser Ser Pro Lys
                485                 490                 495

Ile Ala Pro Phe Arg Ile His Val Thr Cys Ala Leu Val Tyr Asp Lys
                500                 505                 510

Ser Pro Thr Gly Arg Val His Lys Gly Ile Cys Ser Thr Trp Met Lys
            515                 520                 525

Asn Ala Val Pro Leu Glu Glu Ser Asn Asp Cys Ser Trp Ala Pro Ile
530                 535                 540
```

```
Phe Val Arg Asn Ser Asn Phe Lys Leu Pro Thr Asp Pro Lys Val Pro
545                 550                 555                 560

Ile Ile Met Ile Gly Pro Gly Thr Gly Leu Ala Pro Phe Arg Gly Phe
            565                 570                 575

Leu Gln Glu Arg Leu Ala Leu Lys Glu Ser Gly Ala Glu Leu Gly Pro
        580                 585                 590

Ala Ile Leu Phe Phe Gly Cys Arg Asn Arg Lys Met Asp Phe Ile Tyr
        595                 600                 605

Glu Asp Glu Leu Asn Asp Phe Val Lys Ala Gly Val Val Ser Glu Leu
610                 615                 620

Ile Val Ala Phe Ser Arg Glu Gly Pro Met Lys Glu Tyr Val Gln His
625                 630                 635                 640

Lys Met Ser Gln Arg Ala Ser Asp Val Trp Asn Ile Ile Ser Asp Gly
            645                 650                 655

Gly Tyr Val Tyr Val Cys Gly Asp Ala Lys Gly Met Ala Arg Asp Val
            660                 665                 670

His Arg Thr Leu His Thr Ile Ala Gln Glu Gly Ser Met Ser Ser
        675                 680                 685

Ser Glu Ala Glu Gly Met Val Lys Asn Leu Gln Thr Thr Gly Arg Tyr
690                 695                 700

Leu Arg Asp Val Trp
705
```

<210> SEQ ID NO 24
<211> LENGTH: 20
<212> TYPE: PRT
<213> ORGANISM: Artificial Sequence
<220> FEATURE:
<223> OTHER INFORMATION: N-terminal replacement peptide

<400> SEQUENCE: 24

```
Met Ala Leu Leu Leu Ala Val Phe Leu Gly Leu Ser Cys Leu Leu Leu
1               5                   10                  15

Leu Ser Leu Trp
            20
```

<210> SEQ ID NO 25
<211> LENGTH: 66
<212> TYPE: DNA
<213> ORGANISM: Artificial Sequence
<220> FEATURE:
<223> OTHER INFORMATION: polylinker

<400> SEQUENCE: 25

```
gtcgacaatt aaccatggtt aattaagctt atatatggta ccatatatga attcattaat    60
ctcgag                                                              66
```

<210> SEQ ID NO 26
<211> LENGTH: 26
<212> TYPE: DNA
<213> ORGANISM: Artificial Sequence
<220> FEATURE:
<223> OTHER INFORMATION: extension sequence

<400> SEQUENCE: 26

```
gtcgacaatt aggtaaaaaa taaacc                                        26
```

<210> SEQ ID NO 27
<211> LENGTH: 19
<212> TYPE: DNA

```
<213> ORGANISM: Artificial Sequence
<220> FEATURE:
<223> OTHER INFORMATION: 5' non coding sequence

<400> SEQUENCE: 27
aagcttaagg aggtaaaaa                                                19

<210> SEQ ID NO 28
<211> LENGTH: 30
<212> TYPE: DNA
<213> ORGANISM: Artificial Sequence
<220> FEATURE:
<223> OTHER INFORMATION: 3' non coding sequence

<400> SEQUENCE: 28
ggtaccatat atgaattcat taatctcgag                                    30

<210> SEQ ID NO 29
<211> LENGTH: 62
<212> TYPE: DNA
<213> ORGANISM: Artificial Sequence
<220> FEATURE:
<223> OTHER INFORMATION: Forward primer

<400> SEQUENCE: 29
taattttatt ccgaactaag tcgaaggagg taatatggcg ttgctgttgg ctgttttct    60 gg                                                                  62

<210> SEQ ID NO 30
<211> LENGTH: 50
<212> TYPE: DNA
<213> ORGANISM: Artificial Sequence
<220> FEATURE:
<223> OTHER INFORMATION: Reverse primer

<400> SEQUENCE: 30
attttttacc taattgtcga cttagttcgg aataaagtta ttgtacggac              50

<210> SEQ ID NO 31
<211> LENGTH: 1925
<212> TYPE: DNA
<213> ORGANISM: Vetiveria zizanoides
<220> FEATURE:
<221> NAME/KEY: misc_feature
<223> OTHER INFORMATION: Vzctg306, full length cDNA encoding for VzZS1,
      includes non coding regions

<400> SEQUENCE: 31
gaagcaaagc catctgccgt gctatcactc tagcaaatta tactgagtgg ataaacttaa    60
taccacacca gacgttttgc attcatggcg acgactgccg ccttctgcct caccaccact   120
ccgatcggcg agccagtctg tcgccggcag tacctcccaa ccgtctgggg cagcttcttc   180
ctcacctacc agccatgcac gccggaagag gtccagtcca tggaggagag ggctctggcc   240
aagaagacgg aggtggggcg catgttgcag gaggtcgccg cctccagtaa cctcgcacgg   300
aagctgggcc ttgtcgatga gctagagcgg ctcggggtgg actatcacta caagacggag   360
atcaacgact gctgggtgc catttataat ggcaaggacg acgataatgg aggttctgat    420
gacgacctct atatcacatc gcttaagttc tatctgctca ggaagcatgg gtacgcttta    480
tcttcagatg tgtttctgaa gttcagagat gagcaaggaa atatttcaag tgatgatgtg    540
aaatgcctga tcatgttgta tgatgcctca catttgagga ttcatgagga gaaaattctt    600
gacaacatca acagtttcac caagagctgc ctccaatcag ttttagaaac aaatttggaa    660
```

-continued

```
ccggctctcc aagaggaggt gcggtgcaca ttggagacac ctcgattcag aagggttgag    720
agaatcgaag cgaaacgctt tatctcagcg tacgaaaaga acatagcacg agatgacgcc    780
ctactagagt ttgcaaggct ggactacaat atcgtgcaaa ttctctactg caaggagctg    840
aaagaactta cagtatggtg gaaggagttc cattcacgga caaatctgac atttgcacga    900
gatagaattg tggagatgta tttctgggtc atggcaatta tttacgagcc ttgttactcg    960
tattcacgga tatgggttac aaaaatgttt ctatccgtgg cattgttgga tgacatctat   1020
gacaattata cgagcacaga ggagagcaat atctttacta cggccatgga aggtgggat    1080 gtgaaggcca ccgaacaact gccagcaaac atgaggacat tctacgatta cttaatttgt   1140
acaacagatg aggtcgtaga agaattgaaa cttcagaata ataagaatgc tgaattagtc   1200
aagaaagtgc tgattgacgc cgctaaatgc taccattcgg aggtcaaatg gcgtgatgac   1260
cactacgtcc ctaatgatgt tggagagcac ctgcagcttt caatgcgaag cattgcagct   1320
atgcactcca tcaactttgt cttcatttca ctgggagctg tgtgtactag ggaggcggtt   1380
gagtgtgctt tcacttatcc aaaaattatt agaggtatat gtgttcacgc acgtattagt   1440
aacgatatcg cgtcacatga gcgagaacaa gcttcggagc atatggcatc aacgttgcaa   1500
acttgcatga agcagtatgg gattacagta gaggaagctg ctgaaaagct cagagtaata   1560
aacgaggagt catggatgga catcgttgag gaatgccttt ataaggacca gtatcccctg   1620
gcgctttcgg agagggtggt ggcttttgca caatcaatat gtttcatgta caatggtgta   1680
gataaataca ccataccatc aaaactcaag gacagtctag actcattgta cgtcaatttg   1740
attccagttt gacgacatcg catcaagtat taattctagg cttaatataa tgccagtaaa   1800
catcatatgt aagggatatt tactttcgtg aatccaaata atttgagggg tcctgtgttc   1860
ctcttaccaa ggatatgtca tcaagttgaa aaatatagcc agcaaaaaaa aaaaaaaaa    1920 aaaaa                                                                1925
```

<210> SEQ ID NO 32
<211> LENGTH: 1668
<212> TYPE: DNA
<213> ORGANISM: Vetiveria zizanoides
<220> FEATURE:
<221> NAME/KEY: misc_feature
<223> OTHER INFORMATION: VzCtg306-ORF, full length cDNA encoding for
    VzZS1, open reading frame only
<220> FEATURE:
<221> NAME/KEY: CDS
<222> LOCATION: (1)..(1668)

<400> SEQUENCE: 32

```
atg gcg acg act gcc gcc ttc tgc ctc acc acc act ccg atc ggc gag    48
Met Ala Thr Thr Ala Ala Phe Cys Leu Thr Thr Thr Pro Ile Gly Glu
1               5                   10                  15 cca gtc tgt cgc cgg cag tac ctc cca acc gtc tgg ggc agc ttc ttc    96
Pro Val Cys Arg Arg Gln Tyr Leu Pro Thr Val Trp Gly Ser Phe Phe
            20                  25                  30 ctc acc tac cag cca tgc acg ccg gaa gag gtc cag tcc atg gag gag   144
Leu Thr Tyr Gln Pro Cys Thr Pro Glu Glu Val Gln Ser Met Glu Glu
        35                  40                  45 agg gct ctg gcc aag aag acg gag gtg ggg cgc atg ttg cag gag gtc   192
Arg Ala Leu Ala Lys Lys Thr Glu Val Gly Arg Met Leu Gln Glu Val
    50                  55                  60 gcc gcc tcc agt aac ctc gca cgg aag ctg ggc ctt gtc gat gag cta   240
Ala Ala Ser Ser Asn Leu Ala Arg Lys Leu Gly Leu Val Asp Glu Leu
65                  70                  75                  80
```

-continued

```
gag cgg ctc ggg gtg gac tat cac tac aag acg gag atc aac gac ttg      288
Glu Arg Leu Gly Val Asp Tyr His Tyr Lys Thr Glu Ile Asn Asp Leu
                85                  90                  95 ctg ggt gcc att tat aat ggc aag gac gac gat aat gga ggt tct gat      336
Leu Gly Ala Ile Tyr Asn Gly Lys Asp Asp Asp Asn Gly Gly Ser Asp
            100                 105                 110 gac gac ctc tat atc aca tcg ctt aag ttc tat ctg ctc agg aag cat      384
Asp Asp Leu Tyr Ile Thr Ser Leu Lys Phe Tyr Leu Leu Arg Lys His
        115                 120                 125 ggg tac gct tta tct tca gat gtg ttt ctg aag ttc aga gat gag caa      432
Gly Tyr Ala Leu Ser Ser Asp Val Phe Leu Lys Phe Arg Asp Glu Gln
    130                 135                 140 gga aat att tca agt gat gat gtg aaa tgc ctg atc atg ttg tat gat      480
Gly Asn Ile Ser Ser Asp Asp Val Lys Cys Leu Ile Met Leu Tyr Asp
145                 150                 155                 160 gcc tca cat ttg agg att cat gag gag aaa att ctt gac aac atc aac      528
Ala Ser His Leu Arg Ile His Glu Glu Lys Ile Leu Asp Asn Ile Asn
                165                 170                 175 agt ttc acc aag agc tgc ctc caa tca gtt tta gaa aca aat ttg gaa      576
Ser Phe Thr Lys Ser Cys Leu Gln Ser Val Leu Glu Thr Asn Leu Glu
            180                 185                 190 ccg gct ctc caa gag gag gtg cgg tgc aca ttg gag aca cct cga ttc      624
Pro Ala Leu Gln Glu Glu Val Arg Cys Thr Leu Glu Thr Pro Arg Phe
        195                 200                 205 aga agg gtt gag aga atc gaa gcg aaa cgc ttt atc tca gcg tac gaa      672
Arg Arg Val Glu Arg Ile Glu Ala Lys Arg Phe Ile Ser Ala Tyr Glu
    210                 215                 220 aag aac ata gca cga gat gac gcc cta cta gag ttt gca agg ctg gac      720
Lys Asn Ile Ala Arg Asp Asp Ala Leu Leu Glu Phe Ala Arg Leu Asp
225                 230                 235                 240 tac aat atc gtg caa att ctc tac tgc aag gag ctg aaa gaa ctt aca      768
Tyr Asn Ile Val Gln Ile Leu Tyr Cys Lys Glu Leu Lys Glu Leu Thr
                245                 250                 255 gta tgg tgg aag gag ttc cat tca cgg aca aat ctg aca ttt gca cga      816
Val Trp Trp Lys Glu Phe His Ser Arg Thr Asn Leu Thr Phe Ala Arg
            260                 265                 270 gat aga att gtg gag atg tat ttc tgg gtc atg gca att att tac gag      864
Asp Arg Ile Val Glu Met Tyr Phe Trp Val Met Ala Ile Ile Tyr Glu
        275                 280                 285 cct tgt tac tcg tat tca cgg ata tgg gtt aca aaa atg ttt cta tcc      912
Pro Cys Tyr Ser Tyr Ser Arg Ile Trp Val Thr Lys Met Phe Leu Ser
    290                 295                 300 gtg gca ttg ttg gat gac atc tat gac aat tat acg agc aca gag gag      960
Val Ala Leu Leu Asp Asp Ile Tyr Asp Asn Tyr Thr Ser Thr Glu Glu
305                 310                 315                 320 agc aat atc ttt act acg gcc atg gaa agg tgg gat gtg aag gcc acc     1008
Ser Asn Ile Phe Thr Thr Ala Met Glu Arg Trp Asp Val Lys Ala Thr
                325                 330                 335 gaa caa ctg cca gca aac atg agg aca ttc tac gat tac tta att tgt     1056
Glu Gln Leu Pro Ala Asn Met Arg Thr Phe Tyr Asp Tyr Leu Ile Cys
            340                 345                 350 aca aca gat gag gtc gta gaa gaa ttg aaa ctt cag aat aat aag aat     1104
Thr Thr Asp Glu Val Val Glu Glu Leu Lys Leu Gln Asn Asn Lys Asn
        355                 360                 365 gct gaa tta gtc aag aaa gtg ctg att gac gcc gct aaa tgc tac cat     1152
Ala Glu Leu Val Lys Lys Val Leu Ile Asp Ala Ala Lys Cys Tyr His
    370                 375                 380 tcg gag gtc aaa tgg cgt gat gac cac tac gtc cct aat gat gtt gga     1200
Ser Glu Val Lys Trp Arg Asp Asp His Tyr Val Pro Asn Asp Val Gly
```

```
                385                 390                 395                 400
gag cac ctg cag ctt tca atg cga agc att gca gct atg cac tcc atc          1248
Glu His Leu Gln Leu Ser Met Arg Ser Ile Ala Ala Met His Ser Ile
                405                 410                 415 aac ttt gtc ttc att tca ctg gga gct gtg tgt act agg gag gcg gtt          1296
Asn Phe Val Phe Ile Ser Leu Gly Ala Val Cys Thr Arg Glu Ala Val
                420                 425                 430 gag tgt gct ttc act tat cca aaa att att aga ggt ata tgt gtt cac          1344
Glu Cys Ala Phe Thr Tyr Pro Lys Ile Ile Arg Gly Ile Cys Val His
                435                 440                 445 gca cgt att agt aac gat atc gcg tca cat gag cga gaa caa gct tcg          1392
Ala Arg Ile Ser Asn Asp Ile Ala Ser His Glu Arg Glu Gln Ala Ser
            450                 455                 460 gag cat atg gca tca acg ttg caa act tgc atg aag cag tat ggg att          1440
Glu His Met Ala Ser Thr Leu Gln Thr Cys Met Lys Gln Tyr Gly Ile
465                 470                 475                 480 aca gta gag gaa gct gct gaa aag ctc aga gta ata aac gag gag tca          1488
Thr Val Glu Glu Ala Ala Glu Lys Leu Arg Val Ile Asn Glu Glu Ser
                485                 490                 495 tgg atg gac atc gtt gag gaa tgc ctt tat aag gac cag tat ccc ctg          1536
Trp Met Asp Ile Val Glu Glu Cys Leu Tyr Lys Asp Gln Tyr Pro Leu
                500                 505                 510 gcg ctt tcg gag agg gtg gtg gct ttt gca caa tca ata tgt ttc atg          1584
Ala Leu Ser Glu Arg Val Val Ala Phe Ala Gln Ser Ile Cys Phe Met
                515                 520                 525 tac aat ggt gta gat aaa tac acc ata cca tca aaa ctc aag gac agt          1632
Tyr Asn Gly Val Asp Lys Tyr Thr Ile Pro Ser Lys Leu Lys Asp Ser
            530                 535                 540 cta gac tca ttg tac gtc aat ttg att cca gtt tga                          1668
Leu Asp Ser Leu Tyr Val Asn Leu Ile Pro Val
545                 550                 555

<210> SEQ ID NO 33
<211> LENGTH: 555
<212> TYPE: PRT
<213> ORGANISM: Vetiveria zizanoides

<400> SEQUENCE: 33

Met Ala Thr Thr Ala Ala Phe Cys Leu Thr Thr Thr Pro Ile Gly Glu
1               5                   10                  15

Pro Val Cys Arg Arg Gln Tyr Leu Pro Thr Val Trp Gly Ser Phe Phe
            20                  25                  30

Leu Thr Tyr Gln Pro Cys Thr Pro Glu Glu Val Gln Ser Met Glu Glu
        35                  40                  45

Arg Ala Leu Ala Lys Lys Thr Glu Val Gly Arg Met Leu Gln Glu Val
    50                  55                  60

Ala Ala Ser Ser Asn Leu Ala Arg Lys Leu Gly Leu Val Asp Glu Leu
65                  70                  75                  80

Glu Arg Leu Gly Val Asp Tyr His Tyr Lys Thr Glu Ile Asn Asp Leu
                85                  90                  95

Leu Gly Ala Ile Tyr Asn Gly Lys Asp Asp Asn Gly Gly Ser Asp
            100                 105                 110

Asp Asp Leu Tyr Ile Thr Ser Leu Lys Phe Tyr Leu Leu Arg Lys His
        115                 120                 125

Gly Tyr Ala Leu Ser Ser Asp Val Phe Leu Lys Phe Arg Asp Glu Gln
    130                 135                 140

Gly Asn Ile Ser Ser Asp Asp Val Lys Cys Leu Ile Met Leu Tyr Asp
145                 150                 155                 160
```

Ala Ser His Leu Arg Ile His Glu Glu Lys Ile Leu Asp Asn Ile Asn
            165                 170                 175

Ser Phe Thr Lys Ser Cys Leu Gln Ser Val Leu Glu Thr Asn Leu Glu
            180                 185                 190

Pro Ala Leu Gln Glu Glu Val Arg Cys Thr Leu Glu Thr Pro Arg Phe
            195                 200                 205

Arg Arg Val Glu Arg Ile Glu Ala Lys Arg Phe Ile Ser Ala Tyr Glu
            210                 215                 220

Lys Asn Ile Ala Arg Asp Asp Ala Leu Leu Glu Phe Ala Arg Leu Asp
225                 230                 235                 240

Tyr Asn Ile Val Gln Ile Leu Tyr Cys Lys Glu Leu Lys Glu Leu Thr
            245                 250                 255

Val Trp Trp Lys Glu Phe His Ser Arg Thr Asn Leu Thr Phe Ala Arg
            260                 265                 270

Asp Arg Ile Val Glu Met Tyr Phe Trp Val Met Ala Ile Ile Tyr Glu
            275                 280                 285

Pro Cys Tyr Ser Tyr Ser Arg Ile Trp Val Thr Lys Met Phe Leu Ser
            290                 295                 300

Val Ala Leu Leu Asp Asp Ile Tyr Asp Asn Tyr Thr Ser Thr Glu Glu
305                 310                 315                 320

Ser Asn Ile Phe Thr Thr Ala Met Glu Arg Trp Asp Val Lys Ala Thr
            325                 330                 335

Glu Gln Leu Pro Ala Asn Met Arg Thr Phe Tyr Asp Tyr Leu Ile Cys
            340                 345                 350

Thr Thr Asp Glu Val Val Glu Glu Leu Lys Leu Gln Asn Asn Lys Asn
            355                 360                 365

Ala Glu Leu Val Lys Lys Val Leu Ile Asp Ala Ala Lys Cys Tyr His
            370                 375                 380

Ser Glu Val Lys Trp Arg Asp Asp His Tyr Val Pro Asn Asp Val Gly
385                 390                 395                 400

Glu His Leu Gln Leu Ser Met Arg Ser Ile Ala Ala Met His Ser Ile
            405                 410                 415

Asn Phe Val Phe Ile Ser Leu Gly Ala Val Cys Thr Arg Glu Ala Val
            420                 425                 430

Glu Cys Ala Phe Thr Tyr Pro Lys Ile Ile Arg Gly Ile Cys Val His
            435                 440                 445

Ala Arg Ile Ser Asn Asp Ile Ala Ser His Glu Arg Glu Gln Ala Ser
450                 455                 460

Glu His Met Ala Ser Thr Leu Gln Thr Cys Met Lys Gln Tyr Gly Ile
465                 470                 475                 480

Thr Val Glu Glu Ala Ala Glu Lys Leu Arg Val Ile Asn Glu Glu Ser
            485                 490                 495

Trp Met Asp Ile Val Glu Glu Cys Leu Tyr Lys Asp Gln Tyr Pro Leu
            500                 505                 510

Ala Leu Ser Glu Arg Val Val Ala Phe Ala Gln Ser Ile Cys Phe Met
            515                 520                 525

Tyr Asn Gly Val Asp Lys Tyr Thr Ile Pro Ser Lys Leu Lys Asp Ser
            530                 535                 540

Leu Asp Ser Leu Tyr Val Asn Leu Ile Pro Val
545                 550                 555

<210> SEQ ID NO 34
<211> LENGTH: 1691

<212> TYPE: DNA
<213> ORGANISM: Vetiveria zizanoides
<220> FEATURE:
<221> NAME/KEY: misc_feature
<223> OTHER INFORMATION: Codon optimized cDNA encoding for VzZS1

<400> SEQUENCE: 34

```
atggccacga ccgcagcatt ctgcctgacc actaccccga tcggcgaacc agtatgccgc      60
cgtcaatact tgccgaccgt gtgggtagc ttttcctga cctatcagcc gtgtaccccg       120
gaagaggtgc agagcatgga gagcgtgcg ctggctaaaa agaccgaggt gggtcgcatg      180
ctgcaagagg tcgcagcaag cagcaacctg cacgtaaac tgggtttggt cgatgaactg      240
gagcgtctgg gtgtggatta tcactacaag acggagatca atgacctgct gggcgccatt    300
tacaatggta aggacgatga caacggcggc agcgacgacg acctgtatat caccagcctg    360
aaattctacc tgctgcgcaa gcatggctat gcgttgagca gcgatgtgtt cttgaaattc    420
cgtgacgaac agggtaatat cctctagcgac gatgtaaagt gcctgatcat gctgtacgac    480
gcaagccacc tgcgcatcca cgaagaaaag attctggata acattaacag ctttaccaaa   540
tcctgtctgc aaagcgtgtt ggaaacgaat ctggagccgg cactgcaaga agaagtccgc    600
tgcacgctgg aaaccctcg cttccgtcgc gttgagcgca tcgaagcgaa gcgtttcatc     660
agcgcgtatg agaagaatat cgcccgtgac gacgcgctgc tggagtttgc gcgtctggac    720
tacaacatcg ttcagattct gtactgtaaa gaactgaaag agctgacggt gtggtggaaa    780
gaatttcata gccgtactaa tctgaccttt gcccgcgatc gtatcgtcga gatgtatttc    840
tgggtgatgc gatcatttta tgagccgtgt tacagctaca gccgcatctg ggttacgaaa    900
atgttcctgt ccgttgcact gttggatgac atttacgaca actacaccag caccgaagag    960
tccaacatct ttacgaccgc gatggagcgt tgggacgtta aggcgacgga gcagctgccg   1020
gcgaatatgc gtacctttta tgattacttg atttgcacga cggatgaggt cgttgaagag   1080
ctgaaattgc aaaacaacaa gaatgccgag ctggttaaga agttctgat tgacgcggcc    1140
aaatgttacc atagcgaggt caaatggcgt gacgatcact acgtcccgaa tgatgtcggc   1200
gagcacttgc agctgagcat gcgttctatt gcggctatgc actccatcaa ctttgtgttc   1260
atctctctgg gtgcggtctg taccgtgag gccgtggaat gcgcgtttac ctatccgaag   1320
attattcgtg gtatttgcgt gcatgcgcgt atttcgaacg atattgcgag ccatgaacgc   1380
gagcaagcgt ctgaacacat ggcttcgacc ctgcaaactt gcatgaaaca gtacggtatt   1440
acggtcgaag aggcagccga gaagttgcgt gttatcaatg aagagagctg gatggatatt   1500
gtggaagagt gtctgtacaa agaccagtat ccgctggctc tgagcgagcg tgttgttgca   1560
ttcgcgcaga gcatttgctt catgtataat ggtgttgata agtataccat cccgagcaag   1620
ctgaaggata gcctggactc gctgtacgtg aacctgattc cggtttaagg taccatatat   1680
gaattcatta a                                                          1691
```

<210> SEQ ID NO 35
<211> LENGTH: 1862
<212> TYPE: DNA
<213> ORGANISM: Vetiveria zizanoides
<220> FEATURE:
<221> NAME/KEY: misc_feature
<223> OTHER INFORMATION: VzTrspt_4_contig_995, full length cDNA encoding for VzZS2, including non coding regions

<400> SEQUENCE: 35

```
gcattcatgg cgacaactgc cgccttctgc ctcaccacca ctccgatcgg cgagccggtc      60
```

```
tgtcgccggc agtacctccc aagcgtctgg ggcaacttct tcctcaccta ccagccatgc    120
acgcccgaag aggtccagtc catggaggag agggctctgg ccaagaagac ggaggtgggg    180
cgcatgttgc aggaggtcgc cgcctccggt gacctcgcac ggaagctggg ccttgtcgat    240
gagctagagc ggctcggggt ggactatcat tacaagacgg agatcaacga cttgctgggt    300
gccatttata atggcaagga cgacgataat ggaggttctg atgacgacct ctatatcaca    360
tcgcttaagt tctatctgct caggaagcat gggtacgctt taccttcaga tgtgtttctg    420
aagttcagag atgagcaagg aaatatttca agtgatgatg tgaaatgcct gatcatgttg    480
tatgatgcct cacatttgag gattcatgag gagaaaattc ttgacaacat caacagtttc    540
accaagagct gcctccaatc agttttagaa acaaatttgg aaccggctct ccaagaggag    600
gtgcggtgca cattggagac acctcgattc agaagggttg agagaatcga agcgagacgg    660
tttatctcag cgtacgaaaa gaacatagca cgagatgacg ccctactaga gtttgcaaag    720
ctggactaca atatcgtgca aattctctac tgcaaggagc tgaaagaact tacagtatgg    780
tggaaggagt tccactcaca gacaaatctg acatttgcac gagatagaat tgtggagatg    840
tatttctggg tcatggcaat tatttatgag ccttgttact catattcacg gatatgggtt    900
acaaaaatgt ttctatccgt ggcattgttg gatgacatct atgacaatta tacgagcaca    960
gaggagagca atatctttac tacggccatg gaaaggtggg atgcgaaggc cactgaacaa   1020
ctgccagcaa acatgaggac attctacgat tacttaattt gtacaacaga tgaggtcgta   1080
gaagaattga aacttcagaa taataagaat gctgaattag tcaagaaagt gctgattgac   1140
gctgctaaat gctaccattc ggaggtcaaa tggcgtgatg accactacgt ccctaatgat   1200
gttggagagc acctgcagct ttcaatgcga agcattgcag ctatgcactc catcaacttt   1260
atcttcattt cactgggagc tgtgtgtact agggaggcgg ttgagtgtgc tttcacttat   1320
ccaaaaatta ttagaggtat atgtgttcac gcacgtatta gtaacgatat cgcgtcacat   1380
gagcgagaac aagcttcgga gcatatggca tcaacgttgc aaacttgcat gaagcagtat   1440
gggattacag tagaggaagc tgctgaaaag ctcagagtaa taaacgagga gtcatggatg   1500
aacatcgttg aggaatgcct ttataaggac cagtatcccc tggcgctttc ggagagggtg   1560
gtggcctttg cacaatcaat atgtttcatg tacaatggtg tagataaata caccatacca   1620
tcaaaactca aggacagtct agactcattg tacgtcaatt tgatttcagt ttgacgacat   1680
cgcatcaagt attaattcta ggcttaatat aatgccagta acatcatat gtaagggata    1740 tttactttcg tgaatccaaa taatttgaga ggtcctgtgt tcctcttacc aaggatatgt   1800
catcaagttg aaaaatatag ccatcactct ctcgttgctt catttcaata tgaacatata   1860
ta                                                                 1862
```

<210> SEQ ID NO 36
<211> LENGTH: 1668
<212> TYPE: DNA
<213> ORGANISM: Vetiveria zizanoides
<220> FEATURE:
<221> NAME/KEY: misc_feature
<223> OTHER INFORMATION: VzTrspt_4_contig_995, full length cDNA encoding
      for VzZS2, open reading frame only

<400> SEQUENCE: 36

```
atggcgacaa ctgccgcctt ctgcctcacc accactccga tcggcgagcc ggtctgtcgc     60
cggcagtacc tcccaagcgt ctggggcaac ttcttcctca cctaccagcc atgcacgccc    120
```

```
gaagaggtcc agtccatgga ggagagggct ctggccaaga agacggaggt ggggcgcatg    180
ttgcaggagg tcgccgcctc cggtgacctc gcacggaagc tgggccttgt cgatgagcta    240
gagcggctcg gggtggacta tcattacaag acggagatca acgacttgct gggtgccatt    300
tataatggca aggacgacga taatggaggt tctgatgacg acctctatat cacatcgctt    360
aagttctatc tgctcaggaa gcatgggtac gctttacctt cagatgtgtt tctgaagttc    420
agagatgagc aaggaaatat ttcaagtgat gatgtgaaat gcctgatcat gttgtatgat    480
gcctcacatt tgaggattca tgaggagaaa attcttgaca acatcaacag tttcaccaag    540
agctgcctcc aatcagtttt agaaacaaat ttggaaccgg ctctccaaga ggaggtgcgg    600
tgcacattgg agacacctcg attcagaagg gttgagagaa tcgaagcgag acggtttatc    660
tcagcgtacg aaaagaacat agcacgagat gacgccctac tagagtttgc aaagctggac    720
tacaatatcg tgcaaattct ctactgcaag gagctgaaag aacttacagt atggtggaag    780
gagttccact cacagacaaa tctgacattt gcacgagata gaattgtgga gatgtatttc    840
tgggtcatgg caattattta tgagccttgt tactcatatt cacggatatg ggttacaaaa    900
atgtttctat ccgtggcatt gttggatgac atctatgaca attatacgag cacagaggag    960
agcaatatct ttactacggc catggaaagg tgggatgcga aggccactga caactgcca    1020 gcaaacatga ggacattcta cgattactta atttgtacaa cagatgaggt cgtagaagaa    1080
ttgaaacttc agaataataa gaatgctgaa ttagtcaaga aagtgctgat tgacgctgct    1140
aaatgctacc attcggaggt caaatggcgt gatgaccact acgtccctaa tgatgttgga    1200
gagcacctgc agctttcaat gcgaagcatt gcagctatgc actccatcaa ctttatcttc    1260
atttcactgg gagctgtgtg tactagggag gcggttgagt gtgctttcac ttatccaaaa    1320
attattagag gtatatgtgt tcacgcacgt attagtaacg atatcgcgtc acatgagcga    1380
gaacaagctt cggagcatat ggcatcaacg ttgcaaactt gcatgaagca gtatgggatt    1440
acagtagagg aagctgctga aaagctcaga gtaataaacg aggagtcatg gatgaacatc    1500
gttgaggaat gcctttataa ggaccagtat cccctggcgc tttcggagag ggtggtggcc    1560
tttgcacaat caatatgttt catgtacaat ggtgtagata aatacaccat accatcaaaa    1620
ctcaaggaca gtctagactc attgtacgtc aatttgattt cagtttga                 1668
```

<210> SEQ ID NO 37
<211> LENGTH: 1668
<212> TYPE: DNA
<213> ORGANISM: Artificial Sequence
<220> FEATURE:
<223> OTHER INFORMATION: Codon optimized cDNA encoding for VzZS2
<220> FEATURE:
<221> NAME/KEY: misc_feature
<223> OTHER INFORMATION: Codon optimized cDNA encoding for VzZS2
<220> FEATURE:
<221> NAME/KEY: CDS
<222> LOCATION: (1

| | | | | | | | | | | | | | | | | |
|---|---|---|---|---|---|---|---|---|---|---|---|---|---|---|---|---|
| cgt | gcg | ctg | gct | aaa | aag | acc | gag | gtg | ggt | cgc | atg | ctg | caa | gag | gtc | 192 |
| Arg | Ala | Leu | Ala | Lys | Lys | Thr | Glu | Val | Gly | Arg | Met | Leu | Gln | Glu | Val | |
| 50 | | | | 55 | | | | | 60 | | | | | | | |
| gca | gca | agc | ggc | gat | ctg | gca | cgt | aaa | ctg | ggt | ttg | gtc | gat | gaa | ctg | 240 |
| Ala | Ala | Ser | Gly | Asp | Leu | Ala | Arg | Lys | Leu | Gly | Leu | Val | Asp | Glu | Leu | |
| 65 | | | | 70 | | | | 75 | | | | | | 80 | | |
| gag | cgt | ctg | ggt | gtg | gat | tat | cac | tac | aag | acg | gag | atc | aat | gac | ctg | 288 |
| Glu | Arg | Leu | Gly | Val | Asp | Tyr | His | Tyr | Lys | Thr | Glu | Ile | Asn | Asp | Leu | |
| | | | | 85 | | | | 90 | | | | | 95 | | | |
| ctg | ggc | gcc | att | tac | aat | ggt | aag | gac | gat | gac | aac | ggc | ggc | agc | gac | 336 |
| Leu | Gly | Ala | Ile | Tyr | Asn | Gly | Lys | Asp | Asp | Asp | Asn | Gly | Gly | Ser | Asp | |
| | | | 100 | | | | | 105 | | | | | 110 | | | |
| gac | gac | ctg | tat | atc | acc | agc | ctg | aaa | ttc | tac | ctg | ctg | cgc | aag | cat | 384 |
| Asp | Asp | Leu | Tyr | Ile | Thr | Ser | Leu | Lys | Phe | Tyr | Leu | Leu | Arg | Lys | His | |
| | | 115 | | | | | 120 | | | | | 125 | | | | |
| ggc | tat | gcg | ttg | cca | agc | gat | gtg | ttc | ttg | aaa | ttc | cgt | gac | gaa | cag | 432 |
| Gly | Tyr | Ala | Leu | Pro | Ser | Asp | Val | Phe | Leu | Lys | Phe | Arg | Asp | Glu | Gln | |
| 130 | | | | | 135 | | | | | 140 | | | | | | |
| ggt | aat | atc | tct | agc | gac | gat | gta | aag | tgc | ctg | atc | atg | ctg | tac | gac | 480 |
| Gly | Asn | Ile | Ser | Ser | Asp | Asp | Val | Lys | Cys | Leu | Ile | Met | Leu | Tyr | Asp | |
| 145 | | | | | 150 | | | | | 155 | | | | | 160 | |
| gca | agc | cac | ctg | cgc | atc | cac | gaa | gaa | aag | att | ctg | gat | aac | att | aac | 528 |
| Ala | Ser | His | Leu | Arg | Ile | His | Glu | Glu | Lys | Ile | Leu | Asp | Asn | Ile | Asn | |
| | | | | 165 | | | | | 170 | | | | | 175 | | |
| agc | ttt | acc | aaa | tcc | tgt | ctg | caa | agc | gtg | ttg | gaa | acg | aat | ctg | gag | 576 |
| Ser | Phe | Thr | Lys | Ser | Cys | Leu | Gln | Ser | Val | Leu | Glu | Thr | Asn | Leu | Glu | |
| | | | 180 | | | | | 185 | | | | | 190 | | | |
| ccg | gca | ctg | caa | gaa | gaa | gtc | cgc | tgc | acg | ctg | gaa | acc | cct | cgc | ttc | 624 |
| Pro | Ala | Leu | Gln | Glu | Glu | Val | Arg | Cys | Thr | Leu | Glu | Thr | Pro | Arg | Phe | |
| | | 195 | | | | | 200 | | | | | 205 | | | | |
| cgt | cgc | gtt | gag | cgc | atc | gaa | gcg | cgt | cgt | ttc | atc | agc | gcg | tat | gag | 672 |
| Arg | Arg | Val | Glu | Arg | Ile | Glu | Ala | Arg | Arg | Phe | Ile | Ser | Ala | Tyr | Glu | |
| | | 210 | | | | | 215 | | | | | 220 | | | | |
| aag | aat | atc | gcc | cgt | gac | gac | gcg | ctg | ctg | gag | ttt | gcg | aaa | ctg | gac | 720 |
| Lys | Asn | Ile | Ala | Arg | Asp | Asp | Ala | Leu | Leu | Glu | Phe | Ala | Lys | Leu | Asp | |
| 225 | | | | 230 | | | | | 235 | | | | | 240 | | |
| tac | aac | atc | gtt | cag | att | ctg | tac | tgt | aaa | gaa | ctg | aaa | gag | ctg | acg | 768 |
| Tyr | Asn | Ile | Val | Gln | Ile | Leu | Tyr | Cys | Lys | Glu | Leu | Lys | Glu | Leu | Thr | |
| | | | | 245 | | | | | 250 | | | | | 255 | | |
| gtg | tgg | tgg | aaa | gaa | ttt | cat | agc | caa | act | aat | ctg | acc | ttt | gcc | cgc | 816 |
| Val | Trp | Trp | Lys | Glu | Phe | His | Ser | Gln | Thr | Asn | Leu | Thr | Phe | Ala | Arg | |
| | | | 260 | | | | | 265 | | | | | 270 | | | |
| gat | cgt | atc | gtc | gag | atg | tat | ttc | tgg | gtg | atg | gcg | atc | att | tat | gag | 864 |
| Asp | Arg | Ile | Val | Glu | Met | Tyr | Phe | Trp | Val | Met | Ala | Ile | Ile | Tyr | Glu | |
| | | | 275 | | | | | 280 | | | | | 285 | | | |
| ccg | tgt | tac | agc | tac | agc | cgc | atc | tgg | gtt | acg | aaa | atg | ttc | ctg | tcc | 912 |
| Pro | Cys | Tyr | Ser | Tyr | Ser | Arg | Ile | Trp | Val | Thr | Lys | Met | Phe | Leu | Ser | |
| | | | 290 | | | | | 295 | | | | | 300 | | | |
| gtt | gca | ctg | ttg | gat | gac | att | tac | gac | aac | tac | acc | agc | acc | gaa | gag | 960 |
| Val | Ala | Leu | Leu | Asp | Asp | Ile | Tyr | Asp | Asn | Tyr | Thr | Ser | Thr | Glu | Glu | |
| 305 | | | | | 310 | | | | | 315 | | | | | 320 | |
| tcc | aac | atc | ttt | acg | acc | gcg | atg | gag | cgt | tgg | gac | gct | aag | gcg | acg | 1008 |
| Ser | Asn | Ile | Phe | Thr | Thr | Ala | Met | Glu | Arg | Trp | Asp | Ala | Lys | Ala | Thr | |
| | | | | 325 | | | | | 330 | | | | | 335 | | |
| gag | cag | ctg | ccg | gcg | aat | atg | cgt | acc | ttt | tat | gat | tac | ttg | att | tgc | 1056 |
| Glu | Gln | Leu | Pro | Ala | Asn | Met | Arg | Thr | Phe | Tyr | Asp | Tyr | Leu | Ile | Cys | |
| | | | 340 | | | | | 345 | | | | | 350 | | | |
| acg | acg | gat | gag | gtc | gtt | gaa | gag | ctg | aaa | ttg | caa | aac | aac | aag | aat | 1104 |
| Thr | Thr | Asp | Glu | Val | Val | Glu | Glu | Leu | Lys | Leu | Gln | Asn | Asn | Lys | Asn | |

```
                355                 360                 365
gcc gag ctg gtt aag aaa gtt ctg att gac gcg gcc aaa tgt tac cat    1152
Ala Glu Leu Val Lys Lys Val Leu Ile Asp Ala Ala Lys Cys Tyr His
    370                 375                 380 agc gag gtc aaa tgg cgt gac gat cac tac gtc ccg aat gat gtc ggc    1200
Ser Glu Val Lys Trp Arg Asp Asp His Tyr Val Pro Asn Asp Val Gly
385                 390                 395                 400 gag cac ttg cag ctg agc atg cgt tct att gcg gct atg cac tcc atc    1248
Glu His Leu Gln Leu Ser Met Arg Ser Ile Ala Ala Met His Ser Ile
            405                 410                 415 aac ttt atc ttc atc tct ctg ggt gcg gtc tgt acc cgt gag gcc gtg    1296
Asn Phe Ile Phe Ile Ser Leu Gly Ala Val Cys Thr Arg Glu Ala Val
        420                 425                 430 gaa tgc gcg ttt acc tat ccg aag att att cgt ggt att tgc gtg cat    1344
Glu Cys Ala Phe Thr Tyr Pro Lys Ile Ile Arg Gly Ile Cys Val His
                435                 440                 445 gcg cgt att tcg aac gat att gcg agc cat gaa cgc gag caa gcg tct    1392
Ala Arg Ile Ser Asn Asp Ile Ala Ser His Glu Arg Glu Gln Ala Ser
450                 455                 460 gaa cac atg gct tcg acc ctg caa act tgc atg aaa cag tac ggt att    1440
Glu His Met Ala Ser Thr Leu Gln Thr Cys Met Lys Gln Tyr Gly Ile
465                 470                 475                 480 acg gtc gaa gag gca gcc gag aag ttg cgt gtt atc aat gaa gag agc    1488
Thr Val Glu Glu Ala Ala Glu Lys Leu Arg Val Ile Asn Glu Glu Ser
                485                 490                 495 tgg atg aac att gtg gaa gag tgt ctg tac aaa gac cag tat ccg ctg    1536
Trp Met Asn Ile Val Glu Glu Cys Leu Tyr Lys Asp Gln Tyr Pro Leu
            500                 505                 510 gct ctg agc gag cgt gtt gtt gca ttc gcg cag agc att tgc ttc atg    1584
Ala Leu Ser Glu Arg Val Val Ala Phe Ala Gln Ser Ile Cys Phe Met
        515                 520                 525 tat aat ggt gtt gat aag tat acc atc ccg agc aag ctg aag gat agc    1632
Tyr Asn Gly Val Asp Lys Tyr Thr Ile Pro Ser Lys Leu Lys Asp Ser
    530                 535                 540 ctg gac tcg ctg tac gtg aac ctg att tca gtt taa                    1668
Leu Asp Ser Leu Tyr Val Asn Leu Ile Ser Val
545                 550                 555

<210> SEQ ID NO 38
<211> LENGTH: 555
<212> TYPE: PRT
<213> ORGANISM: Artificial Sequence
<220> FEATURE:
<223> OTHER INFORMATION: Synthetic Construct

<400> SEQUENCE: 38

Met Ala Thr Thr Ala Ala Phe Cys Leu Thr Thr Thr Pro Ile Gly Glu
1               5                   10                  15

Pro Val Cys Arg Arg Gln Tyr Leu Pro Ser Val Trp Gly Asn Phe Phe
                20                  25                  30

Leu Thr Tyr Gln Pro Cys Thr Pro Glu Glu Val Gln Ser Met Glu Glu
            35                  40                  45

Arg Ala Leu Ala Lys Lys Thr Glu Val Gly Arg Met Leu Gln Glu Val
        50                  55                  60

Ala Ala Ser Gly Asp Leu Ala Arg Lys Leu Gly Leu Val Asp Glu Leu
65                  70                  75                  80

Glu Arg Leu Gly Val Asp Tyr His Tyr Lys Thr Glu Ile Asn Asp Leu
                85                  90                  95

Leu Gly Ala Ile Tyr Asn Gly Lys Asp Asp Asp Asn Gly Gly Ser Asp
```

-continued

```
              100                 105                 110
Asp Asp Leu Tyr Ile Thr Ser Leu Lys Phe Tyr Leu Arg Lys His
            115                 120                 125
Gly Tyr Ala Leu Pro Ser Asp Val Phe Leu Lys Phe Arg Asp Glu Gln
            130                 135                 140
Gly Asn Ile Ser Ser Asp Val Lys Cys Leu Ile Met Leu Tyr Asp
145                 150                 155                 160
Ala Ser His Leu Arg Ile His Glu Glu Lys Ile Leu Asp Asn Ile Asn
                165                 170                 175
Ser Phe Thr Lys Ser Cys Leu Gln Ser Val Leu Glu Thr Asn Leu Glu
                180                 185                 190
Pro Ala Leu Gln Glu Glu Val Arg Cys Thr Leu Glu Thr Pro Arg Phe
                195                 200                 205
Arg Arg Val Glu Arg Ile Glu Ala Arg Phe Ile Ser Ala Tyr Glu
                210                 215                 220
Lys Asn Ile Ala Arg Asp Asp Ala Leu Leu Glu Phe Ala Lys Leu Asp
225                 230                 235                 240
Tyr Asn Ile Val Gln Ile Leu Tyr Cys Lys Glu Leu Lys Glu Leu Thr
                    245                 250                 255
Val Trp Trp Lys Glu Phe His Ser Gln Thr Asn Leu Thr Phe Ala Arg
                260                 265                 270
Asp Arg Ile Val Glu Met Tyr Phe Trp Val Met Ala Ile Ile Tyr Glu
                275                 280                 285
Pro Cys Tyr Ser Tyr Ser Arg Ile Trp Val Thr Lys Met Phe Leu Ser
                290                 295                 300
Val Ala Leu Leu Asp Asp Ile Tyr Asp Asn Tyr Thr Ser Thr Glu Glu
305                 310                 315                 320
Ser Asn Ile Phe Thr Thr Ala Met Glu Arg Trp Asp Ala Lys Ala Thr
                    325                 330                 335
Glu Gln Leu Pro Ala Asn Met Arg Thr Phe Tyr Asp Tyr Leu Ile Cys
                340                 345                 350
Thr Thr Asp Glu Val Val Glu Glu Leu Lys Leu Gln Asn Asn Lys Asn
                355                 360                 365
Ala Glu Leu Val Lys Lys Val Leu Ile Asp Ala Ala Lys Cys Tyr His
                370                 375                 380
Ser Glu Val Lys Trp Arg Asp Asp His Tyr Val Pro Asn Asp Val Gly
385                 390                 395                 400
Glu His Leu Gln Leu Ser Met Arg Ser Ile Ala Ala Met His Ser Ile
                    405                 410                 415
Asn Phe Ile Phe Ile Ser Leu Gly Ala Val Cys Thr Arg Glu Ala Val
                420                 425                 430
Glu Cys Ala Phe Thr Tyr Pro Lys Ile Ile Arg Gly Ile Cys Val His
                435                 440                 445
Ala Arg Ile Ser Asn Asp Ile Ala Ser His Glu Arg Glu Gln Ala Ser
                450                 455                 460
Glu His Met Ala Ser Thr Leu Gln Thr Cys Met Lys Gln Tyr Gly Ile
465                 470                 475                 480
Thr Val Glu Glu Ala Ala Glu Lys Leu Arg Val Ile Asn Glu Glu Ser
                    485                 490                 495
Trp Met Asn Ile Val Glu Glu Cys Leu Tyr Lys Asp Gln Tyr Pro Leu
                500                 505                 510
Ala Leu Ser Glu Arg Val Val Ala Phe Ala Gln Ser Ile Cys Phe Met
                515                 520                 525
```

Tyr Asn Gly Val Asp Lys Tyr Thr Ile Pro Ser Lys Leu Lys Asp Ser
       530                 535                 540

Leu Asp Ser Leu Tyr Val Asn Leu Ile Ser Val
545                 550                 555

<210> SEQ ID NO 39
<211> LENGTH: 1766
<212> TYPE: DNA
<213> ORGANISM: Vetiveria zizanoides
<220> FEATURE:
<221> NAME/KEY: misc_feature
<223> OTHER INFORMATION: VzTrspt_10_contig_49, full length cDNA encoding
      for VzZS2-Nter2, including non coding regions

<400> SEQUENCE: 39

```
ctgccgtgct atcactctag caaattatac tgagtggatc aacttaccac accagacgtt      60
tgcattcatg gcgacaactg ccaccttctg cctcaccatc actccgatcg caagccgga     120
ctgtcgccgg aagtacctcc caagcgtctg gggcaacttc ttcctcacct accagccatg    180
cacgcccgaa gaggtccagt ccatggagga gagggctctg gccaagaaga cggaggtggg    240
gcgcatgttg caggaggtcg ccgcctccgg tgacctcgca cggaagctgg gccttgtcga    300
tgagctagag cggctcgggg tggactatca ttacaagacg gagatcaacg acttgctggg    360
tgccatttat aatggcaagg acgacgataa tggaggttct gatgacgacc tctatatcac    420
atcgcttaag ttctatctgc tcaggaagca tgggtacgct ttaccttcag atgtgtttct    480
gaagttcaga gatgagcaag gaaatatttc aagtgatgat gtgaaatgcc tgatcatgtt    540
gtatgatgcc tcacatttga ggattcatga ggagaaaatt cttgacaaca tcaacagttt    600
caccaagagc tgcctccaat cagttttaga aacaaatttg gaaccggctc tccaagagga    660
ggtgcggtgc acattggaga cacctcgatt cagaagggtt gagagaatcg aagcgagacg    720
gtttatctca gcgtacgaaa agaacatagc acgagatgac gccctactag agtttgcaaa    780
gctggactac aatatcgtgc aaattctcta ctgcaaggag ctgaaagaac ttacagtatg    840
gtggaaggag ttccactcac agacaaatct gacatttgca cgagatagaa ttgtggagat    900
gtatttctgg gtcatggcaa ttatttatga gccttgttac tcatattcac ggatatgggt    960
tacaaaaatg tttctatccg tggcattgtt ggatgacatc tatgacaatt atacgagcac   1020
agaggagagc aatatcttta ctacggccat ggaaaggtgg gatgcgaagg ccactgaaca   1080
actgccagca acatgagga cattctacga ttacttaatt tgtacaacag atgaggtcgt    1140
agaagaattg aaacttcaga ataataagaa tgctgaatta gtcaagaaag tgctgattga   1200
cgctgctaaa tgctaccatt cggaggtcaa atggcgtgat gaccactacg tccctaatga   1260
tgttggagag cacctgcagc tttcaatgcg aagcattgca gctatgcact ccatcaactt   1320
tatcttcatt tcactgggag ctgtgtgtac tagggaggcg gttgagtgtg ctttcactta   1380
tccaaaaatt attagaggta tatgtgttca cgcacgtatt agtaacgata tcgcgtcaca   1440
tgagcgagaa caagcttcgg agcatatggc atcaacgttg caaacttgca tgaagcagta   1500
tgggattaca gtagaggaag ctgctgaaaa gctcagagta ataaacgagg agtcatggat   1560
gaacatcgtt gaggaatgcc tttataagga ccagtatccc ctggcgcttt cggagagggt   1620
ggtggccttt gcacaatcaa tatgtttcat gtacaatggt gtagataaat acaccatacc   1680
atcaaaactc aaggacagtc tagactcatt gtacgtcaat ttgatttcag tttgacgaca   1740
tcgcatcaag tattaattct aggctt                                         1766
```

<210> SEQ ID NO 40
<211> LENGTH: 1667
<212> TYPE: DNA
<213> ORGANISM: Vetiveria zizanoides
<220> FEATURE:
<221> NAME/KEY: misc_feature
<223> OTHER INFORMATION: VzTrspt_10_contig_49, full length cDNA encoding for VzZS2-Nter2, open reading frame only

<400> SEQUENCE: 40

```
atggcgacaa ctgccacctt ctgcctcacc atcactccga tcggcaagcc ggactgtcgc      60
cggaagtacc tcccaagcgt ctggggcaac ttcttcctca cctaccagcc atgcacgccc     120
gaagaggtcc agtccatgga ggagagggct ctggccaaga agacggaggt ggggcgcatg     180
ttgcaggagg tcgccgcctc cggtgacctc gcacggaagc tgggccttgt cgatgagcta     240
gagcggctcg gggtggacta tcattacaag acggagatca acgacttgct gggtgccatt     300
tataatggca aggacgacga taatggaggt tctgatgacg acctctatat cacatcgctt     360
aagttctatc tgctcaggaa gcatgggtac gctttacctt cagatgtgtt tctgaagttc     420
agagatgagc aaggaaatat ttcaagtgat gatgtgaaat gcctgatcat gttgtatgat     480
gcctcacatt tgaggattca tgaggagaaa attcttgaca catcaacag tttcaccaag      540
agctgcctcc aatcagtttt agaaacaaat ttggaaccgg ctctccaaga ggaggtgcgg     600
tgcacattgg agacacctcg attcagaagg gttgagagaa tcgaagcgag acggtttatc     660
tcagcgtacg aaaagaacat agcacgagat gacgccctac tagagtttgc aaagctggac     720
tacaatatcg tgcaaattct ctactgcaag gagctgaaag aacttacagt atggtggaag     780
gagttccact cacagacaaa tctgacattt gcacgagata gaattgtgga gatgtatttc     840
tgggtcatgg caattattta tgagccttgt tactcatatt cacggatatg ggttacaaaa     900
atgtttctat ccgtggcatt gttggatgac atctatgaca attatacgag cacagaggag     960
agcaatatct ttactacggc catggaaagg tgggatgcga aggccactga caactgccca    1020
gcaaacatga ggacattcta cgattactta atttgtacaa cagatgaggt cgtagaagaa    1080
ttgaaacttc agaataataa gaatgctgaa ttagtcaaga aagtgctgat tgacgctgct    1140
aaatgctacc attcggaggt caaatggcgt gatgaccact acgtccctaa tgatgttgga    1200
gagcacctgc agctttcaat gcgaagcatt cagctatgc actccatcaa ctttatcttc     1260
atttcactgg gagctgtgtg tactagggag gcggttgagt gtgctttcac ttatccaaaa    1320
attattagag gtatatgtgt tcacgcacgt attagtaacg atatcgcgtc acatgagcga    1380
gaacaagctt cggagcatat ggcatcaacg ttgcaaactt gcatgaagca gtatgggatt    1440
acagtagagg aagctgctga aaagctcaga gtaataaacg aggagtcatg gatgaacatc    1500
gttgaggaat gcctttataa ggaccagtat cccctggcgc tttcggagag ggtggtggcc    1560
tttgcacaat caatatgttt catgtacaat ggtgtagata aatacaccat accatcaaaa    1620
ctcaaggaca gtctagactc attgtacgtc aatttgattt cagtttg              1667
```

<210> SEQ ID NO 41
<211> LENGTH: 1668
<212> TYPE: DNA
<213> ORGANISM: Artificial Sequence
<220> FEATURE:
<223> OTHER INFORMATION: Codon optimized cDNA encoding for VzZS2-Nter2 SR opt
<220> FEATURE:
<221> NAME/KEY: misc_feature
<223> OTHER INFORMATION: Codon optimized cDNA encoding for VzZS2-Nter2

```
                SR opt
<220> FEATURE:
<221> NAME/KEY: CDS
<222> LOCATION: (1)..(1668)

<400> SEQUENCE: 41 atg gct acg acc gca act ttc tgt ctg act att acg cct atc ggt aaa        48
Met Ala Thr Thr Ala Thr Phe Cys Leu Thr Ile Thr Pro Ile Gly Lys
1               5                   10                  15 cca gat tgt cgc cgt aag tat tta ccg agc gtg tgg ggt aac ttc ttc        96
Pro Asp Cys Arg Arg Lys Tyr Leu Pro Ser Val Trp Gly Asn Phe Phe
            20                  25                  30 ctg act tat cag ccg tgc acc ccg gaa gag gtg cag agc atg gag gaa       144
Leu Thr Tyr Gln Pro Cys Thr Pro Glu Glu Val Gln Ser Met Glu Glu
        35                  40                  45 cgc gcg ctg gca aag aaa acc gag gtt ggc cgt atg ctg cag gaa gtg       192
Arg Ala Leu Ala Lys Lys Thr Glu Val Gly Arg Met Leu Gln Glu Val
    50                  55                  60 gca gct agc ggt gat ctg gca cgt aaa ctg ggc ctg gta gat gaa ctg       240
Ala Ala Ser Gly Asp Leu Ala Arg Lys Leu Gly Leu Val Asp Glu Leu
65                  70                  75                  80 gag cgt ctg ggt gtt gac tat cac tat aag acc gaa atc aat gac tta       288
Glu Arg Leu Gly Val Asp Tyr His Tyr Lys Thr Glu Ile Asn Asp Leu
                85                  90                  95 ctg ggt gcg att tat aac ggc aaa gac gat gac aac ggc ggc tct gac       336
Leu Gly Ala Ile Tyr Asn Gly Lys Asp Asp Asp Asn Gly Gly Ser Asp
            100                 105                 110 gat gac ttg tac att acg tcg ctg aaa ttc tac ctg ttg cgc aaa cac       384
Asp Asp Leu Tyr Ile Thr Ser Leu Lys Phe Tyr Leu Leu Arg Lys His
        115                 120                 125 ggt tac gcg ttg ccg tcc gat gtt ttt ctg aag ttc cgt gat gaa cag       432
Gly Tyr Ala Leu Pro Ser Asp Val Phe Leu Lys Phe Arg Asp Glu Gln
    130                 135                 140 ggt aat att tct agc gat gac gtt aaa tgt ctg atc atg ctg tat gat       480
Gly Asn Ile Ser Ser Asp Asp Val Lys Cys Leu Ile Met Leu Tyr Asp
145                 150                 155                 160 gca tcc cat ctg cgc att cac gaa gaa aag atc ctg gat aac att aac       528
Ala Ser His Leu Arg Ile His Glu Glu Lys Ile Leu Asp Asn Ile Asn
                165                 170                 175 agc ttt acc aaa agc tgt ctg caa agc gtg ctg gaa acg aat ctg gag       576
Ser Phe Thr Lys Ser Cys Leu Gln Ser Val Leu Glu Thr Asn Leu Glu
            180                 185                 190 ccg gca ctg caa gaa gag gtg cgt tgc acg ctg gaa acc ccg cgt ttt       624
Pro Ala Leu Gln Glu Glu Val Arg Cys Thr Leu Glu Thr Pro Arg Phe
        195                 200                 205 cgt cgc gtt gag cgc atc gaa gcg cgt cgt ttc atc agc gcc tat gag       672
Arg Arg Val Glu Arg Ile Glu Ala Arg Arg Phe Ile Ser Ala Tyr Glu
    210                 215                 220 aag aac att gcg cgt gat gac gca ctg ctg gaa ttt gcg aaa ttg gat       720
Lys Asn Ile Ala Arg Asp Asp Ala Leu Leu Glu Phe Ala Lys Leu Asp
225                 230                 235                 240 tac aat att gtc caa atc ctg tac tgc aaa gaa ctg aaa gaa ctg acc       768
Tyr Asn Ile Val Gln Ile Leu Tyr Cys Lys Glu Leu Lys Glu Leu Thr
                245                 250                 255 gtc tgg tgg aaa gag ttc cac agc cag act aac ctg acc ttc gct cgc       816
Val Trp Trp Lys Glu Phe His Ser Gln Thr Asn Leu Thr Phe Ala Arg
            260                 265                 270 gac cgt atc gtc gag atg tat ttt tgg gtc atg gcc att atc tac gag       864
Asp Arg Ile Val Glu Met Tyr Phe Trp Val Met Ala Ile Ile Tyr Glu
        275                 280                 285
```

```
ccg tgc tac agc tac agc cgt atc tgg gtc acc aaa atg ttc ctg tct      912
Pro Cys Tyr Ser Tyr Ser Arg Ile Trp Val Thr Lys Met Phe Leu Ser
        290                 295                 300 gtc gcg ctg ctg gat gat att tac gac aac tat acc agc acc gaa gag      960
Val Ala Leu Leu Asp Asp Ile Tyr Asp Asn Tyr Thr Ser Thr Glu Glu
305                 310                 315                 320 tcc aac atc ttc acg acc gcg atg gaa cgt tgg gac gcg aag gca acc     1008
Ser Asn Ile Phe Thr Thr Ala Met Glu Arg Trp Asp Ala Lys Ala Thr
                325                 330                 335 gag caa ctg ccg gcc aat atg cgc acc ttc tac gat tat ttg att tgt     1056
Glu Gln Leu Pro Ala Asn Met Arg Thr Phe Tyr Asp Tyr Leu Ile Cys
            340                 345                 350 acc acc gac gaa gtt gtc gaa gaa ctg aag ttg cag aac aat aaa aat     1104
Thr Thr Asp Glu Val Val Glu Glu Leu Lys Leu Gln Asn Asn Lys Asn
        355                 360                 365 gcc gaa ttg gtt aaa aaa gtg ctg att gat gcc gcc aag tgc tac cat     1152
Ala Glu Leu Val Lys Lys Val Leu Ile Asp Ala Ala Lys Cys Tyr His
    370                 375                 380 agc gaa gtt aag tgg cgt gat gat cat tat gtt ccg aat gac gtc ggc     1200
Ser Glu Val Lys Trp Arg Asp Asp His Tyr Val Pro Asn Asp Val Gly
385                 390                 395                 400 gag cat ttg caa ctg tcc atg cgc agc atc gcg gcg atg cac agc att     1248
Glu His Leu Gln Leu Ser Met Arg Ser Ile Ala Ala Met His Ser Ile
                405                 410                 415 aac ttt atc ttt atc agc ctg ggc gct gtc tgc acg cgt gaa gct gtt     1296
Asn Phe Ile Phe Ile Ser Leu Gly Ala Val Cys Thr Arg Glu Ala Val
            420                 425                 430 gag tgc gcg ttt acc tat cca aag att att cgt ggt atc tgc gtt cac     1344
Glu Cys Ala Phe Thr Tyr Pro Lys Ile Ile Arg Gly Ile Cys Val His
        435                 440                 445 gcg cgt att tcg aat gac atc gca agc cat gag cgt gag caa gcg agc     1392
Ala Arg Ile Ser Asn Asp Ile Ala Ser His Glu Arg Glu Gln Ala Ser
    450                 455                 460 gag cac atg gca tct acg ctg cag acg tgt atg aaa cag tac ggt att     1440
Glu His Met Ala Ser Thr Leu Gln Thr Cys Met Lys Gln Tyr Gly Ile
465                 470                 475                 480 acg gtt gaa gag gcc gcg gaa aag ctg cgc gtg atc aac gaa gag agc     1488
Thr Val Glu Glu Ala Ala Glu Lys Leu Arg Val Ile Asn Glu Glu Ser
                485                 490                 495 tgg atg aat atc gtt gag gaa tgc ctg tat aaa gac cag tac ccg ctg     1536
Trp Met Asn Ile Val Glu Glu Cys Leu Tyr Lys Asp Gln Tyr Pro Leu
            500                 505                 510 gcg ctg agc gag cgc gtg gtg gcg ttt gcc cag agc att tgt ttt atg     1584
Ala Leu Ser Glu Arg Val Val Ala Phe Ala Gln Ser Ile Cys Phe Met
        515                 520                 525 tac aat ggt gtg gac aag tac acc att ccg tcc aag ctg aaa gac agc     1632
Tyr Asn Gly Val Asp Lys Tyr Thr Ile Pro Ser Lys Leu Lys Asp Ser
    530                 535                 540 ctg gat agc ctg tac gtg aac ctg atc tca gtg taa                     1668
Leu Asp Ser Leu Tyr Val Asn Leu Ile Ser Val
545                 550                 555

<210> SEQ ID NO 42
<211> LENGTH: 555
<212> TYPE: PRT
<213> ORGANISM: Artificial Sequence
<220> FEATURE:
<223> OTHER INFORMATION: Synthetic Construct

<400> SEQUENCE: 42

Met Ala Thr Thr Ala Thr Phe Cys Leu Thr Ile Thr Pro Ile Gly Lys
```

-continued

```
1               5                   10                  15
Pro Asp Cys Arg Arg Lys Tyr Leu Pro Ser Val Trp Gly Asn Phe Phe
                20                  25                  30
Leu Thr Tyr Gln Pro Cys Thr Pro Glu Glu Val Gln Ser Met Glu Glu
                35                  40                  45
Arg Ala Leu Ala Lys Lys Thr Glu Val Gly Arg Met Leu Gln Glu Val
50                  55                  60
Ala Ala Ser Gly Asp Leu Ala Arg Lys Leu Gly Leu Val Asp Glu Leu
65                  70                  75                  80
Glu Arg Leu Gly Val Asp Tyr His Tyr Lys Thr Glu Ile Asn Asp Leu
                85                  90                  95
Leu Gly Ala Ile Tyr Asn Gly Lys Asp Asp Asn Gly Gly Ser Asp
                100                 105                 110
Asp Asp Leu Tyr Ile Thr Ser Leu Lys Phe Tyr Leu Leu Arg Lys His
                115                 120                 125
Gly Tyr Ala Leu Pro Ser Asp Val Phe Leu Lys Phe Arg Asp Glu Gln
                130                 135                 140
Gly Asn Ile Ser Ser Asp Val Lys Cys Leu Ile Met Leu Tyr Asp
145                 150                 155                 160
Ala Ser His Leu Arg Ile His Glu Glu Lys Ile Leu Asp Asn Ile Asn
                165                 170                 175
Ser Phe Thr Lys Ser Cys Leu Gln Ser Val Leu Glu Thr Asn Leu Glu
                180                 185                 190
Pro Ala Leu Gln Glu Glu Val Arg Cys Thr Leu Glu Thr Pro Arg Phe
                195                 200                 205
Arg Arg Val Glu Arg Ile Glu Ala Arg Arg Phe Ile Ser Ala Tyr Glu
210                 215                 220
Lys Asn Ile Ala Arg Asp Asp Ala Leu Leu Glu Phe Ala Lys Leu Asp
225                 230                 235                 240
Tyr Asn Ile Val Gln Ile Leu Tyr Cys Lys Glu Leu Lys Glu Leu Thr
                245                 250                 255
Val Trp Trp Lys Glu Phe His Ser Gln Thr Asn Leu Thr Phe Ala Arg
                260                 265                 270
Asp Arg Ile Val Glu Met Tyr Phe Trp Val Met Ala Ile Ile Tyr Glu
                275                 280                 285
Pro Cys Tyr Ser Tyr Ser Arg Ile Trp Val Thr Lys Met Phe Leu Ser
                290                 295                 300
Val Ala Leu Leu Asp Asp Ile Tyr Asp Asn Tyr Thr Ser Thr Glu Glu
305                 310                 315                 320
Ser Asn Ile Phe Thr Thr Ala Met Glu Arg Trp Asp Ala Lys Ala Thr
                325                 330                 335
Glu Gln Leu Pro Ala Asn Met Arg Thr Phe Tyr Asp Tyr Leu Ile Cys
                340                 345                 350
Thr Thr Asp Glu Val Val Glu Glu Leu Lys Leu Gln Asn Asn Lys Asn
                355                 360                 365
Ala Glu Leu Val Lys Lys Val Leu Ile Asp Ala Ala Lys Cys Tyr His
                370                 375                 380
Ser Glu Val Lys Trp Arg Asp Asp His Tyr Val Pro Asn Asp Val Gly
385                 390                 395                 400
Glu His Leu Gln Leu Ser Met Arg Ser Ile Ala Ala Met His Ser Ile
                405                 410                 415
Asn Phe Ile Phe Ile Ser Leu Gly Ala Val Cys Thr Arg Glu Ala Val
                420                 425                 430
```

```
Glu Cys Ala Phe Thr Tyr Pro Lys Ile Ile Arg Gly Ile Cys Val His
            435                 440                 445

Ala Arg Ile Ser Asn Asp Ile Ala Ser His Glu Arg Glu Gln Ala Ser
    450                 455                 460

Glu His Met Ala Ser Thr Leu Gln Thr Cys Met Lys Gln Tyr Gly Ile
465                 470                 475                 480

Thr Val Glu Glu Ala Ala Glu Lys Leu Arg Val Ile Asn Glu Ser
                485                 490                 495

Trp Met Asn Ile Val Glu Glu Cys Leu Tyr Lys Asp Gln Tyr Pro Leu
            500                 505                 510

Ala Leu Ser Glu Arg Val Val Ala Phe Ala Gln Ser Ile Cys Phe Met
            515                 520                 525

Tyr Asn Gly Val Asp Lys Tyr Thr Ile Pro Ser Lys Leu Lys Asp Ser
            530                 535                 540

Leu Asp Ser Leu Tyr Val Asn Leu Ile Ser Val
545                 550                 555
```

```
<210> SEQ ID NO 43
<211> LENGTH: 79
<212> TYPE: DNA
<213> ORGANISM: Artificial Sequence
<220> FEATURE:
<223> OTHER INFORMATION: Primer for LEU2 marker PCR

<400> SEQUENCE: 43
aggtgcagtt cgcgtgcaat tataacgtcg tggcaactgt tatcagtcgt accgcgccat    60
tcgactacgt cgtaaggcc                                                 79

<210> SEQ ID NO 44
<211> LENGTH: 80
<212> TYPE: DNA
<213> ORGANISM: Artificial Sequence
<220> FEATURE:
<223> OTHER INFORMATION: Primer for LEU2 marker PCR

<400> SEQUENCE: 44
tcgtggtcaa ggcgtgcaat tctcaacacg agagtgattc ttcggcgttg ttgctgacca    60
tcgacggtcg aggagaactt                                                80

<210> SEQ ID NO 45
<211> LENGTH: 85
<212> TYPE: DNA
<213> ORGANISM: Artificial Sequence
<220> FEATURE:
<223> OTHER INFORMATION: Primer for AmpR, E. coli marker PCR

<400> SEQUENCE: 45
tggtcagcaa caacgccgaa gaatcactct cgtgttgaga attgcacgcc ttgaccacga    60
cacgttaagg gattttggtc atgag                                          85

<210> SEQ ID NO 46
<211> LENGTH: 80
<212> TYPE: DNA
<213> ORGANISM: Artificial Sequence
<220> FEATURE:
<223> OTHER INFORMATION: Primer for AmpR, E. coli marker PCR

<400> SEQUENCE: 46
aacgcgtacc ctaagtacgg caccacagtg actatgcagt ccgcactttg ccaatgccaa    60
```

-continued aaatgtgcgc ggaacccta    80

<210> SEQ ID NO 47
<211> LENGTH: 84
<212> TYPE: DNA
<213> ORGANISM: Artificial Sequence
<220> FEATURE:
<223> OTHER INFORMATION: Primer for Yeast origin of replication PCR

<400> SEQUENCE: 47
ttggcattgg caaagtgcgg actgcatagt cactgtggtg ccgtacttag ggtacgcgtt    60
cctgaacgaa gcatctgtgc ttca    84

<210> SEQ ID NO 48
<211> LENGTH: 85
<212> TYPE: DNA
<213> ORGANISM: Artificial Sequence
<220> FEATURE:
<223> OTHER INFORMATION: Primer for Yeast origin of replication PCR

<400> SEQUENCE: 48
ccgagatgcc aaaggatagg tgctatgttg atgactacga cacagaactg cgggtgacat    60
aatgatagca ttgaaggatg agact    85

<210> SEQ ID NO 49
<211> LENGTH: 82
<212> TYPE: DNA
<213> ORGANISM: Artificial Sequence
<220> FEATURE:
<223> OTHER INFORMATION: Primer for E. coli origin of replication PCR

<400> SEQUENCE: 49
atgtcacccg cagttctgtg tcgtagtcat caacatagca cctatccttt ggcatctcgg    60
tgagcaaaag gccagcaaaa gg    82

<210> SEQ ID NO 50
<211> LENGTH: 81
<212> TYPE: DNA
<213> ORGANISM: Artificial Sequence
<220> FEATURE:
<223> OTHER INFORMATION: Primer for E. coli origin of replication PCR

<400> SEQUENCE: 50
ctcagatgta cggtgatcgc caccatgtga cggaagctat cctgacagtg tagcaagtgc    60
tgagcgtcag accccgtaga a    81

<210> SEQ ID NO 51
<211> LENGTH: 1668
<212> TYPE: DNA
<213> ORGANISM: Artificial Sequence
<220> FEATURE:
<223> OTHER INFORMATION: VzZS1 DNA codon optimized for Saccharomyces
      cerevisiae

<400> SEQUENCE: 51
atggctacta ctgctgcttt ctgtttgact actactccaa tcggtgaacc agtttgtaga    60
agacaatact tgccaactgt ttggggttct ttcttcttga cttaccaacc atgtactcca    120
gaagaagttc aatctatgga agaaagagct ttggctaaga agactgaagt tggtagaatg    180
ttgcaagaag ttgctgcttc ttctaacttg gctagaaagt tgggtttggt tgacgaattg    240
gaaagattgg gtgttgacta ccactacaag actgaaatca acgacttgtt gggtgctatc    300

```
tacaacggta aggacgacga caacggtggt tctgacgacg acttgtacat cacttctttg      360
aagttctact tgttgagaaa gcacggttac gctttgtctt ctgacgtttt cttgaagttc      420
agagacgaac aaggtaacat ctcttctgac gacgttaagt gtttgatcat gttgtacgac      480
gcttctcact tgagaatcca cgaagaaaag atcttggaca acatcaactc tttcactaag      540
tcttgtttgc aatctgtttt ggaaactaac ttggaaccag ctttgcaaga agaagttaga      600
tgtactttgg aaactccaag attcagaaga gttgaaagaa tcgaagctaa agattcatc       660 tctgcttacg aaaagaacat cgctagagac gacgctttgt tggaattcgc tagattggac      720
tacaacatcg ttcaaatctt gtactgtaag gaattgaagg aattgactgt ttggtggaag      780
gaattccact ctagaactaa cttgactttc gctagagaca gaatcgttga aatgtacttc      840
tgggttatgg ctatcatcta cgaaccatgt tactcttact ctagaatctg ggttactaag      900
atgttcttgt ctgttgcttt gttggacgac atctacgaca actacacttc tactgaagaa      960
tctaacatct tcactactgc tatggaaaga tgggacgtta aggctactga acaattgcca     1020
gctaacatga gaactttcta cgactacttg atctgtacta ctgacgaagt tgttgaagaa     1080
ttgaagttgc aaaacaacaa gaacgctgaa ttggttaaga aggttttgat cgacgctgct     1140
aagtgttacc actctgaagt taagtggaga acgaccact acgttccaaa cgacgttggt      1200
gaacacttgc aattgtctat gagatctatc gctgctatgc actctatcaa cttcgttttc     1260
atctctttgg gtgctgtttg tactagaaga gctgttgaat gtgctttcac ttacccaaag     1320
atcatcagag gtatctgtgt tcacgctaga atctctaacg acatcgcttc tcacgaaaga     1380
gaacaagctt ctgaacacat ggcttctact ttgcaaactt gtatgaagca atacggtatc     1440
actgttgaag aagctgctga aaagttgaga gttatcaacg aagaatcttg gatggacatc     1500
gttgaagaat gtttgtacaa ggaccaatac ccattggctt tgtctgaaag agttgttgct     1560
ttcgctcaat ctatctgttt catgtacaac ggtgttgaca agtacactat cccatctaag     1620
ttgaaggact ctttggactc tttgtacgtt aacttgatcc cagtttaa                 1668

<210> SEQ ID NO 52
<211> LENGTH: 1668
<212> TYPE: DNA
<213> ORGANISM: Artificial Sequence
<220> FEATURE:
<223> OTHER INFORMATION: VzZS2 DNA codon optimized for Saccharomyces
      cerevisiae

<400> SEQUENCE: 52
atggctacta ctgctgcttt ctgtttgact actactccaa tcggtgaacc agtttgtaga        60
agacaatact tgccatctgt ttggggtaac ttcttcttga cttaccaacc atgtactcca       120
gaagaagttc aatctatgga agaaagagct tggctaaga agactgaagt tggtagaatg       180
ttgcaagaag ttgctgcttc tggtgacttg gctagaaagt tgggtttggt tgacgaattg      240
gaaagattgg gtgttgacta ccactacaag actgaaatca cgacttgtt gggtgctatc      300 tacaacggta aggacgacga caacggtggt tctgacgacg acttgtacat cacttctttg      360
aagttctact tgttgagaaa gcacggttac gctttgccat ctgacgtttt cttgaagttc      420
agagacgaac aaggtaacat ctcttctgac gacgttaagt gtttgatcat gttgtacgac      480
gcttctcact tgagaatcca cgaagaaaag atcttggaca acatcaactc tttcactaag      540
tcttgtttgc aatctgtttt ggaaactaac ttggaaccag ctttgcaaga agaagttaga      600
tgtactttgg aaactccaag attcagaaga gttgaaagaa tcgaagctag aagattcatc      660
```

```
tctgcttacg aaaagaacat cgctagagac gacgctttgt tggaattcgc taagttggac    720
tacaacatcg ttcaaatctt gtactgtaag gaattgaagg aattgactgt ttggtggaag    780
gaattccact ctcaaactaa cttgactttc gctagagaca gaatcgttga aatgtacttc    840
tgggttatgg ctatcatcta cgaaccatgt tactcttact ctagaatctg ggttactaag    900
atgttcttgt ctgttgcttt gttggacgac atctacgaca actacacttc tactgaagaa    960
tctaacatct tcactactgc tatggaaaga tgggacgcta aggctactga acaattgcca   1020
gctaacatga gaactttcta cgactacttg atctgtacta ctgacgaagt tgttgaagaa   1080
ttgaagttgc aaaacaacaa gaacgctgaa ttggttaaga aggttttgat cgacgctgct   1140
aagtgttacc actctgaagt taagtggaga gacgaccact acgttccaaa cgacgttggt   1200
gaacacttgc aattgtctat gagatctatc gctgctatgc actctatcaa cttcatcttc   1260
atctctttgg gtgctgtttg tactagagaa gctgttgaat gtgctttcac ttacccaaag   1320
atcatcagag gtatctgtgt tcacgctaga atctctaacg catcgcttc tcacgaaaga   1380 gaacaagctt ctgaacacat ggcttctact ttgcaaactt gtatgaagca atacggtatc   1440
actgttgaag aagctgctga aaagttgaga gttatcaacg aagaatcttg gatgaacatc   1500
gttgaagaat gtttgtacaa ggaccaatac ccattggctt tgtctgaaag agttgttgct   1560
ttcgctcaat ctatctgttt catgtacaac ggtgttgaca gtacactat cccatctaag   1620 ttgaaggact ctttggactc tttgtacgtt aacttgatct ctgttta    1668
```

<210> SEQ ID NO 53
<211> LENGTH: 1668
<212> TYPE: DNA
<213> ORGANISM: Artificial Sequence
<220> FEATURE:
<223> OTHER INFORMATION: VzZS2-Nter2 DNA codon optimized for
      Saccharomyces cerevisiae

<400> SEQUENCE: 53

```
atggctacta ctgctacttt ctgtttgact atcactccaa tcggtaagcc agactgtaga     60
agaaagtact tgccatctgt ttggggtaac ttcttcttga cttaccaacc atgtactcca    120
gaagaagttc aatctatgga agaaagagct ttggctaaga gactgaagt tggtagaatg    180 ttgcaagaag ttgctgcttc tggtgacttg gctagaaagt tgggttttggt tgacgaattg    240 gaaagattgg gtgttgacta ccactacaag actgaaatca cgacttgtt gggtgctatc    300 tacaacggta aggacgacga caacggtggt tctgacgacg acttgtacat cacttctttg    360
aagttctact tgttgagaaa gcacggttac gctttgccat ctgacgtttt cttgaagttc    420
agagacgaac aagtaacat ctcttctgac gacgttaagt gtttgatcat gttgtacgac    480
gcttctcact gagaatcca cgaagaaag atcttggaca catcaactc tttcactaag    540 tcttgtttgc aatctgtttt ggaaactaac ttggaaccag ctttgcaaga gaagttaga    600 tgtactttgg aaactccaag attcagaaga gttgaaagaa tcgaagctag aagattcatc    660
tctgcttacg aaaagaacat cgctagagac gacgctttgt tggaattcgc taagttggac    720
tacaacatcg ttcaaatctt gtactgtaag gaattgaagg aattgactgt ttggtggaag    780
gaattccact ctcaaactaa cttgactttc gctagagaca gaatcgttga aatgtacttc    840
tgggttatgg ctatcatcta cgaaccatgt tactcttact ctagaatctg ggttactaag    900
atgttcttgt ctgttgcttt gttggacgac atctacgaca actacacttc tactgaagaa    960
tctaacatct tcactactgc tatggaaaga tgggacgcta aggctactga acaattgcca   1020
```

| | |
|---|---|
| gctaacatga aactttctac gactacttg atctgtacta ctgacgaagt tgttgaagaa | 1080 |
| ttgaagttgc aaaacaacaa gaacgctgaa ttggttaaga aggttttgat cgacgctgct | 1140 |
| aagtgttacc actctgaagt taagtggaga gacgaccact acgttccaaa cgacgttggt | 1200 |
| gaacacttgc aattgtctat gagatctatc gctgctatgc actctatcaa cttcatcttc | 1260 |
| atctctttgg gtgctgtttg tactagagaa gctgttgaat gtgctttcac ttacccaaag | 1320 |
| atcatcagag gtatctgtgt tcacgctaga atctctaacg acatcgcttc tcacgaaaga | 1380 |
| gaacaagctt ctgaacacat ggcttctact ttgcaaactt gtatgaagca atacggtatc | 1440 |
| actgttgaag aagctgctga aaagttgaga gttatcaacg aagaatcttg gatgaacatc | 1500 |
| gttgaagaat gtttgtacaa ggaccaatac ccattggctt tgtctgaaag agttgttgct | 1560 |
| ttcgctcaat ctatctgttt catgtacaac ggtgttgaca agtacactat cccatctaag | 1620 |
| ttgaaggact cttttggactc tttgtacgtt aacttgatct ctgtttaa | 1668 |

<210> SEQ ID NO 54
<211> LENGTH: 1542
<212> TYPE: DNA
<213> ORGANISM: Artificial Sequence
<220> FEATURE:
<223> OTHER INFORMATION: VzCP521-11 DNA codon optimized for
    Saccharomyces cerevisiae

<400> SEQUENCE: 54

| | |
|---|---|
| atggaagaca ctaagatctt ggttgctgct gtttctgttt gtgttttgtt ggttgttttg | 60 |
| tctaagttga gaagtctttt gttgccaggt gctaagccaa agttgaactt gccaccaggt | 120 |
| ccatggactt tgccagttat cggttctttg caccacgtta tcacttaccc aaacttgcac | 180 |
| agagctttgc acggtttggc tcaaaagtac ggtccagtta tgatgttcag attgggtgaa | 240 |
| gttccaatga tggttgtttc ttctccagct gctgctcaag aagctttgaa gactaacgac | 300 |
| atcgcttttcg ctgacagata cactaacgct actatcggtg cttttgacttt ccacggtgaa | 360 |
| gacatggctt tcgctccata cggtgaaaga tggagacaat tgagaaagat ctgtgttttg | 420 |
| gaattgttgt ctgctgctag agttcaatct ttcagacaca tcagagctga agaagtttct | 480 |
| agattggttg gtaagttggc tgcttctgct gctgctggtg aagctgttca cttgaacaag | 540 |
| atcgttgcta agttcgttaa cgacactatc gttagaaag ctgttggttc tggttctaag | 600 |
| caccaagacg aatacttgaa ctctatcgac gttgctttga caaaactat gggtgttgct | 660 |
| ttggctgact gttcccatc ttctagattg atccaaatga cgacactgc tccaagaaag | 720 |
| gttttggctg ctagaaacaa catggaaaga tccttggaag aaatcatcaa cgaaactaag | 780 |
| gaagctatgg acagaggtga cggtcaaaag aaggttgaag gtatcttggg tgttttgttg | 840 |
| agattgcaaa aggaaggttc tactccagtt ccattgacta cgaagttat cgttactgtt | 900 |
| atgttcgaca tgttcggtgc tggttctgac acttcttcta ctttgttgac ttggtgtatg | 960 |
| atggaattgg ttagatctcc accaactatg gctaaggttc aagacgaagt tagagaagct | 1020 |
| ttcaagggta agaaggaatc tactatcatc actgaagacg acttgaaggg tttgacttac | 1080 |
| ttgaagcaag ttatcaagga agctttgaga atgcacccac cagttccatt gttgttgcca | 1140 |
| agaaagtgta gagaaacttg taaggttatg ggttacgaca tcccaaaggg tactgttgtt | 1200 |
| ttcgctaacg cttgggctat cggtagagac ccaaagtact gggaagaccc agaagaattc | 1260 |
| aagccagaaa gattcgacaa gtctaacgtt gactacaagg gtactaactt cgaatacttg | 1320 |
| ccattcggtt ctggtagaag aatctgtcca ggtatcaact ggggtttgtg taacatcgaa | 1380 |

| | |
|---|---|
| ttggctttgg cttctttgtt gtaccacttc gactggaagt tgccaaacgg tatggaacca | 1440 |
| aaggacatcg acatgggtga agctcaaggt ttgatcgctt ctaagaagac taacttgact | 1500 |
| ttgcacccag ttactagaat cgctccagct ggtttcaact aa | 1542 |

<210> SEQ ID NO 55
<211> LENGTH: 1521
<212> TYPE: DNA
<213> ORGANISM: Artificial Sequence
<220> FEATURE:
<223> OTHER INFORMATION: VzCP8201 DNA codon optimized for Saccharomyces cerevisiae

<400> SEQUENCE: 55

| | |
|---|---|
| atggacttct tgagaatccc attcttggtt gctttcgttt tcttggctgt tttgttgaga | 60 |
| ttgatcagat cttacatcac ttcttctgct ttgagattgc caccaggtcc atggcaattg | 120 |
| ccattgatcg gttctttgca ccacttgttg ttgtctagat tctctgactt gccacacaga | 180 |
| gctttgagag aaatgtctgg tacttacggt ccattgatgt tgttgagatt cggttctgtt | 240 |
| ccaactttgg ttgtttcttc tgctgaagct gctagaaag ttatgagaac tcacgacttg | 300 |
| gctttctgtg acagacactt gggtgttact ttggacatcg ttacttgtgg tggtaaggac | 360 |
| atcatctgtt ctccatacaa cgctcactgg agagaattga aaagttgtg tatggttgaa | 420 |
| atcttgtctc aaagaagagt tttgtctttc agatctatca gagaagaaga agttgcttct | 480 |
| ttggttagat ctatctctga cgaatgtggt ggtggtcaac aaccagttaa cttgactgaa | 540 |
| ggtatctcta atgatcaa cgacgttgct gctagaactg ttgttggtga cagatgtaag | 600 |
| taccaagacg aatacatgca cgaattggac gaagttgtta gattggctgg tggtttcaac | 660 |
| ttggctgact tgtacccatc ttctagattg gttagaagat ctctgctgc tgctagagac | 720 |
| gctagaagat gtcaaagaaa catgtacaga atcatccaat ctatcatcca gaaagagaa | 780 |
| gctatgccaa ctccagaaag agacgaagaa gacttgttgg gtgttttgtt gagattgcaa | 840 |
| agagaaggtg gtttgcaatt cgctttgact aacgaaatcg tttctactgt tatctacgac | 900 |
| atcttctctg ctggttctga aacttcttct actgttttgg tttgggctat gtctgaattg | 960 |
| gttaagaacc cacaagttat gagaaaggct caatctgaag ttagagacac tttcaagggt | 1020 |
| aacaacaaga tcactgaatc tgacttgatc aagttgagat acttgcaatt ggttatcaag | 1080 |
| gaaactttga gattgcacgc tccagttcca ttgttgttgc aagagaatg tagagaatct | 1140 |
| tgtcaaatca tgggttacga cgttttgaag ggtactaagg ttttcgttaa cgcttgggct | 1200 |
| atcgctagag acactggttt gtggtgtgac ggtgaagaat tcagaccaga agattcgaa | 1260 |
| tcttctaaca tcgacttcag aggtaacgac ttcgaattca ctccattcgg tgctggtaga | 1320 |
| agagtttgtc aggtatcac tttgggtttg gctaacttgg aattggcttt ggcttctttg | 1380 |
| ttgtaccact tcgactggga cttgccaaac ggtgctagat tggaagactt ggacatggct | 1440 |
| gaagctttcg gtatcacttt gaagagaaag tctatgttgt ggttgaaggc taagccatac | 1500 |
| aacaacttca tcccaaacta a | 1521 |

The invention claimed is:

1. A method for producing an oxidized zizaene compound, which method comprises
   a. contacting zizaene or a zizaene containing composition with a polypeptide having
      Cytochrome P450 monooxygenase activity, selected from:
      i. VzCP8201 comprising an amino acid sequence having at least 90% sequence identity to SEQ ID NO: 19,
      ii. VzCP521-11 comprising an amino acid sequence having at least 90% sequence identity to SEQ ID NO: 21,
      iii. VzCP7186 comprising an amino acid sequence having at least 90% sequence identity to SEQ ID NO: 20,
      iv. or combinations of at least two of said polypeptides;
      thereby predominantly obtaining at least one oxidation product of zizaene, wherein the at least one oxidation product of zizaene comprises zizaenol, wherein the polypeptide catalyzes an oxidation reaction of zizaene in position C3;
   b. optionally isolating a zizaene oxidation product as obtained in step a; and
   c. converting the zizaene oxidation product to zizaenone, or to a mixture comprising zizaenone and epi-zizaenone.

2. The method of claim 1, wherein step a. is performed in vivo in an isolated recombinant host cell in the presence of oxygen; or in vitro in a liquid reaction medium in the presence of oxygen.

3. The method of claim 2, wherein step a. is carried out by cultivating an isolated recombinant host cell expressing at least one of said polypeptides having Cytochrome P450 monooxygenase activity in the presence of zizaene or a zizaene containing composition under conditions conducive to the oxidation of zizaene.

4. The method of claim 1, wherein conversion of zizaene in step a. is performed in the presence of a polypeptide having P450 reductase (CPR) activity.

5. The method of claim 4, wherein said CPR comprising an amino acid sequence having at least 90% sequence identity to SEQ ID NO: 23.

6. The method of claim 1, further comprising, prior to step a. the cyclisation of farnesyl diphosphate (FPP) in the presence of a polypeptide having zizaene synthase activity.

7. The method of claim 6, wherein said polypeptide having zizaene synthase activity comprises an amino acid sequence having at least 90% sequence identity to SEQ ID NO: 33, 38 or 42.

8. The method of claim 1, wherein said polypeptide having Cytochrome P450 monooxygenase activity is selected from:
   i. VzCP8201 comprising an amino acid sequence having at least 90% sequence identity to SEQ ID NO: 19, N-terminally extended by at least one amino acid residue,
   ii. VzCP521-11 comprising an amino acid sequence having at least 90% sequence identity to SEQ ID NO:21, N-terminally extended by at least one amino acid residue; and
   iii. VzCP7186 comprising an amino acid sequence having at least 90% sequence identity to SEQ ID NO:20, N-terminally extended by at least one amino acid residue.

9. The method of claim 1, which method comprises
   a. contacting zizaene or a zizaene containing composition with a polypeptide having
      Cytochrome P450 monooxygenase activity, selected from:
      i. VzCP8201 comprising an amino acid sequence having at least 90% sequence identity to SEQ ID NO: 19,
      ii. VzCP521-11 comprising an amino acid sequence having at least 90% sequence identity to SEQ ID NO: 21,
      iii. VzCP7186 comprising an amino acid sequence having at least 90% sequence identity to SEQ ID NO: 20,
      iv. or combinations of at least two of said polypeptides;
      thereby obtaining at least one oxidation product of zizaene;
   b. isolating a zizaene oxidation product as obtained in step a; and
   c. converting the zizaene oxidation product to zizaenone, or to a mixture comprising zizaenone and epi-zizaenone.

* * * * *